(12) United States Patent
Que

(10) Patent No.: US 7,935,862 B2
(45) Date of Patent: May 3, 2011

(54) TARGETED INTEGRATION AND STACKING OF DNA THROUGH HOMOLOGOUS RECOMBINATION

(75) Inventor: Qiudeng Que, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 474 days.

(21) Appl. No.: 11/001,346

(22) Filed: Dec. 1, 2004

(65) Prior Publication Data
US 2006/0253918 A1    Nov. 9, 2006

Related U.S. Application Data

(60) Provisional application No. 60/526,155, filed on Dec. 2, 2003.

(51) Int. Cl.
*C12N 15/82* (2006.01)
*C12N 15/06* (2006.01)
*C12N 15/63* (2006.01)
*C12N 15/00* (2006.01)
*A01H 5/00* (2006.01)

(52) U.S. Cl. ........ 800/278; 800/295; 435/455; 435/468; 435/471

(58) Field of Classification Search .................. None
See application file for complete search history.

(56) References Cited

U.S. PATENT DOCUMENTS

| | | | |
|---|---|---|---|
| 5,227,288 A | 7/1993 | Blattner | |
| 5,527,695 A * | 6/1996 | Hodges et al. | 800/291 |
| 5,888,732 A | 3/1999 | Hartley et al. | |
| 6,121,014 A | 9/2000 | Koziel et al. | |
| 6,143,557 A | 11/2000 | Hartley et al. | |
| 6,171,861 B1 | 1/2001 | Hartley et al. | |
| 6,187,994 B1 | 2/2001 | Baszczynski et al. | |
| 6,262,341 B1 | 7/2001 | Baszczynski et al. | |
| 6,270,969 B1 | 8/2001 | Hartley et al. | |
| 6,300,545 B1 | 10/2001 | Baszczynski et al. | |
| 6,331,661 B1 | 12/2001 | Baszczynski et al. | |
| 6,410,329 B1 | 6/2002 | Hansen et al. | |
| 6,455,315 B1 | 9/2002 | Baszczynski et al. | |
| 6,458,594 B1 | 10/2002 | Baszczynski et al. | |
| 6,541,231 B1 | 4/2003 | Baszczynski et al. | |
| 6,632,672 B2 | 10/2003 | Calos | |
| 2003/0027337 A1 | 2/2003 | Droge et al. | |
| 2003/0054552 A1 | 3/2003 | Hartley et al. | |
| 2003/0064515 A1 | 4/2003 | Hartley et al. | |
| 2003/0110532 A1 | 6/2003 | Armstrong et al. | |
| 2003/0140376 A1 | 7/2003 | Depicker et al. | |
| 2004/0033596 A1 * | 2/2004 | Threadgill et al. | 435/325 |

FOREIGN PATENT DOCUMENTS

| | | |
|---|---|---|
| EP | 0 160 571 A2 | 11/1985 |
| EP | 0 632 054 A1 | 1/1995 |
| EP | 1 308 516 A1 | 5/2003 |
| WO | WO 94/17176 | 8/1994 |
| WO | WO 95/00555 | 1/1995 |
| WO | WO 99/21977 | 5/1999 |
| WO | WO 99/25821 | 5/1999 |
| WO | WO 99/25841 | 5/1999 |
| WO | WO 99/25854 | 5/1999 |
| WO | WO 99/25855 | 5/1999 |
| WO | WO 99/60842 | 12/1999 |
| WO | WO 01/07572 | 2/2001 |
| WO | WO 01/11058 | 2/2001 |
| WO | WO 01/16345 | 3/2001 |
| WO | WO 01/18222 | 3/2001 |
| WO | WO 02/00875 | 1/2002 |
| WO | WO 02/08409 | 1/2002 |
| WO | WO 02/079409 | 10/2002 |
| WO | WO 02/083867 | 10/2002 |
| WO | WO 02/083910 | 10/2002 |
| WO | WO 02/085104 | 10/2002 |
| WO | WO 02/086144 | 10/2002 |

OTHER PUBLICATIONS

Offringa et al. 1992, Transgenic Research 1:114-123.*
Onouchi et al. 1995, Mol. Gen. Genet. 25:653-660.*
Argos et al., The EMBO Journal, vol. 5, No. 2, pp. 433-440, 1986.
Azaro et al., Mobile DNA II, Edited by N.I. Craig et al. (2002 ASM Press, Washington, DC), pp. 118-148.
Christ amd Droge, Genesis, vol. 32, pp. 203-208, 2002.
Drogai et al., Journal of Molecular Biology, vol. 252, pp. 178-188, 1995.
Esposito et al., Nucleic Acids Research, vol. 25, No. 18, pp. 3605-3614, 1997.
Hoess et al., Nucleic Acids Research, vol. 14, No. 5, pp. 2287-2300, 1986.
Kolot et al., Molecular Biology Reports, vol. 26, pp. 207-213, 1999.
Landy, Current Opinion in Genetics and Development, vol. 3, pp. 699-707, 1993.
Lorbach et al., Journal of Molecular Biology, vol. 296, pp. 1175-1181, 2000.
Nunes-Duby et al., Nucleic Acids Research, vol. 26, No. 2, pp. 391-406, 1998.
Smith et al., Molecular Microbiology, vol. 44, No. 2, pp. 299-307, 2002.
Stanley et al., The EMBO Journal, vol. 5, No. 8, pp. 1761-1767, 1986.
Albert et al., The Plant Journal, 1995, 7, 4, pp. 649-659.
Chilton et al., Plant Physiol., 2003, 133, pp. 956-965.
Chiurazzi et al., The Plant Cell, 1996, 8, pp. 2057-2066.
Day et al., Genes and Dev., 2000, 14, pp. 2869-2880.
Deng et al., Molecular and Cellular Biology, 1992, 12, 8, pp. 3365-3371.
D'Halluin et al., Plant Biotechnology Journal, 2008, 6, pp. 93-102.
Gallego et al., Plant Molecular Biology, 1999, 39, pp. 83-93.
Halfter et al., Mol. Gen. Genet., 1992, 231, pp. 186-193.
Hanin et al., The Plant Journal, 2001, 28, 6, pp. 671-677.

(Continued)

Primary Examiner — Cathy Kingdon Worley
(74) *Attorney, Agent, or Firm* — Womble Carlyle Sandridge & Rice PLLC

(57) ABSTRACT

The invention provides various methods for the targeted integration and stacking of nucleotide sequences in the genome of a host plant cell using homologous recombination.

42 Claims, 32 Drawing Sheets

OTHER PUBLICATIONS

Hrouda et al., Mol. Gen. Genet., 1994, 243, pp. 106-111.
Kempin et al., Nature, 1997, 389, pp. 802-803.
Kirik et al., The EMBO Journal, 2000, 19, 20, pp. 5562-5566.
Lee et al., The Plant Cell, 1990, 2, pp. 415-425.
Lebel et al., Proc. Natl. Acd. Sci., 1993, 90, pp. 422-426.
Lloyd et al., Proc. Natl. Acd. Sci., 2005, 102, 6, pp. 2232-2237.
McElroy et al., The Plant Cell, 1990, 2, pp. 163-171.
Mengeste et al., The EMBO Journal, 1999, 18, 16, pp. 4505-4512.
Miao et al., The Plant Journal, 1995, 7, pp. 359-365.
Narasimhulu et al., Plant Cell, 1996, 8, pp. 873-886.
Offringa et al., The EMBO Journal, 1990, 9, 10, pp. 3077-3084.
Offringa et al., Proc. Natl. Acad. Sci., 1993, 90, pp. 7346-7350.
Paszkowski et al., Plant Molecular Biology, 1992, 19, pp. 825-836.
Puchta et al., Nucleic Acids Research, 1993, 21, 22, pp. 5034-5040.
Puchta et al., The Plant Journal, 1998, 13, 3, pp. 5055-5060.
Reiss et al., Proc. Natl. Acad. Sci., 1996, 93, pp. 3094-3098.
Reiss et al., Proc. Natl. Acad. Sci., 2000, 97, 7, pp. 3358-3363.
Risseeuw et al., The Plant Journal, 1995, 7, 1, pp. 109-119.
Risseeuw et al., The Plant Journal, 1997, 11, 4, pp. 717-728.
Salomon et al., The EMBO Journal, 1998, 17, 20, pp. 6086-6095.
Schaeffer et al., The Plant Journal, 1997, 11, 6, pp. 1195-1206.
Sedivy et al., Trends in Genetics, 1999, 15, 3, pp. 88-90.
Shalev et al., Proc. Natl. Acad. Sci., 1999, 96, pp. 7398-7402.
Shaked et al., Proc. Natl. Acad. Sci., 2005, 102, 34, pp. 12265-12269.
Srivastava et al., Molecular Breeding, 2001, 8, pp. 345-350.
Srivastava et al., Plant Biotechnology Journal, 2004, 2, pp. 169-179.
Maliga, Annu. Rev. Plant Biol., 2004, 55, pp. 289-313.
Terada et al., Nature Biotechnology, 2002, 20, pp. 1030-1034.
Terada et al., Plant Cell Rep., 2004, 22, pp. 653-659.
Thykjaer et al., Plant Molecular Biology, 1997, 35, pp. 523-530.
Vergunst et al., Plant Molecular Biology, 1998, 38, pp. 393-406.
Wright et al., The Plant Journal, 2005, 44, pp. 693-705.
Xiao et al., Genetics, 2000, 156, pp. 2007-2017.
Puchta et al., Proc. Natl. Acad. Sci., 1996, 93, pp. 5055-5060.
Vergunst et al., Nucleic Acids Research, 1998, 26, 11, pp. 2729-2734.
Iida and Terada, "Modification of endogenous natural genes by gene targeting in rice and other higher plants", *Plant Molecular Biology*, (2005) 59:205-219 (2005).

\* cited by examiner

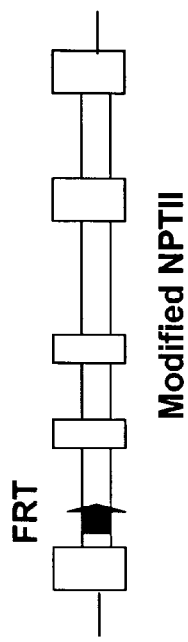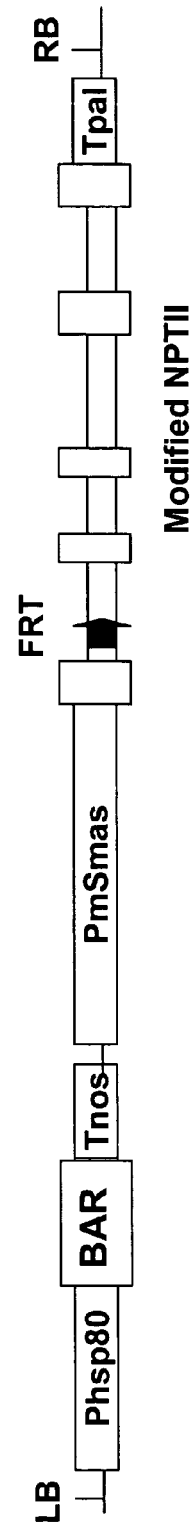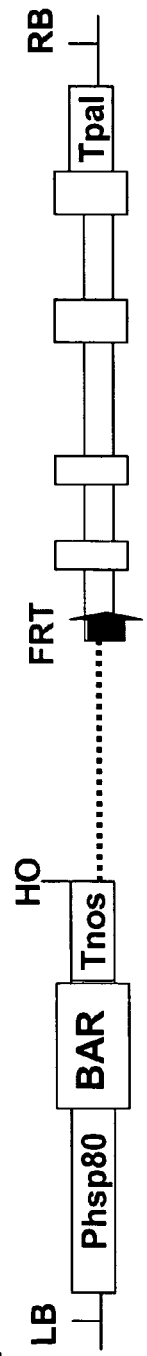
FIG. 13A
FIG. 13B
FIG. 13C

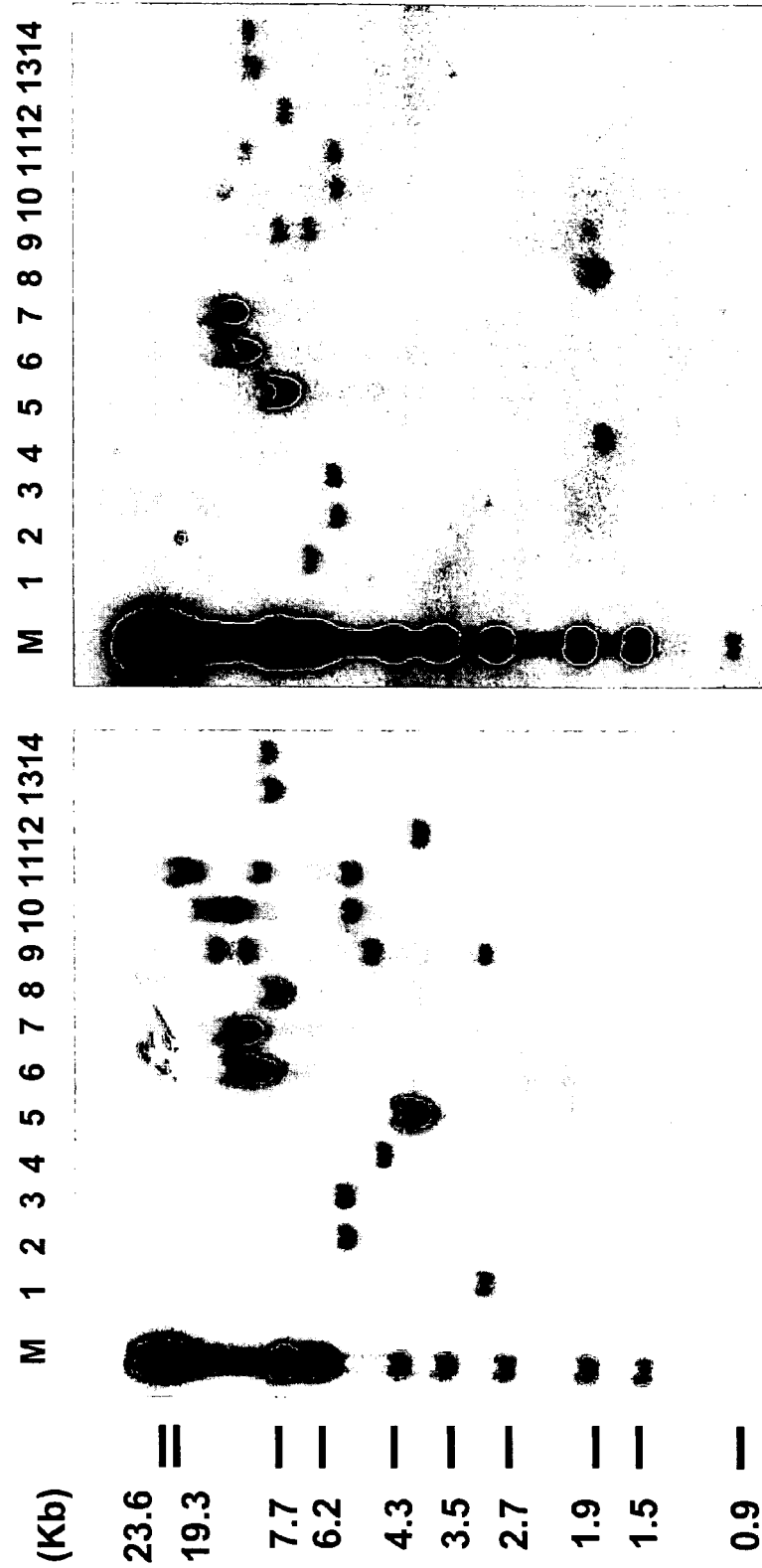

RS: R recombinase recognition sequences; attB and attP: lambda integrase recognition sequences; I-CeuI: I-CeuI cleavage sequence

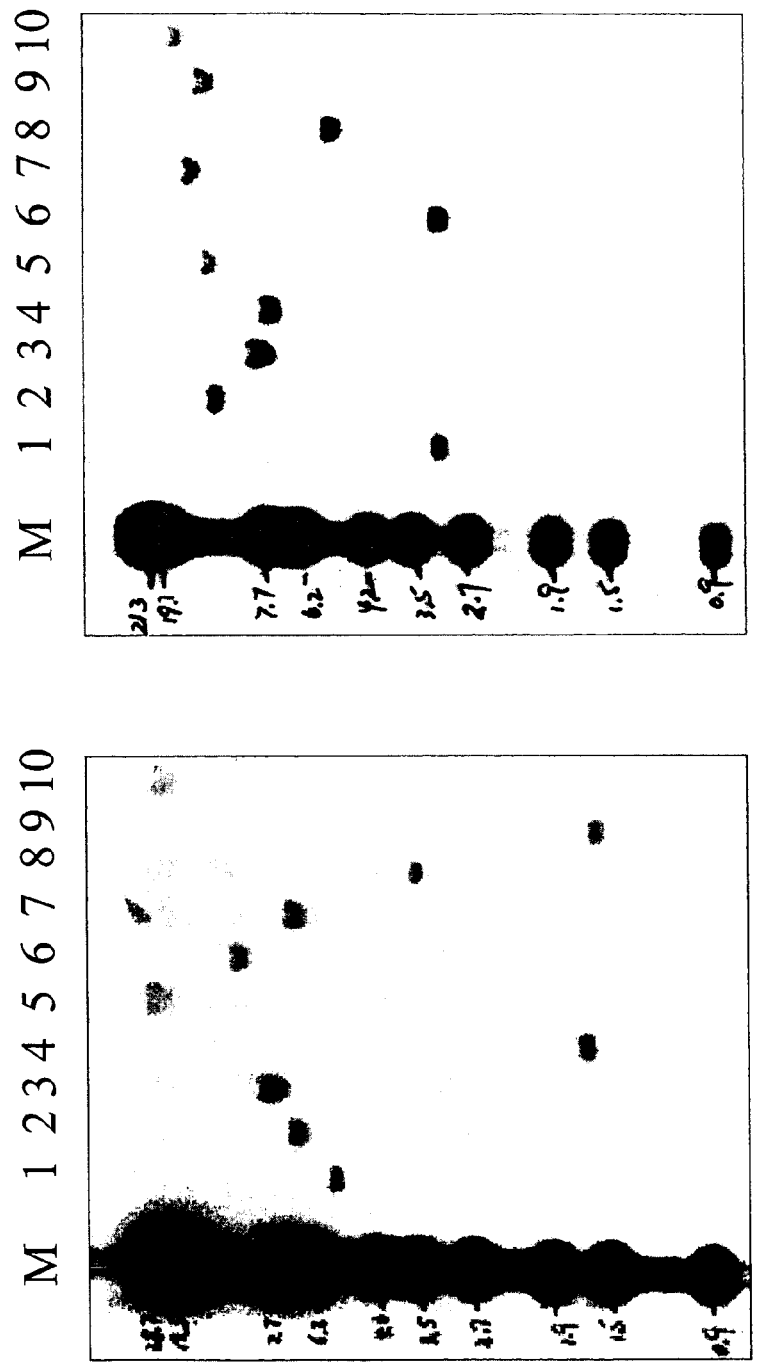
FIG. 20A  PMIintrons 3' probe
FIG. 20B  Actin-1D 5' probe

SEQUENCE LISTING

<160> NUMBER OF SEQ ID NOS: 118

<210> SEQ ID NO 1
<211> LENGTH: 30
<212> TYPE: DNA
<213> ORGANISM: Artificial Sequence
<220> FEATURE:
<223> OTHER INFORMATION: NPTFA primer

<400> SEQUENCE: 1
gatctctaga atgattgaac aagatggatt                                    30

<210> SEQ ID NO 2
<211> LENGTH: 32
<212> TYPE: DNA
<213> ORGANISM: Artificial Sequence
<220> FEATURE:
<223> OTHER INFORMATION: NPTRA primer

<400> SEQUENCE: 2
tcgcagcttg gtacctgcag ttcattcagg gc                                 32

<210> SEQ ID NO 3
<211> LENGTH: 32
<212> TYPE: DNA
<213> ORGANISM: Artificial Sequence
<220> FEATURE:
<223> OTHER INFORMATION: IntBAFFW  primer

<400> SEQUENCE: 3
gccctgaatg aactgcaggt accaagctgc ga                                 32

<210> SEQ ID NO 4
<211> LENGTH: 32
<212> TYPE: DNA
<213> ORGANISM: Artificial Sequence
<220> FEATURE:
<223> OTHER INFORMATION: IntBAFRV primer

<400> SEQUENCE: 4
gccgcgctgc ctcgtcctga aaaattcaga aa                                 32

<210> SEQ ID NO 5
<211> LENGTH: 32
<212> TYPE: DNA
<213> ORGANISM: Artificial sequence
<220> FEATURE:
<223> OTHER INFORMATION: NPTF2 primer

<400> SEQUENCE: 5
tttctgaatt tttcaggacg aggcagcgcg gc                                 32

<210> SEQ ID NO 6
<211> LENGTH: 34
<212> TYPE: DNA
<213> ORGANISM: Artificial sequence
<220> FEATURE:
<223> OTHER INFORMATION: NPTR2 primer

<400> SEQUENCE: 6
gaatagtact aatacctggc acttcgccca atag                               34

<210> SEQ ID NO 7
<211> LENGTH: 30
<212> TYPE: DNA

```
<213> ORGANISM: Artificial sequence
<220> FEATURE:
<223> OTHER INFORMATION: IntPALFW primer

<400> SEQUENCE: 7
ttagtactat tcttttgttc tctaatcaga                                    30

<210> SEQ ID NO 8
<211> LENGTH: 36
<212> TYPE: DNA
<213> ORGANISM: Artificial sequence
<220> FEATURE:
<223> OTHER INFORMATION: IntPALRV primer

<400> SEQUENCE: 8
tgacaggaga tcctgccctg taacgaacaa aaacat                             36

<210> SEQ ID NO 9
<211> LENGTH: 36
<212> TYPE: DNA
<213> ORGANISM: Artificial sequence
<220> FEATURE:
<223> OTHER INFORMATION: NPTFC primer

<400> SEQUENCE: 9 atgttttgt tcgttacagg gcaggatctc ctgtca                              36

<210> SEQ ID NO 10
<211> LENGTH: 36
<212> TYPE: DNA
<213> ORGANISM: Artificial sequence
<220> FEATURE:
<223> OTHER INFORMATION: NPTR3 primer

<400> SEQUENCE: 10
atcgattcat atatataccct ggtcgacaag accggc                            36

<210> SEQ ID NO 11
<211> LENGTH: 30
<212> TYPE: DNA
<213> ORGANISM: Artificial sequence
<220> FEATURE:
<223> OTHER INFORMATION: IntTUBFW primer

<400> SEQUENCE: 11
caggtatata tatgaatcga tttctcccctt                                   30

<210> SEQ ID NO 12
<211> LENGTH: 32
<212> TYPE: DNA
<213> ORGANISM: Artificial sequence
<220> FEATURE:
<223> OTHER INFORMATION: IntTUBRV primer

<400> SEQUENCE: 12
tcgtccagat catcctgtaa tacagaaatg tt                                 32

<210> SEQ ID NO 13
<211> LENGTH: 32
<212> TYPE: DNA
<213> ORGANISM: Artificial sequence
<220> FEATURE:
<223> OTHER INFORMATION: NPTFD primer

<400> SEQUENCE: 13
aacatttctg tattacagga tgatctggac ga                                 32
```

<210> SEQ ID NO 14
<211> LENGTH: 32
<212> TYPE: DNA
<213> ORGANISM: Artificial sequence
<220> FEATURE:
<223> OTHER INFORMATION: NPTR4 primer

<400> SEQUENCE: 14
ggaaaagctt aattacctcg ccgtcgggca tg                          32

<210> SEQ ID NO 15
<211> LENGTH: 28
<212> TYPE: DNA
<213> ORGANISM: Artificial sequence
<220> FEATURE:
<223> OTHER INFORMATION: IntTUAFW primer

<400> SEQUENCE: 15
gtaattaagc ttttccacct ctcttgtt                               28

<210> SEQ ID NO 16
<211> LENGTH: 32
<212> TYPE: DNA
<213> ORGANISM: Artificial sequence
<220> FEATURE:
<223> OTHER INFORMATION: IntTUARV primer

<400> SEQUENCE: 16
gatcctgcag caatggaaaa atatttcaat ac                          32

<210> SEQ ID NO 17
<211> LENGTH: 30
<212> TYPE: DNA
<213> ORGANISM: Artificial sequence
<220> FEATURE:
<223> OTHER INFORMATION: NPTFE primer

<400> SEQUENCE: 17
attgctgcag gatctcgtcg tgacccatgg                             30

<210> SEQ ID NO 18
<211> LENGTH: 28
<212> TYPE: DNA
<213> ORGANISM: Artificial sequence
<220> FEATURE:
<223> OTHER INFORMATION: NPTR5 primer

<400> SEQUENCE: 18
cattaggatc ctcagaagaa ctcgtcaa                               28

<210> SEQ ID NO 19
<211> LENGTH: 40
<212> TYPE: DNA
<213> ORGANISM: Artificial sequence
<220> FEATURE:
<223> OTHER INFORMATION: FRTBGL2 primer

<400> SEQUENCE: 19
gatctgaagt tcctattctc tagaaagtat aggaacttcg                  40

<210> SEQ ID NO 20
<211> LENGTH: 40
<212> TYPE: DNA
<213> ORGANISM: Artificial sequence
<220> FEATURE:
<223> OTHER INFORMATION: FRTBAM1 primer -continued

```
<400> SEQUENCE: 20
gatccgaagt tcctatactt tctagagaat aggaacttca                              40

<210> SEQ ID NO 21
<211> LENGTH: 30
<212> TYPE: DNA
<213> ORGANISM: Artificial sequence
<220> FEATURE:
<223> OTHER INFORMATION: TPALBGLI primer

<400> SEQUENCE: 21
tgttaagatc ttagtcctct gtttttttct                                         30

<210> SEQ ID NO 22
<211> LENGTH: 30
<212> TYPE: DNA
<213> ORGANISM: Artificial sequence
<220> FEATURE:
<223> OTHER INFORMATION: TPALSAC primer

<400> SEQUENCE: 22
cttgagctct tctataaccc tagatggcta                                         30

<210> SEQ ID NO 23
<211> LENGTH: 27
<212> TYPE: DNA
<213> ORGANISM: Artificial sequence
<220> FEATURE:
<223> OTHER INFORMATION: BARCLA primer

<400> SEQUENCE: 23
tcatatcgat gagcccagaa cgacgcc                                            27

<210> SEQ ID NO 24
<211> LENGTH: 32
<212> TYPE: DNA
<213> ORGANISM: Artificial sequence
<220> FEATURE:
<223> OTHER INFORMATION: BARBGL primer

<400> SEQUENCE: 24
tttgagatct tcatatctcg gtgacgggca gg                                      32

<210> SEQ ID NO 25
<211> LENGTH: 30
<212> TYPE: DNA
<213> ORGANISM: Artificial sequence
<220> FEATURE:
<223> OTHER INFORMATION: ISCEBAM1 primer

<400> SEQUENCE: 25
acttggatcc atattaccct gttatcccta                                         30

<210> SEQ ID NO 26
<211> LENGTH: 30
<212> TYPE: DNA
<213> ORGANISM: Artificial sequence
<220> FEATURE:
<223> OTHER INFORMATION: ISCEBGL2 primer

<400> SEQUENCE: 26
tcgaagatct gctagggata acagggtaat                                         30

<210> SEQ ID NO 27
<211> LENGTH: 30
<212> TYPE: DNA
```

```
<213> ORGANISM: Artificial sequence
<220> FEATURE:
<223> OTHER INFORMATION: ICEUBGL2 primer

<400> SEQUENCE: 27
tcgaagatct ctataacggt cgtaaggtag                              30

<210> SEQ ID NO 28
<211> LENGTH: 30
<212> TYPE: DNA
<213> ORGANISM: Artificial sequence
<220> FEATURE:
<223> OTHER INFORMATION: ICEUBAM1 primer

<400> SEQUENCE: 28
acttggatcc tcgctacctt aggaccgtta                              30

<210> SEQ ID NO 29
<211> LENGTH: 30
<212> TYPE: DNA
<213> ORGANISM: Artificial sequence
<220> FEATURE:
<223> OTHER INFORMATION: HOBGL2 primer

<400> SEQUENCE: 29
tcgaagatct agctttccgc aacagtataa                              30

<210> SEQ ID NO 30
<211> LENGTH: 30
<212> TYPE: DNA
<213> ORGANISM: Artificial sequence
<220> FEATURE:
<223> OTHER INFORMATION: HOBAM1 primer

<400> SEQUENCE: 30
acttggatcc attatactgt tgcggaaagc                              30

<210> SEQ ID NO 31
<211> LENGTH: 40
<212> TYPE: DNA
<213> ORGANISM: Artificial sequence
<220> FEATURE:
<223> OTHER INFORMATION: FRTBGL2

<400> SEQUENCE: 31
gatctgaagt tcctattctc tagaaagtat aggaacttcg                   40

<210> SEQ ID NO 32
<211> LENGTH: 40
<212> TYPE: DNA
<213> ORGANISM: Artificial sequence
<220> FEATURE:
<223> OTHER INFORMATION: FRTBAM1

<400> SEQUENCE: 32
gatccgaagt tcctatactt tctagagaat aggaacttca                   40

<210> SEQ ID NO 33
<211> LENGTH: 30
<212> TYPE: DNA
<213> ORGANISM: Artificial sequence
<220> FEATURE:
<223> OTHER INFORMATION: HOATG primer

<400> SEQUENCE: 33
ctactgtcga caaaaatgct ttctgaaaac                              30
```

<210> SEQ ID NO 34
<211> LENGTH: 30
<212> TYPE: DNA
<213> ORGANISM: Artificial sequence
<220> FEATURE:
<223> OTHER INFORMATION: HOBAMH primer

<400> SEQUENCE: 34
ctaggatccg acctggtcgt cacagtagct                                       30

<210> SEQ ID NO 35
<211> LENGTH: 872
<212> TYPE: DNA
<213> ORGANISM: Artificial sequence
<220> FEATURE:
<223> OTHER INFORMATION: I-CeuI endonuclease with maize-preferred codons
      and potato ST-LS1 intron

<400> SEQUENCE: 35
gaattcgccc ttggggatcc atgagcaact tcatcctgaa gcccggcgag aagctgcccc      60
aggacaagct ggaggagctg aagaagatca cgacgccgt gaagaagacc aagaacttca     120
gcaagtacct gatcgacctg cgcaagctgt tccagatcga cgaggtgcag gtgaccagcg     180
agagcaagct gttcctggcc ggcttcctgg agggcgaggc cagcctgaac atcagcacca     240
agaagctggc caccagcaag ttcggcctgg tggtggaccc cgagttcaac gtgacccagc     300
acgtaagttt ctgcttctac ctttgatata tataataa ttatcattaa ttagtagtaa     360
tataatattt caaatatttt tttcaaaata aagaatgta gtatatagca attgcttttc      420
tgtagtttat aagtgtgtat attttaattt ataactttc taatatatga ccaaaatttg     480
ttgatgtgca ggtgaacggc gtgaaggtgc tgtacctggc cctggaggtg ttcaagaccg     540
gccgcatccg ccacaagagc ggcagcaacg ccaccctggt gctgaccatc gacaaccgcc     600
agagcctgga ggagaaggtg atccccttct acgagcagta cgtggtggcc ttcagcagcc     660
ccgagaaggt gaagcgcgtg gccaacttca aggccctgct ggagctgttc aacaacgacg     720
cccaccagga cctggagcag ctggtgaaca agatcctgcc catctgggac cagatgcgca     780
agcagcaggg ccagagcaac gagggcttcc ccaacctgga ggccgcccag gacttcgccc     840
gcaactacaa gaagggcatc aagtaggaat tc                                  872

<210> SEQ ID NO 36
<211> LENGTH: 74
<212> TYPE: DNA
<213> ORGANISM: Artificial sequence
<220> FEATURE:
<223> OTHER INFORMATION: 1A primer

<400> SEQUENCE: 36
ggggatccat gagcaacttc atcctgaagc ccggcgagaa gctgccccgg acaagctgga     60
ggagctgaag aaga                                                       74

<210> SEQ ID NO 37
<211> LENGTH: 75
<212> TYPE: DNA
<213> ORGANISM: Artificial sequence
<220> FEATURE:
<223> OTHER INFORMATION: 1B primer

<400> SEQUENCE: 37
cgcaggtcga tcaggtactt gctgaagttc ttggtcttct tcacggcgtc gttgatcttc     60
ttcagctcct ccagc                                                      75

```
<210> SEQ ID NO 38
<211> LENGTH: 75
<212> TYPE: DNA
<213> ORGANISM: Artificial sequence
<220> FEATURE:
<223> OTHER INFORMATION: 1C primer

<400> SEQUENCE: 38
aagtacctga tcgacctgcg caagctgttc cagatcgacg aggtgcaggt gaccagcgag      60
agcaagctgt tcctg                                                      75

<210> SEQ ID NO 39
<211> LENGTH: 75
<212> TYPE: DNA
<213> ORGANISM: Artificial sequence
<220> FEATURE:
<223> OTHER INFORMATION: 1Dprimer

<400> SEQUENCE: 39
tggccagctt cttggtgctg atgttcaggc tggcctcgcc ctccaggaag ccggccagga      60
acagcttgct ctcgc                                                      75

<210> SEQ ID NO 40
<211> LENGTH: 75
<212> TYPE: DNA
<213> ORGANISM: Artificial sequence
<220> FEATURE:
<223> OTHER INFORMATION: 1E primer

<400> SEQUENCE: 40
cagcaccaag aagctggcca ccagcaagtt cggcctggtg gtggaccccg agttcaacgt      60
gacccagcac gtgaa                                                      75

<210> SEQ ID NO 41
<211> LENGTH: 75
<212> TYPE: DNA
<213> ORGANISM: Artificial sequence
<220> FEATURE:
<223> OTHER INFORMATION: 1F primer

<400> SEQUENCE: 41
cgcaggtcga tcaggtactt gctgaagttc ttggtcttct tcacggcgtc gttgatcttc      60
ttcagctcct ccagc                                                      75

<210> SEQ ID NO 42
<211> LENGTH: 75
<212> TYPE: DNA
<213> ORGANISM: Artificial sequence
<220> FEATURE:
<223> OTHER INFORMATION: 2G primer

<400> SEQUENCE: 42
ccccggccgc atccgccaca agagcggcag caacgccacc ctggtgctga ccatcgacaa      60
ccgccagagc ctgga                                                      75

<210> SEQ ID NO 43
<211> LENGTH: 75
<212> TYPE: DNA
<213> ORGANISM: Artificial sequence
<220> FEATURE:
<223> OTHER INFORMATION: 2H primer

<400> SEQUENCE: 43
```

```
ctcggggctg ctgaaggcca ccacgtactg ctcgtagaag gggatcacct tctcctccag    60
gctctggcgg ttgtc                                                    75

<210> SEQ ID NO 44
<211> LENGTH: 75
<212> TYPE: DNA
<213> ORGANISM: Artificial sequence
<220> FEATURE:
<223> OTHER INFORMATION: 2I primer

<400> SEQUENCE: 44
tggccttcag cagccccgag aaggtgaagc gcgtggccaa cttcaaggcc ctgctggagc    60
tgttcaacaa cgacg                                                    75

<210> SEQ ID NO 45
<211> LENGTH: 75
<212> TYPE: DNA
<213> ORGANISM: Artificial sequence
<220> FEATURE:
<223> OTHER INFORMATION: 2J primer

<400> SEQUENCE: 45
atctggtccc agatgggcag gatcttgttc accagctgct ccaggtcctg gtgggcgtcg    60
ttgttgaaca gctcc                                                    75

<210> SEQ ID NO 46
<211> LENGTH: 75
<212> TYPE: DNA
<213> ORGANISM: Artificial sequence
<220> FEATURE:
<223> OTHER INFORMATION: 2K primer

<400> SEQUENCE: 46
ctgcccatct gggaccagat gcgcaagcag cagggccaga gcaacgaggg cttccccaac    60
ctggaggccg cccag                                                    75

<210> SEQ ID NO 47
<211> LENGTH: 65
<212> TYPE: DNA
<213> ORGANISM: Artificial sequence
<220> FEATURE:
<223> OTHER INFORMATION: 2L primer

<400> SEQUENCE: 47
ggggaattcc tacttgatgc ccttcttgta gttgcgggcg aagtcctggg cggcctccag    60
gttgg                                                               65

<210> SEQ ID NO 48
<211> LENGTH: 29
<212> TYPE: DNA
<213> ORGANISM: Artificial sequence
<220> FEATURE:
<223> OTHER INFORMATION: primer

<400> SEQUENCE: 48
gggtacgtaa gtttctgctt ctacctttg                                     29

<210> SEQ ID NO 49
<211> LENGTH: 29
<212> TYPE: DNA
<213> ORGANISM: Artificial sequence
<220> FEATURE:
<223> OTHER INFORMATION: primer
```

```
<400> SEQUENCE: 49
ccccagctgc acatcaacaa attttggtc                                    29

<210> SEQ ID NO 50
<211> LENGTH: 14
<212> TYPE: DNA
<213> ORGANISM: Artificial sequence
<220> FEATURE:
<223> OTHER INFORMATION: primer

<400> SEQUENCE: 50
gatcggcaat tgcc                                                    14

<210> SEQ ID NO 51
<211> LENGTH: 27
<212> TYPE: DNA
<213> ORGANISM: Artificial sequence
<220> FEATURE:
<223> OTHER INFORMATION: primer

<400> SEQUENCE: 51
ccggtgagta atattgtacg gctaaga                                      27

<210> SEQ ID NO 52
<211> LENGTH: 27
<212> TYPE: DNA
<213> ORGANISM: Artificial sequence
<220> FEATURE:
<223> OTHER INFORMATION: primer

<400> SEQUENCE: 52
agatcctcag aagaactcgt caagaag                                      27

<210> SEQ ID NO 53
<211> LENGTH: 30
<212> TYPE: DNA
<213> ORGANISM: Artificial sequence
<220> FEATURE:
<223> OTHER INFORMATION: primer

<400> SEQUENCE: 53
aatataggcg gtattccggc cattataaca                                   30

<210> SEQ ID NO 54
<211> LENGTH: 30
<212> TYPE: DNA
<213> ORGANISM: Artificial sequence
<220> FEATURE:
<223> OTHER INFORMATION: primer

<400> SEQUENCE: 54
ctaagatcct cagaagaact cgtcaagaag                                   30

<210> SEQ ID NO 55
<211> LENGTH: 30
<212> TYPE: DNA
<213> ORGANISM: Artificial sequence
<220> FEATURE:
<223> OTHER INFORMATION: primer

<400> SEQUENCE: 55
accctccgct acttctccgg gaaaagacgc                                   30

<210> SEQ ID NO 56
<211> LENGTH: 30
```

```
<212> TYPE: DNA
<213> ORGANISM: Artificial sequence
<220> FEATURE:
<223> OTHER INFORMATION: primer

<400> SEQUENCE: 56
actatcggcg agtacttcta cacagccatc                                      30

<210> SEQ ID NO 57
<211> LENGTH: 26
<212> TYPE: DNA
<213> ORGANISM: Artificial sequence
<220> FEATURE:
<223> OTHER INFORMATION: primer

<400> SEQUENCE: 57
gtgtctcatg cacttgggag gtgatc                                          26

<210> SEQ ID NO 58
<211> LENGTH: 40
<212> TYPE: DNA
<213> ORGANISM: Artificial sequence
<220> FEATURE:
<223> OTHER INFORMATION: primer

<400> SEQUENCE: 58
gatccgcggt tgatgaaaga ataacgtatt ctttcatcaa                           40

<210> SEQ ID NO 59
<211> LENGTH: 40
<212> TYPE: DNA
<213> ORGANISM: Artificial sequence
<220> FEATURE:
<223> OTHER INFORMATION: primer

<400> SEQUENCE: 59
gatcttgatg aaagaatacg ttattctttc atcaaccgcg                           40

<210> SEQ ID NO 60
<211> LENGTH: 30
<212> TYPE: DNA
<213> ORGANISM: Artificial sequence
<220> FEATURE:
<223> OTHER INFORMATION: primer

<400> SEQUENCE: 60
atgccgcagg taccaagctg cgaatcttcg                                      30

<210> SEQ ID NO 61
<211> LENGTH: 30
<212> TYPE: DNA
<213> ORGANISM: Artificial sequence
<220> FEATURE:
<223> OTHER INFORMATION: PMIINTRA primer

<400> SEQUENCE: 61
atcgggatac ctgaaaaatt cagaaacaaa                                      30

<210> SEQ ID NO 62
<211> LENGTH: 30
<212> TYPE: DNA
<213> ORGANISM: Artificial sequence
<220> FEATURE:
<223> OTHER INFORMATION: PMIINTFB primer

<400> SEQUENCE: 62
cggtcgcagg tattagtact attcttttgt                                      30
```

<210> SEQ ID NO 63
<211> LENGTH: 30
<212> TYPE: DNA
<213> ORGANISM: Artificial sequence
<220> FEATURE:
<223> OTHER INFORMATION: PMIINTRB primer

<400> SEQUENCE: 63
cggatgtgca cctgtaacga acaaaaacat            30

<210> SEQ ID NO 64
<211> LENGTH: 30
<212> TYPE: DNA
<213> ORGANISM: Artificial sequence
<220> FEATURE:
<223> OTHER INFORMATION: PMIINTFC primer

<400> SEQUENCE: 64
acctgcaagg tatatatatg aatcgatttc            30

<210> SEQ ID NO 65
<211> LENGTH: 30
<212> TYPE: DNA
<213> ORGANISM: Artificial sequence
<220> FEATURE:
<223> OTHER INFORMATION: PMIINTRC primer

<400> SEQUENCE: 65
gcgccacacc tgtaatacag aaatgttaag            30

<210> SEQ ID NO 66
<211> LENGTH: 30
<212> TYPE: DNA
<213> ORGANISM: Artificial sequence
<220> FEATURE:
<223> OTHER INFORMATION: PMIINTFD primer

<400> SEQUENCE: 66
gtgaaacaag gttattaacg ttttccacct            30

<210> SEQ ID NO 67
<211> LENGTH: 30
<212> TYPE: DNA
<213> ORGANISM: Artificial sequence
<220> FEATURE:
<223> OTHER INFORMATION: PMIINTRD primer

<400> SEQUENCE: 67
gttctgcacc tgcatcaatg gaaaaatatt            30

<210> SEQ ID NO 68
<211> LENGTH: 33
<212> TYPE: DNA
<213> ORGANISM: Artificial sequence
<220> FEATURE:
<223> OTHER INFORMATION: PMIEXF1 primer

<400> SEQUENCE: 68
gtggatccgg cagcatgcaa aaactcatta act         33

<210> SEQ ID NO 69
<211> LENGTH: 32
<212> TYPE: DNA
<213> ORGANISM: Artificial sequence
<220> FEATURE:
<223> OTHER INFORMATION: PMIEXR1 primer

```
<400> SEQUENCE: 69
tcgcagcttg gtacctgcgg cattttcttt gg                                    32

<210> SEQ ID NO 70
<211> LENGTH: 30
<212> TYPE: DNA
<213> ORGANISM: Artificial sequence
<220> FEATURE:
<223> OTHER INFORMATION: PMIEXF2 primer

<400> SEQUENCE: 70
aatttttcag gtatcccgat ggatgccgcc                                       30

<210> SEQ ID NO 71
<211> LENGTH: 30
<212> TYPE: DNA
<213> ORGANISM: Artificial sequence
<220> FEATURE:
<223> OTHER INFORMATION: PMIEXR2 primer

<400> SEQUENCE: 71
tagtactaat acctgcgacc ggctggagta                                       30

<210> SEQ ID NO 72
<211> LENGTH: 30
<212> TYPE: DNA
<213> ORGANISM: Artificial sequence
<220> FEATURE:
<223> OTHER INFORMATION: PMIEXF3 primer

<400> SEQUENCE: 72
gttcgttaca ggtgcacatc cggcgattgc                                       30

<210> SEQ ID NO 73
<211> LENGTH: 30
<212> TYPE: DNA
<213> ORGANISM: Artificial sequence
<220> FEATURE:
<223> OTHER INFORMATION: PMIEXR3 primer

<400> SEQUENCE: 73
tcatatatat accttgcagg taagcgtgcg                                       30

<210> SEQ ID NO 74
<211> LENGTH: 30
<212> TYPE: DNA
<213> ORGANISM: Artificial sequence
<220> FEATURE:
<223> OTHER INFORMATION: PMIEXF4 primer

<400> SEQUENCE: 74
ctgtattaca ggtgtggcgc tggaagtgat                                       30

<210> SEQ ID NO 75
<211> LENGTH: 30
<212> TYPE: DNA
<213> ORGANISM: Artificial sequence
<220> FEATURE:
<223> OTHER INFORMATION: PMIEXR4 primer

<400> SEQUENCE: 75
tgttaataac cttgtttcac cggctgggtc                                       30

<210> SEQ ID NO 76
<211> LENGTH: 31
```

```
<212> TYPE: DNA
<213> ORGANISM: Artificial sequence
<220> FEATURE:
<223> OTHER INFORMATION: PMIEXF5 primer

<400> SEQUENCE: 76
cgattgatgc aggtgcagaa ctggacttcc c                          31

<210> SEQ ID NO 77
<211> LENGTH: 32
<212> TYPE: DNA
<213> ORGANISM: Artificial sequence
<220> FEATURE:
<223> OTHER INFORMATION: PMIEXR5 primer

<400> SEQUENCE: 77
tgctcgagtc attagcaaga gatgttaatt tt                         32

<210> SEQ ID NO 78
<211> LENGTH: 32
<212> TYPE: DNA
<213> ORGANISM: Artificial sequence
<220> FEATURE:
<223> OTHER INFORMATION: GUSBAFFW1 primer

<400> SEQUENCE: 78
ttgactggca ggtaccaagc tgcgaatctt cg                         32

<210> SEQ ID NO 79
<211> LENGTH: 29
<212> TYPE: DNA
<213> ORGANISM: Artificial sequence
<220> FEATURE:
<223> OTHER INFORMATION: GUSBAFRV1 primer

<400> SEQUENCE: 79
ggccaccacc tgaaaaattc agaaacaaa                             29

<210> SEQ ID NO 80
<211> LENGTH: 26
<212> TYPE: DNA
<213> ORGANISM: Artificial sequence
<220> FEATURE:
<223> OTHER INFORMATION: GUSBAMHI primer

<400> SEQUENCE: 80
tccaaccatg ttacgtcctg tagaaa                                26

<210> SEQ ID NO 81
<211> LENGTH: 32
<212> TYPE: DNA
<213> ORGANISM: Artificial sequence
<220> FEATURE:
<223> OTHER INFORMATION: BAFGUSRV1 primer

<400> SEQUENCE: 81
cagcttggta cctgccagtc aacagacgcg ac                         32

<210> SEQ ID NO 82
<211> LENGTH: 32
<212> TYPE: DNA
<213> ORGANISM: Artificial sequence
<220> FEATURE:
<223> OTHER INFORMATION: BAFGUSFW primer

<400> SEQUENCE: 82
ttgactggca ggtaccaagc tgcgaatctt cg                         32
```

<210> SEQ ID NO 83
<211> LENGTH: 30
<212> TYPE: DNA
<213> ORGANISM: Artificial sequence
<220> FEATURE:
<223> OTHER INFORMATION: GUSSALI primer

<400> SEQUENCE: 83
gtcgactcat tgtttgcctc cctgctgcgg                                       30

<210> SEQ ID NO 84
<211> LENGTH: 29
<212> TYPE: DNA
<213> ORGANISM: Artificial sequence
<220> FEATURE:
<223> OTHER INFORMATION: GUSBAMHI

<400> SEQUENCE: 84
ggatccaacc atgttacgtc ctgtagaaa                                        29

<210> SEQ ID NO 85
<211> LENGTH: 32
<212> TYPE: DNA
<213> ORGANISM: Artificial sequence
<220> FEATURE:
<223> OTHER INFORMATION: GUSBAFRV1 primer

<400> SEQUENCE: 85
attggccacc acctgaaaaa ttcagaaaca aa                                    32

<210> SEQ ID NO 86
<211> LENGTH: 32
<212> TYPE: DNA
<213> ORGANISM: Artificial sequence
<220> FEATURE:
<223> OTHER INFORMATION: GUSBAFFW1

<400> SEQUENCE: 86
ttgactggca ggtaccaagc tgcgaatctt cg                                    32

<210> SEQ ID NO 87
<211> LENGTH: 30
<212> TYPE: DNA
<213> ORGANISM: Artificial sequence
<220> FEATURE:
<223> OTHER INFORMATION: GUSSALI

<400> SEQUENCE: 87
gtcgactcat tgtttgcctc cctgctgcgg                                       30

<210> SEQ ID NO 88
<211> LENGTH: 30
<212> TYPE: DNA
<213> ORGANISM: Artificial sequence
<220> FEATURE:
<223> OTHER INFORMATION: ICEUBGL2

<400> SEQUENCE: 88
tcgaagatct ctataacggt cctaaggtag                                       30

<210> SEQ ID NO 89
<211> LENGTH: 30
<212> TYPE: DNA
<213> ORGANISM: Artificial sequence
<220> FEATURE:
<223> OTHER INFORMATION: ICEUBAMH primer

<400> SEQUENCE: 89
acttggatcc tcgctacctt aggaccgtta                                    30

<210> SEQ ID NO 90
<211> LENGTH: 38
<212> TYPE: DNA
<213> ORGANISM: Artificial sequence
<220> FEATURE:
<223> OTHER INFORMATION: ATTB1 primer

<400> SEQUENCE: 90
gatccgctca agttagtata aaaaagcagg cttcatga                           38

<210> SEQ ID NO 91
<211> LENGTH: 38
<212> TYPE: DNA
<213> ORGANISM: Artificial sequence
<220> FEATURE:
<223> OTHER INFORMATION: ATTB2 primer

<400> SEQUENCE: 91
gatctcatga agcctgcttt tttatactaa cttgagcg                           38

<210> SEQ ID NO 92
<211> LENGTH: 35
<212> TYPE: DNA
<213> ORGANISM: Artificial sequence
<220> FEATURE:
<223> OTHER INFORMATION: ATTPSPOMI primer

<400> SEQUENCE: 92
gggccctctg ttacaggtca ctaataccat ctaag                              35

<210> SEQ ID NO 93
<211> LENGTH: 31
<212> TYPE: DNA
<213> ORGANISM: Artificial sequence
<220> FEATURE:
<223> OTHER INFORMATION: ATTPSPEI primer

<400> SEQUENCE: 93
actagtgaaa tcaaataatg attttatttt g                                  31

<210> SEQ ID NO 94
<211> LENGTH: 1489
<212> TYPE: DNA
<213> ORGANISM: DNA

<400> SEQUENCE: 94
ctcgagcaac catgcagctg accaaggaca ccgagatcag caccatcaac cgccagatga       60
gcgacttcag cgagctgagc cagatcctgc ccctgcacca gatcagcaag atcaaggaca      120
tcctggagaa cgagaacccc ctgcccaagg agaagctggc cagccacctg accatgatca      180
tcctgatggc caacctggcc agccagaagc gcaaggacgt gcccgtgaag cgcagcacct      240
tcctgaagta ccagcgcagc atcagcaaga ccctgcagta cgacacagc accaagaccg       300 tgagcttcga gtaccacctg aaggacccca gcaagctgat caagggcctg gaggacgtgg      360
tgagccccta ccgcttcgtg gtgggcgtgc acgagaagcc cgacgacgtg atgagccacc      420
tgagcgccgt gcacatgcgc aaggaggccg ccgcaagcg cgacctgggc aacaagatca      480
acgacgagat caccaagatc gccgagaccc aggagaccat ctggggcttc gtgggcaaga      540
ccatggacct gatcgaggcc cgcaccaccc gccccaccac caaggccgcc tacaacctgc      600

```
tgctgcaggc caccttcatg aactgctgcc gcgccgacga cctgaagaac accgacatca    660
agaccttcga ggtgatcccc gacaagcacc tgggccgcat gctgcgcgcc ttcgtgcccg    720
agaccaagac cggcacccgc ttcgtgtact tcttcccctg caagggccgc tgcgaccccc    780
tgctggccct ggacagctac ctgcagtgga ccgaccccat ccccaagacc cgcaccaccg    840
acgaggacgc ccgctacgac taccagctgc tgcgcaacag cctgctgggc agctacgacg    900
gcttcatcag caagcagagc gacgagagca tcttcaagat ccccaacggc cccaaggccc    960
acctgggccg ccacgtgacc gccagctacc tgagcaacaa cgagatggac aaggaggcca   1020
ccctgtacgg caactggagc gccgcccgcg aggagggcgt gagccgcgtg gccaaggccc   1080
gctacatgca caccatcgag aagagccccc ccagctacct gttcgccttc ctgagcggct   1140
tctacaacat caccgccgag cgcgcctgcg agctggtgga ccccaacagc aacccctgcg   1200
agcaggacaa gaacatcccc atgatcagcg acatcgagac cctgatggcc cgctacggca   1260
agaacgccga gatcatcccc atggacgtgc tggtgttcct gagcagctac gcccgcttca   1320
agaacaacga gggcaaggag tacaagctgc aggcccgcag cagccgcggc gtgcccgact   1380
tccccgacaa cggccgcacc gccctgtaca acgccctgac cgccgcccac gtgaagcgcc   1440
gcaagatcag catcgtggtg ggccgcagca tcgacaccag ctgaagctt              1489

<210> SEQ ID NO 95
<211> LENGTH: 34
<212> TYPE: DNA
<213> ORGANISM: Artificial sequence
<220> FEATURE:
<223> OTHER INFORMATION: OsRecQcfw2 primer

<400> SEQUENCE: 95
caccatgaag cacggtgtaa ttgatgataa agaa                                34

<210> SEQ ID NO 96
<211> LENGTH: 30
<212> TYPE: DNA
<213> ORGANISM: Artificial sequence
<220> FEATURE:
<223> OTHER INFORMATION: OsRecQcRv1 primer

<400> SEQUENCE: 96
tcaagaggga atctttatgc agttgtcgca                                     30

<210> SEQ ID NO 97
<211> LENGTH: 34
<212> TYPE: DNA
<213> ORGANISM: Artificial sequence
<220> FEATURE:
<223> OTHER INFORMATION: OsRecQdFW2 primer

<400> SEQUENCE: 97
caccatgata aagccaaggg tcaactggtc ggat                                34

<210> SEQ ID NO 98
<211> LENGTH: 30
<212> TYPE: DNA
<213> ORGANISM: Artificial sequence
<220> FEATURE:
<223> OTHER INFORMATION: RecQdRV1 primer

<400> SEQUENCE: 98
ctaggctatt ctggcggact gccacgcagg                                     30
```

<210> SEQ ID NO 99
<211> LENGTH: 3525
<212> TYPE: DNA
<213> ORGANISM: DNA

<400> SEQUENCE: 99

```
atgataaagc caagggtcaa ctggtcggat catgcaaatg ctgttcaaag ctcctgtatc      60
aaagatgaat tcctgagttc aagttttttg ttctctttac caacacaaag gcctaatcag     120
gaagcagatt gtacgggaat gcttccttta aggtctgctg cttgcagaat tcaaggccta     180
gagcgtcttc aagctccatc cattgagaag gcctggcgtt ctctacgcaa cactcaggtt     240
gcacggaaga attatttaag acctggttta tctggaaaag tgaaagattg tgatagcgac     300
catgctcata cttatgggac aagttcttca tataatgtta acaaagtgga cagtgtgtcc     360
agaaatagga atcccaccca ggaaagtatg catcagacga ctgaaagtgg tactatggag     420
aagaacagta gccatctgcc tgcaggcacc aagtcctgta caaggactta cctgaacaat     480
catgtggtgc aggcagatac cattacaaca caaatcaaa gtcttgcaag aactggtcct     540
gaattattca agactgctcc ttttattgac aacatgtgtg atgatgctaa attagatgcc     600
atggatgagg atgagcttct agcgagtatt gatgtggacc gaatagtcat ggaacattat     660
caagcaacaa atacacccag agggtcatcc aaatctccat tagagaagtg caacttcaat     720
ggatttgatg agaataattt accacaagaa ctctctataa tgtgtgacca cggtagcaag     780
ctagcttttt gcccagaggc gaagtctcat ttgcttgaaa tgaaggataa cttgcttgca     840
atatcccatg agcttattga cggtcaactc agccctcaac aatctgatga tcttcatcaa     900
aagagagcac tcctaaagaa gcagattgag ctgcttgggg agtatacggc gaggttaacc     960
caagatgaag agcgacagca gtctcattct atggcctcca caacagctca tcagggccat    1020
caccccacta gcatcctaag tagctctttt gtaaaggata ccaatatatt ccgatcaccg    1080
atttacacca ggaatgaacc tggggagagt ggtttatgct tttcttctgc tccatattcc    1140
tatatggatg gtttaagcat gccattaccg tctgttcaga gagattacac tccaagggct    1200
attgatatca gttacactga aggttctggt gataaacagt ggagtagtac acactttgca    1260
tggactaagg aactcgaggc caacaacaaa ggagtatttg gaaaccgttc ttttcgccca    1320
aatcaacgag aaataaccaa cgccacaatg agtgggaatg atgttttgt tttgatgcca    1380
actggtggtg gaaaaagttt gacatatcag cttccagcac tcatttgtaa tggcgttaca    1440
ttggtagttt ctcctctcgt atcgctcatc caagaccaga tcatgcattt attgcaggca    1500
aatatttctg cagcttacct tagcgccagc atggagtggt cagaacagca ggagatatta    1560
agagaattaa tgtctcctac atgcacgtac aagttactgt atgttacgcc tgaaaagata    1620
gccaagagtg atgctctgtt gagacaattg gaaaatttat attcgcgagg ccatctctct    1680
agaattgtca ttgatgaagc ccactgtgtt agccagtggg gtcatgattt ccgacctgat    1740
taccagcatc taggcatttt aaaacagaag ttcccgcaga cgccggtcct ggccttgaca    1800
gcaacagcaa ctgcaagtgt caaggaagat gtcgtgcaag ttctaggcct tgcaaactgc    1860
attattttca gacaaggttt taatcgtcca aatctgaggt attttgtatg gccaagaca    1920
aagaagtgcc tcgaggatat ccataacttt atacatgcaa atcataataa gaatgcggc    1980
atcatatatt gcctttcgag gatggattgt gagaaagtgg ctgctaaatt aagggaatat    2040
ggcaccagg catcacatta tcatggtagc atggatcctg aggatagagc aaatatccag    2100
aaacagtgga gcaaggatag gatcaacata atatgtgcta cagttgcatt tgggatgggt    2160
attaataaac ctgatgtccg ttttgttatc catcattccc tgcccaaatc aattgaagga    2220
```

```
tatcatcagg agtgtggacg tgctggtcgt gacagtcagc tttcatcttg tgtcctgttc    2280
tacaattatt ctgattatat tcgtctcaaa cacatggtta cccaaggatt tgcggagcaa    2340
ggaacatcag caccacgagg aggttcttcg caggaacaag cgcttgaaac gcataaggaa    2400
aatctcctgc gaatggttag ttactgcgaa aatgatgtgg actgcagacg tctactacag    2460
ctgatccact ttggagagat gtttaatcct tcatgttgtg caaaaacatg tgataattgc    2520
ttgaaagagt tgagatgggt caaaaaagat gtgaccaaca ttgctagaca attggttgat    2580
ctggtaatga tgacaaagca aacatattca actactcata ttctcgaagt atacagaggt    2640
tcagtaaacc aaaatgtcaa gaagcaccgc catgatactt tgagtcttca tggagctgga    2700
aagcatctag ctaaaggtga agcagcgaga atattgcgcc atctagtaat tgaggaaata    2760
ctcattgagg atgtcaaaaa gagcgaaaac tatggatctg tatcatctgt cttaaagact    2820
aatcataaga aaagtggtga tcttctctct ggcaagcaca acgttgtcct caagttcccc    2880
actcctgaga aggctcctaa gatgggtgta ctcgatgaat cgtcagttcc acgaattaat    2940
aagactaatc aacagagtca agtggacggg agccttgcag ccgagcttta tgaagctttg    3000
caatgcctta ggactcagat aatggatgaa atccacaat tattggcata ccacatattt    3060
aaaaacgaga cattgaagga aatcagcaac cgaatgccaa gaacgaaaga ggaacttgtg    3120
gagataaatg gcatcggcaa gaacaagctg acaagtacg gggaccgcgt gcttgcaacc    3180
atagaggatt tcctcgccag atatccaaat gcgaccagga aaaccagcag cggcggcagc    3240
aacgagcaca gcgaggcggt caagaagcga agaggcttct ccgtcaccaa cacctctacc    3300
aactgtgacg actttgagga acgcacggtc cagtccaaga aacgcgctgc aaagacacgt    3360
acaaggcagg aaatatctga tgctgccagc atcgtccagg acgtccgcta catagatctt    3420
gagctagatg gttgtgaaca agtcaatgaa gtgccataca gtgtacaaaa gcctgtggct    3480
tctggtaggg ttttacctgc gtggcagtcc gccagaatag cctag                   3525
```

<210> SEQ ID NO 100
<211> LENGTH: 1174
<212> TYPE: PRT
<213> ORGANISM: Protein

<400> SEQUENCE: 100

```
Met Ile Lys Pro Arg Val Asn Trp Ser Asp His Ala Asn Ala Val Gln
1               5                   10                  15

Ser Ser Cys Ile Lys Asp Glu Phe Leu Ser Ser Phe Leu Phe Ser
            20                  25                  30

Leu Pro Thr Gln Arg Pro Asn Gln Glu Ala Asp Cys Thr Gly Met Leu
        35                  40                  45

Pro Leu Arg Ser Ala Ala Cys Arg Ile Gln Gly Leu Glu Arg Leu Gln
    50                  55                  60

Ala Pro Ser Ile Glu Lys Ala Trp Arg Ser Leu Arg Asn Thr Gln Val
65                  70                  75                  80

Ala Arg Lys Asn Tyr Leu Arg Pro Gly Leu Ser Gly Lys Val Lys Asp
                85                  90                  95

Cys Asp Ser Asp His Ala His Thr Tyr Gly Thr Ser Ser Tyr Asn
            100                 105                 110

Val Asn Lys Val Asp Ser Val Ser Arg Asn Arg Asn Pro Thr Gln Glu
        115                 120                 125

Ser Met His Gln Thr Thr Glu Ser Gly Thr Met Glu Lys Asn Ser Ser
    130                 135                 140
```

```
His Leu Pro Ala Gly Thr Lys Ser Cys Thr Arg Thr Tyr Leu Asn Asn
145                 150                 155                 160

His Val Val Gln Ala Asp Thr Ile Thr Thr Asn Gln Ser Leu Ala
        165                 170                 175

Arg Thr Gly Pro Glu Leu Phe Lys Thr Ala Pro Phe Ile Asp Asn Met
            180                 185                 190

Cys Asp Asp Ala Lys Leu Asp Ala Met Asp Glu Asp Leu Leu Ala
        195                 200                 205

Ser Ile Asp Val Asp Arg Ile Val Met Glu His Tyr Gln Ala Thr Asn
210                 215                 220

Thr Pro Arg Gly Ser Ser Lys Ser Pro Leu Glu Lys Cys Asn Phe Asn
225                 230                 235                 240

Gly Phe Asp Glu Asn Asn Leu Pro Gln Glu Leu Ser Ile Met Cys Asp
                245                 250                 255

His Gly Ser Lys Leu Ala Phe Cys Pro Glu Ala Lys Ser His Leu Leu
            260                 265                 270

Glu Met Lys Asp Asn Leu Leu Ala Ile Ser His Glu Leu Ile Asp Gly
        275                 280                 285

Gln Leu Ser Pro Gln Gln Ser Asp Asp Leu His Gln Lys Arg Ala Leu
    290                 295                 300

Leu Lys Lys Gln Ile Glu Leu Leu Gly Glu Tyr Thr Ala Arg Leu Thr
305                 310                 315                 320

Gln Asp Glu Glu Arg Gln Gln Ser His Ser Met Ala Ser Thr Thr Ala
                325                 330                 335

His Gln Gly His His Pro Thr Ser Ile Leu Ser Ser Ser Phe Val Lys
            340                 345                 350

Asp Thr Asn Ile Phe Arg Ser Pro Ile Tyr Thr Arg Asn Glu Pro Gly
        355                 360                 365

Glu Ser Gly Leu Cys Phe Ser Ser Ala Pro Tyr Ser Tyr Met Asp Gly
    370                 375                 380

Leu Ser Met Pro Leu Pro Ser Val Gln Arg Asp Tyr Thr Pro Arg Ala
385                 390                 395                 400

Ile Asp Ile Ser Tyr Thr Glu Gly Ser Gly Asp Lys Gln Trp Ser Ser
                405                 410                 415

Thr His Phe Ala Trp Thr Lys Glu Leu Glu Ala Asn Asn Lys Gly Val
            420                 425                 430

Phe Gly Asn Arg Ser Phe Arg Pro Asn Gln Arg Glu Ile Thr Asn Ala
        435                 440                 445

Thr Met Ser Gly Asn Asp Val Phe Val Leu Met Pro Thr Gly Gly Gly
    450                 455                 460

Lys Ser Leu Thr Tyr Gln Leu Pro Ala Leu Ile Cys Asn Gly Val Thr
465                 470                 475                 480

Leu Val Val Ser Pro Leu Val Ser Leu Ile Gln Asp Gln Ile Met His
                485                 490                 495

Leu Leu Gln Ala Asn Ile Ser Ala Ala Tyr Leu Ser Ala Ser Met Glu
            500                 505                 510

Trp Ser Glu Gln Gln Glu Ile Leu Arg Glu Leu Met Ser Pro Thr Cys
        515                 520                 525

Thr Tyr Lys Leu Leu Tyr Val Thr Pro Glu Lys Ile Ala Lys Ser Asp
    530                 535                 540

Ala Leu Leu Arg Gln Leu Glu Asn Leu Tyr Ser Arg Gly His Leu Ser
545                 550                 555                 560

Arg Ile Val Ile Asp Glu Ala His Cys Val Ser Gln Trp Gly His Asp
                565                 570                 575
```

```
Phe Arg Pro Asp Tyr Gln His Leu Gly Ile Leu Lys Gln Lys Phe Pro
            580                 585                 590

Gln Thr Pro Val Leu Ala Leu Thr Ala Thr Ala Ser Val Lys
            595                 600                 605

Glu Asp Val Val Gln Val Leu Gly Leu Ala Asn Cys Ile Ile Phe Arg
            610                 615                 620

Gln Gly Phe Asn Arg Pro Asn Leu Arg Tyr Phe Val Trp Pro Lys Thr
625                 630                 635                 640

Lys Lys Cys Leu Glu Asp Ile His Asn Phe Ile His Ala Asn His Asn
                645                 650                 655

Lys Glu Cys Gly Ile Ile Tyr Cys Leu Ser Arg Met Asp Cys Glu Lys
                660                 665                 670

Val Ala Ala Lys Leu Arg Glu Tyr Gly His Gln Ala Ser His Tyr His
                675                 680                 685

Gly Ser Met Asp Pro Glu Asp Arg Ala Asn Ile Gln Lys Gln Trp Ser
            690                 695                 700

Lys Asp Arg Ile Asn Ile Ile Cys Ala Thr Val Ala Phe Gly Met Gly
705                 710                 715                 720

Ile Asn Lys Pro Asp Val Arg Phe Val Ile His Ser Leu Pro Lys
                725                 730                 735

Ser Ile Glu Gly Tyr His Gln Glu Cys Gly Arg Ala Gly Arg Asp Ser
            740                 745                 750

Gln Leu Ser Ser Cys Val Leu Phe Tyr Asn Tyr Ser Asp Tyr Ile Arg
            755                 760                 765

Leu Lys His Met Val Thr Gln Gly Phe Ala Glu Gln Gly Thr Ser Ala
        770                 775                 780

Pro Arg Gly Gly Ser Ser Gln Glu Gln Ala Leu Glu Thr His Lys Glu
785                 790                 795                 800

Asn Leu Leu Arg Met Val Ser Tyr Cys Glu Asn Asp Val Asp Cys Arg
                805                 810                 815

Arg Leu Leu Gln Leu Ile His Phe Gly Glu Met Phe Asn Pro Ser Cys
                820                 825                 830

Cys Ala Lys Thr Cys Asp Asn Cys Leu Lys Glu Leu Arg Trp Val Lys
                835                 840                 845

Lys Asp Val Thr Asn Ile Ala Arg Gln Leu Val Asp Leu Val Met Met
        850                 855                 860

Thr Lys Gln Thr Tyr Ser Thr His Ile Leu Glu Val Tyr Arg Gly
865                 870                 875                 880

Ser Val Asn Gln Asn Val Lys Lys His Arg His Asp Thr Leu Ser Leu
                885                 890                 895

His Gly Ala Gly Lys His Leu Ala Lys Gly Ala Ala Arg Ile Leu
                900                 905                 910

Arg His Leu Val Ile Glu Glu Ile Leu Ile Glu Asp Val Lys Lys Ser
        915                 920                 925

Glu Asn Tyr Gly Ser Val Ser Ser Val Leu Lys Thr Asn His Lys Lys
        930                 935                 940

Ser Gly Asp Leu Leu Ser Gly Lys His Asn Val Val Leu Lys Phe Pro
945                 950                 955                 960

Thr Pro Glu Lys Ala Pro Lys Met Gly Val Leu Asp Glu Ser Ser Val
                965                 970                 975

Pro Arg Ile Asn Lys Thr Asn Gln Gln Ser Gln Val Asp Gly Ser Leu
                980                 985                 990

Ala Ala Glu Leu Tyr Glu Ala Leu  Gln Cys Leu Arg Thr  Gln Ile Met
```

```
                995                1000               1005
Asp Glu Asn Pro Gln Leu Leu Ala Tyr His Ile Phe Lys Asn Glu
    1010                1015                1020

Thr Leu Lys Glu Ile Ser Asn Arg Met Pro Arg Thr Lys Glu Glu
    1025                1030                1035

Leu Val Glu Ile Asn Gly Ile Gly Lys Asn Lys Leu Asn Lys Tyr
    1040                1045                1050

Gly Asp Arg Val Leu Ala Thr Ile Glu Asp Phe Leu Ala Arg Tyr
    1055                1060                1065

Pro Asn Ala Thr Arg Lys Thr Ser Ser Gly Gly Ser Asn Glu His
    1070                1075                1080

Ser Glu Ala Val Lys Lys Arg Arg Gly Phe Ser Val Thr Asn Thr
    1085                1090                1095

Ser Thr Asn Cys Asp Asp Phe Glu Glu Arg Thr Val Gln Ser Lys
    1100                1105                1110

Lys Arg Ala Ala Lys Thr Arg Thr Arg Gln Glu Ile Ser Asp Ala
    1115                1120                1125

Ala Ser Ile Val Gln Asp Val Arg Tyr Ile Asp Leu Glu Leu Asp
    1130                1135                1140

Gly Cys Glu Gln Val Asn Glu Val Pro Tyr Ser Val Gln Lys Pro
    1145                1150                1155

Val Ala Ser Gly Arg Val Leu Pro Ala Trp Gln Ser Ala Arg Ile
    1160                1165                1170

Ala

<210> SEQ ID NO 101
<211> LENGTH: 1419
<212> TYPE: PRT
<213> ORGANISM: Protein

<400> SEQUENCE: 101

Ala Thr Gly Ala Ala Gly Cys Ala Cys Gly Gly Thr Gly Thr Ala Ala
1               5                   10                  15

Thr Thr Gly Ala Thr Gly Ala Thr Ala Ala Gly Ala Ala Gly Thr
                20                  25                  30

Thr Gly Ala Gly Gly Thr Gly Ala Gly Ala Ala Cys Thr Cys Cys Thr
                35                  40                  45

Thr Thr Gly Thr Thr Cys Ala Gly Ala Cys Gly Gly Cys Ala Gly
            50                  55                  60

Ala Ala Thr Cys Cys Thr Cys Thr Gly Cys Thr Cys Gly Ala Cys Ala
65                  70                  75                  80

Gly Ala Cys Thr Cys Gly Cys Ala Thr Cys Ala Ala Thr Cys Thr Gly
                85                  90                  95

Gly Ala Cys Thr Cys Cys Thr Thr Cys Gly Gly Gly Thr Thr Cys Thr
                100                 105                 110

Cys Cys Thr Cys Ala Gly Ala Thr Gly Ala Thr Gly Ala Cys Thr Thr
            115                 120                 125

Thr Gly Ala Ala Ala Cys Gly Thr Thr Gly Gly Ala Gly Thr Cys Cys
            130                 135                 140

Cys Ala Thr Thr Gly Thr Gly Ala Thr Cys Gly Thr Thr Cys Ala Gly
145                 150                 155                 160

Thr Cys Ala Gly Thr Ala Cys Cys Cys Ala Gly Ala Ala Gly Ala Ala
                165                 170                 175

Gly Gly Thr Gly Ala Ala Cys Ala Gly Ala Gly Gly Ala Ala Ala Cys
                180                 185                 190
```

```
Ala Ala Thr Ala Gly Ala Thr Gly Thr Gly Ala Gly Thr Cys Ala Thr
        195                 200                 205
Cys Cys Ala Cys Thr Thr Cys Ala Ala Cys Thr Thr Cys Ala Ala Ala
    210                 215                 220

Cys Ala Gly Ala Gly Ala Ala Ala Cys Thr Cys Thr Ala Ala Gly Thr
225                 230                 235                 240
Thr Ala Thr Cys Ala Gly Cys Ala Gly Cys Thr Cys Ala Ala Cys Ala
                245                 250                 255
Thr Gly Gly Ala Cys Ala Cys Cys Thr Thr Thr Gly Thr Gly Cys Thr
            260                 265                 270

Thr Ala Thr Gly Cys Cys Ala Ala Cys Ala Gly Gly Thr Gly Gly Thr
        275                 280                 285
Gly Gly Gly Ala Ala Gly Ala Gly Cys Thr Thr Gly Thr Gly Thr Thr
    290                 295                 300

Ala Thr Cys Ala Gly Cys Thr Ala Cys Cys Thr Gly Cys Ala Ala Cys
305                 310                 315                 320

Ala Cys Thr Gly Cys Ala Cys Cys Cys Ala Gly Gly Thr Gly Thr Thr
                325                 330                 335
Ala Cys Gly Gly Thr Thr Gly Thr Thr Gly Thr Ala Thr Gly Cys Cys
            340                 345                 350

Cys Thr Cys Thr Ala Cys Thr Gly Thr Cys Ala Cys Thr Thr Ala Thr
        355                 360                 365

Thr Gly Ala Gly Gly Ala Thr Cys Ala Ala Ala Thr Thr Gly Thr Gly
    370                 375                 380

Gly Cys Ala Thr Thr Ala Ala Ala Cys Thr Thr Cys Ala Ala Gly Thr
385                 390                 395                 400

Thr Thr Gly Cys Thr Ala Thr Ala Cys Cys Ala Gly Cys Ala Gly Cys
                405                 410                 415

Ala Thr Thr Thr Thr Thr Gly Ala Ala Cys Thr Cys Thr Cys Ala Gly
            420                 425                 430

Cys Ala Gly Ala Cys Ala Cys Cys Thr Thr Cys Ala Cys Ala Gly Thr
        435                 440                 445

Cys Ala Thr Cys Thr Gly Cys Ala Gly Thr Ala Ala Thr Cys Cys Ala
    450                 455                 460

Ala Gly Ala Gly Cys Thr Thr Ala Gly Ala Ala Gly Thr Gly Gly Thr
465                 470                 475                 480

Ala Ala Ala Cys Cys Gly Thr Cys Ala Thr Thr Cys Ala Ala Ala Cys
                485                 490                 495

Thr Cys Cys Thr Cys Thr Ala Cys Gly Thr Cys Ala Cys Thr Cys Cys
            500                 505                 510

Thr Gly Ala Ala Ala Gly Ala Ala Thr Gly Gly Cys Thr Gly Gly Ala
        515                 520                 525

Ala Ala Cys Ala Gly Cys Thr Cys Ala Thr Thr Thr Ala Thr Thr Gly
    530                 535                 540

Gly Gly Ala Thr Cys Cys Thr Cys Ala Thr Ala Gly Gly Thr Thr Thr
545                 550                 555                 560

Ala Cys Ala Cys Cys Ala Gly Ala Gly Gly Gly Gly Thr Thr Thr Ala
                565                 570                 575

Cys Thr Gly Gly Cys Gly Ala Gly Ala Thr Thr Thr Gly Thr Gly Ala
            580                 585                 590

Thr Thr Gly Ala Thr Gly Ala Ala Gly Cys Cys Cys Ala Thr Thr Gly
        595                 600                 605

Thr Gly Thr Ala Ala Gly Thr Cys Ala Ala Thr Gly Gly Gly Gly Ala
```

```
    610                 615                 620

Cys Ala Thr Gly Ala Cys Thr Thr Cys Cys Gly Cys Cys Cys Ala Gly
625                 630                 635                 640

Ala Thr Thr Ala Cys Cys Gly Ala Gly Gly Cys Cys Thr Gly Gly Gly
                645                 650                 655

Ala Thr Gly Cys Cys Thr Cys Ala Ala Ala Cys Ala Gly Ala Ala Cys
            660                 665                 670

Thr Thr Cys Cys Cys Thr Cys Gly Ala Gly Thr Ala Cys Cys Ala Ala
        675                 680                 685

Thr Thr Ala Thr Gly Gly Cys Thr Thr Thr Ala Ala Cys Ala Gly Cys
    690                 695                 700

Thr Ala Cys Ala Gly Cys Gly Ala Cys Thr Gly Cys Ala Thr Cys Thr
705                 710                 715                 720

Gly Thr Cys Thr Gly Cys Ala Ala Gly Gly Ala Cys Ala Thr Ala Cys
                725                 730                 735

Thr Ala Ala Gly Thr Ala Cys Cys Thr Thr Gly Ala Gly Gly Ala Thr
            740                 745                 750

Cys Cys Cys Thr Ala Ala Thr Gly Cys Ala Ala Cys Gly Gly Thr Ala
        755                 760                 765

Cys Thr Cys Ala Ala Gly Ala Gly Gly Ala Gly Cys Thr Thr Thr Gly
    770                 775                 780

Ala Cys Ala Gly Ala Ala Cys Ala Ala Ala Cys Cys Thr Gly Ala Ala
785                 790                 795                 800

Thr Thr Ala Thr Gly Ala Gly Gly Thr Gly Ala Thr Thr Gly Gly Cys
                805                 810                 815

Ala Ala Gly Ala Cys Ala Ala Ala Ala Ala Cys Thr Cys Cys Ala Cys
            820                 825                 830

Ala Gly Ala Ala Gly Cys Ala Gly Cys Thr Gly Gly Gly Thr Gly Ala
        835                 840                 845

Thr Ala Thr Cys Cys Thr Ala Ala Ala Ala Gly Ala Gly Cys Gly Thr
    850                 855                 860

Thr Thr Cys Ala Thr Gly Ala Ala Cys Ala Thr Gly Thr Cys Thr Gly
865                 870                 875                 880

Gly Thr Ala Thr Cys Gly Thr Gly Thr Ala Cys Thr Gly Thr Cys Thr
                885                 890                 895

Gly Thr Cys Cys Ala Ala Ala Ala Ala Thr Gly Ala Ala Thr Gly Thr
            900                 905                 910

Gly Cys Thr Gly Ala Cys Ala Cys Thr Gly Cys Cys Ala Ala Gly Thr
        915                 920                 925

Thr Cys Thr Thr Gly Ala Gly Gly Gly Ala Gly Ala Ala Gly Thr Ala
    930                 935                 940

Cys Ala Ala Gly Ala Thr Ala Ala Ala Ala Thr Gly Cys Gly Cys Ala
945                 950                 955                 960

Cys Ala Thr Thr Ala Cys Cys Ala Cys Gly Cys Thr Gly Gly Cys Thr
                965                 970                 975

Thr Gly Gly Cys Thr Gly Cys Thr Cys Gly Thr Cys Ala Ala Cys Gly
            980                 985                 990

Ala Thr Cys Cys Ala Ala Thr Gly  Thr Ala Cys Ala Ala  Gly Gly Ala
        995                 1000                 1005

Ala Ala  Ala Thr Gly Gly Cys  Ala Cys Ala Gly Cys  Gly Gly Ala
    1010                 1015                 1020

Gly Ala  Gly Gly Thr Cys Ala  Ala Ala Gly Thr Cys  Ala Thr Thr
    1025                 1030                 1035
```

```
Thr Gly Thr Gly Cys Gly Ala Cys Cys Ala Thr Ala Gly Cys Ala
1040                1045                1050

Thr Thr Thr Gly Gly Cys Ala Thr Gly Gly Gly Ala Ala Thr Ala
1055                1060                1065

Gly Ala Cys Ala Ala Ala Cys Cys Thr Gly Ala Thr Gly Thr Gly
1070                1075                1080

Cys Gly Cys Thr Thr Thr Gly Thr Thr Ala Thr Cys Cys Ala Cys
1085                1090                1095

Ala Ala Cys Ala Cys Cys Ala Thr Gly Thr Cys Ala Ala Ala Ala
1100                1105                1110

Thr Cys Gly Ala Thr Ala Gly Ala Ala Ala Gly Cys Thr Ala Cys
1115                1120                1125

Thr Ala Thr Cys Ala Gly Gly Ala Gly Thr Cys Ala Gly Gly Gly
1130                1135                1140

Ala Gly Ala Gly Cys Ala Gly Ala Ala Gly Ala Gly Ala Cys
1145                1150                1155

Ala Ala Thr Cys Thr Thr Cys Cys Gly Gly Cys Ala Cys Ala Thr
1160                1165                1170

Thr Gly Cys Ala Thr Thr Gly Thr Gly Thr Thr Ala Thr Ala Thr
1175                1180                1185

Cys Ala Gly Ala Ala Ala Ala Gly Gly Ala Cys Cys Thr Cys
1190                1195                1200

Gly Gly Thr Cys Gly Ala Ala Thr Thr Gly Thr Ala Thr Gly Cys
1205                1210                1215

Ala Thr Gly Cys Thr Gly Ala Gly Gly Ala Ala Thr Thr Cys Ala
1220                1225                1230

Gly Gly Gly Ala Ala Cys Thr Thr Cys Ala Ala Gly Ala Gly Thr
1235                1240                1245

Gly Ala Gly Ala Gly Cys Thr Thr Cys Ala Ala Gly Gly Thr Thr
1250                1255                1260

Gly Cys Ala Ala Thr Gly Gly Ala Gly Cys Ala Ala Gly Cys Ala
1265                1270                1275

Ala Ala Gly Ala Ala Ala Ala Thr Gly Cys Ala Ala Ala Cys Ala
1280                1285                1290

Thr Ala Thr Thr Gly Cys Gly Ala Gly Cys Thr Gly Ala Ala Gly
1295                1300                1305

Ala Cys Ala Gly Ala Ala Thr Gly Cys Cys Gly Gly Ala Gly Gly
1310                1315                1320

Cys Ala Ala Ala Cys Thr Cys Thr Thr Cys Thr Thr Gly Gly Cys
1325                1330                1335

Cys Ala Cys Thr Thr Cys Gly Gly Thr Gly Ala Gly Cys Ala Gly
1340                1345                1350

Thr Ala Thr Gly Ala Cys Ala Gly Gly Cys Ala Ala Ala Gly Gly
1355                1360                1365

Thr Gly Cys Ala Ala Ala Cys Ala Thr Gly Gly Thr Thr Gly Thr
1370                1375                1380

Ala Gly Cys Cys Cys Thr Thr Gly Cys Gly Ala Cys Ala Ala Cys
1385                1390                1395

Thr Gly Cys Ala Thr Ala Ala Ala Gly Ala Thr Thr Cys Cys Cys
1400                1405                1410

Thr Cys Thr Thr Gly Ala
1415

<210> SEQ ID NO 102
```

<211> LENGTH: 472
<212> TYPE: PRT
<213> ORGANISM: Protein

<400> SEQUENCE: 102

```
Met Lys His Gly Val Ile Asp Asp Lys Glu Val Glu Val Arg Thr Pro
1               5                   10                  15

Leu Phe Arg Gln Ala Glu Ser Ser Ala Arg Gln Thr Arg Ile Asn Leu
            20                  25                  30

Asp Ser Phe Gly Phe Ser Ser Asp Asp Phe Glu Thr Leu Glu Ser
        35                  40                  45

His Cys Asp Arg Ser Val Ser Thr Gln Lys Lys Val Asn Arg Gly Asn
    50                  55                  60

Asn Arg Cys Glu Ser Ser Thr Ser Thr Ser Asn Arg Glu Thr Leu Ser
65                  70                  75                  80

Tyr Gln Gln Leu Asn Met Asp Thr Phe Val Leu Met Pro Thr Gly Gly
                85                  90                  95

Gly Lys Ser Leu Cys Tyr Gln Leu Pro Ala Thr Leu His Pro Gly Val
            100                 105                 110

Thr Val Val Cys Pro Leu Leu Ser Leu Ile Glu Asp Gln Ile Val
        115                 120                 125

Ala Leu Asn Phe Lys Phe Ala Ile Pro Ala Ala Phe Leu Asn Ser Gln
130                 135                 140

Gln Thr Pro Ser Gln Ser Ser Ala Val Ile Gln Glu Leu Arg Ser Gly
145                 150                 155                 160

Lys Pro Ser Phe Lys Leu Leu Tyr Val Thr Pro Glu Arg Met Ala Gly
                165                 170                 175

Asn Ser Ser Phe Ile Gly Ile Leu Ile Gly Leu His Gln Arg Gly Leu
            180                 185                 190

Leu Ala Arg Phe Val Ile Asp Glu Ala His Cys Val Ser Gln Trp Gly
        195                 200                 205

His Asp Phe Arg Pro Asp Tyr Arg Gly Leu Gly Cys Leu Lys Gln Asn
    210                 215                 220

Phe Pro Arg Val Pro Ile Met Ala Leu Thr Ala Thr Ala Thr Ala Ser
225                 230                 235                 240

Val Cys Lys Asp Ile Leu Ser Thr Leu Arg Ile Pro Asn Ala Thr Val
                245                 250                 255

Leu Lys Arg Ser Phe Asp Arg Thr Asn Leu Asn Tyr Glu Val Ile Gly
            260                 265                 270

Lys Thr Lys Thr Pro Gln Lys Gln Leu Gly Asp Ile Leu Lys Glu Arg
        275                 280                 285

Phe Met Asn Met Ser Gly Ile Val Tyr Cys Leu Ser Lys Asn Glu Cys
    290                 295                 300

Ala Asp Thr Ala Lys Phe Leu Arg Glu Lys Tyr Lys Ile Lys Cys Ala
305                 310                 315                 320

His Tyr His Ala Gly Leu Ala Ala Arg Gln Arg Ser Asn Val Gln Gly
                325                 330                 335

Lys Trp His Ser Gly Glu Val Lys Val Ile Cys Ala Thr Ile Ala Phe
            340                 345                 350

Gly Met Gly Ile Asp Lys Pro Asp Val Arg Phe Val Ile His Asn Thr
        355                 360                 365

Met Ser Lys Ser Ile Glu Ser Tyr Tyr Gln Glu Ser Gly Arg Ala Gly
    370                 375                 380

Arg Asp Asn Leu Pro Ala His Cys Ile Val Leu Tyr Gln Lys Lys Asp
385                 390                 395                 400
```

```
Leu Gly Arg Ile Val Cys Met Leu Arg Asn Ser Gly Asn Phe Lys Ser
            405                 410                 415
Glu Ser Phe Lys Val Ala Met Glu Gln Ala Lys Lys Met Gln Thr Tyr
            420                 425                 430
Cys Glu Leu Lys Thr Glu Cys Arg Arg Gln Thr Leu Leu Gly His Phe
            435                 440                 445
Gly Glu Gln Tyr Asp Arg Gln Arg Cys Lys His Gly Cys Ser Pro Cys
    450                 455                 460
Asp Asn Cys Ile Lys Ile Pro Ser
465                 470

<210> SEQ ID NO 103
<211> LENGTH: 4692
<212> TYPE: DNA
<213> ORGANISM: DNA

<400> SEQUENCE: 103
atggcttccc gtcccgcgca cgacctgctt caacgcgtct ttggttacga cgatttccgt      60
ggtccgcagc aggacatcgt ggagcatgtg gctgccggtc acgacgccct ggtgctgatg     120
cccaccggcg gcggcaaatc gctgtgctac caggtcccag ccctgctgcg tgacggttgc     180
ggcatcgtca tctcgccgct gatcgcactg atgcaggacc aggtcgaagc cctgcgccag     240
ctcggcgtgc gcgccgagta cctgaattca accctggacg ccgagaccgc cggccgcgtc     300
gagcgcgagc tgctcgccgg cgaactggac atgctgtatg tcgcccctga gcggctgctg     360
agcgggcgtt tcctgtcgct gctgtcgcgc agccagatcg ccctgttcgc catcgacgaa     420
gcacactgcg tgtcgcagtg gggccatgac ttcgcccccg aatatcgcca gttgaccgtg     480
ctgcacgagc gttggccgca gatcccgcgg atcgcgctga ccgccaccgc cgatccgccg     540
acccagcgcg agatcgccga gcgcctcgat ctgcaggaag cgcgccattt tgtcagttcc     600
ttcgaccgcc ccaacatccg ctacaccgtc gtgcagaagg acaacgcccg caagcagctg     660
accgacttcc tgcgcggcca ccgtggcgag gccggcatcg tctactgcat gtcgcggcgc     720
aaggtcgagg agaccgctga attcctctgc ggccaaggcg tcaacgctct gccttaccac     780
gccggcctgc cgccggaagt gcgcgccagc aaccagcgcc gcttcctgcg cgaggacggc     840
atcgtgatgt gtgccaccat cgccttcggc atgggcatcg acaagccgga cgtgcgtttc     900
gtcgcgcata ccgacctgcc caagtcgatg gagggctact accaggaaac cggacgcgca     960
ggccgcgatg gcgaagccgc cgaggcctgg ctgtgctacg gctgggtga  tgtggtactg    1020
ctcaagcaga tgatcgagca gtccgaggcg ggcgaagagc gcaagcagct ggaacgggcc    1080
aagctcgacc atctgctggg ctactgcgaa tcgatgcagt gccgccgcca ggtgctgctg    1140
gccggcttcg gcgaaaccta cccccaaccg tgcggcaact gcgacaactg cctgacgcca    1200
ccggcctcgt gggacgcgac cataccggca cagaaggcgc tgagctgcgt ctaccgcagc    1260
ggccagcgct tcggtgtcgg ccacctgatc gacatcctgc gcggcagcga gaacgagaag    1320
gtgaggcagc agggccacga caagctgagc acttatgcca tcggccgcga cctggatgca    1380
cgcacctggc gcagcgtgtt ccgccagctg gtcgcggcca gcctgctgga agtggacagc    1440
gagggccacg gcggcctgcg cctgaccgac gccagccgcg acgtgctgac cggccgccgc    1500
cagatcagca tgccgccgcg acccggccag cagcagcagcg gacgcgagcg cagtgcgcag    1560
cgcaccggcc tgtcggtact gccgcaggac ctggccctgt tcaacgcgct gcgcggcctg    1620
cgcgccgaac tggcccggga acagaacgta ccggcgttcg tgatcttcca cgacagcacc    1680
```

```
ctgcgcaaca tcgccgagcg gcgcccgacc agcctggatg aactggcccg ggtcggcggc    1740
atcggcggta ccaagctgag ccgctatggc ccgcgcctgg tcgagatcgt gcgcgaagaa    1800
ggcctgttgc tcaacgggct gaacgcggcc atggcccgtg gtcacgaaga aatggggcgg    1860
atggcccacg ccgcagccgc tgctgttgat ggcggcactg ccgactgcca ccaccacgcc    1920
gccatgcagg ccgacccggc cccgcaggcc aaggccccgg cccacgacgc ccactgccag    1980
atcaaggact gcgtgcgcag ctgcgcccag caccccgctgc tggtggtgca gccgttgccg    2040
ttcatggccg gaccggcact gtcgctggcc ccgcagccga tgccggccac cggccggccg    2100
gcgcccccgt ctgccgccga tctcacgccc tcccatcggc tgattccaca cgcaccggcc    2160
tggccgccgg tggcgtggtt gccggcatcg ccgctgtcgg cgtgccgcag cgcgtgctcg    2220
ccgccgccac tgccgcccca cgcctggccg gcgcccccgc cgtgctcagc gacacccgca    2280
tcgaactggc catcggcgaa tcgctggcca actttcactg gccgcacccg tccggcgatc    2340
accgtcaatg gatcgctgcc ggcaccgatc ctgcgctggc gcgaaggcca gaccgtggac    2400
ctgttcgtgc gcaacacgct ggaccgccac ccgacctcga tccattggca cggcattctg    2460
ctgccggcca acatggacgg cgtgcccggc ctgagcttca atggcatcgg ccccggtgag    2520
acctaccact accacttcga actgaagcag tcgggtacct actggtacca cagccactcg    2580
atgttccagg agcaggccgg cctgtacgga gcgctgatca tcgacccggc cgagccggcg    2640
ccctaccagc acgaccgcga gcacgtgatc ctgctgtccg actggaccga catggacccc    2700
ggcgcgctgt tccggcgcat gaagaagctc gccgagcatg acaactacta caagcgcacc    2760
ctgcccgact tcctgcgtga cgtgaagcgc gacggttggt cggccgcgtt gtccgaccgt    2820
ggcatgtggg gcggatgcg gatgacgccc accgacatct ccgacatcaa tgcgcacacc    2880
tacacctacc tgatgaatgg caccgcgccg gccggcaact ggaccgggct gttccgcagc    2940
ggcgagaaag tactgctgcg cttcatcaac ggcgcctcga tgacctactt cgacgtgcgc    3000
attcccggcc tgaagatgac cgtggtcgcc gccgacggcc agtacatcca tccggtcagc    3060
atcgacgagt tccgcatcgc gccggccgaa acctacgacg tgctggtgga accgaccggg    3120
caggacgcgt tcaccatctt ctgccaggac atgggccgca ccggttcccg cgcgcgaccc    3180
acgcccgttg ctgacgatag cgacatgggg cacgacatgg gtagtggtgg ccatggtggc    3240
cacgacatgg ccgcgatgaa gggcatgaa ggcggctgcg gcgccagcat ggaccacggt    3300
gcgcacggcg gtagcgatgc cgccagcaag gcaccgaagc acccggccag cgaacgcaac    3360
aacccgctgg tggacatgca gagctcggcc accgaaccga agctggacga tcccggcatc    3420
ggcctgcgcg acaacggtcg ccaggtactc acctacggcg cgatgcgcag cctgttcgag    3480
gaccccgatg gccgcgagcc gagccgcgag atcgagctgc acctgaccgg ccatatggag    3540
aagttctcct ggtcattcga tggcattccg ttcgccagcg ccgagccgct gcggctgaac    3600 tacgcgagc gcatgccatc tgatctggag aacgcgcagg gcgaattcca gctgcgcaag    3660
cacaccatcg acatgccacc cggcacccgc cgcagttacc gcgtgcgcgc cgatgcgctc    3720
ggtcgctggg cctaccactg ccatctgctc taccacatgg aagcgggcat gatgcgcgaa    3780
aacagcaccg gccaggcctg ggaggccacc ggctggatcg gtggcaacat caaccgcctg    3840
tggttgcgca ccgatggcga acgcagccgc ggccgcacgg aatcgtcgtc actggaagca    3900
ctgtatggtc gcagcgtatc gccgtggtgg gacgtgctgg gcggcgtgcg ccaggacttc    3960
cggccggccg actcgcgcac ctgggcggcc atcggcatcc agggccttgc accgtacaag    4020
ttcgagagct cggcaacgct gtacatgggt tccggcggcc aggtgctggc caaggccgag    4080
```

-continued

```
gtcgagtacg acgtgctgct gaccaaccgc ctgatcctgc agccgctgct ggaagccacc      4140
atcgcagcca aggatgaacc ggagtacggc attggtcgcg gactgaacaa gatccgccgc      4200
gccacccttg ccgatgtcga cgcgctgtcg accatcgcca tcaccaccta caacgaaacc      4260
tggggcgact cgtatccggc gcaggagctg caggatttcc tgcaggcgca ctacagcagc      4320
gaaccgcagc gcgccgagtt gtccgacccg cgcagtgcga tctggctgct gttggacggc      4380
gacaacgtgg tcggctacct ggccgccggt gccaacaccc tgccgcatgc cgaagcccgc      4440
gagggcgaca tcgaactgaa gcgcttctac atcctggccg actaccagaa cggcggccac      4500
ggcgcgcgcc tgatggacgc gttcatggcc tggctggacc agccgcagcg ccgcaccctg      4560
tgggtgggcg tctgggagga gaacttcggc gcgcagcgct tctacgcgcg ctacggctgc      4620
agcaaggtcg gcgagtacga cttcatcgtc ggggatacgc gcgaccgcga gttcatcctg      4680
cgccggctgt ga                                                          4692
```

<210> SEQ ID NO 104
<211> LENGTH: 1563
<212> TYPE: PRT
<213> ORGANISM: Protein

<400> SEQUENCE: 104

```
Met Ala Ser Arg Pro Ala His Asp Leu Leu Gln Arg Val Phe Gly Tyr
1               5                   10                  15

Asp Asp Phe Arg Gly Pro Gln Gln Asp Ile Val Glu His Val Ala Ala
            20                  25                  30

Gly His Asp Ala Leu Val Leu Met Pro Thr Gly Gly Lys Ser Leu
        35                  40                  45

Cys Tyr Gln Val Pro Ala Leu Leu Arg Asp Gly Cys Gly Ile Val Ile
    50                  55                  60

Ser Pro Leu Ile Ala Leu Met Gln Asp Gln Val Glu Ala Leu Arg Gln
65                  70                  75                  80

Leu Gly Val Arg Ala Glu Tyr Leu Asn Ser Thr Leu Asp Ala Glu Thr
                85                  90                  95

Ala Gly Arg Val Glu Arg Glu Leu Leu Ala Gly Glu Leu Asp Met Leu
            100                 105                 110

Tyr Val Ala Pro Glu Arg Leu Leu Ser Gly Arg Phe Leu Ser Leu Leu
        115                 120                 125

Ser Arg Ser Gln Ile Ala Leu Phe Ala Ile Asp Glu Ala His Cys Val
    130                 135                 140

Ser Gln Trp Gly His Asp Phe Arg Pro Glu Tyr Arg Gln Leu Thr Val
145                 150                 155                 160

Leu His Glu Arg Trp Pro Gln Ile Pro Arg Ile Ala Leu Thr Ala Thr
                165                 170                 175

Ala Asp Pro Pro Thr Gln Arg Glu Ile Ala Glu Arg Leu Asp Leu Gln
            180                 185                 190

Glu Ala Arg His Phe Val Ser Ser Phe Asp Arg Pro Asn Ile Arg Tyr
        195                 200                 205

Thr Val Val Gln Lys Asp Asn Ala Arg Lys Gln Leu Thr Asp Phe Leu
    210                 215                 220

Arg Gly His Arg Gly Glu Ala Gly Ile Val Tyr Cys Met Ser Arg Arg
225                 230                 235                 240

Lys Val Glu Glu Thr Ala Glu Phe Leu Cys Gly Gln Gly Val Asn Ala
                245                 250                 255

Leu Pro Tyr His Ala Gly Leu Pro Pro Glu Val Arg Ala Ser Asn Gln
            260                 265                 270
```

-continued

```
Arg Arg Phe Leu Arg Glu Asp Gly Ile Val Met Cys Ala Thr Ile Ala
        275                 280                 285
Phe Gly Met Gly Ile Asp Lys Pro Asp Val Arg Phe Val Ala His Thr
        290                 295                 300
Asp Leu Pro Lys Ser Met Glu Gly Tyr Tyr Gln Glu Thr Gly Arg Ala
305                 310                 315                 320
Gly Arg Asp Gly Glu Ala Ala Glu Ala Trp Leu Cys Tyr Gly Leu Gly
                325                 330                 335
Asp Val Val Leu Leu Lys Gln Met Ile Glu Gln Ser Glu Ala Gly Glu
            340                 345                 350
Glu Arg Lys Gln Leu Glu Arg Ala Lys Leu Asp His Leu Leu Gly Tyr
        355                 360                 365
Cys Glu Ser Met Gln Cys Arg Arg Gln Val Leu Leu Ala Gly Phe Gly
        370                 375                 380
Glu Thr Tyr Pro Gln Pro Cys Gly Asn Cys Asp Asn Cys Leu Thr Pro
385                 390                 395                 400
Pro Ala Ser Trp Asp Ala Thr Ile Pro Ala Gln Lys Ala Leu Ser Cys
                405                 410                 415
Val Tyr Arg Ser Gly Gln Arg Phe Gly Val Gly His Leu Ile Asp Ile
            420                 425                 430
Leu Arg Gly Ser Glu Asn Glu Lys Val Arg Gln Gly His Asp Lys
        435                 440                 445
Leu Ser Thr Tyr Ala Ile Gly Arg Asp Leu Asp Ala Arg Thr Trp Arg
        450                 455                 460
Ser Val Phe Arg Gln Leu Val Ala Ala Ser Leu Leu Glu Val Asp Ser
465                 470                 475                 480
Glu Gly His Gly Gly Leu Arg Leu Thr Asp Ala Ser Arg Asp Val Leu
                485                 490                 495
Thr Gly Arg Arg Gln Ile Ser Met Arg Arg Asp Pro Ala Ser Ser Ser
            500                 505                 510
Ser Gly Arg Glu Arg Ser Ala Gln Arg Thr Gly Leu Ser Val Leu Pro
        515                 520                 525
Gln Asp Leu Ala Leu Phe Asn Ala Leu Arg Gly Leu Arg Ala Glu Leu
        530                 535                 540
Ala Arg Glu Gln Asn Val Pro Ala Phe Val Ile Phe His Asp Ser Thr
545                 550                 555                 560
Leu Arg Asn Ile Ala Glu Arg Arg Pro Thr Ser Leu Asp Glu Leu Ala
                565                 570                 575
Arg Val Gly Gly Ile Gly Gly Thr Lys Leu Ser Arg Tyr Gly Pro Arg
            580                 585                 590
Leu Val Glu Ile Val Arg Glu Glu Gly Leu Leu Leu Asn Gly Leu Asn
        595                 600                 605
Ala Ala Met Ala Arg Gly His Glu Glu Met Gly Arg Met Ala His Ala
        610                 615                 620
Ala Ala Ala Val Asp Gly Gly Thr Ala Asp Cys His His His Ala
625                 630                 635                 640
Ala Met Gln Ala Asp Pro Ala Pro Gln Ala Lys Ala Pro Ala His Asp
                645                 650                 655
Ala His Cys Gln Ile Lys Asp Cys Val Arg Ser Cys Ala Gln His Pro
            660                 665                 670
Leu Leu Val Val Gln Pro Leu Pro Phe Met Ala Gly Pro Ala Leu Ser
        675                 680                 685
Leu Ala Pro Gln Pro Met Pro Ala Thr Gly Arg Pro Ala Pro Pro Ser
```

```
                690               695               700
Ala Ala Asp Leu Thr Pro Ser His Arg Leu Ile Pro His Ala Pro Ala
705               710               715               720

Trp Pro Pro Val Ala Trp Leu Pro Ala Ser Pro Leu Ser Ala Cys Arg
            725               730               735

Ser Ala Cys Ser Pro Pro Leu Pro Pro His Ala Trp Pro Ala Pro
            740               745               750

Pro Pro Cys Ser Ala Thr Pro Ser Asn Trp Pro Ser Ala Asn Arg
            755               760               765

Trp Pro Thr Phe Thr Gly Arg Thr Arg Pro Ala Ile Thr Val Asn Gly
770               775               780

Ser Leu Pro Ala Pro Ile Leu Arg Trp Arg Glu Gly Gln Thr Val Asp
785               790               795               800

Leu Phe Val Arg Asn Thr Leu Asp Arg His Pro Thr Ser Ile His Trp
                805               810               815

His Gly Ile Leu Leu Pro Ala Asn Met Asp Gly Val Pro Gly Leu Ser
            820               825               830

Phe Asn Gly Ile Gly Pro Gly Glu Thr Tyr His Tyr His Phe Glu Leu
            835               840               845

Lys Gln Ser Gly Thr Tyr Trp Tyr His Ser His Ser Met Phe Gln Glu
850               855               860

Gln Ala Gly Leu Tyr Gly Ala Leu Ile Ile Asp Pro Ala Glu Pro Ala
865               870               875               880

Pro Tyr Gln His Asp Arg Glu His Val Ile Leu Leu Ser Asp Trp Thr
            885               890               895

Asp Met Asp Pro Gly Ala Leu Phe Arg Arg Met Lys Lys Leu Ala Glu
            900               905               910

His Asp Asn Tyr Tyr Lys Arg Thr Leu Pro Asp Phe Leu Arg Asp Val
            915               920               925

Lys Arg Asp Gly Trp Ser Ala Ala Leu Ser Asp Arg Gly Met Trp Gly
            930               935               940

Arg Met Arg Met Thr Pro Thr Asp Ile Ser Asp Ile Asn Ala His Thr
945               950               955               960

Tyr Thr Tyr Leu Met Asn Gly Thr Ala Pro Ala Gly Asn Trp Thr Gly
            965               970               975

Leu Phe Arg Ser Gly Glu Lys Val Leu Leu Arg Phe Ile Asn Gly Ala
            980               985               990

Ser Met Thr Tyr Phe Asp Val Arg Ile Pro Gly Leu Lys Met Thr Val
            995               1000              1005

Val Ala Ala Asp Gly Gln Tyr Ile His Pro Val Ser Ile Asp Glu
1010              1015              1020

Phe Arg Ile Ala Pro Ala Glu Thr Tyr Asp Val Leu Val Glu Pro
1025              1030              1035

Thr Gly Gln Asp Ala Phe Thr Ile Phe Cys Gln Asp Met Gly Arg
1040              1045              1050

Thr Gly Ser Arg Ala Arg Pro Thr Pro Val Ala Asp Asp Ser Asp
1055              1060              1065

Met Gly His Asp Met Gly Ser Gly Gly His Gly His Asp Met
1070              1075              1080

Ala Ala Met Lys Gly Met Glu Gly Gly Cys Gly Ala Ser Met Asp
1085              1090              1095

His Gly Ala His Gly Gly Ser Asp Ala Ala Ser Lys Ala Pro Lys
1100              1105              1110
```

```
His Pro Ala Ser Glu Arg Asn Asn Pro Leu Val Asp Met Gln Ser
1115                1120                1125

Ser Ala Thr Glu Pro Lys Leu Asp Asp Pro Gly Ile Gly Leu Arg
1130                1135                1140

Asp Asn Gly Arg Gln Val Leu Thr Tyr Gly Ala Met Arg Ser Leu
1145                1150                1155

Phe Glu Asp Pro Asp Gly Arg Glu Pro Ser Arg Glu Ile Glu Leu
1160                1165                1170

His Leu Thr Gly His Met Glu Lys Phe Ser Trp Ser Phe Asp Gly
1175                1180                1185

Ile Pro Phe Ala Ser Ala Glu Pro Leu Arg Leu Asn Tyr Gly Glu
1190                1195                1200

Arg Met Pro Ser Asp Leu Glu Asn Ala Gln Gly Glu Phe Gln Leu
1205                1210                1215

Arg Lys His Thr Ile Asp Met Pro Pro Gly Thr Arg Arg Ser Tyr
1220                1225                1230

Arg Val Arg Ala Asp Ala Leu Gly Arg Trp Ala Tyr His Cys His
1235                1240                1245

Leu Leu Tyr His Met Glu Ala Gly Met Met Arg Glu Asn Ser Thr
1250                1255                1260

Gly Gln Ala Trp Glu Ala Thr Gly Trp Ile Gly Gly Asn Ile Asn
1265                1270                1275

Arg Leu Trp Leu Arg Thr Asp Gly Glu Arg Ser Arg Gly Arg Thr
1280                1285                1290

Glu Ser Ser Ser Leu Glu Ala Leu Tyr Gly Arg Ser Val Ser Pro
1295                1300                1305

Trp Trp Asp Val Leu Gly Gly Val Arg Gln Asp Phe Arg Pro Ala
1310                1315                1320

Asp Ser Arg Thr Trp Ala Ala Ile Gly Ile Gln Gly Leu Ala Pro
1325                1330                1335

Tyr Lys Phe Glu Ser Ser Ala Thr Leu Tyr Met Gly Ser Gly Gly
1340                1345                1350

Gln Val Leu Ala Lys Ala Glu Val Glu Tyr Asp Val Leu Leu Thr
1355                1360                1365

Asn Arg Leu Ile Leu Gln Pro Leu Leu Glu Ala Thr Ile Ala Ala
1370                1375                1380

Lys Asp Glu Pro Glu Tyr Gly Ile Gly Arg Gly Leu Asn Lys Ile
1385                1390                1395

Arg Arg Ala Thr Leu Ala Asp Val Asp Ala Leu Ser Thr Ile Ala
1400                1405                1410

Ile Thr Thr Tyr Asn Glu Thr Trp Gly Asp Ser Tyr Pro Ala Gln
1415                1420                1425

Glu Leu Gln Asp Phe Leu Gln Ala His Tyr Ser Ser Glu Pro Gln
1430                1435                1440

Arg Ala Glu Leu Ser Asp Pro Arg Ser Ala Ile Trp Leu Leu Leu
1445                1450                1455

Asp Gly Asp Asn Val Val Gly Tyr Leu Ala Ala Gly Ala Asn Thr
1460                1465                1470

Leu Pro His Ala Glu Ala Arg Glu Gly Asp Ile Glu Leu Lys Arg
1475                1480                1485

Phe Tyr Ile Leu Ala Asp Tyr Gln Asn Gly Gly His Gly Ala Arg
1490                1495                1500

Leu Met Asp Ala Phe Met Ala Trp Leu Asp Gln Pro Gln Arg Arg
1505                1510                1515
```

Thr Leu Trp Val Gly Val Trp Glu Glu Asn Phe Gly Ala Gln Arg
    1520                1525                1530

Phe Tyr Ala Arg Tyr Gly Cys Ser Lys Val Gly Glu Tyr Asp Phe
    1535                1540                1545

Ile Val Gly Asp Thr Arg Asp Arg Glu Phe Ile Leu Arg Arg Leu
    1550                1555                1560

<210> SEQ ID NO 105
<211> LENGTH: 1185
<212> TYPE: DNA
<213> ORGANISM: DNA

<400> SEQUENCE: 105
gcacgagcgc aaggcaagct ttccgcttcc tatttcggat tgggatcatc agcggctgta      60
gcgtggaccc gacggggtg tccggaccac atccctattt catcttggta ccccgtccgt     120
ctccgatttc agaagcacgg cgggctcccc ggcagcctct accgagcaga aagctgagtt     180
ctaccccaga accgaggcat ggaggacgaa gaaaacatcg agggagaact gttgctcgtg     240
gagtcacaac tccacgacat ccaaggacaa attaaaacat tactcgatcg ccaagaggag     300
ttgtatgaac gccaggcaca gttgaaggct ttgctcgaag catctaaatt gaccagaaat     360
acaacaatta acacatcttc agttgctccg gaagattggt ctgggagctt cccatgggat     420
ctggaggctg acgataccag gttcaatata tttggcattt cctcctaccg atcaaatcaa     480
cgagaaataa ttaatgcagt catgagtgga agagatgttc tggtcataat ggcagctggt     540
ggagggaaga gtctatgtta ccagctccca gctgtacttc gtgatggaat tgcactggtt     600
gtcagtcctt tactttccct tattcaggac caggtcatgg gactgtcagc tttaggtata     660
ccagcataca tgctaacttc aactaccaac aaggaagttg agaagttcat ctataagaca     720
cttgataaag gagaaggaga actaaagata ttatatgtga cacctgaaaa gatctcaaaa     780
agtaaaaggt tcatgtctaa gctcgagaaa tgccatcatg ccggtcgtct ttctctgatt     840
gcaatagatg aggctcactg ctgtagccaa tggggtcatg attttcgtcc tgactacaag     900
aatcttggca ttttgaaaat tcaatttccc agtgttccaa tgatagcttt aactgcaact     960
gcaacaagta aggtccaaat ggatttaatg gagatgctcc acatcccgag atgcatcaag    1020
tttgtcagca cagttaacag gcccaacctt ttttataagg tgtctgagaa tcgccagtt    1080
ggaaaggttg tcattgatga gatcacaaag tttataagtg aatcataccc aaataatgag    1140
tctggaatta tatactgctt ttcaaggaag gaatgtgaac aggtt                    1185

<210> SEQ ID NO 106
<211> LENGTH: 870
<212> TYPE: DNA
<213> ORGANISM: DNA

<400> SEQUENCE: 106
cttgaggatc cccaacgctg tggtactgaa gaggagcttc gacagactga acctcaacta      60
cgaggtaatc ggcaagacga aactttcca gaagcagctg gcgatctcc tgaaagagcg     120
cttcatgaac gaatctggta tcgtgtactg tctctcgaag aacgagtgtg cagacactgc     180
caagttttg aggaagaaat acaagatcaa atgcgcgcac taccacgcta gcctggcagc     240
tcgtcagcga accagtgtcc aggagaaatg gcacaacggg gaggttaagg tcatctgcgc     300
taccatagcc ttcggcatgg ggatcgacaa acctgacgtg cgttttgtta tccacaacac     360
attgtccaag tcaatagaaa gctactacca ggagtccggg agggcagggc gagatgagct     420

| | |
|---|---|
| tccggcacac tgtatcgtct tgtaccagaa gaaagacttc agccgtatcg tgtgcatgtt | 480 |
| gaggaacggt gagaacttca ggagcgagag cttcagggtt gcgatggagc aagctaagaa | 540 |
| gatgcaggca tactgcgagc tcaagaccga gtgccggaga caggcacttc tgcagcactt | 600 |
| cggcgaacag tacgacaggc gaaggtgccg agacgggcct agccctgcg acaactgcct | 660 |
| caagacatag tttagggtaa taaactatgg cgataaaaaa tgccatgacg cttggttatg | 720 |
| ctctgaactt gtgaggtgtg tgccacttcc acagtacatt cgtctgtgta tatgtagcat | 780 |
| ccatagctca aacaagtggc cgcaactgca ctgtgtgtaa cgatggtctt tgttttcagt | 840 |
| tggattgtga ggttcggggc tttaaaaaaa | 870 |

<210> SEQ ID NO 107
<211> LENGTH: 3569
<212> TYPE: DNA
<213> ORGANISM: DNA

<400> SEQUENCE: 107

| | |
|---|---|
| atggaggacg atgacgatga ccaacgcttg cttcacagcc ttggtgtcac gtccgcagac | 60 |
| atccacgata ttgaaaggag aatcatatca caggcaacaa ctgatcctgc cgactcatct | 120 |
| ggaccaacca tcaatggagg tcatcagcct gatgatgctc tcgccaaact gcatcacaaa | 180 |
| ctgcgctctg tgcaaattga aattgatgct gtagcctcca ccatcaaagg agctaagctt | 240 |
| aagcaaccat ccggaaataa accacatgag cataaaggca aggaccagcc agatcatcat | 300 |
| ggagcaggac acctccagca agcccttgct gccgaccgtc ttacaagcct caggaaagct | 360 |
| aaagcacaga tacagaaaga gatactacag tcacatcttt ctccatctgc ctccaatcga | 420 |
| aaagataaaa tgctggccat gctggtccaa gacgagccga ggcacaaaaa gccacccgta | 480 |
| gggcctaaaa acatcgtgaa acgcccgatg aaaactgtca cctatgatga tgacaacaac | 540 |
| ttcgatgcag tgcttgatgg agcctctgcg ggatttatgg aaactgaaag ggaagaactg | 600 |
| atcaggaagg gtttgttgac accattccat aagttgaagg gcttcgagaa acgtgtggaa | 660 |
| ctacccgaac cttctcatag acaagatgat tctgcaggac aaaactgaaga agccatggaa | 720 |
| gcttccagga ttgctagagt tgctcagtcg ctaaagcaga ttgcacagaa ccgcccagca | 780 |
| accaaattgc ttgattcaga gtctttacct aagctagatg cacctgctgc cccatttcag | 840 |
| agacttggaa aaccccctaaa gcgtcctgtc tctcccagtt cagatgagca ggaaaagaag | 900 |
| agaccaagaa ataagaccaa aagaccactg cctggcaaga atggaggaa agcaaactca | 960 |
| attaaggaat catcattgga tgacaacgat gttggagagg cagctgtgtc agtttcagat | 1020 |
| gatgatgaag atcaggttac agaaggctct gatgagttaa ctgatgttac ccttgaagga | 1080 |
| ggtttgagaa ttcctggcac actttacacg caactatttg actaccagaa agtgggagtg | 1140 |
| cagtggctat gggagttgca ttgtcaaagg gctggtggaa taattggaga tgaaatgggc | 1200 |
| ctgggaaaga ctgtgcaggt cttgtcattt cttggttcct tgcataacag tgggctctac | 1260 |
| aagcctagca ttgttgtttg tcctgtaacc cttttgcaac agtggcgaag ggaggccagt | 1320 |
| agatggtatc caaagttcaa ggttgagatc ttacatgact ctgcaaacag ttcatctaaa | 1380 |
| aagagcaaga ggtctagtga ttctgacagt gaagcttcct gggatagtga tcaggaagaa | 1440 |
| gcggttacat gttcaaaacc cgcaaagaag tgggatgact tgatttcacg tgttgtgagt | 1500 |
| tcaggatcag gtttgcttct gaccacatat gagcagttaa ggatcctagg ggagaagttg | 1560 |
| cttgatatag aatgggggata tgctgtattg atgagggtc accgcattag gaatcctaat | 1620 |
| gctgagatta ctcttgtgtg caagcaattg cagaccgtgc acaggataat tatgacaggt | 1680 |

-continued

```
gcacctattc aaaacaaact ttcggagctt tggtctctct ttgattttgt gttccctgga    1740
aaactaggtg tcctgcctgt gtttgaggct gagttttctg ttccaattac tgttggtggg    1800
tacgctaatg caacaccatt gcaagtgtcc acggcgtatc gatgtgctgt tgtcctacgt    1860
gacctggtca tgccgtacct tcttagaaga atgaaagctg atgtcaatgc acagcttccc    1920
aagaaaacag agcatgttct tttctgtagt ctaactactg agcaacgtgc tacttatcgt    1980
gcatttcttg ctagttcgga ggtggaacaa atctttgatg gtaacagaaa ttccctttat    2040
gggatagatg ttctaaggaa gatatgcaat catcctgatc tacttgagag agaacatgct    2100
gctcagaatc ctgactatgg gaatccagaa agaagtggaa agatgaaagt ggttgagcaa    2160
gttcttaaag tatggaaaga acaaggtcat cgtgttcttc ttttcactca gacacaacaa    2220
atgcttgaca ttatgggaa cttcttgaca gcttgcgaat accaataccg aagaatggat     2280
ggacttacac ctgcaaagca aagaatggca cttattgatg aattcaataa cacagatgaa    2340 attttattt tcattctgac cacgaaagtt ggtggactgg gtacgaattt gactggtgca     2400
aaccggatta ttatatatga tcctgactgg aatccttcaa ctgacatgca ggctagggaa    2460
cgtgcatggc gaattgggca aactagagat gtgacagttt atagactgat cacgcgtggg    2520
acaatagagg agaaagtcta ccatcgtcag gtatacaagc atttcctcac aaacaaagta    2580
ctgaaagacc ctcagcagag gcggtttttt aaagccagag acatgaagga tttgtttacg    2640
ctgcaagatg atgacaataa tggctcaact gaaacatcaa atattttcag ccaattgtct    2700
gaggatgtga atatcggagt tccgagtgac aagcaacaag accagctata tgcagcctct    2760
gctacaccga caacctctgg gactgaaccg agctcatcca ggcatggaca gggtaaagaa    2820
gaccattgcc ctgaccaagc agatgaagaa tgcaacattt tgaagagcct ttttgatgct    2880
caaggcattc atagtgcgat caatcatgat gccataatga acgctaatga tgaccagaag    2940
ctgcgcctag aagcagaagc tacacaggtg gcacaaaggg cagctgaagc tttacgccaa    3000
tcacggatgc tcagaagtca tgaaagtttt tctgttccta catggactgg aagagctggt    3060
gctgcggggg caccatcctc tgtccgcagg aagtttgggt caacactcaa tacccagttg    3120
gttaattctt ctcagccatc agaaacttca atggcaggg gccaaagtct tcaggtgggt     3180
gctctaaatg gcaaagcact gtcctccgct gagcttctgg ccaggatacg tggaacccga    3240
gagggagcag cttcagatgc actagaacat caactcaacc tgggatcagc ttccaatcac    3300
acatcgagtt catcagggaa tggccgtgca tcaagctctt ctactaggag catgatcgta    3360
cagcctgaag tcctaatccg ccaattgtgc accttcatac agcagcatgg tggttccgcc    3420
agctcaacaa gtataactga acacttcaag aaccggatac tgtccaagga tatgctgctg    3480
tttaagaatc tgctgaagga aatagctacg ttgcaaagag gtgcaaatgg tgcaacgtgg    3540
gtgctgaaac ctgactacca gtaactagt                                      3569
```

<210> SEQ ID NO 108
<211> LENGTH: 3453
<212> TYPE: DNA
<213> ORGANISM: DNA

<400> SEQUENCE: 108

```
atgcgcacaa gcaccacatc agatagccca tccccatctc cacaaaacaa agcctctttt      60
aacacatcac gtggtgctgc atttagggat gaagaaccag gtgcaaaaga caatgaagtt    120
gagaaaagga aaccattgat attacatttg aagaagcgtt caaccaagga actatctaca    180
gataccacat catcaaagtc agggttactt ggaaagtctt cagaagagaa acaggagaaa    240
```

```
cacggaagtg ctttgaaagt gaagaaacat ctgcatccca tggaattatc tccaaagaaa    300
tataagaaca agaagcaaca caatcacaga gacagtaaga gatccgaagc aaaaaaggtc    360
caatatttgg catcagatgt ggacagtgat tcttcaatgg aaccatctac ttctcttgag    420
cacagcgaat cgccgccccc aaaaagaaaa tcgttggatg gaagaacacc tgcatcaagt    480
accaagaaag gaaaaagaa agtgaaattt attgataaaa agcaccctga gaatgctgtt    540
catataactg aaaaggagca tggtggtgca ggagacaaaa taacaactca gggggatctg    600
caggttgatc gcatcctagg ctgtcgactt cagacaagcc aaatcatttc acctgcccat    660
gcttcatcag agcagattga tatggcccct cctagtgcat ccggtgcaac agaacctagt    720
caagcccttt caaaaggact tcatgaagaa attcagtctt ctaatagtga tactaatgtg    780
acagaggatg catgtgctga tgaattagca acgatggtg gggaaaataa tttggattgt    840
tctgatgctc aaaaggagag taatgttaga tcccatggac acaaggaatc acttaacgca    900
aaagaaatca tgaatacagc atcagcatgt tccgctgatc aaattgtcac agttaaggat    960
gctggagcag tacagacata tgtaacggct tcagtaaatg gtgaatatga gacagtaact   1020
gatattccag aagaaaagaa tgacaccaaa catccagttt ccaaagctga cacagaagtc   1080
cacactaaac aagaacatac acctgatagt aaattgcatg ggaaactaga aaactacaaa   1140
gcaaagtacg gaacaggttt gataaacatc tgcaaagaac aatggtgcca accgcaacga   1200
gttattgctc tgcgcacttc tttagatgaa atagaagagg ctttgatcaa atggtgtgcc   1260
cttccatatg acgaatgcac gtgggaaaga ttagatgaac ctacaatggt gaagtatgca   1320
catttggtca ctcagttcaa aaaatttgaa tcccaggctt tggataagga taagggaggt   1380
agccatgcaa agccaaggga acaccaagag tttaatatgc tggttgagca gccaaaagaa   1440
ctccagggag gcatgctctt ccctcatcaa ctggaagcat tgaactggct acgcaaatgc   1500
tggtacaagt caaaaaatgt tatccttgct gatgagatgg gtcttggaaa gactgtgtct   1560
gcctgtgctt ttctatcatc cctatgttgt gaatataaga ttaacttgcc atgtcttgtc   1620
ttggttcctc tttctactat gcccaactgg atggctgaat ttgcatcatg ggcacctcat   1680
ttaaatgttg tggagtatca tggttctgca cgggcaagat ctattattcg tcaatatgag   1740
tggcatgagg gtgatgcaag ccagatgggt aaaatcaaga atctcataa gttcaatgta   1800 ttgctcacta cttatgaaat ggtgcttgtt gatgctgcat atcttcggtc tgtgtcatgg   1860
gaggttctta tagtcgatga gggtcatcgt ctgaagaatt ctagcagcaa acttttcagt   1920
ttactcaata cattatcatt tcagcataga gttttgctga ctggaactcc gttacagaat   1980
aacattggtg aaatgtataa cttattgaac ttcttacaac ctgcttcttt cccttctcta   2040
gcttcatttg aggagaaatt caatgacctt acaacaacag agaaagtgga ggagctgaag   2100
aaccttgtag ctccacatat gcttcgaaga ctgaaaaagg atgcaatgca aaatatccct   2160
ccaaagactg aacgaatggt gcctgttgaa ttgacatcaa tccaggctga atactaccgt   2220
gctatgctta caaagaacta ccaagtattg cgcaatattg ggaaaggtgg tgctcaccag   2280
tcattgttga acatagtaat gcaacttcgg aaagtctgca atcatccgta tcttattcct   2340
ggaactgaac ctgaatcagg atcaccagag ttcttgcatg aaatgcgaat aaaggcctca   2400
gcaaagttaa ctttgttgca ctctatgctt aaaatcctac acaaggatgg tcatcgagtt   2460
cttatttttt ctcagatgac aaagcttctt gacatccttg aagattacct gacctgggag   2520
tttggtccga aaacatttga aagagtggat ggttcagtat ctgtggcaga acgccaggca   2580
gcaattgctc gttttaatca ggacaagagt cgttttgtat tcctgctatc tacgcggtca   2640
```

-continued

```
tgtgggcttg gaattaattt ggcaactgca gatactgtta tcatatatga ttctgatttc    2700
aatccacatg ctgatataca ggcaatgaac agagcacaca gaattggaca gtcaaacaga    2760
cttttagttt acaggcttgt cgtgcgtgct agtgttgagg agcgtatctt gcaccttgcg    2820
aagaaaaaat tgatgcttga tcaacttttt gttaacaaat cagaatcaca gaaggaagtg    2880
gaagatatca ttcgctgggg aacagaggaa ctcttcagga atagcgatgt tgcagttaaa    2940
gataataatg aagcttctgg tgctaaaaat gatgtagcag aggttgagtt taagcataaa    3000
agaaaaactg gtggactagg cgatgtttat gaagacagat gtgctgatgg ttctgctaaa    3060
tttaattggg atgaaaatgc tatcacaaag cttcttgaca gatccaacgt tccatcaaca    3120
gtagctgaaa gcactgatgg ggacttggac aatgatatgc ttggcactgt aaagtcaata    3180
gattggaacg atgagctgaa tgatgaccct ggtgccaccg aggacatccc aaatattgat    3240
aatgatggtt gcgagcaggc atctgaagca aagcaggatg cagctaatcg tgttgaagaa    3300
aatgaatggg ataaactctt acgtgtcaga tgggagcagt atcaaactga ggaggaagca    3360
tctcttggtc gaggtaagcg tttaaggaag gctgtttctt acagggaaac atttgcaacc    3420
attcctaatg aagctttaag cgagtagaac tag    3453
```

<210> SEQ ID NO 109
<211> LENGTH: 2964
<212> TYPE: DNA
<213> ORGANISM: DNA

<400> SEQUENCE: 109

```
atggcggaca cggggagcct ggagaagatg gggcgagagc tcaagtgccc catctgcctg      60
agccttctca gttcggcggt atccatctcc tgcaaccacg tcttctgcaa tgattgcctc     120
acggaatcga tgaaatccac gtcgagctgc cccgtgtgca aggtcccgtt ccgacgacga     180
gaaatgcgac cagcacctca catggacaat ctggtcagca ttttcaaaag catggaggct     240
gcagcaggta ccaatgttgt ctcaacacag gaggctcctg tggtaaaact tgcagatgga     300
tcagattgtg tcaacagcgg gaaaaattcc aaaaggtcac aaaaatcatt gacacgaaaa     360
aggaaggtaa catccgagat ggaaaaaaat acagcaaagg atgctacagc ttctgcatcc     420
caacctacta caaagccttc cttctctact aacaaaagaa tacaagtgaa accattccct     480
gaatctgaga caccaataag agctgagaag attatgaagc tgaagagcc aaaaaataat      540 ctgaataatg atgttgaagg aaagaataaa gcagtggcat cgggtcaacc tggaagtcct     600
tcattgtcac cctttttttg gctaaggaa caagaagaac aagaaggctg taccgctgag      660
acgttaagtg aaacgcaatc tttagacaca cccttgcgtc ataatgcacc ctcttttagc     720
gatattaaag attctgatga cgaaatccct ttaaatacaa ctccaaatag caaagctgcg     780
gctacagaac tctttgacag tgaaatattt gaatggaccc agagaccatg ctctcctgaa     840
ttgtattcca ctccattgaa aaagcagagt aaagctaaga gtaaactaga tcaaattgaa     900
gagaagggtg atgaagaaga tgtgcatatt ggtggttcat ttgataagct gggcagtgca     960
agtaatgcag ctcagcttgt caatacaaaa gcaacaaagc agaagagaaa gaaaacaagt    1020
cccagtaaca aaacagtgc aaaattgtcc aatcgtgctg agccctgcat aaaaaagtct    1080
gatgccaatc aacaaggttc aaatagacgt aaaagtgctg ccctaaaatc ttgtcagaaa    1140
agcagcagtg ctgtagggag gaatacttca ggtagaagaa acaaggcctc tagcaacagc    1200
aagccaattc atggctctag tgataactcc ccagagtcat atcttcctaa ggagggtttg    1260
gatgttgaag cacctgacaa acccctttct gaaaggatcc aaaacttgga gaaaactagt    1320
```

| | |
|---|---:|
| cgacgaaagg gaagtgcaag gaagctggaa atggcaggga aaactatttc agatactaca | 1380 |
| gagaagaata gtgagccaag aagtaagaga gtcagaagaa tgtctgacca cgctatagct | 1440 |
| aaaccggttg aagttccttc aggatctgga aatgaaacag aaataccaca gcttcacacc | 1500 |
| ctcacaaaag gcagcattca acgcaaatcc tccaacgcta aagacatag caaagtttgt | 1560 |
| ggagaacagg aaggtaagaa taaacttgag aacacgacaa tgacacctat tattttacat | 1620 |
| gggaaatgcc aaaataaaga ggcagtatgt acagctcctt cagtaaggac tgcatctgtt | 1680 |
| aagtacaagc aagcaaaatt tagcgaacaa ccagattgtt ttggaacgga aactttgga | 1740 |
| aaccttcaag catgccctgc acgtaatgtt ttactgaaga agtgtgaggt atctactttg | 1800 |
| aaggtttcct gtgctttctg ccagaccgat gtcatcacag aggagtctgg agagatggtt | 1860 |
| cattatcaaa atgggaagca agtccctgca gagttcaatg gaggagccaa tgtggtgcac | 1920 |
| tctcacaaga actgccttga gtgggctcct gatgtctact tcgaagatga ttctgccttt | 1980 |
| aatcttacaa ctgaattggc gagaagcaga cggatcaaat gtgcttgctg tggaattaaa | 2040 |
| ggagctgcac ttggatgctt tgagatgagt tgtcggagaa gtttccactt cacctgtgct | 2100 |
| aaactaatcc cagaatgcag atgggataat gaaaattttg tgatgttatg ccctctacat | 2160 |
| cggtctacaa agttacccaa tgaaaattct gaacagcaaa agcaacctaa aaggaaaaca | 2220 |
| acactcaaag ggtcatctca ataggatcc aatcaagatt gtggtaataa ctggaaatgg | 2280 |
| ccatctggat caccacagaa gtgggttctc tgctgctcat cactttctag ttctgagaag | 2340 |
| ggacttgtat cagaatttgc aaagttagct ggcgtgccta tttcggcaac ttggagtcca | 2400 |
| aatgttaccc atgttattgc atcaactgat ctctctggtg cttgcaaacg gacgctgaag | 2460 |
| tttctcatgg caatcttgaa tggcagatgg attgtctcca tagattgggt taaaacttgc | 2520 |
| atggagtgca tggaaccaat tgatgagcac aaatttgaag tcgctactga tgttcatggg | 2580 |
| atcactgatg gtcctaggtt aggaagatgc agggttattg acaggcaacc taagctgttc | 2640 |
| gacagcatga ggttctacct ccatggggac tacacaaaat cctacagagg ctacctgcaa | 2700 |
| gatctcgtgg ttgcagcagg tggaatagtt cttcagagga agcccgtatc aagagaccag | 2760 |
| caaaagcttc ttgatgacag ctctgacctc ctcatcgttt acagcttcga gaatcaagat | 2820 |
| agggcaaaat ccaaggccga aaccaaggct gctgatcgca ggcaggctga tgctcaggct | 2880 |
| cttgcttgcg cttctggagg cagagttgtg agcagtgcat gggtgattga ctcaattgca | 2940 |
| gcctgcaatc tgcaacctct ttga | 2964 |

<210> SEQ ID NO 110
<211> LENGTH: 4500
<212> TYPE: DNA
<213> ORGANISM: DNA

<400> SEQUENCE: 110

| | |
|---|---:|
| atggctgacc tcttcaacca agctttggat aagctggttg ctgctgatgg aatggccgaa | 60 |
| gcgatcgagg attcagggaa aggtgcggtg ttctgcactg ggttgggggg atcagttgcc | 120 |
| gtcagcgaga gggctgtaga gagggccaag gcattggttg ggaggtcgc ggaggagata | 180 |
| agtaatgaga ggaggcaacc atttggtgat ggttctaatt tggagtgcgg attgggagaa | 240 |
| agtaatgttt catttaaagg tggtgtacat aaagatagtt tgtctccgat gttccaaacc | 300 |
| ggatcgggta aaatggtttc gctgagcaag ggctcaattc agaaggctag agctgtttta | 360 |
| gaaggaaatg ccgagaattc ttctgtcatt gctgtacagt ctatgttcca tactggattg | 420 |
| gttaggccag acccagtcag caggagctcc actgataatg caatgactgt tttggaggga | 480 |

```
caaacaaatc caaaacaagg agatgtggca gatgtgtatg acaaggaaaa ttttccattg      540
ttccaaactg gttcaggtaa agctgtatcg gtcagtgtag catctatcca gaaagctaag      600
gctgtcctgg agcaaaataa tacagaaaac acggaagatt ttggtaggcc tgaccaatct      660
ctgattttcc aaactggttc gcgaagacca gtcttgatca gtgaaagatc tagctctgtg      720
gtgaaggatg gaggtgctga aaatattgtg ttccaaacgg ggttagggag gcctgttgtg      780
gtgagccaga cctcaattca aaaggcaagg acagtattag atcaagaatg tgccaaaaga      840
agtggacatg gagatactaa tgtctccacc actacttttc aaactgaaac accaacgcct      900
gttctgatga gtggtggcct gactatgaat gatagatctg ttacacctga gggggtgtt       960 tcaatgcaag gaaattttttt ggaggctgat ggtcacttgc cattatttca aactgggtta    1020
gggaggtcca tttcagtaag taaaggctca attaagagag caagtgcact tctggagcca    1080
aggaacatta caaaagaact ggaagatgaa gctcactcag atgatggctg tgccactcca    1140
atgttcaaaa ctggatcagg aaggtctatc acagcaagtg aaaattctag aaagaaagcc    1200
cacgttgtct tagagggcga ggaaccagta aaaaatgtaa ataatgacac tggagaagcc    1260
attgctccaa tgctccatgc tggaatgcag aagtttgcac cccaaaatag aaactcaagt    1320
cataaggcga tcaccctcat ggagcaaggg agctctatgg aagaagaccg tggaaacgaa    1380
ccaccaatgt ttcgaactgg atctgggaag tcagtcttga ttagtcacag ctccgtgcag    1440
aaggcaaggg cggttctgga ggaagaaggc aatatgaaga agaaaatca caaacaactt     1500 agcaatgtgg acaaatatat tccgatcttt acttcacctc tcaagacaag ctatgcaagg    1560
actgtacata tatcttcagt tggtgtttct cgagctgcaa ctttgttggg tttggaggag    1620
aatacccttt caacacaact tttaggacat gtgggtgata agctaggtac aaagataact    1680
gttgagaggg aaaattcaga gcaccagttt ggtgtagcat cagtcagtgg aatttctggt    1740
ggctgcccta taagctctgg cccagctgaa aaccaagtac ttatggatcc acatcagcat    1800
tttgcatttt ctaaaacaac gttctctgat tccagtgagc aagctatcag gttcagcact    1860
gctggcggca gaacaatggc tattcctagt gatgcacttc agcgtgcgaa aaatcttctg    1920
ggtgaatcgg atttagaggt ttcaccaaat aatttattag gccactcttc agcatctgct    1980
tgtaaagaga atatacaaaa ttcaactggt ctgcgaaaag aaggtgaacc tgatttattg    2040
aaaagtaggg ggaacagcaa aactgagcca gcacaatttt ccattccagc aaaacctgat    2100
aggaagcaca cagattcctt ggaatatgct gtacctgatg ccactttggc taacggaaac    2160
tccgtcaggc ttcatgcggc aagagatttt catcctatca atgaaattcc aaagatatcc    2220
aagccttctt ccagatgttc atttggaact gaaaatgcaa gtgacactaa agataaggct    2280
cgaagactcc aaatgccatc tggaccattg attgacatca ctaattacat cgatacacat    2340
tctgttaata ctgactacct ggccggtgag aagagaagat ttgggggaag aaactccata    2400
tctcccttta aacgtcctcg ttcttccagg ttcatcgcac ctatcaacat caataatcca    2460
tccccttctg gagtatccaa actacctatt cagattaatc cctgtcgaac aaagctatct    2520
tcatgctatc cttttcaaca tcaaagaaaa tcgtgtgaag agtattttgg tggtccccca    2580
tgcttcaaat atttgacaga agatgtaaca gatgaagtga agctcatgga tgcaaaaaag    2640
gctgagaagt acaagtttaa aacagatact ggtgcagaag aatttcagaa gatgcttctt    2700
gcctgtggtg cttcattgac atacacaact aaagaatggg tcagcaacca ctacaaatgg    2760
attgtttgga agcttgcttc attggagaga tgctatccaa ctagagctgc tggcaaattc    2820
ttaaaagttg gtaatgtttt ggaagagctg aagtacaggt atgacagaga agtgaacaat    2880
```

```
ggccaccgct cagccataaa gaaaattttg aagggaatg cttcaccatc tttgatgatg    2940
gtgctgtgca tttctgctat ttactcttgt cctgacctaa acaacagtaa gccagaggat   3000
gatagggcac atacagacga cgacaacagt gagaataaaa gcttgagacc tgctaaaagg   3060
aacatgtcta caaagattga actaactgat ggatggtatt ctctagatgc gtcattagat   3120
ctggcacttt tggagcaact agagaaaaga aaacttttta taggacagaa gcttcggata   3180
tggggagctt cactatgtgg gtgggctggg cctgtgtcat ttcatgaggc atcgggtacc   3240
gtcaaattaa tgatccacat aaatggcacc tatcgtgcaa gatgggatga actttgggg   3300 ttatgcaagc atgctggagt cccactggca ttcaagtgca taaaagcttc aggtggcaga   3360
gttcctagga cactggttgg agttacaagg atttatcctg ttatgtacag ggagaggttt   3420
tctgacggtc gttttgtggt gaggtctgaa aggatggaaa gaaaagcact acagctgtat   3480
caccagagag tgtctaagat tgcagaagac attcagtcag aacatggaga acactgcgac   3540
aacactgatg ataacgatga aggggcaaaa atatgcaaaa tgctagagag ggcagctgag   3600
cctgaaattc ttatgtccag catgagttca gagcagctgc tgtctttctc atattatcaa   3660
gaaaagcaaa agattgtcag gcaaaatgaa gtagctaaga aggttgaaaa tgctcttaaa   3720
gttgctgggc ttagttcaag agatgttaca ccattttga aagtgagggt gacgggcctt   3780
atcagcaaac actccgccac aaaatctggc tgcaggaag ggttaataac aatttggaac   3840
cctaccgaga agcaaaaatc cgacctggtg gagggacaaa tttattctgt cacaggactg   3900
ttggcttcaa gctactttac agaagtatcc tacttgagtg gtagaggatc atctacagca   3960
tggacgcctt tagcaaccgc acagactaca aattttgaac cattttttcac ccctcgtaaa   4020 gcagttgaat tgtcacattt tggtgaagtg ccacttacaa gcgaatttga cattgcaggt   4080 gttatttttgt atgttgggaa tgtttatttta ttgaacaacc agaataggca gtggctcttt   4140
ttgacagatg gatctaaatt tatctctgga gaaaagtatg aagagcaaga tgactgtctt   4200
ctggcagtta gcttttcttc caaaaccact ggcgaggatt ctgcattctt caattatgcc   4260 cttttctggac atatagttgg ttttagtaat ctggtcaagc gagataaaga ccagatgagg   4320
cacgtgtggg tagctgaggc gacagagagc tccacctata gtctctccca cgagatacct   4380
aaaaaatcac atctcaaaga ggctgccact tctgctgaaa aatgggcttc aaattctcat   4440
cctatgattc agcatctgaa ggaaagagtt ctgcaaatag ttggtgacag tggtggctga   4500
```

<210> SEQ ID NO 111
<211> LENGTH: 1329
<212> TYPE: DNA
<213> ORGANISM: DNA

<400> SEQUENCE: 111

```
atgtcggaga agaagcgccg cggcggggca ggcgcggggg ccgcgtcggg ctccgcctcc     60
aagaagccgc gggtctccac ggcggcgtcg tacgccgagt cgctccgctc gaagctccgc   120
cccgacgcct ccatcctcgc caccctccgc tccctggcct ccgcctgctc caaacccaag   180
cccgcggggt cgtcgtcgtc gtcgtcgtcc gcctcgaagg cgctcgcagc cgaggacgac   240
ccggccgcca gctacatcgt ggtggccgac caggactccg cctccgtcac ctcccgcatc   300
aaccgcctcg tgctcgccgc ggcgcgcagc atcctgtccg gccggggctt ctccttcgcg   360
gtgccctccc gcgccgcctc caaccaggtc tacctcccgg acctcgaccg catcgtgctc   420
gtccgccgcg agtccgccag gcccttcgcc aacgtcgcca ccgcgcggaa ggccaccatc   480
accgcgcgcg tcctctcctt ggtccacgcc gtcctccgca gggggatcca cgtcaccaag   540
```

```
cgtgacctct tctacaccga cgtcaagctc ttcggcgacc aggcgcagtc cgacgccgtc    600
ctcgacgacg tctcctgtat gctcggctgc acccgctcct ccctccacgt cgtcgcgtcc    660
gagaagggcg tcgtcgtcgg gcgcctcacc ttcgccgacg acggcgaccg gatcgactgc    720
acgcgcatgg gcgtcggcgg gaaggccatc ccgcccaaca tcgacagggt ctcaggcatc    780
gagagcgacg ctctcttcat cttgctggtg gagaaggacg ccgcgttcat gcgtctcgcc    840
gaggaccggt tctacaaccg cttcccgtgc atcatcttga cggcgaaggg gcagccggat    900
gtcgccacac ggctgttctt gcggcggctt aaggtggagc tgaagctgcc agtgctggca    960
ttggtggact ccgacccata tgggctgaag atcttgtcag tgtacatgtg tggttccaag    1020
aacatgtcat atgacagtgc caacctgaca acaccggata tcaagtggct cggagtgcgg    1080
ccaagcgatc tggacaagta tcgggtgccg gagcagtgcc ggcttccgat gactgatcac    1140
gatatcaagg tggggaagga gctgcttgag gaggactttg tgaagcagaa tgaaggatgg    1200
gtgaaggagc tggagacgat gttgcggacg aggcagaagg ctgagataca ggctctcagt    1260
tcatttggtt tccagtatct cactgaggtc tatctacctc tcaagctgca gcaacaggac    1320
tggatttga                                                            1329

<210> SEQ ID NO 112
<211> LENGTH: 1456
<212> TYPE: DNA
<213> ORGANISM: DNA

<400> SEQUENCE: 112
agcaaccatg gatgattcaa cggatgacga ttcgtatcat ccaagaaaac actatgctta     60
tgatcgtcag gtttcttcaa gcagatggcg taccagccgc gagtatatca gaggtcccgg    120
ccccgaaact catactactg agagtgctca agatggacag gatccacctg ctggagtata    180
ttcctatggt tatttttctg gcagtggtaa tgatcctcaa gttcaaggac actttgttcc    240
ggagattcaa aagtacaacc cttacgtgat tttcaaaggt gaacaactcc cggttcctat    300
atgggaactg ccagaggaga aggtccaaga ttttcatgat aggtacttta ttgcaaaaga    360
caagagtcga gttgaagcca ggaagactct gaataggttg ttagagggga acatcaatac    420
aattgaaagg ggacatggat ataaattcaa tattccaaaa tatacagata acatggagtt    480
taatgaggaa gtcaaggttt ctctagcaaa agcaggcaag accataagcc gttccttttg    540
caatgcgaat cagcgggaag ttgcatctag gactggctat accattgatc taatagaacg    600
gacacttggg gctggattga acatctcgaa gagaactgtc ttatacacaa acaaggatct    660
gtttggggat caaagtaaat cagatcaagc gatcaatgac atctgcgctt tgacaaatat    720
cagaaggggc tctttgggta ataggcagc tgaaaaagga attgtagttg gaaacatttt    780
cctggaattg acaaatggca atcgattag ttgttctatt ggagtgcaga taccacacag    840
gcttgaccag atcaaagatg tttgtgttga ataggttca cgcaacatag agtatattct    900
tgttgtggaa aagcatacaa tgttgaatta tctactagag atggactatc acaccaataa    960
caactgtata attctgacag gatgtggcat gccaaccctc caaacaaggg atttcctcag    1020
attcttgaaa caacgcactg gactacctgt ctttggactt tgtgatccag atcctgaagg    1080
tataagtatt cttgctacgt atgctagagg gtcttgcaat tcagcatatg acaatttcaa    1140
tatttccgtg ccatctattt gttgggttgg attgtcatcc tcagacatga taagttgaa    1200
tttgtctgag accaactact cacgtttgtc tcgcgaggac aaaactatgt tgaagaacct    1260
ttggcaggac gatttgtccg atgtatggaa acgcagaatc gaagaaatga taagtttga    1320
```

```
caagaaggcc tcttttgaag ctattcatag tttggggttt gattattttg caaccaatt    1380 gcttccggat atgattaaca aagtacgaga aggctatgtt caggtatatt tctcactcct    1440
atagcaactt gtattt                                                    1456
```

<210> SEQ ID NO 113
<211> LENGTH: 1187
<212> TYPE: PRT
<213> ORGANISM: Protein

<400> SEQUENCE: 113

```
Met Glu Asp Asp Asp Asp Gln Arg Leu Leu His Ser Leu Gly Val
1               5                   10                  15

Thr Ser Ala Asp Ile His Asp Ile Glu Arg Arg Ile Ile Ser Gln Ala
                20                  25                  30

Thr Thr Asp Pro Ala Asp Ser Ser Gly Pro Thr Ile Asn Gly Gly His
            35                  40                  45

Gln Pro Asp Asp Ala Leu Ala Lys Leu His His Lys Leu Arg Ser Val
    50                  55                  60

Gln Ile Glu Ile Asp Ala Val Ala Ser Thr Ile Lys Gly Ala Lys Leu
65                  70                  75                  80

Lys Gln Pro Ser Gly Asn Lys Pro His Glu His Lys Gly Lys Asp Gln
                85                  90                  95

Pro Asp His His Gly Ala Gly His Leu Gln Gln Ala Leu Ala Ala Asp
            100                 105                 110

Arg Leu Thr Ser Leu Arg Lys Ala Lys Ala Gln Ile Gln Lys Glu Ile
        115                 120                 125

Leu Gln Ser His Leu Ser Pro Ser Ala Ser Asn Arg Lys Asp Lys Met
    130                 135                 140

Leu Ala Met Leu Val Gln Asp Glu Pro Arg His Lys Lys Pro Pro Val
145                 150                 155                 160

Gly Pro Lys Asn Ile Val Lys Arg Pro Met Lys Thr Val Thr Tyr Asp
                165                 170                 175

Asp Asp Asn Asn Phe Asp Ala Val Leu Asp Gly Ala Ser Ala Gly Phe
            180                 185                 190

Met Glu Thr Glu Arg Glu Glu Leu Ile Arg Lys Gly Leu Leu Thr Pro
        195                 200                 205

Phe His Lys Leu Lys Gly Phe Glu Lys Arg Val Glu Leu Pro Glu Pro
    210                 215                 220

Ser His Arg Gln Asp Asp Ser Ala Gly Gln Thr Glu Glu Ala Met Glu
225                 230                 235                 240

Ala Ser Arg Ile Ala Arg Val Ala Gln Ser Leu Lys Gln Ile Ala Gln
                245                 250                 255

Asn Arg Pro Ala Thr Lys Leu Leu Asp Ser Glu Ser Leu Pro Lys Leu
            260                 265                 270

Asp Ala Pro Ala Ala Pro Phe Gln Arg Leu Gly Lys Pro Leu Lys Arg
        275                 280                 285

Pro Val Ser Pro Ser Ser Asp Glu Gln Glu Lys Lys Arg Pro Arg Asn
    290                 295                 300

Lys Thr Lys Arg Pro Leu Pro Gly Lys Lys Trp Arg Lys Ala Asn Ser
305                 310                 315                 320

Ile Lys Glu Ser Ser Leu Asp Asp Asn Asp Val Gly Glu Ala Ala Val
                325                 330                 335

Ser Val Ser Asp Asp Asp Glu Asp Gln Val Thr Glu Gly Ser Asp Glu
            340                 345                 350
```

-continued

```
Leu Thr Asp Val Thr Leu Glu Gly Gly Leu Arg Ile Pro Gly Thr Leu
            355                 360                 365

Tyr Thr Gln Leu Phe Asp Tyr Gln Lys Val Gly Val Gln Trp Leu Trp
    370                 375                 380

Glu Leu His Cys Gln Arg Ala Gly Gly Ile Ile Gly Asp Glu Met Gly
385                 390                 395                 400

Leu Gly Lys Thr Val Gln Val Leu Ser Phe Leu Gly Ser Leu His Asn
                405                 410                 415

Ser Gly Leu Tyr Lys Pro Ser Ile Val Val Cys Pro Val Thr Leu Leu
            420                 425                 430

Gln Gln Trp Arg Arg Glu Ala Ser Arg Trp Tyr Pro Lys Phe Lys Val
        435                 440                 445

Glu Ile Leu His Asp Ser Ala Asn Ser Ser Lys Lys Ser Lys Arg
    450                 455                 460

Ser Ser Asp Ser Asp Ser Glu Ala Ser Trp Asp Ser Asp Gln Glu Glu
465                 470                 475                 480

Ala Val Thr Cys Ser Lys Pro Ala Lys Lys Trp Asp Leu Ile Ser
                485                 490                 495

Arg Val Val Ser Ser Gly Ser Gly Leu Leu Leu Thr Thr Tyr Glu Gln
            500                 505                 510

Leu Arg Ile Leu Gly Glu Lys Leu Leu Asp Ile Glu Trp Gly Tyr Ala
    515                 520                 525

Val Leu Asp Glu Gly His Arg Ile Arg Asn Pro Asn Ala Glu Ile Thr
530                 535                 540

Leu Val Cys Lys Gln Leu Gln Thr Val His Arg Ile Ile Met Thr Gly
545                 550                 555                 560

Ala Pro Ile Gln Asn Lys Leu Ser Glu Leu Trp Ser Leu Phe Asp Phe
                565                 570                 575

Val Phe Pro Gly Lys Leu Gly Val Leu Pro Val Phe Glu Ala Glu Phe
            580                 585                 590

Ser Val Pro Ile Thr Val Gly Gly Tyr Ala Asn Ala Thr Pro Leu Gln
    595                 600                 605

Val Ser Thr Ala Tyr Arg Cys Ala Val Val Leu Arg Asp Leu Val Met
610                 615                 620

Pro Tyr Leu Leu Arg Arg Met Lys Ala Asp Val Asn Ala Gln Leu Pro
625                 630                 635                 640

Lys Lys Thr Glu His Val Leu Phe Cys Ser Leu Thr Thr Glu Gln Arg
                645                 650                 655

Ala Thr Tyr Arg Ala Phe Leu Ala Ser Ser Glu Val Glu Gln Ile Phe
            660                 665                 670

Asp Gly Asn Arg Asn Ser Leu Tyr Gly Ile Asp Val Leu Arg Lys Ile
    675                 680                 685

Cys Asn His Pro Asp Leu Leu Glu Arg Glu His Ala Ala Gln Asn Pro
690                 695                 700

Asp Tyr Gly Asn Pro Glu Arg Ser Gly Lys Met Lys Val Val Glu Gln
705                 710                 715                 720

Val Leu Lys Val Trp Lys Glu Gln Gly His Arg Val Leu Leu Phe Thr
                725                 730                 735

Gln Thr Gln Gln Met Leu Asp Ile Met Gly Asn Phe Leu Thr Ala Cys
            740                 745                 750

Glu Tyr Gln Tyr Arg Arg Met Asp Gly Leu Thr Pro Ala Lys Gln Arg
    755                 760                 765

Met Ala Leu Ile Asp Glu Phe Asn Asn Thr Asp Glu Ile Phe Ile Phe
770                 775                 780
```

-continued

```
Ile Leu Thr Thr Lys Val Gly Leu Gly Thr Asn Leu Thr Gly Ala
785                 790                 795                 800

Asn Arg Ile Ile Ile Tyr Asp Pro Asp Trp Asn Pro Ser Thr Asp Met
            805                 810                 815

Gln Ala Arg Glu Arg Ala Trp Arg Ile Gly Gln Thr Arg Asp Val Thr
            820                 825                 830

Val Tyr Arg Leu Ile Thr Arg Gly Thr Ile Glu Glu Lys Val Tyr His
        835                 840                 845

Arg Gln Val Tyr Lys His Phe Leu Thr Asn Lys Val Leu Lys Asp Pro
    850                 855                 860

Gln Gln Arg Arg Phe Phe Lys Ala Arg Asp Met Lys Asp Leu Phe Thr
865                 870                 875                 880

Leu Gln Asp Asp Asp Asn Asn Gly Ser Thr Glu Thr Ser Asn Ile Phe
                885                 890                 895

Ser Gln Leu Ser Glu Asp Val Asn Ile Gly Val Pro Ser Asp Lys Gln
            900                 905                 910

Gln Asp Gln Leu Tyr Ala Ala Ser Ala Thr Pro Thr Ser Gly Thr
        915                 920                 925

Glu Pro Ser Ser Ser Arg His Gly Gln Gly Lys Glu Asp His Cys Pro
930                 935                 940

Asp Gln Ala Asp Glu Glu Cys Asn Ile Leu Lys Ser Leu Phe Asp Ala
945                 950                 955                 960

Gln Gly Ile His Ser Ala Ile Asn His Asp Ala Ile Met Asn Ala Asn
            965                 970                 975

Asp Asp Gln Lys Leu Arg Leu Glu Ala Glu Ala Thr Gln Val Ala Gln
            980                 985                 990

Arg Ala Ala Glu Ala Leu Arg Gln Ser Arg Met Leu Arg Ser His Glu
            995                 1000                1005

Ser Phe Ser Val Pro Thr Trp Thr Gly Arg Ala Gly Ala Ala Gly
    1010                1015                1020

Ala Pro Ser Ser Val Arg Arg Lys Phe Gly Ser Thr Leu Asn Thr
    1025                1030                1035

Gln Leu Val Asn Ser Ser Gln Pro Ser Glu Thr Ser Asn Gly Arg
    1040                1045                1050

Gly Gln Ser Leu Gln Val Gly Ala Leu Asn Gly Lys Ala Leu Ser
    1055                1060                1065

Ser Ala Glu Leu Leu Ala Arg Ile Arg Gly Thr Arg Glu Gly Ala
    1070                1075                1080

Ala Ser Asp Ala Leu Glu His Gln Leu Asn Leu Gly Ser Ala Ser
    1085                1090                1095

Asn His Thr Ser Ser Ser Ser Gly Asn Gly Arg Ala Ser Ser Ser
    1100                1105                1110

Ser Thr Arg Ser Met Ile Val Gln Pro Glu Val Leu Ile Arg Gln
    1115                1120                1125

Leu Cys Thr Phe Ile Gln Gln His Gly Gly Ser Ala Ser Ser Thr
    1130                1135                1140

Ser Ile Thr Glu His Phe Lys Asn Arg Ile Leu Ser Lys Asp Met
    1145                1150                1155

Leu Leu Phe Lys Asn Leu Leu Lys Glu Ile Ala Thr Leu Gln Arg
    1160                1165                1170

Gly Ala Asn Gly Ala Thr Trp Val Leu Lys Pro Asp Tyr Gln
    1175                1180                1185
```

<210> SEQ ID NO 114
<211> LENGTH: 1148
<212> TYPE: PRT
<213> ORGANISM: Protein

<400> SEQUENCE: 114

```
Met Arg Thr Ser Thr Thr Ser Asp Ser Pro Ser Pro Ser Pro Gln Asn
1               5                   10                  15

Lys Ala Ser Phe Asn Thr Ser Arg Gly Ala Ala Phe Arg Asp Glu Glu
            20                  25                  30

Pro Gly Ala Lys Asp Asn Glu Val Glu Lys Arg Lys Pro Leu Ile Leu
        35                  40                  45

His Leu Lys Lys Arg Ser Thr Lys Glu Leu Ser Thr Asp Thr Thr Ser
    50                  55                  60

Ser Lys Ser Gly Leu Leu Gly Lys Ser Glu Glu Lys Gln Glu Lys
65                  70                  75                  80

His Gly Ser Ala Leu Lys Val Lys Lys His Leu His Pro Met Glu Leu
                85                  90                  95

Ser Pro Lys Lys Tyr Lys Asn Lys Lys Gln His Asn His Arg Asp Ser
            100                 105                 110

Lys Arg Ser Glu Ala Lys Lys Val Gln Tyr Leu Ala Ser Asp Val Asp
            115                 120                 125

Ser Asp Ser Ser Met Glu Pro Ser Thr Ser Leu Glu His Ser Glu Ser
130                 135                 140

Pro Pro Pro Lys Arg Lys Ser Leu Asp Gly Arg Thr Pro Ala Ser Ser
145                 150                 155                 160

Thr Lys Lys Gly Lys Lys Val Lys Phe Ile Asp Lys Lys His Pro
                165                 170                 175

Glu Asn Ala Val His Ile Thr Glu Lys Glu His Gly Gly Ala Gly Asp
            180                 185                 190

Lys Ile Thr Thr Gln Gly Asp Leu Gln Val Asp Arg Ile Leu Gly Cys
        195                 200                 205

Arg Leu Gln Thr Ser Gln Ile Ile Ser Pro Ala His Ala Ser Ser Glu
210                 215                 220

Gln Ile Asp Met Ala Pro Pro Ser Ala Ser Gly Ala Thr Glu Pro Ser
225                 230                 235                 240

Gln Ala Leu Ser Lys Gly Leu His Glu Glu Ile Gln Ser Ser Asn Ser
            245                 250                 255

Asp Thr Asn Val Thr Glu Asp Ala Cys Ala Asp Glu Leu Ala Asn Asp
            260                 265                 270

Gly Gly Glu Asn Asn Leu Asp Cys Ser Asp Ala Gln Lys Glu Ser Asn
        275                 280                 285

Val Arg Ser His Gly His Lys Glu Ser Leu Asn Ala Lys Glu Ile Met
    290                 295                 300

Asn Thr Ala Ser Ala Cys Ser Ala Asp Gln Ile Val Thr Val Lys Asp
305                 310                 315                 320

Ala Gly Ala Val Gln Thr Tyr Val Thr Ala Ser Val Asn Gly Glu Tyr
                325                 330                 335

Glu Thr Val Thr Asp Ile Pro Glu Glu Lys Asn Asp Thr Lys His Pro
            340                 345                 350

Val Ser Lys Ala Asp Thr Glu Val His Thr Lys Gln Glu His Thr Pro
        355                 360                 365

Asp Ser Lys Leu His Gly Lys Leu Glu Asn Tyr Lys Ala Lys Tyr Gly
    370                 375                 380

Thr Gly Leu Ile Asn Ile Cys Lys Glu Gln Trp Cys Gln Pro Gln Arg
```

```
         385                 390                 395                 400
Val Ile Ala Leu Arg Thr Ser Leu Asp Glu Ile Glu Glu Ala Leu Ile
                    405                 410                 415
Lys Trp Cys Ala Leu Pro Tyr Asp Glu Cys Thr Trp Glu Arg Leu Asp
                    420                 425                 430
Glu Pro Thr Met Val Lys Tyr Ala His Leu Val Thr Gln Phe Lys Lys
                    435                 440                 445
Phe Glu Ser Gln Ala Leu Asp Lys Asp Lys Gly Gly Ser His Ala Lys
450                 455                 460
Pro Arg Glu His Gln Glu Phe Asn Met Leu Val Glu Gln Pro Lys Glu
465                 470                 475                 480
Leu Gln Gly Gly Met Leu Phe Pro His Gln Leu Glu Ala Leu Asn Trp
                    485                 490                 495
Leu Arg Lys Cys Trp Tyr Lys Ser Lys Asn Val Ile Leu Ala Asp Glu
                    500                 505                 510
Met Gly Leu Gly Lys Thr Val Ser Ala Cys Ala Phe Leu Ser Ser Leu
                    515                 520                 525
Cys Cys Glu Tyr Lys Ile Asn Leu Pro Cys Leu Val Leu Val Pro Leu
            530                 535                 540
Ser Thr Met Pro Asn Trp Met Ala Glu Phe Ala Ser Trp Ala Pro His
545                 550                 555                 560
Leu Asn Val Val Glu Tyr His Gly Ser Ala Arg Ala Arg Ser Ile Ile
                    565                 570                 575
Arg Gln Tyr Glu Trp His Glu Gly Asp Ala Ser Gln Met Gly Lys Ile
                    580                 585                 590
Lys Lys Ser His Lys Phe Asn Val Leu Leu Thr Thr Tyr Glu Met Val
            595                 600                 605
Leu Val Asp Ala Ala Tyr Leu Arg Ser Val Ser Trp Glu Val Leu Ile
610                 615                 620
Val Asp Glu Gly His Arg Leu Lys Asn Ser Ser Ser Lys Leu Phe Ser
625                 630                 635                 640
Leu Leu Asn Thr Leu Ser Phe Gln His Arg Val Leu Leu Thr Gly Thr
                    645                 650                 655
Pro Leu Gln Asn Asn Ile Gly Glu Met Tyr Asn Leu Leu Asn Phe Leu
                    660                 665                 670
Gln Pro Ala Ser Phe Pro Ser Leu Ala Ser Phe Glu Glu Lys Phe Asn
            675                 680                 685
Asp Leu Thr Thr Thr Glu Lys Val Glu Glu Leu Lys Asn Leu Val Ala
            690                 695                 700
Pro His Met Leu Arg Arg Leu Lys Lys Asp Ala Met Gln Asn Ile Pro
705                 710                 715                 720
Pro Lys Thr Glu Arg Met Val Pro Val Glu Leu Thr Ser Ile Gln Ala
                    725                 730                 735
Glu Tyr Tyr Arg Ala Met Leu Thr Lys Asn Tyr Gln Val Leu Arg Asn
                    740                 745                 750
Ile Gly Lys Gly Gly Ala His Gln Ser Leu Leu Asn Ile Val Met Gln
            755                 760                 765
Leu Arg Lys Val Cys Asn His Pro Tyr Leu Ile Pro Gly Thr Glu Pro
            770                 775                 780
Glu Ser Gly Ser Pro Glu Phe Leu His Glu Met Arg Ile Lys Ala Ser
785                 790                 795                 800
Ala Lys Leu Thr Leu Leu His Ser Met Leu Lys Ile Leu His Lys Asp
                    805                 810                 815
```

Gly His Arg Val Leu Ile Phe Ser Gln Met Thr Lys Leu Leu Asp Ile
             820                 825                 830

Leu Glu Asp Tyr Leu Thr Trp Glu Phe Gly Pro Lys Thr Phe Glu Arg
             835                 840                 845

Val Asp Gly Ser Val Ser Val Ala Glu Arg Gln Ala Ala Ile Ala Arg
         850                 855                 860

Phe Asn Gln Asp Lys Ser Arg Phe Val Phe Leu Leu Ser Thr Arg Ser
865                 870                 875                 880

Cys Gly Leu Gly Ile Asn Leu Ala Thr Ala Asp Thr Val Ile Ile Tyr
                885                 890                 895

Asp Ser Asp Phe Asn Pro His Ala Asp Ile Gln Ala Met Asn Arg Ala
            900                 905                 910

His Arg Ile Gly Gln Ser Asn Arg Leu Leu Val Tyr Arg Leu Val Val
        915                 920                 925

Arg Ala Ser Val Glu Glu Arg Ile Leu His Leu Ala Lys Lys Lys Leu
930                 935                 940

Met Leu Asp Gln Leu Phe Val Asn Lys Ser Glu Ser Gln Lys Glu Val
945                 950                 955                 960

Glu Asp Ile Ile Arg Trp Gly Thr Glu Glu Leu Phe Arg Asn Ser Asp
                965                 970                 975

Val Ala Val Lys Asp Asn Asn Glu Ala Ser Gly Ala Lys Asn Asp Val
            980                 985                 990

Ala Glu Val Glu Phe Lys His Lys Arg Lys Thr Gly Gly Leu Gly Asp
        995                 1000                1005

Val Tyr Glu Asp Arg Cys Ala Asp Gly Ser Ala Lys Phe Asn Trp
    1010                1015                1020

Asp Glu Asn Ala Ile Thr Lys Leu Leu Asp Arg Ser Asn Val Pro
    1025                1030                1035

Ser Thr Val Ala Glu Ser Asp Gly Asp Leu Asp Asn Asp Met
    1040                1045                1050

Leu Gly Thr Val Lys Ser Ile Asp Trp Asn Asp Glu Leu Asn Asp
    1055                1060                1065

Asp Pro Gly Ala Thr Glu Asp Ile Pro Asn Ile Asp Asn Asp Gly
    1070                1075                1080

Cys Glu Gln Ala Ser Glu Ala Lys Gln Asp Ala Ala Asn Arg Val
    1085                1090                1095

Glu Glu Asn Glu Trp Asp Lys Leu Leu Arg Val Arg Trp Glu Gln
    1100                1105                1110

Tyr Gln Thr Glu Glu Ala Ser Leu Gly Arg Gly Lys Arg Leu
    1115                1120                1125

Arg Lys Ala Val Ser Tyr Arg Glu Thr Phe Ala Thr Ile Pro Asn
    1130                1135                1140

Glu Ala Leu Ser Glu
    1145

<210> SEQ ID NO 115
<211> LENGTH: 987
<212> TYPE: PRT
<213> ORGANISM: Protein

<400> SEQUENCE: 115

Met Ala Asp Thr Gly Ser Leu Glu Lys Met Gly Arg Glu Leu Lys Cys
1               5                   10                  15

Pro Ile Cys Leu Ser Leu Leu Ser Ser Ala Val Ser Ile Ser Cys Asn
            20                  25                  30

His Val Phe Cys Asn Asp Cys Leu Thr Glu Ser Met Lys Ser Thr Ser
             35                  40                  45

Ser Cys Pro Val Cys Lys Val Pro Phe Arg Arg Glu Met Arg Pro
 50                  55                  60

Ala Pro His Met Asp Asn Leu Val Ser Ile Phe Lys Ser Met Glu Ala
 65                  70                  75                  80

Ala Ala Gly Thr Asn Val Val Ser Thr Gln Glu Ala Pro Val Val Lys
                 85                  90                  95

Leu Ala Asp Gly Ser Asp Cys Val Asn Ser Gly Lys Asn Ser Lys Arg
                100                 105                 110

Ser Gln Lys Ser Leu Thr Arg Lys Arg Lys Val Thr Ser Glu Met Glu
            115                 120                 125

Lys Asn Thr Ala Lys Asp Ala Thr Ala Ser Ala Ser Gln Pro Thr Thr
130                 135                 140

Lys Pro Ser Phe Ser Thr Asn Lys Arg Ile Gln Val Lys Pro Phe Pro
145                 150                 155                 160

Glu Ser Glu Thr Pro Ile Arg Ala Glu Lys Ile Met Lys Pro Glu Glu
                165                 170                 175

Pro Lys Asn Asn Leu Asn Asn Asp Val Glu Gly Lys Asn Lys Ala Val
            180                 185                 190

Ala Ser Gly Gln Pro Gly Ser Pro Ser Leu Ser Pro Phe Phe Trp Leu
            195                 200                 205

Arg Glu Gln Glu Gln Glu Gly Cys Thr Ala Glu Thr Leu Ser Glu
210                 215                 220

Thr Gln Ser Leu Asp Thr Pro Leu Arg His Asn Ala Pro Ser Phe Ser
225                 230                 235                 240

Asp Ile Lys Asp Ser Asp Glu Ile Pro Leu Asn Thr Thr Pro Asn
                245                 250                 255

Ser Lys Ala Ala Ala Thr Glu Leu Phe Asp Ser Glu Ile Phe Glu Trp
            260                 265                 270

Thr Gln Arg Pro Cys Ser Pro Glu Leu Tyr Ser Thr Pro Leu Lys Lys
            275                 280                 285

Gln Ser Lys Ala Lys Ser Lys Leu Asp Gln Ile Glu Glu Lys Gly Asp
290                 295                 300

Glu Glu Asp Val His Ile Gly Gly Ser Phe Asp Lys Leu Gly Ser Ala
305                 310                 315                 320

Ser Asn Ala Ala Gln Leu Val Asn Thr Lys Ala Thr Lys Gln Lys Arg
                325                 330                 335

Lys Lys Thr Ser Pro Ser Asn Lys Asn Ser Ala Lys Leu Ser Asn Arg
            340                 345                 350

Ala Glu Pro Cys Ile Lys Lys Ser Asp Ala Asn Gln Gln Gly Ser Asn
            355                 360                 365

Arg Arg Lys Ser Ala Ala Leu Lys Ser Cys Gln Lys Ser Ser Ser Ala
370                 375                 380

Val Gly Arg Asn Thr Ser Gly Arg Arg Asn Lys Ala Ser Ser Asn Ser
385                 390                 395                 400

Lys Pro Ile His Gly Ser Ser Asp Asn Ser Pro Glu Ser Tyr Leu Pro
                405                 410                 415

Lys Glu Gly Leu Asp Val Glu Ala Pro Asp Lys Pro Leu Ser Glu Arg
            420                 425                 430

Ile Gln Asn Leu Glu Lys Thr Ser Arg Arg Lys Gly Ser Ala Arg Lys
            435                 440                 445

Leu Glu Met Ala Gly Lys Thr Ile Ser Asp Thr Thr Glu Lys Asn Ser
450                 455                 460

-continued

```
Glu Pro Arg Ser Lys Arg Val Arg Arg Met Ser Asp His Ala Ile Ala
465                 470                 475                 480
Lys Pro Val Glu Val Pro Ser Gly Ser Gly Asn Glu Thr Glu Ile Pro
            485                 490                 495
Gln Leu His Thr Leu Thr Lys Gly Ser Ile Gln Arg Lys Ser Ser Asn
            500                 505                 510
Ala Arg Arg His Ser Lys Val Cys Gly Glu Gln Glu Gly Lys Asn Lys
            515                 520                 525
Leu Glu Asn Thr Thr Met Thr Pro Ile Ile Leu His Gly Lys Cys Gln
            530                 535                 540
Asn Lys Glu Ala Val Cys Thr Ala Pro Ser Val Arg Thr Ala Ser Val
545                 550                 555                 560
Lys Tyr Lys Gln Ala Lys Phe Ser Glu Gln Pro Asp Cys Phe Gly Thr
            565                 570                 575
Glu Asn Phe Gly Asn Leu Gln Ala Cys Pro Ala Arg Asn Val Leu Leu
            580                 585                 590
Lys Lys Cys Glu Val Ser Thr Leu Lys Val Ser Cys Ala Phe Cys Gln
            595                 600                 605
Thr Asp Val Ile Thr Glu Glu Ser Gly Glu Met Val His Tyr Gln Asn
            610                 615                 620
Gly Lys Gln Val Pro Ala Glu Phe Asn Gly Gly Ala Asn Val Val His
625                 630                 635                 640
Ser His Lys Asn Cys Leu Glu Trp Ala Pro Asp Val Tyr Phe Glu Asp
            645                 650                 655
Asp Ser Ala Phe Asn Leu Thr Thr Glu Leu Ala Arg Ser Arg Arg Ile
            660                 665                 670
Lys Cys Ala Cys Cys Gly Ile Lys Gly Ala Ala Leu Gly Cys Phe Glu
            675                 680                 685
Met Ser Cys Arg Arg Ser Phe His Phe Thr Cys Ala Lys Leu Ile Pro
            690                 695                 700
Glu Cys Arg Trp Asp Asn Glu Asn Phe Val Met Leu Cys Pro Leu His
705                 710                 715                 720
Arg Ser Thr Lys Leu Pro Asn Glu Asn Ser Glu Gln Lys Gln Pro
            725                 730                 735
Lys Arg Lys Thr Thr Leu Lys Gly Ser Ser Gln Ile Gly Ser Asn Gln
            740                 745                 750
Asp Cys Gly Asn Asn Trp Lys Trp Pro Ser Gly Ser Pro Gln Lys Trp
            755                 760                 765
Val Leu Cys Cys Ser Ser Leu Ser Ser Ser Glu Lys Gly Leu Val Ser
            770                 775                 780
Glu Phe Ala Lys Leu Ala Gly Val Pro Ile Ser Ala Thr Trp Ser Pro
785                 790                 795                 800
Asn Val Thr His Val Ile Ala Ser Thr Asp Leu Ser Gly Ala Cys Lys
            805                 810                 815
Arg Thr Leu Lys Phe Leu Met Ala Ile Leu Asn Gly Arg Trp Ile Val
            820                 825                 830
Ser Ile Asp Trp Val Lys Thr Cys Met Glu Cys Met Glu Pro Ile Asp
            835                 840                 845
Glu His Lys Phe Glu Val Ala Thr Asp Val His Gly Ile Thr Asp Gly
            850                 855                 860
Pro Arg Leu Gly Arg Cys Arg Val Ile Asp Arg Gln Pro Lys Leu Phe
865                 870                 875                 880
Asp Ser Met Arg Phe Tyr Leu His Gly Asp Tyr Thr Lys Ser Tyr Arg
```

```
                       885                 890                 895
Gly Tyr Leu Gln Asp Leu Val Val Ala Ala Gly Gly Ile Val Leu Gln
                900                 905                 910

Arg Lys Pro Val Ser Arg Asp Gln Gln Lys Leu Leu Asp Asp Ser Ser
            915                 920                 925

Asp Leu Leu Ile Val Tyr Ser Phe Glu Asn Gln Asp Arg Ala Lys Ser
        930                 935                 940

Lys Ala Glu Thr Lys Ala Ala Asp Arg Arg Gln Ala Asp Ala Gln Ala
945                 950                 955                 960

Leu Ala Cys Ala Ser Gly Gly Arg Val Val Ser Ser Ala Trp Val Ile
                965                 970                 975

Asp Ser Ile Ala Ala Cys Asn Leu Gln Pro Leu
            980                 985

<210> SEQ ID NO 116
<211> LENGTH: 1499
<212> TYPE: PRT
<213> ORGANISM: Protein

<400> SEQUENCE: 116

Met Ala Asp Leu Phe Asn Gln Ala Leu Asp Lys Leu Val Ala Ala Asp
1               5                   10                  15

Gly Met Ala Glu Ala Ile Glu Asp Ser Gly Lys Gly Ala Val Phe Cys
            20                  25                  30

Thr Gly Leu Gly Gly Ser Val Ala Val Ser Glu Arg Ala Val Glu Arg
        35                  40                  45

Ala Lys Ala Leu Val Gly Glu Val Ala Glu Glu Ile Ser Asn Glu Arg
    50                  55                  60

Arg Gln Pro Phe Gly Asp Gly Ser Asn Leu Glu Cys Gly Leu Gly Glu
65                  70                  75                  80

Ser Asn Val Ser Phe Lys Gly Gly Val His Lys Asp Ser Leu Ser Pro
                85                  90                  95

Met Phe Gln Thr Gly Ser Gly Lys Met Val Ser Leu Ser Lys Gly Ser
            100                 105                 110

Ile Gln Lys Ala Arg Ala Val Leu Glu Gly Asn Ala Glu Asn Ser Ser
        115                 120                 125

Val Ile Ala Val Gln Ser Met Phe His Thr Gly Leu Val Arg Pro Asp
    130                 135                 140

Pro Val Ser Arg Ser Ser Thr Asp Asn Ala Met Thr Val Leu Glu Gly
145                 150                 155                 160

Gln Thr Asn Pro Lys Gln Gly Asp Val Ala Asp Val Tyr Asp Lys Glu
                165                 170                 175

Asn Phe Pro Leu Phe Gln Thr Gly Ser Gly Lys Ala Val Ser Val Ser
            180                 185                 190

Val Ala Ser Ile Gln Lys Ala Lys Ala Val Leu Glu Gln Asn Asn Thr
        195                 200                 205

Glu Asn Thr Glu Asp Phe Gly Arg Pro Asp Gln Ser Leu Ile Phe Gln
    210                 215                 220

Thr Gly Ser Arg Arg Pro Val Leu Ile Ser Glu Arg Ser Ser Ser Val
225                 230                 235                 240

Val Lys Asp Gly Gly Ala Glu Asn Ile Val Phe Gln Thr Gly Leu Gly
                245                 250                 255

Arg Pro Val Val Ser Gln Thr Ser Ile Gln Lys Ala Arg Thr Val
            260                 265                 270

Leu Asp Gln Glu Cys Ala Lys Arg Ser Gly His Gly Asp Thr Asn Val
```

```
                275                 280                 285
Ser Thr Thr Thr Phe Gln Thr Glu Thr Pro Thr Pro Val Leu Met Ser
290                 295                 300
Gly Gly Leu Thr Met Asn Asp Arg Ser Val Thr Pro Glu Gly Gly Val
305                 310                 315                 320
Ser Met Gln Gly Asn Phe Leu Glu Ala Asp Gly His Leu Pro Leu Phe
                325                 330                 335
Gln Thr Gly Leu Gly Arg Ser Ile Ser Val Ser Lys Gly Ser Ile Lys
            340                 345                 350
Arg Ala Ser Ala Leu Leu Glu Pro Arg Asn Ile Thr Lys Glu Leu Glu
            355                 360                 365
Asp Glu Ala His Ser Asp Asp Gly Cys Ala Thr Pro Met Phe Lys Thr
        370                 375                 380
Gly Ser Gly Arg Ser Ile Thr Ala Ser Glu Asn Ser Arg Lys Lys Ala
385                 390                 395                 400
His Val Val Leu Glu Gly Glu Pro Val Lys Asn Val Asn Asn Asp
                405                 410                 415
Thr Gly Glu Ala Ile Ala Pro Met Leu His Ala Gly Met Gln Lys Phe
            420                 425                 430
Ala Pro Gln Asn Arg Asn Ser Ser His Lys Ala Ile Thr Leu Met Glu
            435                 440                 445
Gln Gly Ser Ser Met Glu Glu Asp Arg Gly Asn Glu Pro Pro Met Phe
        450                 455                 460
Arg Thr Gly Ser Gly Lys Ser Val Leu Ile Ser His Ser Ser Val Gln
465                 470                 475                 480
Lys Ala Arg Ala Val Leu Glu Glu Gly Asn Met Lys Lys Glu Asn
                485                 490                 495
His Lys Gln Leu Ser Asn Val Asp Lys Tyr Ile Pro Ile Phe Thr Ser
                500                 505                 510
Pro Leu Lys Thr Ser Tyr Ala Arg Thr Val His Ile Ser Ser Val Gly
            515                 520                 525
Val Ser Arg Ala Ala Thr Leu Leu Gly Leu Glu Glu Asn Thr Leu Ser
530                 535                 540
Thr Gln Leu Leu Gly His Val Gly Asp Lys Leu Gly Thr Lys Ile Thr
545                 550                 555                 560
Val Glu Arg Glu Asn Ser Glu His Gln Phe Gly Val Ala Ser Val Ser
                565                 570                 575
Gly Ile Ser Gly Gly Cys Pro Ile Ser Ser Gly Pro Ala Glu Asn Gln
            580                 585                 590
Val Leu Met Asp Pro His Gln His Phe Ala Phe Ser Lys Thr Thr Phe
            595                 600                 605
Ser Asp Ser Ser Glu Gln Ala Ile Arg Phe Ser Thr Ala Gly Gly Arg
        610                 615                 620
Thr Met Ala Ile Pro Ser Asp Ala Leu Gln Arg Ala Lys Asn Leu Leu
625                 630                 635                 640
Gly Glu Ser Asp Leu Glu Val Ser Pro Asn Asn Leu Leu Gly His Ser
                645                 650                 655
Ser Ala Ser Ala Cys Lys Glu Asn Ile Gln Asn Ser Thr Gly Leu Arg
                660                 665                 670
Lys Glu Gly Glu Pro Asp Leu Leu Lys Ser Arg Gly Asn Ser Lys Thr
            675                 680                 685
Glu Pro Ala Gln Phe Ser Ile Pro Ala Lys Pro Asp Arg Lys His Thr
        690                 695                 700
```

-continued

```
Asp Ser Leu Glu Tyr Ala Val Pro Asp Ala Thr Leu Ala Asn Gly Asn
705                 710                 715                 720

Ser Val Arg Leu His Ala Ala Arg Asp Phe His Pro Ile Asn Glu Ile
            725                 730                 735

Pro Lys Ile Ser Lys Pro Ser Ser Arg Cys Ser Phe Gly Thr Glu Asn
        740                 745                 750

Ala Ser Asp Thr Lys Asp Lys Ala Arg Arg Leu Gln Met Pro Ser Gly
    755                 760                 765

Pro Leu Ile Asp Ile Thr Asn Tyr Ile Asp Thr His Ser Val Asn Thr
770                 775                 780

Asp Tyr Leu Ala Gly Glu Lys Arg Arg Phe Gly Gly Arg Asn Ser Ile
785                 790                 795                 800

Ser Pro Phe Lys Arg Pro Arg Ser Ser Arg Phe Ile Ala Pro Ile Asn
            805                 810                 815

Ile Asn Asn Pro Ser Pro Ser Gly Val Ser Lys Leu Pro Ile Gln Ile
        820                 825                 830

Asn Pro Cys Arg Thr Lys Leu Ser Ser Cys Tyr Pro Phe Gln His Gln
    835                 840                 845

Arg Lys Ser Cys Glu Gly Tyr Phe Gly Gly Pro Pro Cys Phe Lys Tyr
850                 855                 860

Leu Thr Glu Asp Val Thr Asp Glu Val Lys Leu Met Asp Ala Lys Lys
865                 870                 875                 880

Ala Glu Lys Tyr Lys Phe Lys Thr Asp Thr Gly Ala Glu Glu Phe Gln
            885                 890                 895

Lys Met Leu Leu Ala Cys Gly Ala Ser Leu Thr Tyr Thr Thr Lys Glu
        900                 905                 910

Trp Val Ser Asn His Tyr Lys Trp Ile Val Trp Lys Leu Ala Ser Leu
    915                 920                 925

Glu Arg Cys Tyr Pro Thr Arg Ala Ala Gly Lys Phe Leu Lys Val Gly
930                 935                 940

Asn Val Leu Glu Glu Leu Lys Tyr Arg Tyr Asp Arg Glu Val Asn Asn
945                 950                 955                 960

Gly His Arg Ser Ala Ile Lys Lys Ile Leu Glu Gly Asn Ala Ser Pro
            965                 970                 975

Ser Leu Met Met Val Leu Cys Ile Ser Ala Ile Tyr Ser Cys Pro Asp
        980                 985                 990

Leu Asn Asn Ser Lys Pro Glu Asp Asp Arg Ala His Thr Asp Asp Asp
    995                 1000                1005

Asn Ser Glu Asn Lys Ser Leu Arg Pro Ala Lys Arg Asn Met Ser
    1010                1015                1020

Thr Lys Ile Glu Leu Thr Asp Gly Trp Tyr Ser Leu Asp Ala Ser
    1025                1030                1035

Leu Asp Leu Ala Leu Leu Glu Gln Leu Glu Lys Arg Lys Leu Phe
    1040                1045                1050

Ile Gly Gln Lys Leu Arg Ile Trp Gly Ala Ser Leu Cys Gly Trp
    1055                1060                1065

Ala Gly Pro Val Ser Phe His Glu Ala Ser Gly Thr Val Lys Leu
    1070                1075                1080

Met Ile His Ile Asn Gly Thr Tyr Arg Ala Arg Trp Asp Glu Thr
    1085                1090                1095

Leu Gly Leu Cys Lys His Ala Gly Val Pro Leu Ala Phe Lys Cys
    1100                1105                1110

Ile Lys Ala Ser Gly Gly Arg Val Pro Arg Thr Leu Val Gly Val
    1115                1120                1125
```

```
Thr Arg Ile Tyr Pro Val Met Tyr Arg Glu Arg Phe Ser Asp Gly
    1130                1135                1140
Arg Phe Val Val Arg Ser Glu Arg Met Glu Arg Lys Ala Leu Gln
    1145                1150                1155
Leu Tyr His Gln Arg Val Ser Lys Ile Ala Glu Asp Ile Gln Ser
    1160                1165                1170
Glu His Gly Glu His Cys Asp Asn Thr Asp Asp Asn Asp Glu Gly
    1175                1180                1185
Ala Lys Ile Cys Lys Met Leu Glu Arg Ala Ala Glu Pro Glu Ile
    1190                1195                1200
Leu Met Ser Ser Met Ser Ser Glu Gln Leu Leu Ser Phe Ser Tyr
    1205                1210                1215
Tyr Gln Glu Lys Gln Lys Ile Val Arg Gln Asn Glu Val Ala Lys
    1220                1225                1230
Lys Val Glu Asn Ala Leu Lys Val Ala Gly Leu Ser Ser Arg Asp
    1235                1240                1245
Val Thr Pro Phe Leu Lys Val Arg Val Thr Gly Leu Ile Ser Lys
    1250                1255                1260
His Ser Ala Thr Lys Ser Gly Cys Arg Glu Gly Leu Ile Thr Ile
    1265                1270                1275
Trp Asn Pro Thr Glu Lys Gln Lys Ser Asp Leu Val Glu Gly Gln
    1280                1285                1290
Ile Tyr Ser Val Thr Gly Leu Leu Ala Ser Ser Tyr Phe Thr Glu
    1295                1300                1305
Val Ser Tyr Leu Ser Gly Arg Gly Ser Ser Thr Ala Trp Thr Pro
    1310                1315                1320
Leu Ala Thr Ala Gln Thr Thr Asn Phe Glu Pro Phe Phe Thr Pro
    1325                1330                1335
Arg Lys Ala Val Glu Leu Ser His Phe Gly Glu Val Pro Leu Thr
    1340                1345                1350
Ser Glu Phe Asp Ile Ala Gly Val Ile Leu Tyr Val Gly Asn Val
    1355                1360                1365
Tyr Leu Leu Asn Asn Gln Asn Arg Gln Trp Leu Phe Leu Thr Asp
    1370                1375                1380
Gly Ser Lys Phe Ile Ser Gly Glu Lys Tyr Glu Glu Gln Asp Asp
    1385                1390                1395
Cys Leu Leu Ala Val Ser Phe Ser Ser Lys Thr Thr Gly Glu Asp
    1400                1405                1410
Ser Ala Phe Phe Asn Tyr Ala Leu Ser Gly His Ile Val Gly Phe
    1415                1420                1425
Ser Asn Leu Val Lys Arg Asp Lys Asp Gln Met Arg His Val Trp
    1430                1435                1440
Val Ala Glu Ala Thr Glu Ser Ser Thr Tyr Ser Leu Ser His Glu
    1445                1450                1455
Ile Pro Lys Lys Ser His Leu Lys Glu Ala Ala Thr Ser Ala Glu
    1460                1465                1470
Lys Trp Ala Ser Asn Ser His Pro Met Ile Gln His Leu Lys Glu
    1475                1480                1485
Arg Val Leu Gln Ile Val Gly Asp Ser Gly Gly
    1490                1495

<210> SEQ ID NO 117
<211> LENGTH: 442
<212> TYPE: PRT
```

<213> ORGANISM: Protein

<400> SEQUENCE: 117

```
Met Ser Glu Lys Lys Arg Arg Gly Ala Gly Ala Gly Ala Ala Ser
1               5                   10                  15

Gly Ser Ala Ser Lys Lys Pro Arg Val Ser Thr Ala Ala Ser Tyr Ala
                20                  25                  30

Glu Ser Leu Arg Ser Lys Leu Arg Pro Asp Ala Ser Ile Leu Ala Thr
            35                  40                  45

Leu Arg Ser Leu Ala Ser Ala Cys Ser Lys Pro Lys Pro Ala Gly Ser
    50                  55                  60

Ser Ser Ser Ser Ser Ala Ser Lys Ala Leu Ala Ala Glu Asp Asp
65                  70                  75                  80

Pro Ala Ala Ser Tyr Ile Val Val Ala Asp Gln Asp Ser Ala Ser Val
                85                  90                  95

Thr Ser Arg Ile Asn Arg Leu Val Leu Ala Ala Arg Ser Ile Leu
            100                 105                 110

Ser Gly Arg Gly Phe Ser Phe Ala Val Pro Ser Arg Ala Ala Ser Asn
            115                 120                 125

Gln Val Tyr Leu Pro Asp Leu Asp Arg Ile Val Leu Val Arg Arg Glu
130                 135                 140

Ser Ala Arg Pro Phe Ala Asn Val Ala Thr Ala Arg Lys Ala Thr Ile
145                 150                 155                 160

Thr Ala Arg Val Leu Ser Leu Val His Ala Val Leu Arg Arg Gly Ile
                165                 170                 175

His Val Thr Lys Arg Asp Leu Phe Tyr Thr Asp Val Lys Leu Phe Gly
            180                 185                 190

Asp Gln Ala Gln Ser Asp Ala Val Leu Asp Asp Val Ser Cys Met Leu
        195                 200                 205

Gly Cys Thr Arg Ser Ser Leu His Val Val Ala Ser Glu Lys Gly Val
210                 215                 220

Val Val Gly Arg Leu Thr Phe Ala Asp Asp Gly Asp Arg Ile Asp Cys
225                 230                 235                 240

Thr Arg Met Gly Val Gly Gly Lys Ala Ile Pro Pro Asn Ile Asp Arg
                245                 250                 255

Val Ser Gly Ile Glu Ser Asp Ala Leu Phe Ile Leu Leu Val Glu Lys
            260                 265                 270

Asp Ala Ala Phe Met Arg Leu Ala Glu Asp Arg Phe Tyr Asn Arg Phe
        275                 280                 285

Pro Cys Ile Ile Leu Thr Ala Lys Gly Gln Pro Asp Val Ala Thr Arg
290                 295                 300

Leu Phe Leu Arg Arg Leu Lys Val Glu Leu Lys Leu Pro Val Leu Ala
305                 310                 315                 320

Leu Val Asp Ser Asp Pro Tyr Gly Leu Lys Ile Leu Ser Val Tyr Met
                325                 330                 335

Cys Gly Ser Lys Asn Met Ser Tyr Asp Ser Ala Asn Leu Thr Thr Pro
            340                 345                 350

Asp Ile Lys Trp Leu Gly Val Arg Pro Ser Asp Leu Asp Lys Tyr Arg
        355                 360                 365

Val Pro Glu Gln Cys Arg Leu Pro Met Thr Asp His Asp Ile Lys Val
370                 375                 380

Gly Lys Glu Leu Leu Glu Glu Asp Phe Val Lys Gln Asn Glu Gly Trp
385                 390                 395                 400

Val Lys Glu Leu Glu Thr Met Leu Arg Thr Arg Gln Lys Ala Glu Ile
```

```
                        405                 410                 415
Gln Ala Leu Ser Ser Phe Gly Phe Gln Tyr Leu Thr Glu Val Tyr Leu
            420                 425                 430

Pro Leu Lys Leu Gln Gln Gln Asp Trp Ile
            435                 440

<210> SEQ ID NO 118
<211> LENGTH: 478
<212> TYPE: PRT
<213> ORGANISM: Protein

<400> SEQUENCE: 118

Met Asp Asp Ser Thr Asp Asp Ser Tyr His Pro Arg Lys His Tyr
 1               5                  10                  15

Ala Tyr Asp Arg Gln Val Ser Ser Arg Trp Arg Thr Ser Arg Glu
            20                  25                  30

Tyr Ile Arg Gly Pro Gly Pro Glu Thr His Thr Thr Glu Ser Ala Gln
            35                  40                  45

Asp Gly Gln Asp Pro Pro Ala Gly Val Tyr Ser Tyr Gly Tyr Phe Ser
        50                  55                  60

Gly Ser Gly Asn Asp Pro Gln Val Gln Gly His Phe Val Pro Glu Ile
 65                  70                  75                  80

Gln Lys Tyr Asn Pro Tyr Val Ile Phe Lys Gly Glu Gln Leu Pro Val
                85                  90                  95

Pro Ile Trp Glu Leu Pro Glu Glu Lys Val Gln Asp Phe His Asp Arg
            100                 105                 110

Tyr Phe Ile Ala Lys Asp Lys Ser Arg Val Glu Ala Arg Lys Thr Leu
        115                 120                 125

Asn Arg Leu Leu Glu Gly Asn Ile Asn Thr Ile Glu Arg Gly His Gly
    130                 135                 140

Tyr Lys Phe Asn Ile Pro Lys Tyr Thr Asp Asn Met Glu Phe Asn Glu
145                 150                 155                 160

Glu Val Lys Val Ser Leu Ala Lys Ala Gly Lys Thr Ile Ser Arg Ser
                165                 170                 175

Phe Cys Asn Ala Asn Gln Arg Glu Val Ala Ser Arg Thr Gly Tyr Thr
            180                 185                 190

Ile Asp Leu Ile Glu Arg Thr Leu Gly Ala Gly Leu Asn Ile Ser Lys
        195                 200                 205

Arg Thr Val Leu Tyr Thr Asn Lys Asp Leu Phe Gly Asp Gln Ser Lys
    210                 215                 220

Ser Asp Gln Ala Ile Asn Asp Ile Cys Ala Leu Thr Asn Ile Arg Arg
225                 230                 235                 240

Gly Ser Leu Gly Ile Ile Ala Ala Glu Lys Gly Ile Val Val Gly Asn
                245                 250                 255

Ile Phe Leu Glu Leu Thr Asn Gly Lys Ser Ile Ser Cys Ser Ile Gly
            260                 265                 270

Val Gln Ile Pro His Arg Leu Asp Gln Ile Lys Asp Val Cys Val Glu
        275                 280                 285

Ile Gly Ser Arg Asn Ile Glu Tyr Ile Leu Val Val Glu Lys His Thr
    290                 295                 300

Met Leu Asn Tyr Leu Leu Glu Met Asp Tyr His Thr Asn Asn Asn Cys
305                 310                 315                 320

Ile Ile Leu Thr Gly Cys Gly Met Pro Thr Leu Gln Thr Arg Asp Phe
                325                 330                 335

Leu Arg Phe Leu Lys Gln Arg Thr Gly Leu Pro Val Phe Gly Leu Cys
```

-continued

```
               340                 345                 350
Asp Pro Asp Pro Glu Gly Ile Ser Ile Leu Ala Thr Tyr Ala Arg Gly
        355                 360                 365

Ser Cys Asn Ser Ala Tyr Asp Asn Phe Asn Ile Ser Val Pro Ser Ile
    370                 375                 380

Cys Trp Val Gly Leu Ser Ser Ser Asp Met Ile Lys Leu Asn Leu Ser
385                 390                 395                 400

Glu Thr Asn Tyr Ser Arg Leu Ser Arg Glu Asp Lys Thr Met Leu Lys
                405                 410                 415

Asn Leu Trp Gln Asp Asp Leu Ser Asp Val Trp Lys Arg Arg Ile Glu
            420                 425                 430

Glu Met Ile Ser Phe Asp Lys Lys Ala Ser Phe Glu Ala Ile His Ser
        435                 440                 445

Leu Gly Phe Asp Tyr Phe Ala Thr Asn Leu Leu Pro Asp Met Ile Asn
    450                 455                 460

Lys Val Arg Glu Gly Tyr Val Gln Val Tyr Phe Ser Leu Leu
465                 470                 475
```

TARGETED INTEGRATION AND STACKING OF DNA THROUGH HOMOLOGOUS RECOMBINATION

FIELD OF THE INVENTION

The present invention relates generally to transgenic plants and, more particularly, to site-specific integration and stacking of nucleotide sequences in the genome of a host cell through homologous recombination.

BACKGROUND

In recent years, the development of genetic engineering techniques has had dramatic implications in the field of crop improvement. Using these techniques, beneficial traits can be introduced into almost any crop and improved crops can be rapidly obtained. The use of genetic engineering obviates the need for lengthy procedures to introduce the desired trait by conventional breeding methods.

Present plant transformation methods generally integrate a single transgene into the host genome. Successful integration of each transgene requires repeated confrontation of various issues, such as variability in transgene expression caused by different integration loci, so-called "positions effects," and the risk of creating a mutation in the genome upon integration of the transgene into the host. Consequently, a large number of transformation events must be screened and tested before obtaining a transgenic plant that exhibits the desired level of transgene expression without also exhibiting abnormalities resulting from the inadvertent insertion of the transgene into an important locus in the host genome. Moreover, if an additional transgene is subsequently added to a transgenic plant, the additional transgene likely will be integrated into the genome at a location that is different from the location of the pre-existing transgene, rendering the breeding of elite plant lines with both genes difficult and cumbersome.

An inherent problem with such single-round integration techniques is that sequence stacking, or the successive integration of multiple nucleotide sequences at a predetermined locus in the host genome, is difficult to accomplish. However, efficient sequence stacking is desirable for a variety of reasons. For example, the ability to achieve targeted insertion of multiple transgenes into a host would facilitate registration of a transgenic plant with government regulatory agencies, since the potential for random alteration of the plant's genetic material would be minimized. Further, in some cases, such as the engineering of traits or metabolic pathways that involve multiple genes, for example, co-location of the transgenes would be highly desirable. Additionally, since only a limited number of selectable and scoreable marker sequences may be available for use in transforming a given crop, the ability to re-use a marker sequence when introducing successive nucleotide sequences into the host genome would also be desirable.

SUMMARY

The present disclosure provides methods for the targeted integration and stacking of nucleotide sequences in the genome of a host cell using homologous recombination. A target sequence in the genome of a host cell and a donor sequence introduced into the host cell each comprises a homology sequence that permits homologous recombination to occur between the target and donor sequences. In one embodiment, a homology sequence shared by a target sequence and a donor sequence comprises at least one intron sequence that lengthens the region of homology and thereby enhances the frequency of homologous recombination between the target and donor sequences.

BRIEF DESCRIPTION OF THE FIGURES

FIGS. 13A-13F are schematic representations of a modified nptII gene with multiple introns, target and donor DNA constructs, endonucleases, and a FLP expression construct. FIG. 13A: A schematic representation of a modified nptII gene with four *Arabidopsis* intron insertions (i.e., the nptII-intron gene sequence). "FRT" indicates a FLP recognition sequence. FIG. 13B: A positive control construct (pNOV2731) containing the full-length nptII-intron. "Phsp80" indicates an HSP80 promoter; "BAR" indicates a glufosinate herbicide resistance gene; "Tnos" indicates a nos terminator; "Pmsmas" indicates a modified SMAS promoter; "Tpal" indicates the Arabidopsis PAL1 terminator. FIG. 13C: A target DNA construct (pNOV2701) containing the modified nptII gene truncated at the 5'-region. FIG. 13D: Donor DNA constructs (pNOV2736, pNOV2737, pNOV2755, pNOV2757) containing the nptII-intron gene truncated at different places in the 3'-coding region. "Hpt" indicates a hygromycin phosphotransferase gene; hpt includes the *Arabidopsis* ubq3 promoter and terminator. FIG. 13E: A yeast HO endonuclease expression cassette. FIG. 13F: A FLP recombinase expression vector (pNOV2762) with *Arabidopsis* PPO(dm) as a selectable marker. PPO(dm) is under the control of its native *Arabidopsis* ptx promoter.

FIG. 14A: A schematic representation of a target locus derived from pNOV2701, T-DNA of donor pNOV2736, a recombination product, and PCR primers. Striped boxes represent genomic DNA sequences flanking the T-DNA insertion. FIG. 14B: PCR analysis of events targeted to a predetermined location in the genome of tobacco line T2701.06 using PSMASFW2 and NPTR6 primers. Targeted events produce a 3.5 kb fragment. "M" indicates a DNA size marker (i.e., Lambda DNA digested with StyI (19.3, 7.7, 6.2, 3.5, 2.7, 1.9, 1.5, 0.9, 0.4 kb). Lane 1, negative control, untransformed SR1 tobacco; lane 2, positive control T2731.1; lane 3, negative control, target line T2701.6; lane 4, HR-01AB.1; lane 5, HR-01AB.2; lane 6, HR-01AB.3; lane 7, HR-01AC.1; lane 8, HR-01AD.1; lane 9, HR-01AD.4; lane 10, HR-01AE.1; lane 11, HR-01AE.2. FIG. 14C: PCR amplification of targeted events with primers from flanking genomic DNA sequences. "M" is a DNA ladder (10, 8, 6, 5, 4, 3, 2, 1.5, 1.0, 0.5 kb; 3 kb band has the strongest signal, New England Biolab, Beverly Mass.). Lanes 1 to 5 with PDFSP1 and HYGRV1 primers; lane 1, HR-01AB.1; lane 2, HR-03AB.1, lane 3, HR-03AD.2, lane 4, HR-05AA.2; lane 5, HR-02AC.1. Lanes 6 to 9 with PDFSP1 and PALEXONV primers; lane 6, HR-01AB.1; lane 7, HR-01AB.1×SRI kanamycin resistant progeny; lane 8, HR-03AB.1×SR1 kanamycin resistant progeny, lane 9, HR-03AD.2.

FIGS. 15A-15C represent a Southern blot analysis of targeted events. FIG. 15A: A schematic representation of target and donor vectors, restriction sites, and probes. FIG. 15B A blot probed with an HSP80 promoter fragment. "M" is a DNA marker (Lambda DNA digested with StyI). Lanes 1-4, target line T2701.6; lanes 5-8, HR-03AD.2; lanes 9-11, HR-05AA.1; lanes 12-14, HR-05AA.2. Lanes 1, 5, 9, 12 with EcoRV; Lanes 2, 6, 10, 13 with SacI; Lanes 3, 7, 11, 14 with NheI; Lanes 4 and 8 with SpeI. FIG. 15C: The same blot was stripped and re-probed with the nptII exon 5::Pa11 3'-UTR fragment.

FIG. 16A: Tubq3fw and NptR3 primers were used for PCR amplification of lines obtained from HR-03AD.2 progeny re-transformed with pNOV2762. The 1.5 kb band indicates excision of the mSMAS promoter and part of the nptII-intron sequence. FIG. 16B: Tubq3fw and NptR2 primers are used for PCR amplification of progeny of HR-08AA32R2× SR1. The 932 bb band indicates excision of the mSMAS promoter and part of the nptII-intron sequence. Lane 1, recombinant HR-03AD.2 control; lanes 2-4, progeny with complete excision of the mSMAS promoter and part of the nptII-intron sequence.

FIG. 17A: A schematic drawing showing a PMI-intron gene sequence, the T-DNA region of monocot target vector pNOV5025, pAdF55, and the positive control vector pNOV5026. "SRRS" indicates a site-specific recombinase recognition sequence. "OsAct1" is a rice actin 1 promoter; "Hpt" is a hygromycin phsosphotransferase gene; "CMPS" is a Cestrum virus promoter; "ZmUbi" indicates a maize ubiquitin promoter; "GUS" is a β-glucuronidase gene; "PPO" is a mutant *Arabidopsis* protoporphyrin oxidase gene. FIG. 17B: Donor vectors pNOV503 1, pNOV5045, pNOV5096, and pQD20OC6.

FIGS. 20A-20D illustrate Southern blot analyses of a maize target plant AW289B1A and a targeted recombination event HR-18FB.1M. The blot was hybridized with the following probes: FIG. 20A: the PMI-intron 3'-region (intron 4-exon 5) that is present in the target T-DNA but not in the donor; FIG. 20B: the rice actin-1 5'-region fragment that is present in the target T-DNA but not in the donor; FIG. 20C: the GUS 3'-probe hybridizes to sequence present only in the donor; and FIG. 20D: the PPO 3'-probe hybridizes to sequences present in both the target and donor. The hybridization probes were spiked with one microliter of labeled Lambda DNA to show the molecular weight marker. Lane M had Lambda DNA digested with StyI. The fragment sizes are: 23578 bps, 19324 bps, 7743 bps, 6225 bps, 4254 bps, 3472 bps, 2690 bps, 1882 bps, 1489 bps, 925 bps, and 421 bps. The 421 bp fragment is not shown in the figures. Lanes 1 to 5 include DNA from target plant AW289B1A; lanes 6-10 include DNA from targeted event HR-18FB.1M. The restriction enzymes used to digest DNA in each lane are: lane 1 and 6, SacI; lane 2 and 7, ScaI; lane 3 and 8, KpnI; lane 4 and 9, SpeI; lane 5 and 10, HpaI.

DETAILED DESCRIPTION OF EXEMPLARY EMBODIMENTS

Figure 1:
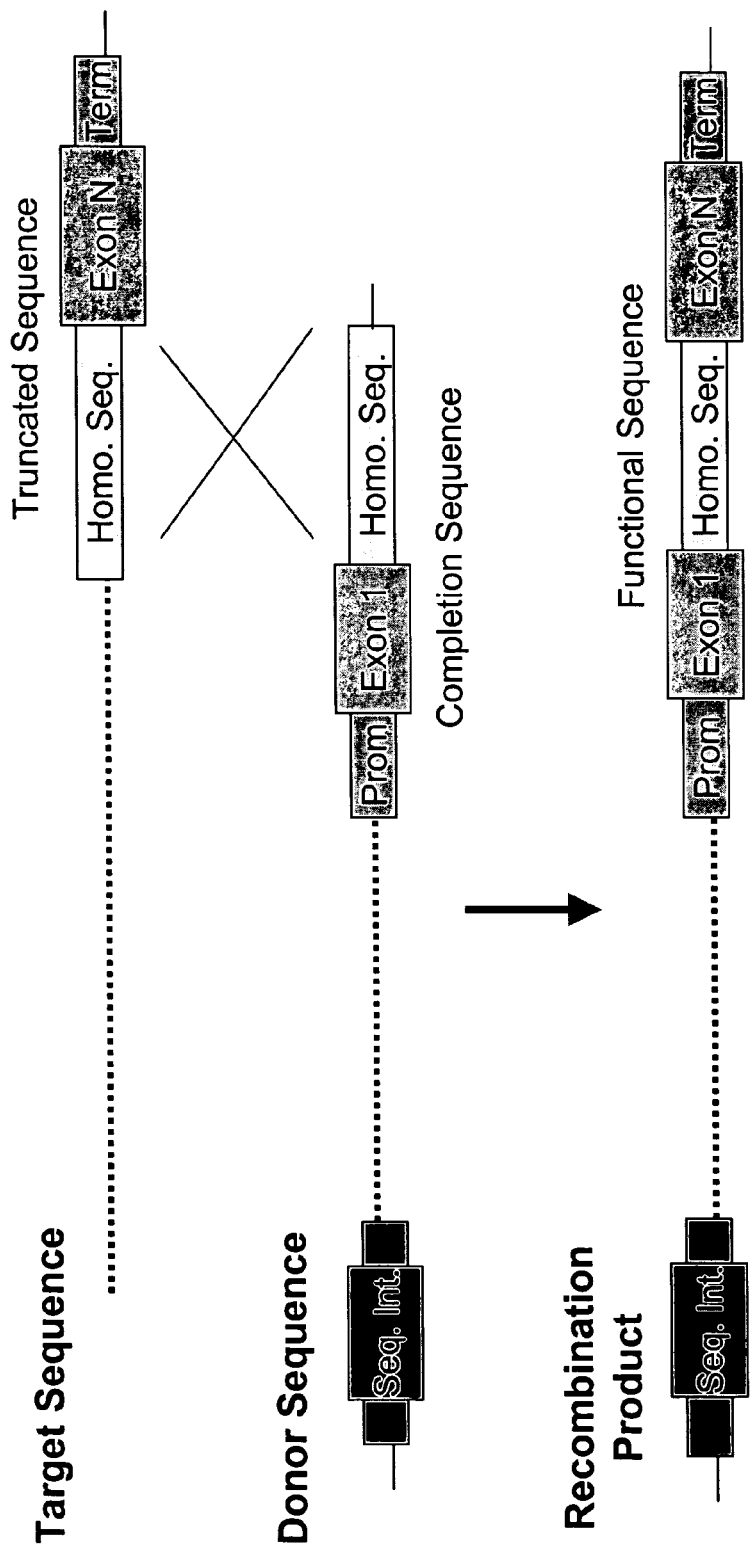
FIGS. 1-12B illustrate various exemplary embodiments of the invention.

The following definitions are provided to enable a clear and consistent understanding of the specification and the claims. Unless otherwise noted, terms are to be understood according to conventional usage by those of ordinary skill in the relevant art. The nomenclature for DNA bases as set forth at 37 C.F.R. §1.822 as well as the standard one- and three-letter nomenclature for amino acid residues are used throughout the disclosure.

A "coding sequence" is a nucleic acid sequence that can be transcribed into RNA, such as mRNA, rRNA, tRNA, snRNA, sense RNA, or antisense RNA, within a host cell into which the coding sequence has been introduced. In the case of mRNA, for example, the mRNA then can be translated within the host cell to produce a protein. A "coding region" comprises a coding sequence.

"Donor," "donor molecule," "donor DNA," and "donor sequence" are used interchangeably to refer to a desired nucleotide sequence that one wishes to recombine into a target DNA sequence using site-directed homologous recombination. The donor sequence can include any desired nucleotide sequence, such as, for example, a gene, an expression cassette, a promoter, a molecular marker, a selectable marker, a visible marker, a portion of any of these, or the like. A "donor construct" or "donor vector" contains a donor sequence.

"Endogenous," as used herein, means "of the same origin," i.e., derived from a host cell.

An "excisable sequence" refers to a nucleotide sequence comprising at least a portion of a marker sequence as well as at least one recombinase recognition site. An excisable sequence is contained within a target sequence.

"Expression" of a gene or other nucleotide sequence of interest refers to the transcription of the nucleotide sequence of interest to produce a corresponding RNA. In the case of an mRNA, the RNA may then be translated to produce a corresponding gene product (i.e., a peptide, a polypeptide, or a protein). Gene expression is controlled or modulated by regulatory elements, including 5' regulatory elements, such as a promoter, for example.

"Expression cassette," as used herein, includes a DNA sequence capable of directing expression of a particular nucleotide sequence in an appropriate host cell. An expression cassette typically comprises a promoter operably linked to a nucleotide sequence of interest, which is operably linked to a terminator or termination signal or to sequences containing an RNA polyadenylation signal. The expression cassette may also comprise sequences that permit proper translation of the nucleotide sequence, such as a translation initiation site and a translation termination sequence. Unique endonuclease restriction sites may also be included at the ends of an expression cassette to allow the cassette to be easily inserted or removed when creating a DNA construct. The nucleotide sequence of interest usually codes for a protein of interest but may also code for a functional RNA of interest, for example antisense RNA or a nontranslated RNA that, in the sense or antisense direction, inhibits expression of a particular gene, e.g., antisense RNA or double-stranded interference RNA. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, that is, the particular DNA sequence of the expression cassette does not occur naturally in the host cell and must be introduced into the host cell or an ancestor of the host cell by a transformation event. The expression of the nucleotide sequence in the expression cassette may be under the control of either a constitutive promoter or an inducible promoter that initiates transcription only when the host cell is exposed to some particular external stimulus. In the case of a multicellular organism, such as a plant, the promoter may also be specific to a particular tissue or organ or stage of development.

A "foreign" gene or DNA sequence includes a gene or other nucleotide sequence of interest that is not normally found in the host organism but that may be introduced by gene transfer. Foreign genes and DNA that are not integrated into the genome are referred to as "extrachromosomal".

The term "gene" is used broadly to include any segment of a nucleotide sequence associated with a biological function. Thus, a gene can include a coding sequence either with or without the regulatory sequences needed for their expression. A gene can also include nonexpressed DNA segments, such as 5' and 3' untranslated sequences, recognition sequences for proteins, and/or termination sequences, for example. Further elements that may be present include, for example, introns. Some genes can be transcribed into mRNA and then translated into polypeptides (e.g., structural genes); other genes can be transcribed into RNA (e.g., rRNA and tRNA); and other types of genes function as regulators of expression (i.e., regulatory genes).

"Gene of interest," "sequence of interest," and "DNA of interest" are used interchangeably and include any nucleotide sequence which, when transferred to a plant, confers upon the plant a desired trait, characteristic, or biological function, such as, for example, virus resistance, insect resistance, resistance to other pests, disease resistance, herbicide tolerance, improved nutritional value, improved performance in an industrial process, or altered reproductive capability, for example. A sequence of interest can be a marker sequence. A sequence of interest can also encode an enzyme involved in a biochemical pathway, the expression of which alters a trait that is important or useful in food, feed, nutraceutical, and/or pharmaceutical production.

"Genome" refers to the complete genetic material of an organism.

"Heterologous," as used herein, means "of different natural origin," that is, representing a non-natural state. For example, if a host cell is transformed with a gene derived from another organism, particularly from another species, that gene is heterologous with respect to the host cell and also with respect to descendants of the host cell that carry the gene. Further, "heterologous" may also be used to refer to a nucleotide sequence which is derived from a natural or original cell type and is inserted into that same natural or original cell type, but which is present in a non-natural state, such as, for example, in a different copy number, under the control of different regulatory elements, or the like.

"Homologous recombination" refers to a reaction between any pair of nucleotide sequences having corresponding sites containing a similar nucleotide sequence (i.e., homologous sequences) through which the two molecules can interact (recombine) to form a new, recombinant DNA sequence. The sites of similar nucleotide sequence are each referred to herein as a "homology sequence". Generally, the frequency of homologous recombination increases as the length of the homology sequence increases. Thus, while homologous recombination can occur between two nucleotide sequences that are less than identical, the recombination frequency (or efficiency) declines as the divergence between the two sequences increases. Recombination may be accomplished using one homology sequence on each of the donor and target molecules, thereby generating a "single-crossover" recombination product. Alternatively, two homology sequences may be placed on each of the target and donor nucleotide sequences. Recombination between two homology sequences on the donor with two homology sequences on the target generates a "double-crossover" recombination product. If the homology sequences on the donor molecule flank a sequence that is to be manipulated (e.g., a sequence of interest), the double-crossover recombination with the target molecule will result in a recombination product wherein the sequence of interest replaces a DNA sequence that was originally between the homology sequences on the target molecule. The exchange of DNA sequence between the target and donor through a double-crossover recombination event is termed "sequence replacement."

To "identify" a recombination product means that the recombination product is detected and distinguished from the starting target and donor sequences. There are many means of identifying a recombination product. For example, a selectable marker gene can be used, whereby site-specific integration results in the selectable marker gene becoming operatively linked with a promoter only in a recombination product. Alternatively, a visible marker gene can be used, whereby a gain or loss of marker gene expression identifies a recombination product. Alternatively, a negative selectable marker gene can be used, whereby a loss or lack of expression of the marker gene identifies a recombination product. Additionally, molecular markers that are characteristic of the target sequence and/or donor sequence can be used, such that the molecular marker pattern is unique for the recombination product.

"Integration" refers to the incorporation of a foreign gene or other nucleotide sequence into a host genome through covalent bonding to the host DNA.

An "isolated" nucleic acid molecule or an isolated protein or toxin is a nucleic acid molecule or protein or toxin that, by the hand of man, exists apart from its native environment and is therefore not a product of nature. An isolated nucleic acid molecule or protein or toxin may exist in a purified form or may exist in a non-native environment, such as, for example, a recombinant host cell or a transgenic plant.

A "marker sequence" refers to any nucleotide sequence that can be used to differentiate a transformed cell from a nontransformed cell. Marker sequences include, but are not limited to, selectable markers, scoreable markers, and molecular markers. Exemplary marker sequences include antibiotic resistance genes (such as, e.g., those conferring resistance to tetracycline, ampicillin, kanamycin, neomycin, hygromycin, and spectinomycin), luminescence genes (such as, e.g., genes encoding luciferase, β-galactosidase, green fluorescence protein (GFP), β-lactamase, or choramphenicol acetyl transferase (CAT)), and genes conferring an enhanced capacity, relative to non-transformed cells, to utilize a particular compound as a nutrient, growth factor, or energy source (such as, e.g., a gene encoding phosphomannose isomerase (PMI)).

"Mega-endonuclease" refers to a rare-cutting endonuclease that is capable of making a site-specific double-strand break in DNA at a particular recognition sequence comprising at least about 12 base pairs. The recognition sequence may be somewhat lengthy and can be as long as about 40 base pairs. One type of mega-endonuclease is referred to as a homing endonuclease, which is an enzyme that is encoded by an intron or an intein (Belfort and Roberts, 1997 Nucl. Acids. Res. 25(17): 3379-3388; see also, Gauthier et al., 1991 Current Genet. 19:43-47). Exemplary mega-endonucleases include, but are not limited to, I-SceI, I-CeuI, I-PpoI, I-CreI, I-DmoI, I-SceII, I-TevI, I-TevII, PI-PfuI, PI-PspI, PI-SceI, and HO, as described herein or otherwise known in the art (see, e.g., Belfort and Roberts (1997).

"Native" refers to a gene that is present in the genome of an untransformed (e.g., a "wild-type") cell.

"Naturally occurring" is used to describe an object that can be found in nature, as distinct from being artificially produced by man. For example, a protein or nucleotide sequence present in an organism (including a virus), which can be isolated from a source in nature and which has not been intentionally modified by man in the laboratory, is naturally occurring.

A "nucleic acid molecule," "nucleic acid sequence," or "nucleotide sequence" is a segment of single- or double-stranded DNA or RNA that can be isolated from any source. In the context of the present invention, the nucleic acid molecule is preferably a segment of DNA.

"Operably linked" and "operatively linked" refers to a relationship between two or more nucleotide sequences that interact physically or functionally. For example, a promoter or regulatory nucleotide sequence is said to be operably linked to a nucleotide sequence that encodes an RNA or a protein if the two sequences are situated such that the regulatory nucleotide sequence will affect the expression level of the coding or structural nucleotide sequence. A 5' portion of a gene is operatively or operably linked with a 3' portion of a gene if the two portions are situated to form a functional gene.

The term "plant", as used herein, refers to, without limitation, whole plants, plant organs (e.g., leaves, stems, roots, fruit, etc.), seeds, plant cells and progeny of plant cells, plant tissue, plant cell or tissue cultures, protoplasts, callus, and any groups of plant cells organized into structural and/or functional units. A plant "regenerated" from a plant cell means that all cells of the plant are derived from that plant cell. The class of plants that can be used in the methods of the invention is generally as broad as the class of higher plants amenable to transformation techniques, including both monocotyledonous and dicotyledonous plants. Exemplary plants include, without limitation, *Acacia*, alfalfa, aneth, apple, apricot, artichoke, *Arabidopsis*, arugula, asparagus, avocado, banana, barley, bean, beet, blackberry, blueberry, broccoli, Brussels sprouts, cabbage, canola, cantaloupe, carrot, cassava, cauliflower, celery, cherry, chicory, clover, cilantro, citrus, clementines, coffee, corn, cotton, cucumber, eggplant, endive, escarole, eucalyptus, fennel, figs, garlic, gourd, grape, grapefruit, hemp, honey dew, jicama, kiwifruit, lettuce, leeks, lemon, lime, mango, maize, melon, mushroom, nectarine, nut, oat, okra, onion, orange, an ornamental plant, papaya, parsley, pea, peach, peanut, pear, pepper, persimmon, pineapple, plantain, plum, pomegranate, potato, pumpkin, quince, radicchio, radish, raspberry, rice, rye, safflower, sorghum, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, zucchini, and woody plants such as coniferous and deciduous trees. Once a gene of interest has been transformed into a particular plant species, the gene may be propagated in that species or may be moved into other varieties of the same species, including commercial varieties, using traditional breeding techniques.

"Plant cell" refers to a structural and physiological unit of a plant, comprising a protoplast and a cell wall, and includes, without limitation, seed suspension cultures, embryos, meristematic regions, callus tissue, leaves, roots, shoots, gametophytes, sporophytes, pollen, and microspores. The plant cell may be in the form of an isolated single cell, a cultured cell, or a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes, and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant, such as a root, stem, leaf, flower bud, or embryo.

"Plant tissue" as used herein means a group of plant cells, including any tissue of a plant either in planta or in culture, organized into a structural and functional unit. The term includes, but is not limited to, whole plants, plant organs, plant seeds, tissue culture, and any groups of plant cells organized into structural and/or functional units. The use of this term in conjunction with, or in the absence of, any specific type of plant tissue, as listed above or otherwise embraced by this definition, is not intended to be exclusive of any other type of plant tissue.

A "promoter" is an untranslated DNA sequence that is located upstream of a coding region, contains a binding site for RNA polymerase II, and initiates transcription of the DNA. The promoter region may also include other elements that act as regulators of gene expression.

A "protoplast" is an isolated plant cell without a cell wall or with only parts of the cell wall.

"Recognition site" or "recognition sequence" refers to a DNA sequence recognized by an enzymatic protein, such as, for example, a recombinase or an endonuclease. In the case of a recombinase, the recognition site or sequence is the location on the DNA at which the recombinase binds to the DNA and cleavage and strand exchange occur.

"Recombinase" refers to any enzyme that is capable of performing site-specific recombination of DNA. Recombinase enzymes possess endonuclease and ligase activities. A recombinase may work as a single protein or as a complex of proteins.

"Regulatory element" includes a nucleotide sequence that is involved in conferring upon a host cell the expression of another nucleotide sequence, such as, for example, a sequence of interest. A regulatory element can comprise a promoter that is operably linked to the nucleotide sequence of interest and to a termination signal. Regulatory elements also typically encompass sequences useful for proper translation of the nucleotide sequence of interest.

"Selectable marker" or "selectable marker gene" refers to a nucleotide sequence whose expression in a plant cell gives the cell a selective advantage under particular conditions. The selective advantage possessed by the cell transformed with the selectable marker gene can be an improved ability to grow in the presence of a negative selective agent, such as an antibiotic or an herbicide, for example, as compared to the ability of non-transformed cells. Alternatively, the selective advantage possessed by the transformed cells can be an enhanced capacity, relative to non-transformed cells, to utilize a particular compound (such as a particular carbohydrate source like mannose, for example) as a nutrient, growth factor, or energy source, thereby effecting what is termed "positive selection." Alternatively, the selective advantage possessed by the transformed cell can be the loss of a previously possessed trait or characteristic, effecting what is termed "negative selection" or "counter selection." In this last case, the host cell is exposed to or contacted by a compound that is toxic only to cells that have not lost the ability to express a specific trait or characteristic (such as a negative selectable marker gene, for example) that was present in the parent cell, which is typically a transgenic parent cell.

"Site-directed recombination," as used herein, refers to a recombination of two nucleotide sequences, wherein the recombination occurs between particular recognition sites located on each of the nucleotide sequences.

"Site-specific" means at a particular nucleotide sequence, which can be in a specific location in the genome of a host cell. The nucleotide sequence can be endogenous to the host cell, either in its natural location in the host genome or at some other location in the genome, or it can be a heterologous nucleotide sequence, which has been previously inserted into the genome of the host cell by any of a variety of known methods.

"Stably transformed" refers to a host cell that contains a nucleotide sequence of interest that has been integrated into the host cell genome and is capable of being passed to progeny of that host cell.

"Subcellular organelles" includes intracellular organs of characteristic structure and function. Subcellular organelles include, for example, vacuoles, plastids, mitochondria, the cell nucleus, the endoplasmic reticulum, and the plasma membrane.

"Substantially identical," as used in the context of two nucleic acid or protein sequences, refers to two or more sequences or subsequences that have at least 60%, preferably 80%, more preferably 90%, even more preferably 95%, and most preferably at least 99% nucleotide or amino acid residue identity, when compared and aligned for maximum correspondence, as measured using one of the following sequence comparison algorithms or by visual inspection. In one embodiment, the substantial identity exists over a region of nucleotide sequences that is at least about 50 residues in length, more preferably over a region of at least about 100 residues, and most preferably the nucleotide sequences are substantially identical over at least about 150 residues. In one embodiment, the nucleotide sequences are substantially identical over the entire length of their coding regions. In another embodiment, the substantial identity exists over a region of protein sequences that is at least about 15 residues in length, more preferably over a region of at least about 30 residues, and most preferably the protein sequences are substantially identical over at least about 50 residues. Furthermore, substantially identical nucleic acid or protein sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based upon the designated program parameters.

Optimal alignment of compared sequences can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, Proc. *Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis. or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered to be similar to a reference sequence if the smallest sum probability in a comparison of the test nucleic acid sequence to the reference nucleic acid sequence is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) of DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions," in the context of nucleic acid hybridization experiments such as Southern and Northern hybridizations, are sequence dependent and are different under different environmental parameters. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes*, part I, chapter 2, "Overview of principles of hybridization and the strategy of nucleic acid probe assays," Elsevier, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The "$T_m$" is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or Northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An exemplary medium stringency wash for a duplex of, e.g., more than 100 nucleotides, is 1×SSC at 45° C. for 15 minutes. An exemplary low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1× SSC, 0.1% SDS at 65° C.

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

"Target," "target molecule," "target DNA," and "target sequence" are used interchangeably to refer to a nucleotide sequence that is present naturally in the genome or that has been previously introduced into a chromosome of a host cell and can be inherited stably as part of the genome (i.e., "chromosomally integrated"). The target nucleotide sequence may be a sequence of interest, an expression cassette, a promoter, a molecular marker, a marker sequence, a selectable marker, a portion of any of these, or the like. The target sequence can be stably transformed into a plant cell to create a "target line" comprising the target sequence integrated at a particular chromosomal location in the plant genome. A "target construct" or "target vector" contains a target sequence.

A "targeted integration event" or "targeted event" is used interchangeably with an "HR-mediated recombination product" to refer to a recombination product formed by target and donor DNA sequences through homologous recombination (i.e., HR).

"Transformation" is a process for introducing a nucleotide sequence into a host cell or organism. In particular, "transformation" means the stable integration of a DNA molecule into the genome of a cell or an organism of interest.

"Transformed," "transgenic," or "recombinant" refers to a cell, tissue, organ, or organism, such as a bacterium or a plant, into which a particular nucleic acid molecule, such as a recombinant vector, has been introduced. The nucleic acid molecule can be stably integrated into the genome of the recipient cell, tissue, organ, or organism and can also be present as an extra-chromosomal or episomal molecule. Such an extra-chromosomal molecule can be auto-replicating. Transformed or transgenic cells, tissues, organs, or organisms are understood to encompass not only the end product of a transformation process but also the progeny thereof, which includes progeny produced from a breeding program employing a transgenic plant as a parent in a cross and exhibiting an altered genotype resulting from the presence of a heterologous nucleic acid molecule. A "non-transformed," "non-transgenic," or "non-recombinant" host refers to an organism, e.g., a bacterium or plant, which does not contain the particular nucleic acid molecule.

A "visible marker," "screenable marker," or "scoreable marker" refers to a gene or nucleotide sequence whose expression in a transformed cell may not confer an advantage to that cell but can be made visible or otherwise detectable. Examples of visible markers include, but are not limited to, β-glucuronidase (GUS), luciferase (LUC), and fluorescent proteins (such as green fluorescent protein (GFP) or cyan fluorescent protein (CFP), for example).

The present disclosure relates to the targeted integration and stacking of nucleotide sequences within the genome of a host cell using homologous recombination. In one embodiment, a homology sequence shared by a target sequence and a donor sequence comprises at least one intron sequence that lengthens the region of homology and thereby enhances the frequency of homologous recombination between the target and donor sequences. In another embodiment, the homology sequence shared by the target and donor sequences comprises two or more intron sequences that lengthen the region of homology shared between the target and donor. In a further embodiment, a site-specific recombination system can be used to mediate the modification of a chromosomally integrated target sequence to prepare the target site for insertion of a subsequent donor sequence. In yet another embodiment, an endonuclease can be used to enhance recombination frequency and to facilitate introduction of the donor sequence into the host cell's genome at the target site. In a further embodiment, the expression level of at least one RecQ gene present in the genome of the host cell is down-regulated to enhance homologous recombination activity in the host cell. In still another embodiment, the expression level of at least one recombination-related gene present in the genome of the host cell is up-regulated to enhance homologous recombination activity in the host cell.

In one embodiment, a method for targeted nucleotide sequence stacking is provided, the method comprising: (a) providing a host cell comprising a chromosomally integrated target sequence, the target sequence comprising a truncated sequence comprising a homology sequence, the homology sequence comprising at least one intron sequence; (b) introducing into the host cell a donor sequence comprising a sequence of interest and a completion sequence, the completion sequence comprising the homology sequence; and (c) obtaining in the host cell a recombination product comprising the sequence of interest and a functional sequence, the functional sequence comprising the homology sequence (FIG. 1). In another embodiment, the target sequence further comprises a mega-endonuclease recognition sequence, and the method further comprises, prior to obtaining the recombination product, introducing into the host cell a mega-endonuclease or a mega-endonuclease coding sequence, the mega-endonuclease or an expression product of the mega-endonuclease coding sequence being capable of recognizing the mega-endonuclease recognition sequence. Optionally, either of these embodiments may be used in conjunction with a method for down-regulating the expression level of at least one RecQ gene that is present in the genome of the host cell. Optionally, any of these embodiments may be used in conjunction with a method for up-regulating the expression level of at least one recombination-related gene that is present in the genome of the host cell.

Figure 2:
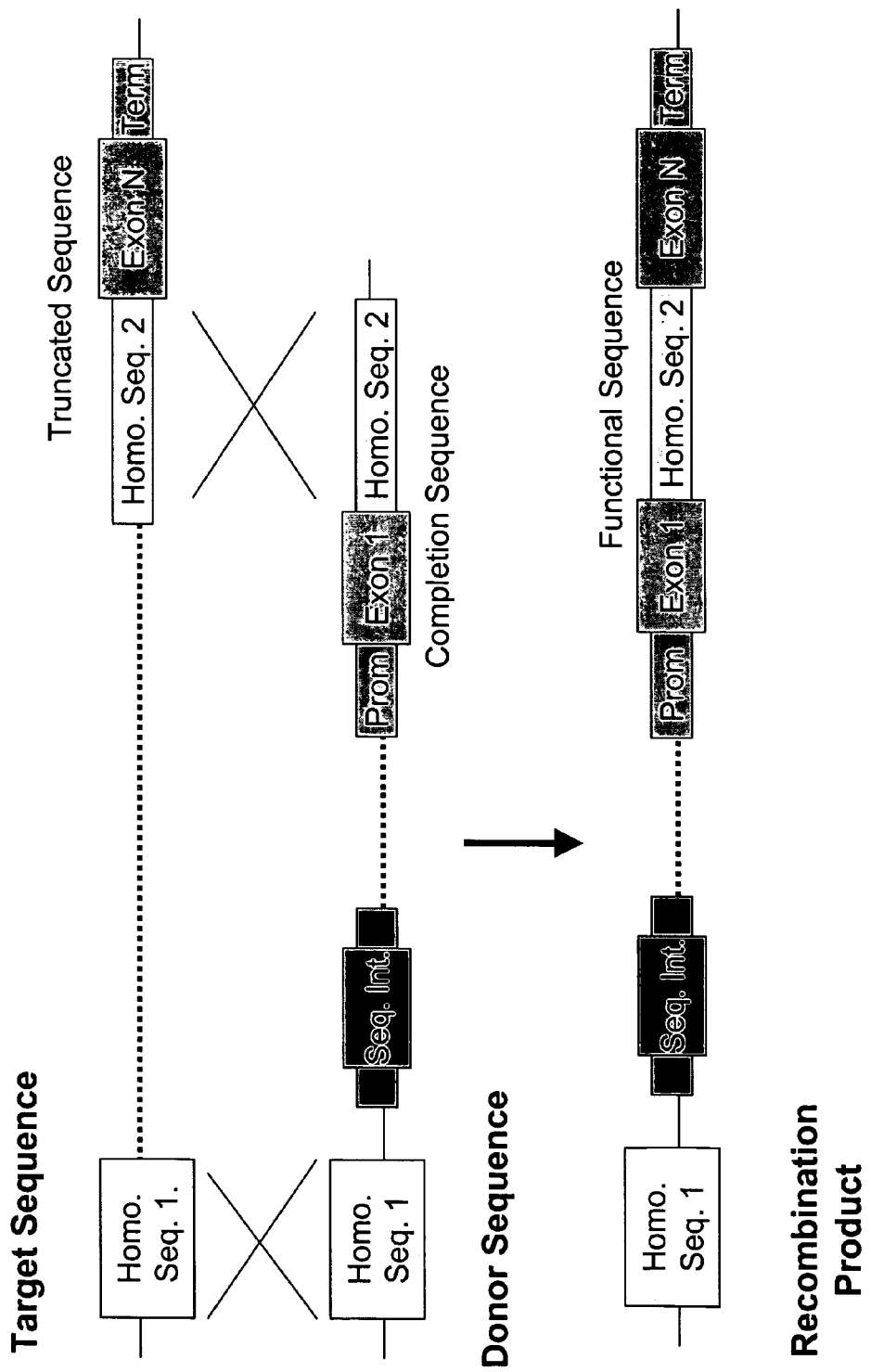

In another embodiment, a method for targeted nucleotide sequence stacking is provided, the method comprising: (a) providing a host cell comprising a chromosomally integrated target sequence, the target sequence comprising (i) a first homology sequence and (ii) a truncated sequence comprising a second homology sequence, the second homology sequence comprising at least one intron sequence; (b) introducing into the host cell a donor sequence comprising the first homology sequence, a sequence of interest, and a completion sequence, the completion sequence comprising the second homology sequence; and (c) obtaining in the host cell a recombination product comprising the first homology sequence, the sequence of interest, and a functional sequence, the functional sequence comprising the second homology sequence (FIG. 2). Optionally, this embodiment may be used in conjunction with a method for down-regulating the expression level of at least one RecQ gene that is present in the genome of the host cell. Optionally, either of these embodiments may be used in conjunction with a method for up-regulating the expression level of at least one recombination-related gene that is present in the genome of the host cell.

Figure 3:
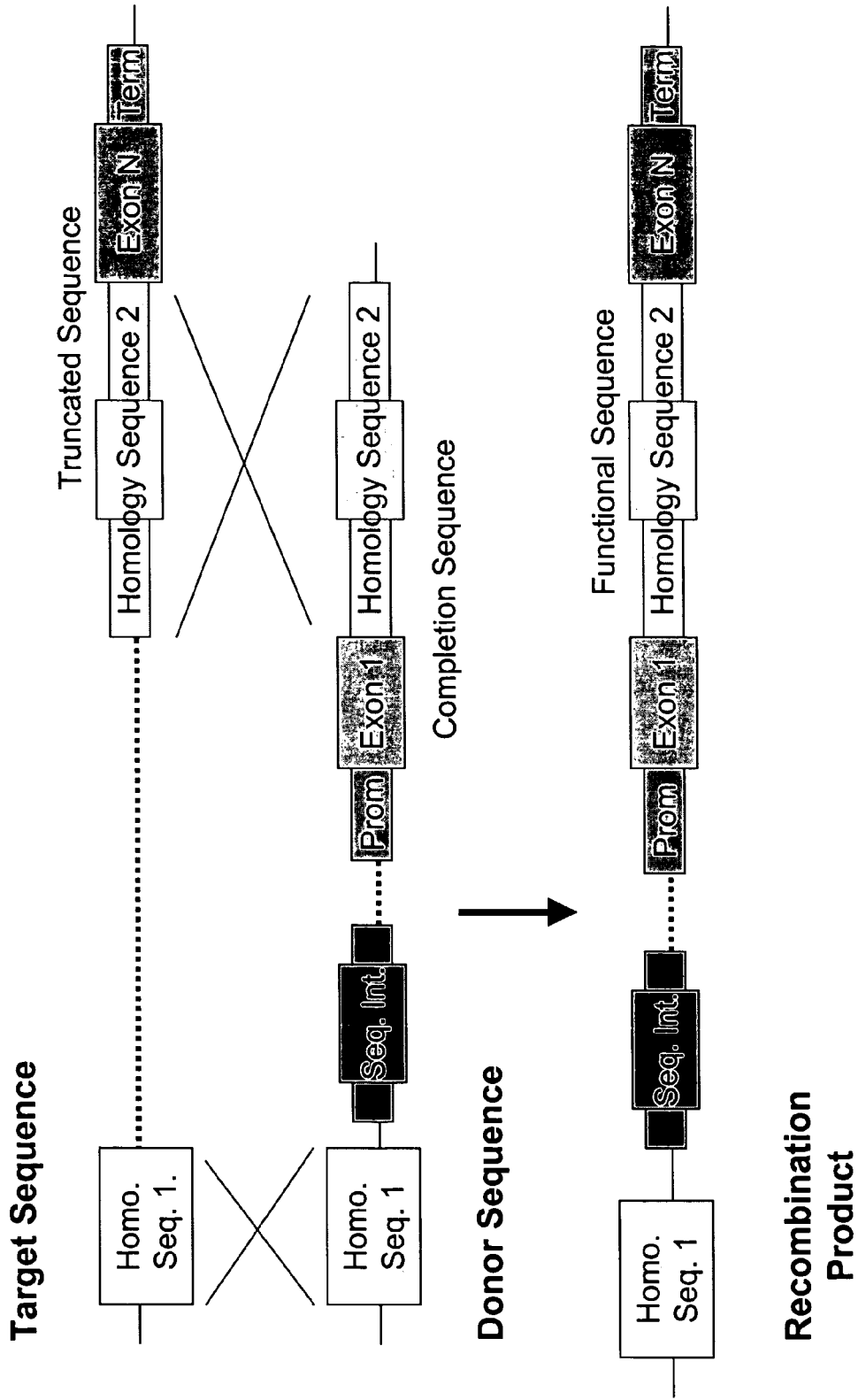

In another embodiment, a method for targeted nucleotide sequence stacking is provided, the method comprising: (a) providing a host cell comprising a chromosomally integrated target sequence, the target sequence comprising (i) a first homology sequence and (ii) a truncated sequence comprising a second homology sequence, the second homology sequence comprising two or more intron sequences; (b) introducing into the host cell a donor sequence comprising the first homology sequence, a sequence of interest, and a completion sequence, the completion sequence comprising the second homology sequence; and (c) obtaining in the host cell a recombination product comprising the first homology sequence, the sequence of interest, and a functional sequence, the functional sequence comprising the second homology sequence (FIG. 3). In another embodiment, the target sequence further comprises a mega-endonuclease recognition sequence positioned between the first homology sequence and the truncated sequence, and the method further comprises, prior to obtaining the recombination product, introducing into the host cell a mega-endonuclease or a mega-endonuclease coding sequence, the mega-endonuclease or an expression product of the mega-endonuclease coding sequence being capable of recognizing the mega-endonuclease recognition sequence. Optionally, either of these embodiments may be used in conjunction with a method for down-regulating the expression level of at least one RecQ gene that is present in the genome of the host cell. Optionally, any of these embodiments may be used in conjunction with a method for up-regulating the expression level of at least one recombination-related gene that is present in the genome of the host cell.

Figure 4:
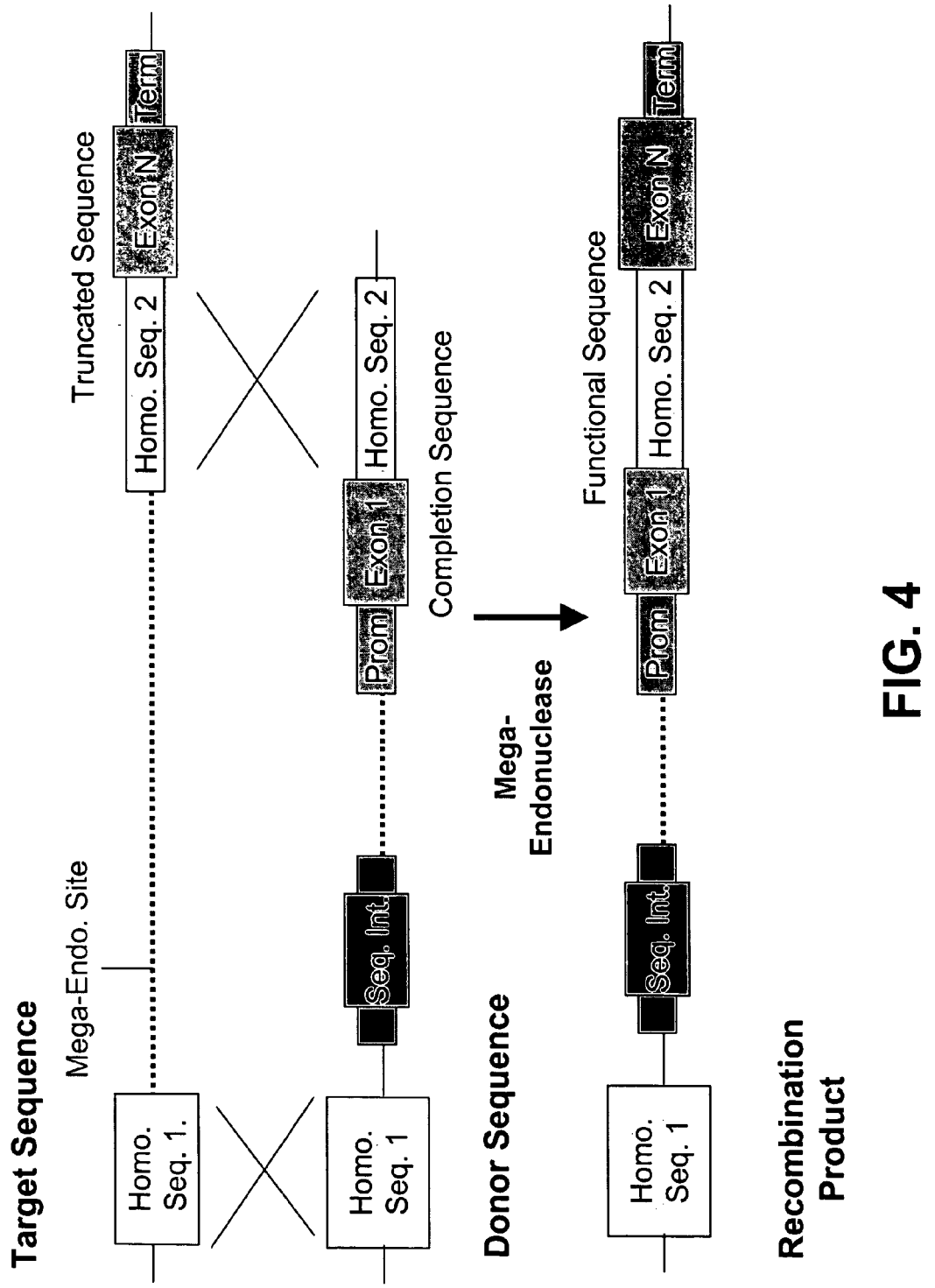

In another embodiment, a method for targeted nucleotide sequence stacking is provided, the method comprising: (a) providing a host cell comprising a chromosomally integrated target sequence, the target sequence comprising (i) a first homology sequence, (ii) a truncated sequence comprising a second homology sequence, the second homology sequence comprising at least one intron sequence, and (iii) a mega-endonuclease recognition sequence positioned between the first homology sequence and the truncated sequence; (b) introducing into the host cell a donor sequence comprising the first homology sequence, a sequence of interest, and a completion sequence, the completion sequence comprising the second homology sequence; (c) introducing into the host cell a mega-endonuclease or a mega-endonuclease coding sequence, the mega-endonuclease or an expression product of the mega-endonuclease coding sequence being capable of recognizing the mega-endonuclease recognition sequence; and (d) obtaining in the host cell a recombination product comprising the first homology sequence, the sequence of interest, and a functional sequence, the functional sequence comprising the second homology sequence; wherein (b) and (c) can be performed in any order or simultaneously (FIG. 4). Optionally, this embodiment may be used in conjunction with a method for down-regulating the expression level of at least one RecQ gene that is present in the genome of the host cell. Optionally, either of these embodiments may be used in conjunction with a method for up-regulating the expression level of at least one recombination-related gene that is present in the genome of the host cell.

Figure 5:
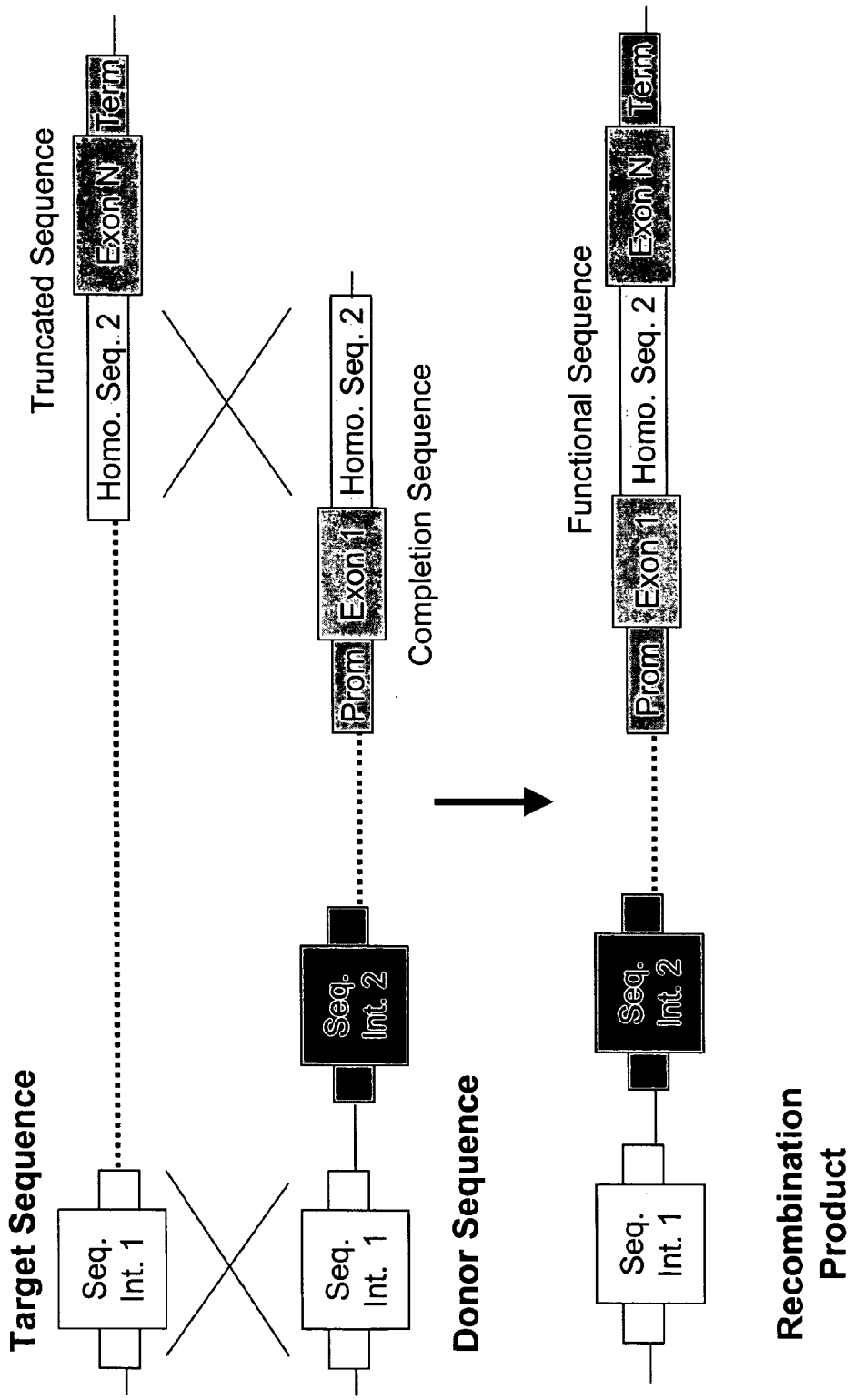

In another embodiment, a method for targeted nucleotide sequence stacking is provided, the method comprising: (a) providing a host cell comprising a chromosomally integrated target sequence, the target sequence comprising (i) a first homology sequence comprising a first sequence of interest and (ii) a truncated sequence comprising a second homology sequence, the second homology sequence comprising at least one intron sequence; (b) introducing into the host cell a donor sequence comprising the first homology sequence, a second sequence of interest, and a completion sequence, the completion sequence comprising the second homology sequence; and (c) obtaining in the host cell a recombination product comprising the first homology sequence, the second sequence of interest, and a functional sequence, the functional sequence comprising the second homology sequence (FIG. 5). In another embodiment, the target sequence further comprises a mega-endonuclease recognition sequence positioned between the first homology sequence and the truncated sequence, and the method further comprises, prior to obtaining the recombination product, introducing into the host cell a mega-endonuclease or a mega-endonuclease coding sequence, the mega-endonuclease or an expression product of the mega-endonuclease coding sequence being capable of recognizing the mega-endonuclease recognition sequence. Optionally, either of these embodiments may be used in conjunction with a method for down-regulating the expression level of at least one RecQ gene that is present in the genome of the host cell. Optionally, any of these embodiments may be used in conjunction with a method for up-regulating the expression level of at least one recombination-related gene that is present in the genome of the host cell.

In accordance with the methods described herein, a target nucleotide sequence is introduced into a host plant cell. In one embodiment, the target sequence is chromosomally integrated into the plant genome by transformation methods described herein or by methods otherwise known in the art. A plant or plant cell transformed with the target sequence may be used to obtain a target cell line or plant line. Such a target cell line or plant line may comprise a single copy of the target sequence integrated into its genome. Once such a target line has been obtained and identified, it may be further characterized. For example, the location of the target sequence can be precisely determined by genetic methods well known in the art or by using molecular markers, such as restriction fragment length polymorphism (RFLP), amplified fragment length polymorphism (AFLP), simple sequence repeat (SSR), and the like. Additionally, host-plant DNA flanking the site of insertion may be sequenced to ensure that no essential gene has been mutated or otherwise disrupted by the insertion of the target sequence. Once a well-characterized target line is obtained, it may be used as a recipient of one or more subsequently introduced nucleotide sequences. Such additional sequences can be comprised in a donor sequence and can be introduced into the target line by any suitable transformation method, including, but not limited to, *Agrobacterium*-mediated transformation, biolistic bombardment, electroporation, PEG-mediated transformation, and whiskers technology, as described herein or otherwise known in the art.

The target sequence comprises a target homology sequence that is used to effect homologous recombination between the target sequence and a donor sequence that comprises a corresponding donor homology sequence. Absolute limits for the length of the homology sequence or the degree of homology are not fixed. Rather, the desired length of the homology sequence and/or the degree of homology depends upon the frequency and/or efficiency that is sought for a particular application. Generally, the longer the homology sequence and the greater the degree of homology, the greater the recombination frequency between the target and donor sequences.

In one embodiment, the homology sequence contained within each of the target and donor sequences can be any nucleotide sequence that is at least about 200 base pairs in length. The length of the homology sequence can vary and includes unit integral values in the ranges of about 150-300 bp, 200-400 bp, 250-500 bp, 300-600 bp, 350-700 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, and 5-10 kb or more. These exemplary ranges include both endpoints as well as every integer within the range; for example, the range of 1-2.5 kb includes both 1000 bp and 2500 bp as well as every integer between those endpoints (i.e., 1000 bp, 1001 bp, 1002 bp, ..., 2498 bp, 2499 bp, and 2500 bp).

In another embodiment, the homology sequence includes at least one intron sequence that serves to extend the region of homology shared between the target and donor sequences and thereby enhances targeting efficiency. Any suitable intron sequence can be employed in accordance with the various embodiment of the invention, so long as the intron sequence is capable of being spliced by the host cell from the RNA transcript(s) of a recombination product. As will be appreciated by those of skill in the art, the intron splicing junctions must be properly recognized by the host cell in order to produce an appropriate expression product. Generally, an intron derived from a monocotyledonous plant will tend to be more effectively spliced from an RNA transcript produced by a monocotyledonous host cell. Likewise, an intron derived from a dicotyledonous plant will tend to be more effectively spliced from an RNA transcript produced by a dicotyledonous host cell.

In one embodiment, each intron sequence is at least about 50 base pairs in length. The length of the intron sequence can vary and includes unit integral values in the ranges of about 40-100 bp, 80-150 bp, 120-200 bp, 160-250 bp, 200-300 bp, 240-350 bp, 280-400 bp, 320-450 bp, 360-500 bp, 400-600 bp, 450-700 bp, 500-800 bp, 550-900 bp, 600-1000 bp, 700-1250 bp, 800-1500 bp, 900-1750 bp, 1-2 kb, and 1.5-3 kb or more. These exemplary ranges include both endpoints as well as every integer within the range; for example, the range of 1.5-3 kb includes both 1500 bp and 3000 bp as well as every integer between those endpoints (i.e., 1500 bp, 1501 bp, 1502 bp, ..., 2998 bp, 2999 bp, and 3000 bp).

In a further embodiment, each homology sequence comprises two or more intron sequences, and each intron sequence is separated from another intron sequence by at least one exon sequence.

In another embodiment, each homology sequence includes at least one recombinase recognition site (as described in greater detail below).

In one embodiment, each of the target and donor sequences comprises two homology sequences. In this embodiment, each of the two homology sequences is independently selected. That is, the first and second homology sequences can be the same or they can be different from each other. In one embodiment, at least one of the first and second homology sequences comprises a sequence of interest.

In one embodiment, the target homology sequence is contained within a truncated, and therefore inactive, nucleotide sequence. The truncated sequence can be, for example, a truncated sequence of interest, a truncated gene, a truncated selectable marker, a truncated visible marker, a truncated negative selectable marker, a truncated promoter sequence, a truncated expression cassette, or the like. In this embodiment, a donor sequence is constructed to include a completion sequence that contains the donor homology sequence. The donor completion sequence completes the truncated nucleotide sequence, in that homologous recombination between the target, which includes the truncated sequence, and the donor, which includes the completion sequence, produces a functional or complete sequence. For example, the truncated sequence can include a 5' portion (or, alternatively, a 3' portion) of a sequence of interest, which optionally may be operably linked to a promoter sequence. The corresponding donor completion sequence then includes the 3' portion (or, alternatively, the 5' portion) of the sequence of interest and optionally may also include a termination sequence. In this manner, homologous recombination between the target and donor sequences ligates or otherwise operably links the 5' portion of the sequence of interest with the 3' portion of the sequence of interest to reconstitute a functional or complete sequence of interest in the recombination product. Only a host cell comprising a desired recombination product has the appropriate expression product (i.e., as derived from a functional sequence of interest).

In one embodiment, the target's truncated sequence can be a truncated marker sequence. The truncated marker sequence can include either a 5' portion of a marker sequence or a 3' portion of a marker sequence. In one embodiment, the truncated marker sequence includes a 5' portion of a marker sequence, which can be operably linked to a promoter sequence. The corresponding donor completion sequence includes the 3' portion of the marker sequence and can also include a termination sequence. In this manner, homologous recombination between the target and donor sequences ligates or otherwise operably links the 5' portion of the marker sequence with the 3' portion of the marker sequence to reconstitute a functional marker sequence in the recombination product. In another embodiment, the truncated marker sequence includes a 3' portion of a marker sequence and can also include a termination sequence. The corresponding donor completion sequence includes the 5' portion of the marker sequence, which can be operably linked to a promoter sequence. Homologous recombination between the target and donor sequences ligates or otherwise operably links the 5' portion of the marker sequence with the 3' portion of the marker sequence to reconstitute a functional marker sequence in the recombination product.

In one embodiment, the target sequence comprises a mega-endonuclease recognition sequence. Exemplary mega-endonuclease recognition sequences include those sequences that are recognized and cleaved by various endonucleases, such as, for example, I-SceI I-CueI, I-PpoI, PI-PspI, PI-SceI, and HO. Other mega-endonuclease recognition sequences may also be used, such as any sequence recognized by I-CreI, I-DmoI, I-SceII, I-TevI, I-TevII, PI-PfuI, or any sequence recognized by other mega-endonucleases that are known in the art. See, e.g., Belfort and Roberts, p.3382, Table 3.

As will be appreciated by those of skill in the art, mega-endonucleases do not have stringent recognition sequences. The above recognition sequences are but single examples of the recognition sequences that may be used with each of the indicated mega-endonucleases. Other recognition sequences, such as, for example, degenerate variations of the sequences indicated above, may also be used, including recognition sequences having single or multiple base changes. See, e.g., Argast et al. 1998 J. Mol. Biol. 280: 345-353; and Gimble and Wang 1996 J. Mol. Biol. 256: 163-180.

A mega-endonuclease or a sequence encoding a mega-endonuclease can be introduced into the host plant cell prior to, after, or simultaneously with the introduction of the donor sequence. In one embodiment, a mega-endonuclease is introduced into the host cell as a nucleic acid molecule (DNA and/or RNA) that comprises a coding sequence for the mega-endonuclease. The mega-endonuclease can be introduced as an expression cassette comprising the coding sequence operatively linked to a plant expressible promoter and an appropriate termination sequence. As used herein, "plant expressible" means that the promoter is operable within a plant cell and is therefore capable of driving expression of a nucleotide sequence to which the promoter is operably linked within the plant cell. The promoter may be selected such that expression of the mega-endonuclease can be spatially or temporally regulated in any desired manner. For example, a promoter can be selected such that expression of the mega-endonuclease is constitutive, developmentally regulated, tissue specific, tissue preferred, cell specific, specific to a particular cellular compartment (i.e., organellar-specific), or the like. Additionally, the promoter can be chosen so that expression of the mega-endonuclease can be chemically induced in a plant, resulting in expression of the mega-endonuclease only in response to treatment of the plant cell or tissue with a chemical ligand. By combining promoter elements that confer specific expression with those conferring chemically induced expression, the mega-endonuclease can be expressed or activated within specific cells or tissues of the plant in response to a chemical application. Any of a variety of plant expressible promoters can be used to drive expression of the mega-endonuclease. Several of such promoters are described herein, and other such promoters are known in the art.

In another embodiment, the mega-endonuclease is introduced into the plant cell by being stably transformed into the genome of the plant cell. For example, the mega-endonuclease can be comprised in an expression cassette comprising the coding sequence of the mega-endonuclease operatively linked to a promoter capable of expression in plant tissues and cells. Suitable methods for stably transforming plant cells are known in the art and are described herein. In one embodiment, a plant cell that is stably transformed with the mega-endonuclease is also stably transformed with a target sequence. In another embodiment, a plant cell that is stably transformed with the mega-endonuclease is also stably transformed with a donor sequence.

As will be appreciated by one of skill in the art, a whole plant can be regenerated from a plant cell or a group of plant cells that has been stably transformed with a selected nucleotide sequence. This regenerated whole plant is then also referred to as being transformed with the selected nucleotide sequence. Thus, for example, in accordance with the methods disclosed herein, a first plant can be stably transformed with one or more expression cassettes comprising a mega-endonuclease and a donor sequence, and this first plant then can be crossed with a second plant that is stably transformed with a target sequence. Accordingly, expression of the mega-endonuclease in an F1 plant or seed can facilitate recombination between the target and donor sequences such that the HR-mediated recombination product is formed in the F1 plant or seed. The nucleotide sequence encoding the mega-endonuclease and the unrecombined portion(s) of the donor sequence can then be segregated from a nucleotide sequence comprising the recombination product sequence(s) through breeding.

In another embodiment, the mega-endonuclease can be introduced into a plant cell such that the plant cell transiently expresses the mega-endonuclease. For example, the mega-endonuclease coding sequence can be introduced into a plant cell through any known means for plant transformation, such as, for example, Agrobacterium or microprojectile bombardment. Frequently, the introduced nucleotide sequence is not integrated into the genome but can be transcribed nonetheless into mRNA.

In another embodiment, the coding sequence of the mega-endonuclease is supplied to the host cell in the form of messenger RNAs (mRNA). In this manner, the mega-endonuclease is provided to the host cell only transiently. The coding sequence for the mega-endonuclease can be inserted into a vector for in-vitro transcription of the RNA using methods described in Lebel et al. 1995 Theor. Appl. Genet. 91:899-906 and U.S. Pat. No. 6,051,409. The RNA then can be transformed into a host cell, such as a cell from a donor line or a target line, for example. In one embodiment, the RNA can be co-transformed into a host cell with a donor sequence. In an exemplary embodiment, the RNA can be transferred to a host cell using microprojectile bombardment, as described in U.S. Pat. No. 6,051,409. In another embodiment, the RNA can be introduced into protoplasts of a host cell by PEG-mediated transformation (see, e.g., Lebel et al. 1995 Theor. Appl. Genet. 91:899-906) or by electroporation. In another embodiment, other transformation techniques, such as microinjection of the RNA, can be used to introduce the RNA into the host cell.

In a further embodiment, an active mega-endonuclease can be introduced into a host cell as a protein, such as a purified protein, for example. The mega-endonuclease protein can be introduced into the cell by any suitable method known in the art, such as, for example, microinjection or electroporation. In another embodiment, the mega-endonuclease can be introduced into the host cell by microinjection together with a donor DNA sequence (see, e.g., Neuhaus et al. 1993 Cell 73:937-952). In another embodiment, the mega-endonuclease protein is introduced into the host cell through infection with *Agrobacterium* comprising a VirE2 or VirF fusion protein (see, e.g., Vergunst et al. 2000 Science 290:979-82).

In one embodiment, the coding sequence of the mega-endonuclease can be optimized for expression in a particular plant host. It is known in the art that the expression of heterologous proteins in plants can be enhanced by optimizing the coding sequences of the proteins according to the codon preference of the host plant. The preferred codon usage in plants differs from the preferred codon usage in certain microorganisms. A comparison of the codon usage within a cloned microbial ORF (open reading frame) to the codon usage in plant genes (and, in particular, genes from the selected host plant) enables an identification of the codons within the ORF that can be changed in an effort to optimize the coding sequence for expression in the host plant.

In one embodiment, the donor sequence comprises at least one sequence of interest. The sequence of interest may be included in an expression cassette, and expression of the sequence of interest may be controlled by any of the promoters described herein or by any other plant expressible promoter known in the art. The promoter that controls or drives expression of the sequence of interest can be included in the expression cassette that comprises the sequence of interest, or the promoter can be otherwise operably linked to the sequence of interest. Exemplary sequences of interest include, but are not limited to, sequences encoding traits related to any of the following desirable characteristics: waxy starch; herbicide tolerance; resistance to bacterial, fungal, or viral disease; insect resistance; abiotic stress resistance; enhanced nutritional quality; improved performance in an industrial process; altered reproductive capability, such as male sterility or male fertility; yield stability; yield enhancement; and the production of commercially valuable enzymes or metabolites in plants.

In another embodiment, the donor sequence may also include a donor marker sequence, such as a selectable or visible marker gene, for example. The donor marker sequence can be any marker sequence described herein or otherwise known in the art but is typically different from any marker sequence associated with the target homology sequence. In this context, "associated with the target homology sequence" means that the marker sequence, or a truncated form of the marker sequence, is part of the target sequence and includes the target homology sequence, such that the target sequence would be capable of expressing the marker sequence upon recombination with a donor that included the corresponding completion sequence, as described above. In such a case, the donor marker sequence can be selected such that the donor marker sequence is different from the marker sequence associated with the target homology sequence, and recombination of the target and donor results in a recombination product that includes two different marker sequences. As described herein, the donor marker sequence can be operably linked to a suitable promoter and/or a suitable termination sequence.

In another embodiment, the donor sequence can be stably integrated into a plant genome. A plant or plant cell transformed with the donor sequence can be obtained by any suitable transformation method, as described herein or by methods otherwise known in the art, and is used to form a donor cell line or plant line. Such a donor cell line or plant line may include a single copy of the donor sequence integrated into its genome. Once such a donor line has been obtained and identified, it may be further characterized, as described above with respect to the target line.

In one embodiment, a target line can be crossed with a donor line by methods of sexual reproduction known in the art, such as, for example, by pollinating the target line with pollen of the donor line and obtaining seed comprising both the target and donor sequences. An HR-mediated recombination product can result from an exchange of nucleotide sequences between a target sequence locus and a donor sequence locus.

In accordance with another aspect of the methods disclosed herein, a site-specific recombinase can be used to excise a portion of a target sequence that has been introduced into a host cell prior to introducing a donor sequence into that host cell. Exemplary site-specific recombinases (and corresponding recognition sites) include, but are not limited to, FLP (FRT), Cre (Lox), R (RS), Gin (gix), β (six), an integrase from any of bacteriophage-λ, HK022, φC31, or R4 (and their corresponding attB/attP or attL/attR sites), as well as any of several other recombinases that are known in the art (see, e.g., Nunes-Duby et al. 1998 Nucleic Acid Research 26:391-406; Smith and Thorpe 2002 Molecular Microbiology 44:299-307).

In accordance with another aspect of the methods disclosed herein, recombinase recognition sites and a corresponding site-specific recombinase can be used to modify an HR-recombination product in preparation for a successive round of targeted sequence integration and stacking.

Figure 6:
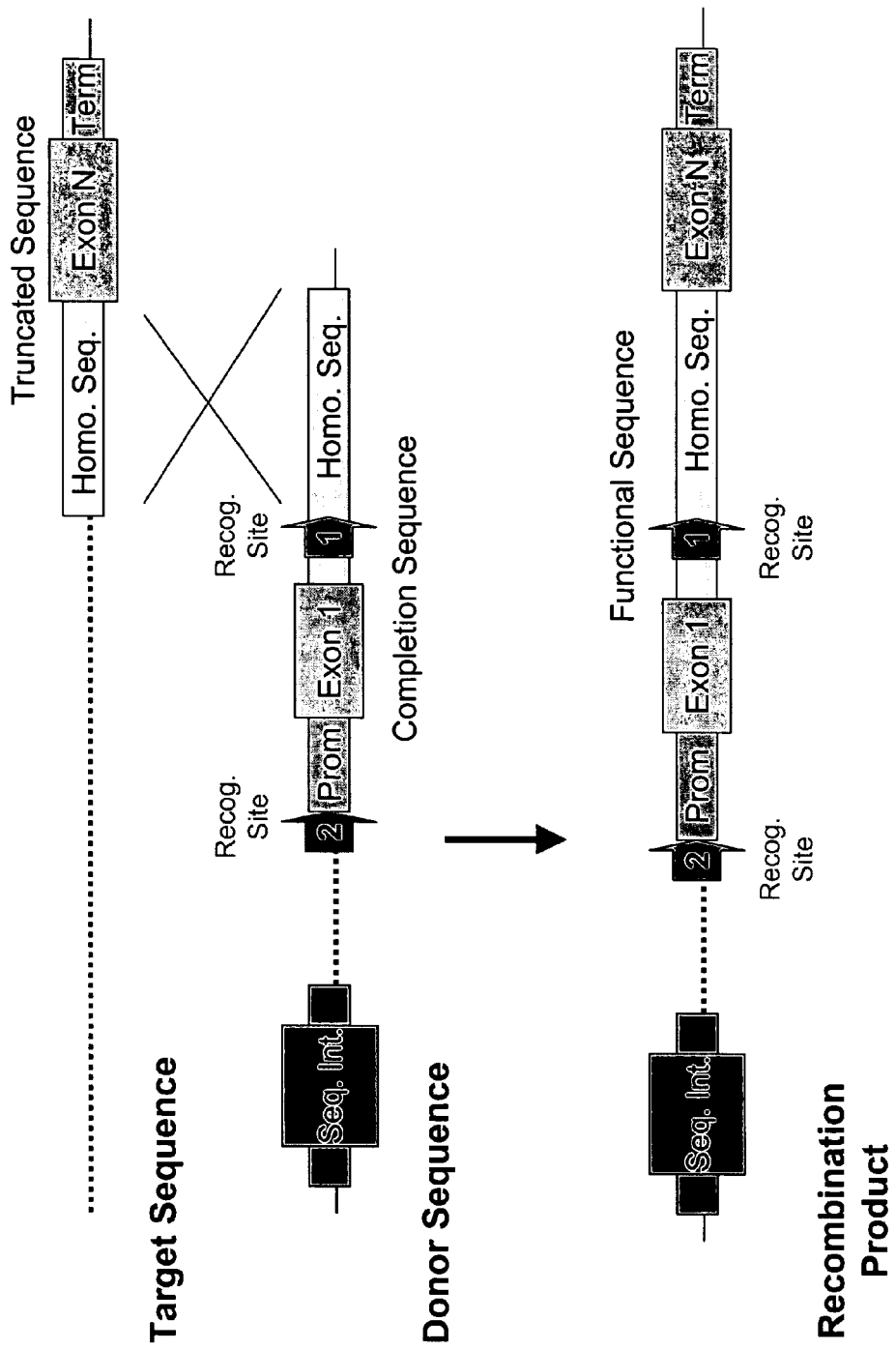

In one embodiment, a method for targeted nucleotide sequence stacking is provided, the method comprising: (a) providing a host cell comprising a chromosomally integrated target sequence, the target sequence comprising a truncated sequence comprising a homology sequence, the homology sequence comprising at least one intron sequence; (b) introducing into the host cell a donor sequence comprising (i) a sequence of interest, (ii) a completion sequence comprising a first recombinase recognition site and the homology sequence, and (iii) a second recombinase recognition site positioned between the sequence of interest and the completion sequence; and (c) obtaining in the host cell a recombination product comprising the sequence of interest, the second recombinase recognition site, and a functional sequence, the functional sequence comprising the first recombinase recognition site and the homology sequence; wherein the first and second recombinase recognition sites can be the same or different (FIG. 6). In another embodiment, the target sequence further comprises a first mega-endonuclease recognition sequence, the donor sequence further comprises a second mega-endonuclease recognition sequence positioned between the sequence of interest and the completion sequence, and the method further comprises, prior to obtaining the recombination product, introducing into the host cell a mega-endonuclease or a mega-endonuclease coding sequence, the mega-endonuclease or an expression product of the mega-endonuclease coding sequence being capable of recognizing the first mega-endonuclease recognition sequence. Optionally, either of these embodiments may be used in conjunction with a method for down-regulating the expression level of at least one RecQ gene that is present in the genome of the host cell. Optionally, any of these embodiments may be used in conjunction with a method for up-regulating the expression level of at least one recombination-related gene that is present in the genome of the host cell.

Figure 7A:
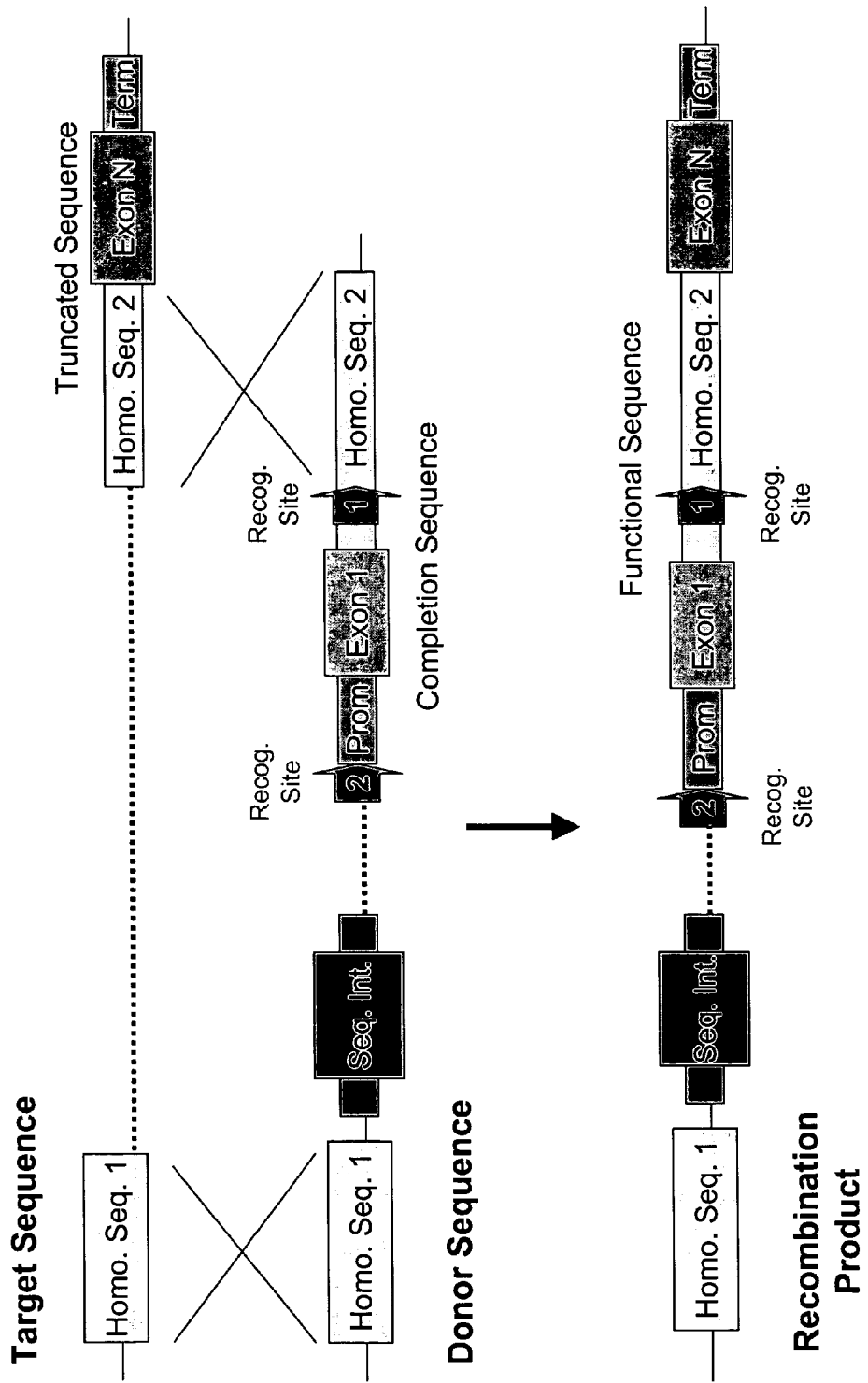

In another embodiment, a method for targeted nucleotide sequence stacking is provided, the method comprising: (a) providing a host cell comprising a chromosomally integrated target sequence, the target sequence comprising (i) a first homology sequence and (ii) a truncated sequence comprising a second homology sequence, the second homology sequence comprising at least one intron sequence; (b) introducing into the host cell a donor sequence comprising (i) the first homology sequence, (ii) a sequence of interest, (iii) a completion sequence comprising a first recombinase recognition site and the second homology sequence, and (iv) a second recombinase recognition site positioned between the sequence of interest and the completion sequence; and (c) obtaining in the host cell a recombination product comprising the first homology sequence, the sequence of interest, the second recombinase recognition site, and a functional sequence, the functional sequence comprising the first recombinase recognition site and the second homology sequence; wherein the first and second recombinase recognition sites can be the same or different (FIG. 7A). In another embodiment, the target sequence further comprises a first mega-endonuclease recognition sequence positioned between the first homology sequence and the truncated sequence, the donor sequence further comprises a second mega-endonuclease recognition sequence positioned between the sequence of interest and the completion sequence, and the method further comprises, prior to obtaining the recombination product, introducing into the host cell a mega-endonuclease or a mega-endonuclease coding sequence, the mega-endonuclease or an expression product of the mega-endonuclease coding sequence being capable of recognizing the first mega-endonuclease recognition sequence. Optionally, either of these embodiments may be used in conjunction with a method for down-regulating the expression level of at least one RecQ gene that is present in the genome of the host cell. Optionally, any of these embodiments may be used in conjunction with a method for up-regulating the expression level of at least one recombination-related gene that is present in the genome of the host cell.

Figure 7B:
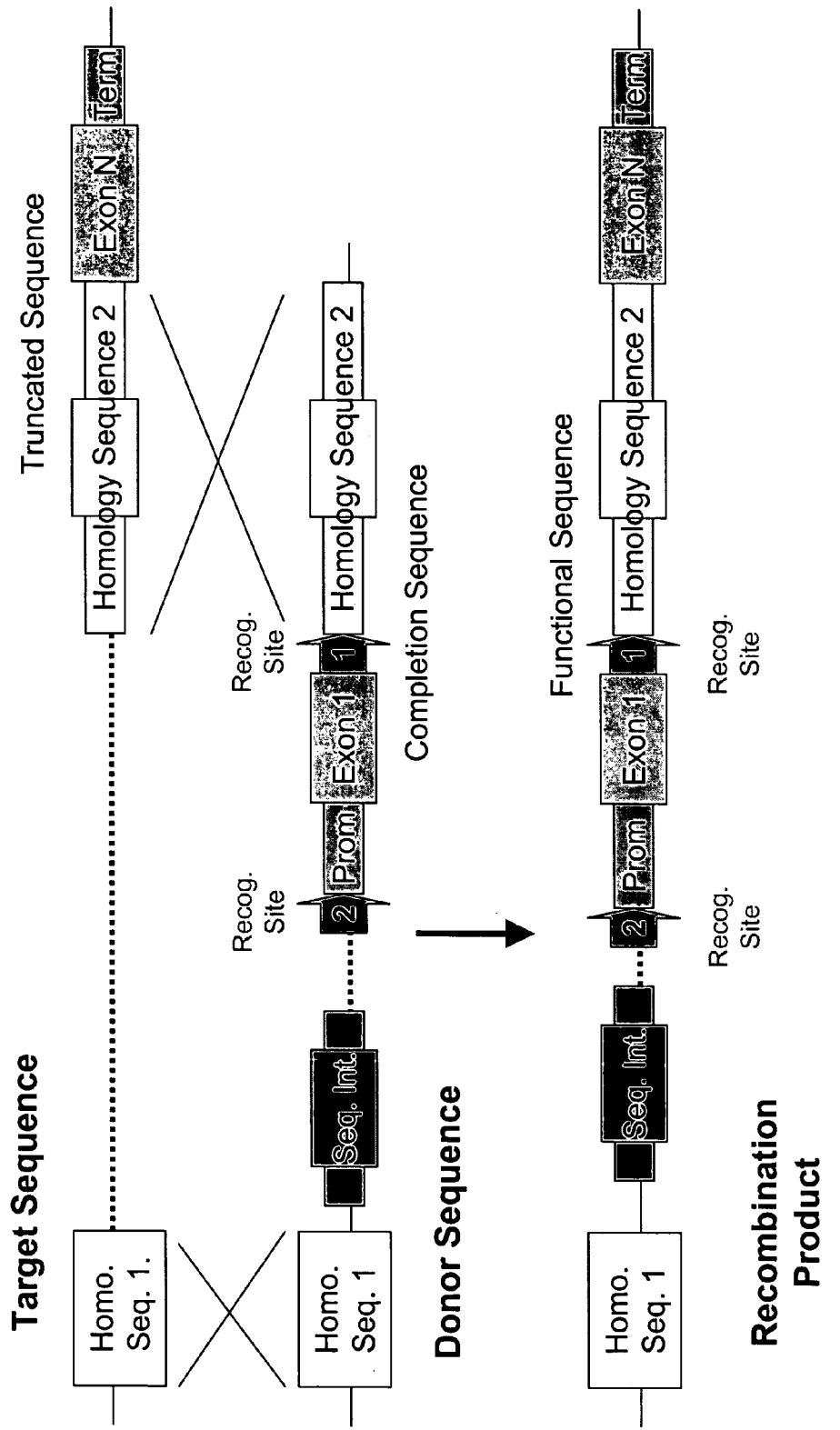

In another embodiment, a method for targeted nucleotide sequence stacking is provided, the method comprising: (a) providing a host cell comprising a chromosomally integrated target sequence, the target sequence comprising (i) a first homology sequence and (ii) a truncated sequence comprising a second homology sequence, the second homology sequence comprising two or more intron sequences; (b) introducing into the host cell a donor sequence comprising (i) the first homology sequence, (ii) a sequence of interest, (iii) a completion sequence comprising a first recombinase recognition site and the second homology sequence, and (iv) a second recombinase recognition site positioned between the sequence of interest and the completion sequence; and (c) obtaining in the host cell a recombination product comprising the first homology sequence, the sequence of interest, the second recombinase recognition site, and a functional sequence, the functional sequence comprising the first recombinase recognition site and the second homology sequence; wherein the first and second recombinase recognition sites can be the same or different (FIG. 7B). In another embodiment, the target sequence further comprises a first mega-endonuclease recognition sequence positioned between the first homology sequence and the truncated sequence, the donor sequence further comprises a second mega-endonuclease recognition sequence positioned between the sequence of interest and the completion sequence, and the method further comprises, prior to obtaining the recombination product, introducing into the host cell a mega-endonuclease or a mega-endonuclease coding sequence, the mega-endonuclease or an expression product of the mega-endonuclease coding sequence being capable of recognizing the first mega-endonuclease recognition sequence. Optionally, either of these embodiments may be used in conjunction with a method for down-regulating the expression level of at least one RecQ gene that is present in the genome of the host cell. Optionally, any of these embodiments may be used in conjunction with a method for up-regulating the expression level of at least one recombination-related gene that is present in the genome of the host cell.

Figure 8:
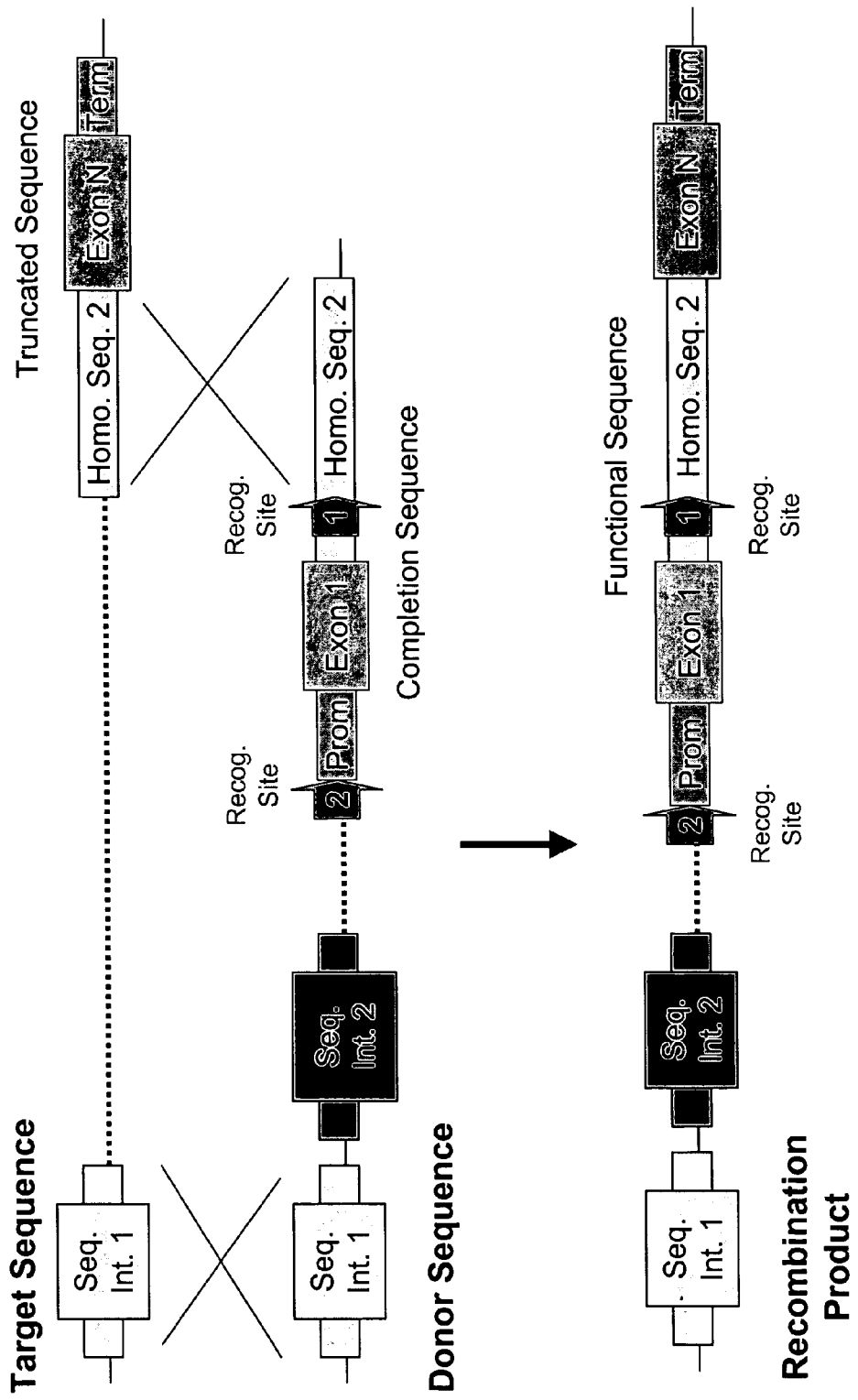

In another embodiment, a method for targeted nucleotide sequence stacking is provided, the method comprising: (a) providing a host cell comprising a chromosomally integrated target sequence, the target sequence comprising (i) a first homology sequence comprising a first sequence of interest and (ii) a truncated sequence comprising a second homology sequence, the second homology sequence comprising at least one intron sequence; (b) introducing into the host cell a donor sequence comprising (i) the first homology sequence, (ii) a second sequence of interest, (iii) a completion sequence comprising a first recombinase recognition site and the second homology sequence, and (iv) a second recombinase recognition site positioned between the second sequence of interest and the completion sequence; and (c) obtaining in the host cell a recombination product comprising the first homology sequence, the second sequence of interest, the second recombinase recognition site, and a functional sequence, the functional sequence comprising the first recombinase recognition site and the second homology sequence; wherein the first and second recombinase recognition sites can be the same or different (FIG. 8). In another embodiment, the target sequence further comprises a first mega-endonuclease recognition sequence positioned between the first homology sequence and the truncated sequence, the donor sequence further comprises a second mega-endonuclease recognition sequence positioned between the second sequence of interest and the completion sequence, and the method further comprises, prior to obtaining the recombination product, introducing into the host cell a mega-endonuclease or a mega-endonuclease coding sequence, the mega-endonuclease or an expression product of the mega-endonuclease coding sequence being capable of recognizing the first mega-endonuclease recognition sequence. Optionally, either of these embodiments may be used in conjunction with a method for down-regulating the expression level of at least one RecQ gene that is present in the genome of the host cell. Optionally, any of these embodiments may be used in conjunction with a method for up-regulating the expression level of at least one recombination-related gene that is present in the genome of the host cell.

Figure 9A:
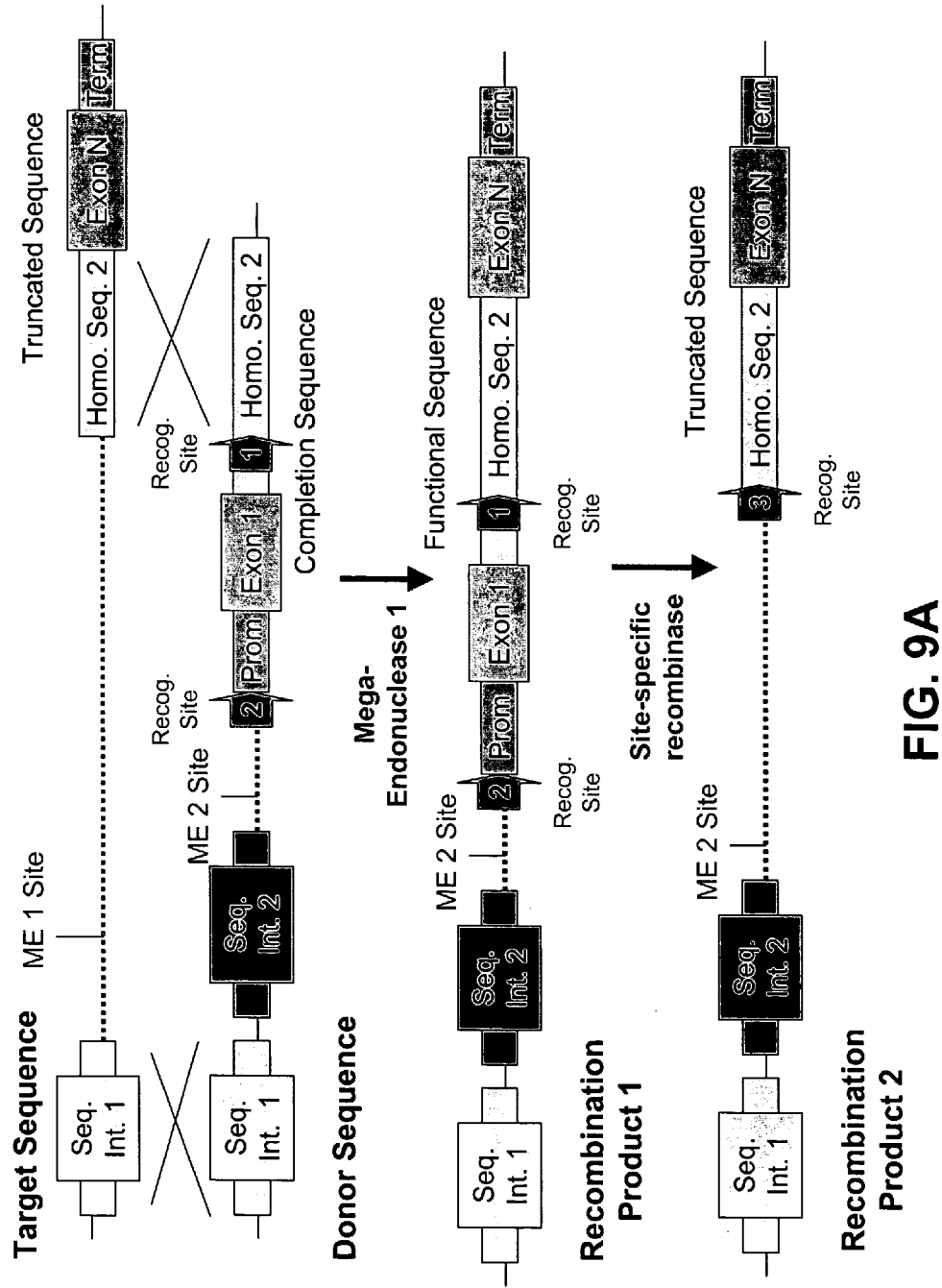

In one embodiment, a method for targeted nucleotide sequence stacking is provided, the method comprising: (a) providing a host cell comprising a chromosomally integrated target sequence, the target sequence comprising (i) a first homology sequence comprising a first sequence of interest, (ii) a truncated sequence comprising a second homology sequence, the second homology sequence comprising at least one intron sequence, and (iii) a first mega-endonuclease recognition sequence positioned between the first homology sequence and the truncated sequence; (b) introducing into the host cell a donor sequence comprising (i) the first homology sequence, (ii) a second sequence of interest, (iii) a completion sequence comprising a first recombinase recognition site and the second homology sequence, (iv) a second mega-endonuclease recognition sequence positioned between the second sequence of interest and the completion sequence, and (v) a second recombinase recognition site positioned between the second mega-endonuclease recognition sequence and the completion sequence; (c) introducing into the host cell a mega-endonuclease or a mega-endonuclease coding sequence, the mega-endonuclease or an expression product of the mega-endonuclease coding sequence being capable of recognizing the first mega-endonuclease recognition sequence; (d) obtaining in the host cell a recombination product comprising the first homology sequence, the second sequence of interest, the second recombinase recognition site, and a functional sequence, the functional sequence comprising the first recombinase recognition site and the second homology sequence; (e) introducing into the host cell a recombinase or a recombinase coding sequence, the recombinase or an expression product of the recombinase coding sequence being capable of recognizing the first and second recombinase recognition sites; and (f) obtaining in the host cell a recombination product comprising the first homology sequence, the second sequence of interest, the second mega-endonuclease recognition sequence, and a truncated sequence comprising a third recombinase recognition site and the second homology sequence; wherein the first and second recombinase recognition sites can be the same or different; wherein the second and third recombinase recognition sites can be the same or different; and wherein (b) and (c) may be performed in any order or simultaneously (FIG. 9A). Optionally, this embodiment may be used in conjunction with a method for down-regulating the expression level of at least one RecQ gene that is present in the genome of the host cell. Optionally, either of these embodiments may be used in conjunction with a method for up-regulating the expression level of at least one recombination-related gene that is present in the genome of the host cell.

Figure 9B:
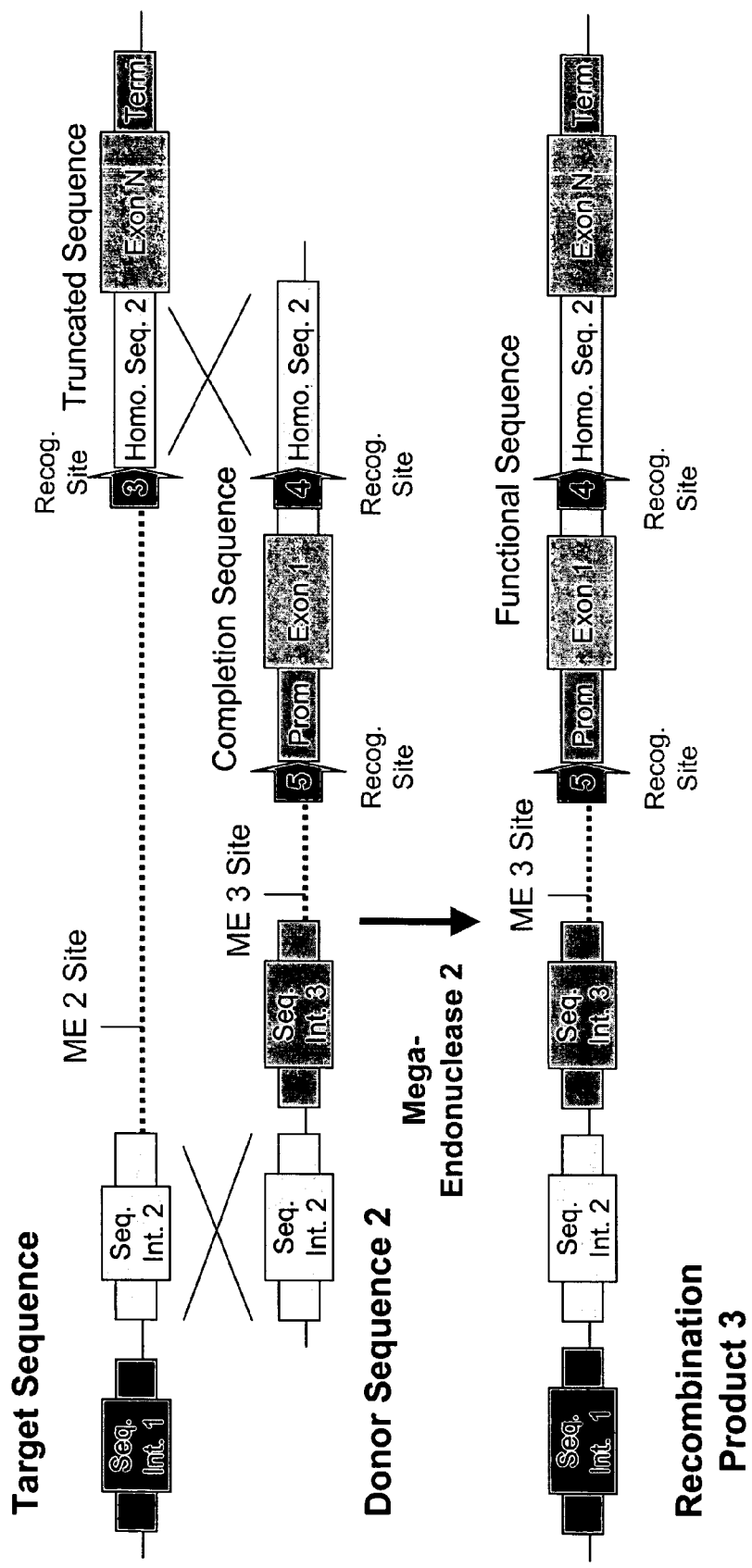

In another embodiment, a method for targeted nucleotide sequence stacking is provided, the method comprising: (a) providing a host cell comprising a chromosomally integrated target sequence, the target sequence comprising (i) a first homology sequence comprising a first sequence of interest, (ii) a truncated sequence comprising a second homology sequence, the second homology sequence comprising at least one intron sequence, and (iii) a first mega-endonuclease recognition sequence positioned between the first homology sequence and the truncated sequence; (b) introducing into the host cell a donor sequence comprising (i) the first homology sequence, (ii) a second sequence of interest, (iii) a first completion sequence comprising a first recombinase recognition site and the second homology sequence, (iv) a second mega-endonuclease recognition sequence positioned between the second sequence of interest and the completion sequence, and (v) a second recombinase recognition site positioned between the second mega-endonuclease recognition sequence and the completion sequence; (c) introducing into the host cell a mega-endonuclease or a mega-endonuclease coding sequence, the mega-endonuclease or an expression product of the mega-endonuclease coding sequence being capable of recognizing the first mega-endonuclease recognition sequence; (d) obtaining in the host cell a recombination product comprising the first homology sequence, the second sequence of interest, the second mega-endonuclease recognition sequence, the second recombinase recognition site, and a functional sequence, the functional sequence comprising the first recombinase recognition site and the second homology sequence; (e) introducing into the host cell a recombinase or a recombinase coding sequence, the recombinase or an expression product of the recombinase coding sequence being capable of recognizing the first and second recombinase recognition sites; (f) obtaining in the host cell a recombination product comprising the first homology sequence, the second sequence of interest, the second mega-endonuclease recognition sequence, and a truncated sequence comprising a third recombinase recognition site and the second homology sequence; (g) introducing into the host cell a second donor sequence comprising (i) a third homology sequence comprising the second sequence of interest, (ii) a third sequence of interest, (iii) a second completion sequence comprising a fourth recombinase recognition site and the second homology sequence, (iv) a third mega-endonuclease recognition sequence positioned between the third sequence of interest and the second completion sequence, and (v) a fifth recombinase recognition site positioned between the third mega-endonuclease recognition sequence and the second completion sequence; (h) introducing into the host cell a second mega-endonuclease or a second mega-endonuclease coding sequence, the second mega-endonuclease or an expression product of the second mega-endonuclease coding sequence being capable of recognizing the second mega-endonuclease recognition sequence; (i) obtaining in the host cell a recombination product comprising the first sequence of interest, the third homology sequence comprising the second sequence of interest, the third sequence of interest, the third mega-endonuclease recognition sequence, the fifth recombinase recognition site, and a functional sequence comprising the fourth recombinase recognition site and the second homology sequence; wherein the first and third mega-endonuclease recognition sequences may be the same or different; wherein the first and second recombinase recognition sites can be the same or different; wherein the second and third recombinase recognition sites can be the same or different; wherein the third and fifth recombinase recognition sites can be the same or different; wherein the fourth and fifth recombinase recognition sites can be the same or different; wherein (b) and (c) may be performed in any order or simultaneously; and wherein (g) and (h) may be performed in any order or simultaneously. As will be readily appreciated by one skilled in the art, steps (e) through (h) may be repeated as desired to obtain a host cell comprising multiple sequences of interest (FIGS. 9A and 9B). Optionally, this embodiment may be used in conjunction with a method for down-regulating the expression level of at least one RecQ gene that is present in the genome of the host cell. Optionally, either of these embodiments may be used in conjunction with a method for up-regulating the expression level of at least one recombination-related gene that is present in the genome of the host cell.

In accordance with another aspect of the methods disclosed herein, a target sequence that has been chromosomally integrated into the host cell genome can include a first recombinase recognition site and a functional sequence, such as a marker sequence, for example. The functional sequence can comprise a target homology sequence that includes a second recombinase recognition site. The portion of the target sequence that is positioned between the first and second recombination recognition sequences is an excisable sequence, which can be removed by a suitable recombinase that is introduced into the cell and is capable of recognizing the first and second recognition sequences. Removal of the exisable sequence by the recombinase transforms the functional sequence into a truncated sequence.

Figure 10:
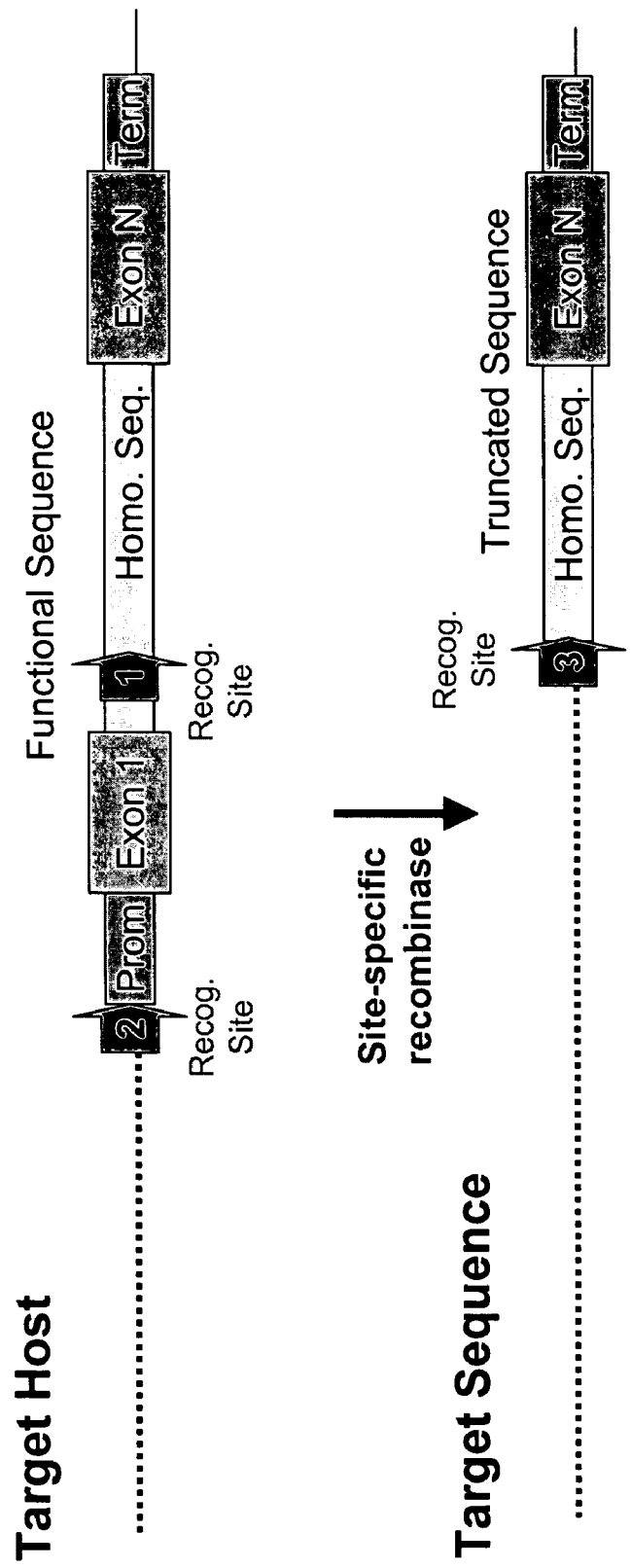

In one embodiment, a method for preparing a target sequence for targeted integration and stacking is provided, the method comprising: (a) providing a host cell comprising a chromosomally integrated target sequence, the target sequence comprising (i) a functional sequence comprising a homology sequence, the homology sequence comprising a first recombinase recognition site and at least one intron sequenceand and (ii) a second recombinase recognition site positioned upstream (i.e., to the 5' side) of the functional sequence; (b) introducing into the host cell a recombinase or a recombinase coding sequence, the recombinase or an expression product of the recombinase coding sequence being capable of recognizing the first and second recombinase recognition sites; and (c) obtaining in the host cell a recombination product comprising a truncated sequence comprising a third recombinase recognition site and the homology sequence; wherein the first and second recombinase recognition sites can be the same or different; and wherein the second and third recombinase recognition sites can be the same or different (FIG. 10). Optionally, the target sequence may further comprise a mega-endonuclease recognition sequence positioned upstream of the second recombinase recognition site.

Figure 11:
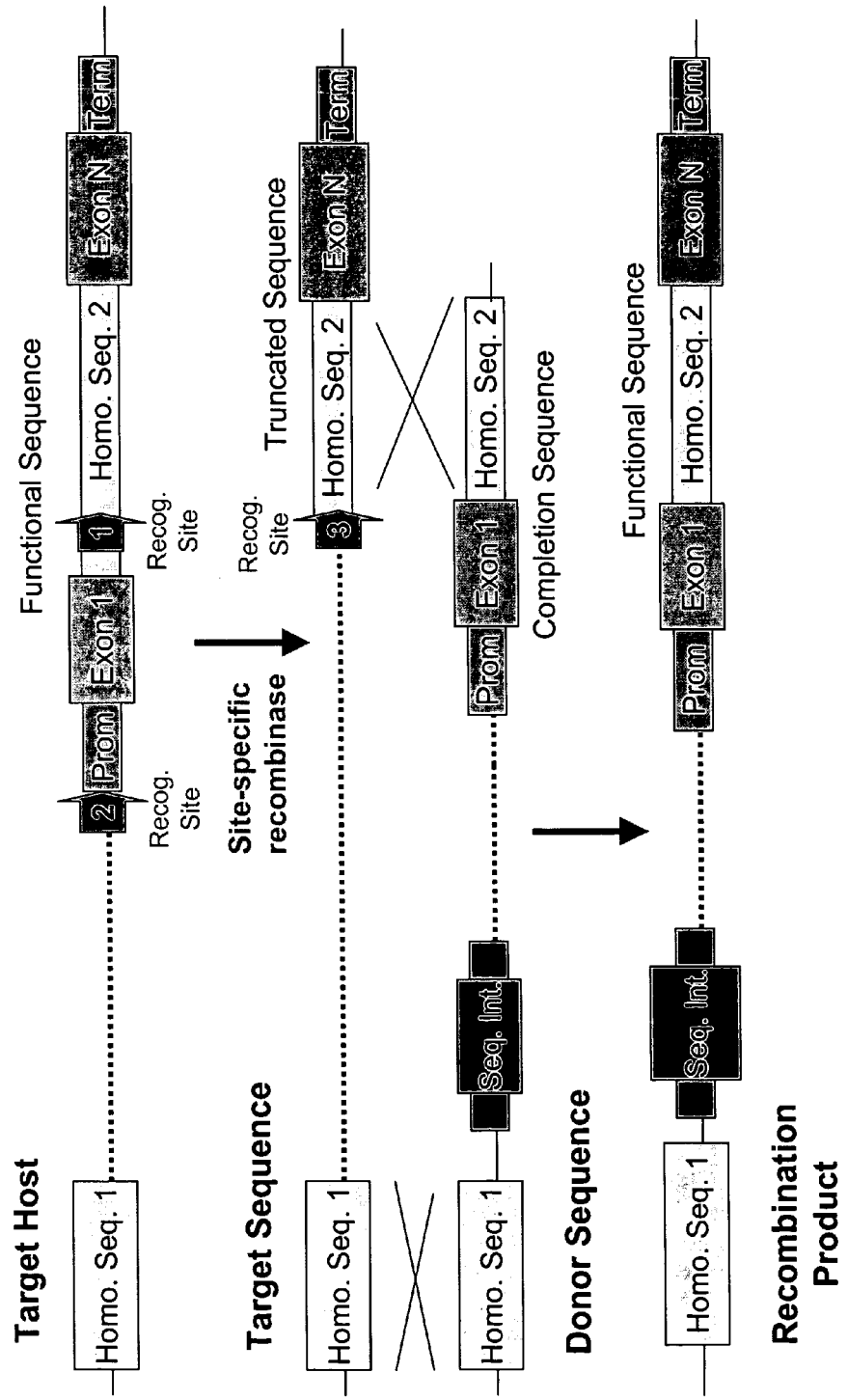

In another embodiment, a method for targeted nucleotide sequence stacking is provided, the method comprising: (a) providing a host cell comprising a chromosomally integrated target sequence, the target sequence comprising (i) a first homology sequence, (ii) a functional sequence comprising a second homology sequence, the second homology sequence comprising a first recombinase recognition site and at least one intron sequence, and (iii) a second recombinase recognition site positioned between the first homology sequence and the functional sequence; (b) introducing into the host cell a recombinase or a recombinase coding sequence, the recombinase or an expression product of the recombinase coding sequence being capable of recognizing the first and second recombinase recognition sites; (c) obtaining in the host cell a recombination product comprising the first homology sequence and a truncated sequence comprising a third recombinase recognition site and the second homology sequence; (d) introducing into the host cell a donor sequence comprising the first homology sequence, a sequence of interest, and a completion sequence, the completion sequence comprising the second homology sequence; and (e) obtaining in the host cell a recombination product comprising the first homology sequence, the sequence of interest, and the functional sequence comprising the second homology sequence; wherein the first and second recombinase recognition sites can be the same or different; and wherein the second and third recombinase recognition sites can be the same or different (FIG. 11). In another embodiment, the target sequence further comprises a mega-endonuclease recognition sequence positioned between the first homology sequence and the functional sequence, and the method further comprises, any time after step (c) and prior to step (e), introducing into the host cell a mega-endonuclease or a mega-endonuclease coding sequence, the mega-endonuclease or an expression product of the mega-endonuclease coding sequence being capable of recognizing the mega-endonuclease recognition sequence. Optionally, either of these embodiments may be used in conjunction with a method for down-regulating the expression level of at least one RecQ gene that is present in the genome of the host cell. Optionally, any of these embodiments may be used in conjunction with a method for up-regulating the expression level of at least one recombination-related gene that is present in the genome of the host cell.

Figure 12A:
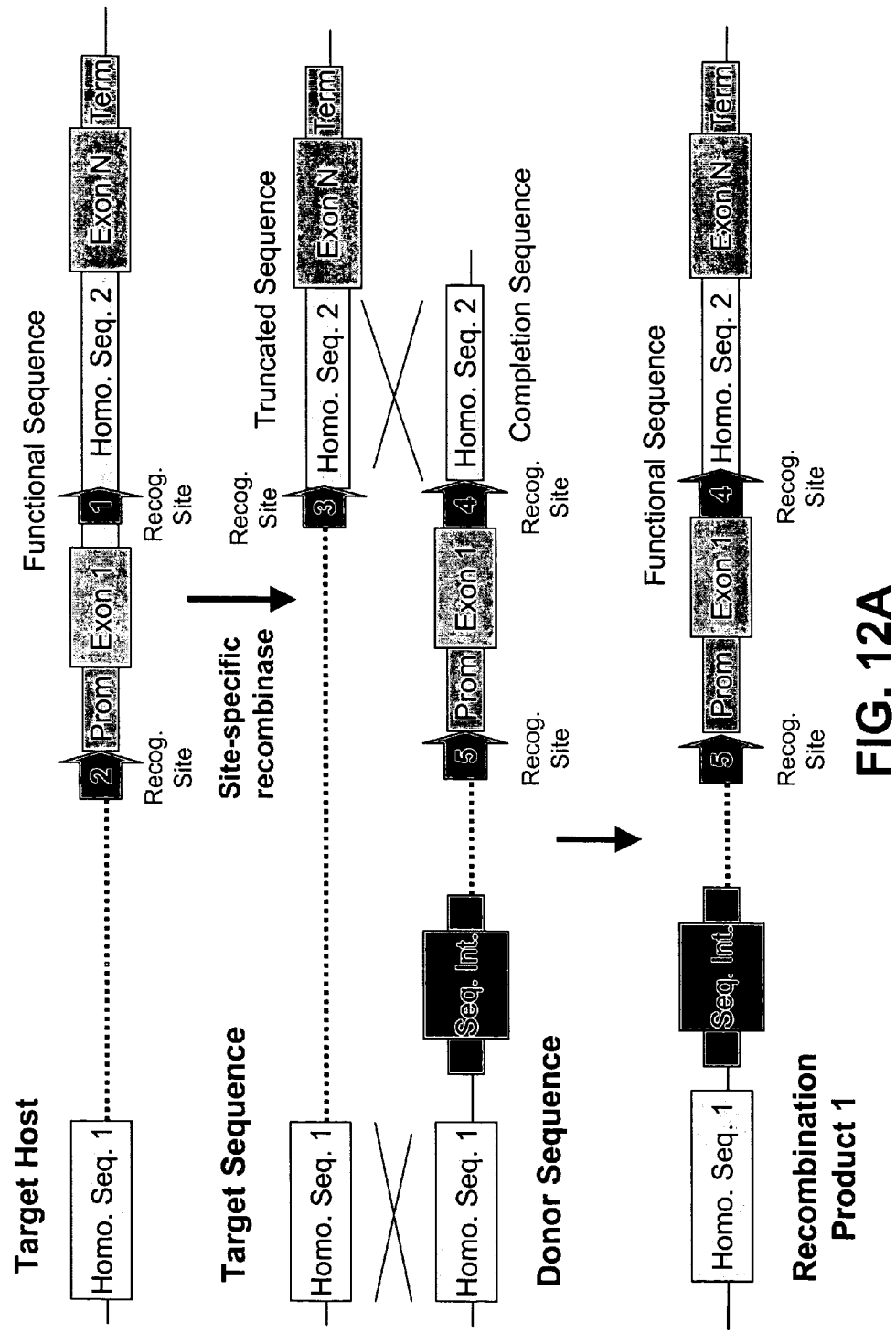
Figure 12B:
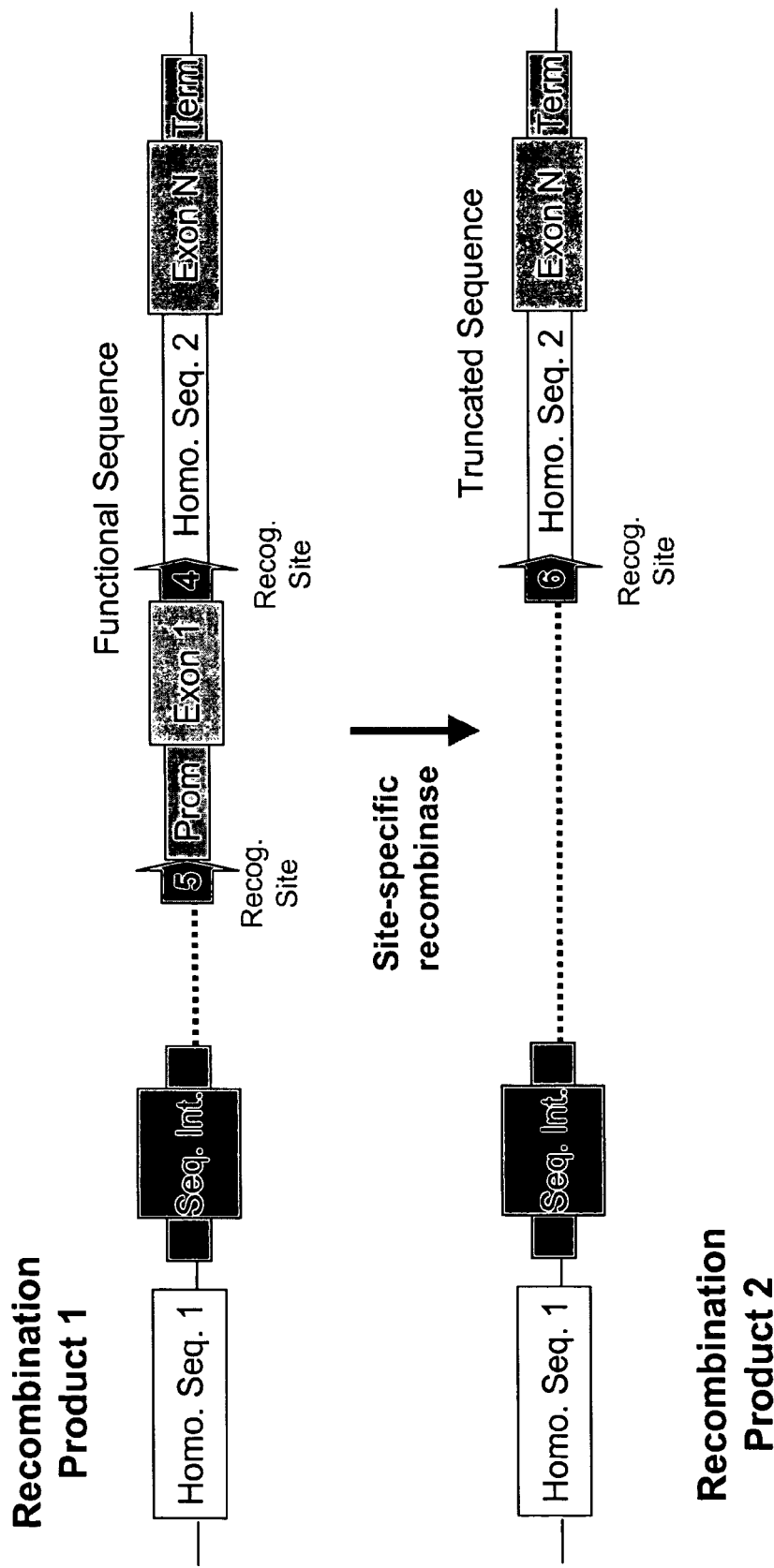

In another embodiment, a method for targeted nucleotide sequence stacking is provided, the method comprising: (a) providing a host cell comprising a chromosomally integrated target sequence, the target sequence comprising (i) a first homology sequence, (ii) a functional sequence comprising a second homology sequence, the second homology sequence comprising a first recombinase recognition site and at least one intron sequence, and (iii) a second recombinase recognition site positioned between the first homology sequence and the functional sequence; (b) introducing into the host cell a recombinase or a recombinase coding sequence, the recombinase or an expression product of the recombinase coding sequence being capable of recognizing the first and second recombinase recognition sites; (c) obtaining in the host cell a recombination product comprising the first homology sequence and a truncated sequence comprising a third recombinase recognition site and the second homology sequence; (d) introducing into the host cell a donor sequence comprising (i) the first homology sequence, (ii) a sequence of interest, (iii) a completion sequence, the completion sequence comprising a fourth recombinase recognition site and the second homology sequence, and (iii) a fifth recombinase recognition site positioned between the sequence of interest and the completion sequence; (e) obtaining in the host cell a recombination product comprising the first homology sequence, the sequence of interest, the fifth recombinase recognition site, and a functional sequence comprising the fourth recombinase recognition site and the second homology sequence; (f) introducing into the host cell the recombinase or the recombinase coding sequence; and (g) obtaining in the host cell a recombination product comprising the first homology sequence, the sequence of interest, and a truncated sequence comprising a sixth recombinase recognition site and the second homology sequence; wherein the first and second recombinase recognition sites can be the same or different; wherein the second and third recombinase recognition sites can be the same or different; wherein the third and fifth recombinase recognition sites can be the same or different; wherein the fourth and fifth recombinase recognition sites can be the same or different; and wherein the fifth and sixth recombinase recognition sites can be the same or different. Steps (d) through (f) may be repeated as desired, as detailed in a previously described embodiment, to obtain a host cell comprising multiple sequences of interest (FIGS. 12A-12B). In another embodiment, the target sequence further comprises a first mega-endonuclease recognition sequence positioned between the first homology sequence and the functional sequence, the donor sequence further comprises a second mega-endonuclease recognition sequence positioned between the sequence of interest and the completion sequence, and the method further comprises, any time after step (c) and prior to step (e), introducing into the host cell a mega-endonuclease or a mega-endonuclease coding sequence, the mega-endonuclease or an expression product of the mega-endonuclease coding sequence being capable of recognizing the first mega-endonuclease recognition sequence. Optionally, either of these embodiments may be used in conjunction with a method for down-regulating the expression level of at least one RecQ gene that is present in the genome of the host cell. Optionally, any of these embodiments may be used in conjunction with a method for up-regulating the expression level of at least one recombination-related gene that is present in the genome of the host cell.

In one embodiment, the recombinase can be introduced into the host cell as one or more nucleic acid molecules (DNA and/or RNA) that comprise the coding sequence for each constituent protein of the recombinase. The recombinase can be introduced as one or more expression cassettes comprising a coding region for each constituent protein, wherein each coding region is operatively linked to a promoter capable of expression in plant cells. Promoters for each expression cassette can be selected such that expression of the recombinase can be spatially or temporally regulated in any desired manner. For example, a promoter can be selected such that expression of the recombinase is constitutive, developmentally regulated, tissue specific, tissue preferred, cell specific, specific to a particular cellular compartment (i.e., organellar-specific), or the like. Additionally, promoters can be chosen so that expression of the recombinase can be chemically induced in a plant, resulting in expression of the recombinase only in response to treatment of the plant cell or tissue with a chemical ligand. By combining promoter elements that confer specific expression with those conferring chemically induced expression, the recombinase can be expressed or activated within specific cells or tissues of the plant in response to a chemical application. Any of a variety of plant expressible promoters can be used to drive expression of the recombinase. Several of such promoters are described herein, and others of such promoters are known in the art.

In another embodiment, the recombinase can be introduced into the plant cell by being stably transformed into the genome of the plant cell. For example, the recombinase can be comprised in one or more expression cassettes comprising the coding sequences of the recombinase, whereby the coding sequence for each protein component of the recombinase is operatively linked to a promoter capable of expression in plant tissues and cells. Suitable methods for stably transforming plant cells are known in the art and are described herein. In one embodiment, a plant cell that is stably transformed with the recombinase is also stably transformed with a donor sequence.

In one embodiment, the recombinase can be introduced into a plant cell such that the plant cell transiently expresses the recombinase. For example, one or more nucleotide sequences comprising the recombinase coding sequence can be introduced into a plant cell through *Agrobacterium* or microprojectile bombardment, for example. Much of the introduced nucleotide sequences are not integrated into the genome but can be transcribed into mRNA.

In another embodiment, the coding sequence(s) of the recombinase can be supplied to the host cell in the form of messenger RNAs (mRNA). In this manner, the recombinase can be provided to the host cell only transiently. The coding sequence for each of the proteins of the recombinase can be inserted into a vector for in-vitro transcription of the RNA using methods described in Lebel et al. 1995 Theor. Appl. Genet. 91:899-906 and U.S. Pat. No. 6,51,409. The RNA then can be transformed into a host cell, such as a cell from a donor line or a target line, for example. In one embodiment, the RNA is co-transformed into a host cell with a donor sequence. In an exemplary embodiment, the RNA is transferred to a host cell using microprojectile bombardment, as described in U.S. Pat. No. 6,051,409. In another embodiment, the RNA is introduced into protoplasts of a host cell by PEG-mediated transformation (see, e.g., Lebel et al. 1995 Theor. Appl. Genet. 91:899-906) or by electroporation. In another embodiment, other transformation techniques, such as microinjection of the RNA, are used to introduce the RNA into the host cell.

In a further embodiment, an active recombinase can be introduced into a host cell as one or more proteins, such as one or more purified proteins, for example. The recombinase protein can be introduced into the cell by any suitable method known in the art, such as, for example, microinjection or electroporation. In another embodiment, the recombinase is introduced into the host cell by microinjection together with a donor DNA sequence (see, e.g., Neuhaus et al. 1993 Cell 73:937-952). In another embodiment, the recombinase protein is introduced into the host cell through infection with *Agrobacterium* comprising a VirE2 or VirF fusion protein (see, e.g., Vergunst et al. 2000 Science 290:979-82).

In one embodiment, the coding sequence(s) of the recombinase can be optimized for expression in a particular plant host. It is known in the art that the expression of heterologous proteins in plants can be enhanced by optimizing the coding sequences of the proteins according to the codon preference of the host plant. The preferred codon usage in plants differs from the preferred codon usage in certain microorganisms. A comparison of the codon usage within a cloned microbial ORF (open reading frame) to the codon usage in plant genes (and, in particular, genes from the selected host plant) enables an identification of the codons within the ORF that can be changed in an effort to optimize the coding sequence for expression in the host plant.

General Methods and Components

Nucleotide sequences utilized in accordance with various embodiments of the invention can be incorporated into a host cell using conventional recombinant DNA technology. Generally, this involves using standard cloning procedures known in the art to insert a nucleotide sequence into an expression system, such as a vector, for example, with respect to which the nucleotide sequence is heterologous. The vector may contain additional elements that may be used during transcription and/or translation of the inserted coding sequence by the host cell that contains the vector. A large number of vector systems known in the art can be used, such as plasmids, bacteriophage viruses, other modified viruses, and the like. The components of the expression system may also be modified to increase expression levels of the inserted coding sequence. For example, truncated sequences, nucleotide substitutions, or other modifications may be employed. Expression systems known in the art can be used to transform virtually any crop plant cell under suitable conditions. Transformed cells may then be regenerated into whole plants. Methods for transforming dicots and monocots are known to those skilled in the art, as described below.

I. Expression Cassettes

Coding sequences intended for expression in transgenic plants are first assembled in expression cassettes 3' to a suitable promoter expressible in plants. The expression cassettes can also comprise any further sequences needed or selected for the expression of the transgene. Such sequences include, but are not restricted to, transcription terminators, extraneous sequences to enhance expression such as introns, viral sequences, and sequences intended for the targeting of the gene product to specific organelles and cell compartments. These expression cassettes can then be transferred to the plant transformation vectors described herein.

The following is a description of various components of typical expression cassettes.

A. Promoters

Selection of the promoter to be used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and selection should reflect the desired location of accumulation of the gene product. Alternatively, the selected promoter can drive expression of the gene under various inducing conditions. Promoters vary in their strength, i.e., ability to promote transcription. Depending upon the host cell system utilized, any one of a number of suitable promoters can be used, including the gene's native promoter. The following are non-limiting examples of promoters that can be used in the expression cassettes employed in the present invention.

1. Constitutive Promoters a. Ubiquitin Promoters

Ubiquitin is a gene product known to accumulate in many cell types and its promoter has been cloned from several species for use in transgenic plants (e.g. sunflower—Binet et al. 1991 Plant Science 79: 87-94; maize—Christensen et al. 1989 Plant Molec. Biol. 12: 619-632; and *Arabidopsis*—Norris et al. 1993 *Plant Mol. Biol.* 21:895-906). The maize ubiquitin promoter has been developed in transgenic monocot systems and its sequence and vectors constructed for monocot transformation are disclosed in the patent publication EP 0 342 926. Taylor et al. (1993 Plant Cell Rep. 12: 491-495) describe a vector (pAHC25) that comprises the maize ubiquitin promoter and first intron and its high activity in cell suspensions of numerous monocotyledons when introduced via microprojectile bombardment. The *Arabidopsis* ubiquitin promoter may also be used with the nucleotide sequences of the present invention. The ubiquitin promoter is suitable for gene expression in transgenic plants, including both monocotyledons and dicotyledons. Suitable vectors include derivatives of pAHC25 or any of the transformation vectors described in this application. The vectors can be modified by the introduction of appropriate ubiquitin promoter and/or intron sequences.

b. The CaMV 35S Promoter

Construction of the plasmid pCGN1761 is described in published patent application EP 0 392 225 (Example 23). The plasmid contains the "double" CaMV 35S promoter and the tml transcriptional terminator with a unique EcoRI site between the promoter and the terminator and has a pUC-type backbone. A derivative of pCGN1761 is constructed which has a modified polylinker, which includes NotI and XhoI sites in addition to the existing EcoRI site. This derivative, designated pCGN1761ENX, is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and XbaI sites 5' to the promoter and XbaI, BamHI and BglI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that can enhance translation. This is particularly useful when over-expression is desired. For example, pCGN1761ENX can be modified by optimization of the translational initiation site as described in Example 37 of U.S. Pat. No. 5,639,949.

c. The Actin Promoter

Several isoforms of actin are known to be expressed in most cell types and consequently the actin promoter is suitable for use as a constitutive promoter. In particular, the promoter from the rice ActI gene has been cloned and characterized (McElroy et al. 1990 Plant Cell 2: 163-171). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al. 1991 Mol. Gen. Genet. 231: 150-160). These incorporate the ActI-intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy et al. (1991 Mol. Gen. Genet. 231: 150-160)) can be easily modified for gene expression and are particularly suitable for use in monocotyledonous hosts. For example, promoter-containing fragments can be removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al. 1993 Plant Cell Rep. 12: 506-509).

2. Inducible Expression a. PR-1 Promoters

The double 35S promoter in pCGN1761ENX can be replaced with any other promoter of choice that will result in suitably high expression levels. By way of example, one of the chemically regulatable promoters described in U.S. Pat. No. 5,614,395, such as the tobacco PR-1a promoter, can replace the double 35S promoter. Alternatively, the *Arabidopsis* PR-1 promoter described in Lebel et al. 1998 *Plant J.* 16:223-233 can be used. The promoter of choice can be excised from its source by restriction enzymes; alternatively, it can be PCR-amplified using primers that carry appropriate terminal restriction sites. If PCR-amplification is undertaken, then the promoter can be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104) and transferred to plasmid pCGN1761ENX (Uknes et al. 1992 *Plant Cell* 4: 645-656). The plasmid pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators can be employed to induce expression of the selected coding sequence in plants transformed in accordance with various embodiments of the invention, including the benzothiadiazole, isonicotinic acid, and salicylic acid compounds disclosed in U.S. Pat. Nos. 5,523,311 and 5,614,395.

b. Ethanol-Inducible Promoters

A promoter inducible by certain alcohols or ketones, such as ethanol, can also be used to confer inducible expression of a coding sequence in accordance with various embodiments of the invention. Such a promoter is, for example, the alcA gene promoter from *Aspergillus nidulans* (Caddick et al. 1998 *Nat. Biotechnol* 16:177-180). In *A. nidulans*, the alcA gene encodes alcohol dehydrogenase I, the expression of which is regulated by the AlcR transcription factors in presence of the chemical inducer. For the purposes of the present disclosure, the CAT coding sequences in plasmid palcA:CAT comprising a alcA gene promoter sequence fused to a minimal 35S promoter (Caddick et al. 1998 *Nat. Biotechnol* 16:177-180) can be replaced by a selected coding sequence to form an expression cassette having the coding sequence under the control of the alcA gene promoter. This is carried out using methods well known in the art.

c. Glucocorticoid-Inducible Promoter

Induction of expression of a nucleic acid sequence using systems based on steroid hormones is also contemplated. For example, a glucocorticoid-mediated induction system is used (Aoyama and Chua 1997 *The Plant Journal* 11: 605-612) and gene expression is induced by application of a glucocorticoid, such as a synthetic glucocorticoid (e.g., dexamethasone). In one embodiment, the glutocorticoid is present at a concentration ranging from about 0.1 mM to about 1 mM. In another embodiment, the glutocorticoid is present at a concentration ranging from about 10 mM to 100 mM. For the purposes of the present disclosure, the luciferase gene sequences can be replaced by a sequence of interest to form an expression cassette having a sequence of interest under the control of six copies of the GAL4 upstream activating sequences fused to the 35S minimal promoter. This is carried out using methods well known in the art. The transacting factor comprises the GAL4 DNA-binding domain (Keegan et al. 1986 *Science* 231: 699-704) fused to the transactivating domain of the herpes viral protein VP16 (Triezenberg et al. 1988 *Genes Devel.* 2: 718-729) fused to the hormone-binding domain of the rat glucocorticoid receptor (Picard et al. 1988 *Cell* 54: 1073-1080). The expression of the fusion protein can be controlled by any promoter suitable for expression in plants, as known in the art or described here. This expression cassette can also comprise a sequence of interest fused to the 6×GAL4/minimal promoter. Thus, tissue- or organ-specificity of the fusion protein can be achieved, leading to inducible tissue- or organ-specificity of the expression cassette.

d. Wound-Inducible Promoters

Wound-inducible promoters can also be suitable for gene expression. Numerous such promoters have been described (e.g. Xu et al. 1993 Plant Molec. Biol. 22: 573-588, Logemann et al. 1989 Plant Cell 1: 151-158, Rohrmeier & Lehle 1993 Plant Molec. Biol. 22: 783-792, Firek et al. 1993 Plant Molec. Biol. 22: 129-142, Warner et al. 1993 Plant J. 3: 191-201) and all are suitable for use with various embodiments of the invention. Logemann et al. describe the 5' upstream sequences of the dicotyledonous potato wunI gene. Xu et al. show that a wound-inducible promoter from the dicotyledon potato (pin2) is active in the monocotyledon rice. Further, Rohrmeier & Lehle describe the cloning of the maize WipI cDNA, which is wound induced and which can be used to isolate the cognate promoter using standard techniques. Similar, Firek et al. and Warner et al. have described a wound-induced gene from the monocotyledon *Asparagus officinalis*, which is expressed at local wound and pathogen invasion sites. Using cloning techniques well known in the art, these promoters can be transferred to suitable vectors, fused to a sequence of interest, for example, and used to express the sequence of interest at sites of plant wounding.

3. Tissue-Specific or Tissue-Preferred Expression a. Root-Preferred Expression

Another pattern of gene expression is root expression. A suitable root promoter for use with various embodiments of the invention is the promoter of the maize metallothionein-like (MTL) gene described by de Framond (FEBS 290: 103-106 (1991)) and also in U.S. Pat. No. 5,466,785. This "MTL" promoter is transferred to a suitable vector such as pCGN1761ENX for the insertion of a selected gene and subsequent transfer of the entire promoter-gene-terminator cassette to a transformation vector of interest.

b. Pith-Preferred Expression

Patent Application WO 93/07278 describes the isolation of the maize trpA gene, which is preferentially expressed in pith cells. The gene sequence and promoter extending up to −1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

c. Leaf-Specific Expression

A maize gene encoding phosphoenol carboxylase (PEPC) has been described by Hudspeth & Grula (1989 Plant Molec Biol 12: 579-589). Using standard molecular biological techniques the promoter for this gene can be used to drive the expression of any gene in a leaf-specific manner in transgenic plants.

d. Pollen-Specific Expression

WO 93/07278 (published Apr. 15, 1993; Ciba Geigy) describes the isolation of the maize calcium-dependent protein kinase (CDPK) gene, which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a sequence of interest in a pollen-specific manner.

B. Transcriptional Terminators

A variety of transcriptional terminators are available for use in the expression cassettes of the present invention. These are responsible for the termination of transcription beyond the transgene and correct mRNA polyadenylation. Suitable transcriptional terminators are those that are known to function in plants and include, but are not limited to, the CaMV 35S terminator, the tml terminator, the nopaline synthase terminator and the pea rbcS E9 terminator. These can be used in both monocotyledons and dicotyledons. In addition, a gene's native transcription terminator can be used.

C. Sequences for the Enhancement or Regulation of Expression

Numerous sequences have been found to enhance gene expression from within the transcriptional unit, and these sequences can be used in conjunction with various genes to increase their expression in transgenic plants.

Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al. 1987 *Genes Develop.* 1: 1183-1200). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. 1987 *Nucl. Acids Res.* 15: 8693-8711; Skuzeski et al. 1990 *Plant Molec. Biol.* 15: 65-79). Other leader sequences known in the art include but are not limited to: picornavirus leaders, for example, EMCV leader (*Encephalomyocarditis* 5' noncoding region)

(Elroy-Stein, Fuerst, and Moss 1989 *PNAS USA* 86:6126-6130); potyvirus leaders, for example, TEV leader (Tobacco Etch Virus) (Allison et al., 1986); MDMV leader (Maize Dwarf Mosaic Virus); *Virology* 154:9-20); human immunoglobulin heavy-chain binding protein (BiP) leader, (Macejak and Sarnow 1991 *Nature* 353: 90-94); untranslated leader from the coat protein mRNA of alfalfa mosaic virus (AMV RNA 4), (Jobling and Gehrke 1987 *Nature* 325:622-625; tobacco mosaic virus leader (TMV), (Gallie et al. 1989 *Molecular Biology of RNA*, pages 237-256); and Maize Chlorotic Mottle Virus leader (MCMV) (Lommel et al. 1991 *Virology* 81:382-385). See also, Della-Cioppa et al. 1987 *Plant Physiology* 84:965-968.

D. Synthetic Genes

In various embodiments of the invention, coding sequences for selected proteins, such as a mega-endonuclease or a site-specific recombinase, for example, can be optimized for expression in a particular plant host. It is known in the art that the optimization of protein expression in plants can be enhanced by optimizing the coding regions of genes to the codon preference of the host. Accordingly, the preferred codon usage in plants differs from the preferred codon usage in certain microorganisms. Comparison of the usage of codons within a cloned microbial ORF to usage in plant genes (and in particular genes from the target plant) enables an identification of the codons within the ORF that can be changed. Typically, plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

Plant genes typically have a GC content of more than 35%. ORF sequences which are rich in A and T nucleotides can cause several problems in plants. Firstly, motifs of ATTTA are believed to cause destabilization of message RNA (mRNA) and are found at the 3' end of many short-lived mRNAs. Secondly, the occurrence of polyadenylation signals, such as AATAAA, at inappropriate positions within the mRNA is believed to cause premature truncation of transcription. In addition, monocotyledons may recognize AT-rich sequences as introns and may identify flanking splice sites (see below).

Plants differ from microorganisms in that their mRNAs do not possess a defined ribosome-binding site. Rather, it is believed that ribosomes attach to the 5' end of the mRNA and scan for the first available ATG at which to start translation. Nevertheless, it is believed that there is a preference for certain nucleotides adjacent to the ATG and that expression of microbial genes can be achieved by the inclusion of a eukaryotic consensus translation initiator at the ATG. Clontech (1993/1994 catalog, page 210, incorporated herein by reference) have suggested one sequence as a consensus translation initiator for the expression of the *E. coli* uidA gene in plants. Further, Joshi (1987 NAR 15: 6643-6653) has compared many plant sequences adjacent to the ATG and suggests another consensus sequence. In situations where difficulties are encountered in the expression of microbial ORFs in plants, inclusion of one of these sequences at the initiating ATG may improve translation. In such cases, the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

| Position Before the Initiating ATG in 14 Maize Genes: | | | | | | | | | |
|---|---|---|---|---|---|---|---|---|---|
| −10 | −9 | −8 | −7 | −6 | −5 | −4 | −3 | −2 | −1 |

|   | −10 | −9 | −8 | −7 | −6 | −5 | −4 | −3 | −2 | −1 |
|---|---|---|---|---|---|---|---|---|---|---|
| C | 3 | 8 | 4 | 6 | 2 | 5 | 6 | 0 | 10 | 7 |
| T | 3 | 0 | 3 | 4 | 3 | 2 | 1 | 1 | 1 | 0 |
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which the nucleotide sequence is being incorporated, and the sequence adjacent to the ATG modified to incorporate the preferred nucleotides.

Genes cloned from non-plant sources and not optimized for expression in plants may also contain motifs which may be recognized in plants as 5' or 3' splice sites and may be cleaved, thus generating truncated or deleted mRNAs. These sites can be removed using techniques well known in the art.

Techniques for modifying coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. See, e.g., EP 0 385 962, EP 0 359 472, and WO 93/07278. In most cases, it is preferable to assay the expression of gene constructions using transient assay protocols (which are well known in the art) prior to their use in generating transgenic plants.

II. Plant Transformation Vectors and Selectable Markers

Numerous transformation vectors known to those of ordinary skill in the plant transformation arts are available for plant transformation, and the nucleotide sequences pertinent to the invention can be used in conjunction with any such vectors. The selection of a particular vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. 1982 Gene 19: 259-268; Bevan et al. 1983 Nature 304:184-187), the bar gene, which confers resistance to the herbicide phosphinothricin (White et al. 1990 Nucl. Acids Res 18: 1062, Spencer et al. 1990 Theor. Appl. Genet 79: 625-631), the hpt gene, which confers resistance to the antibiotic hygromycin (Blochinger & Diggelmann Mol Cell Biol 4: 2929-2931), and the dhfr gene, which confers resistance to methotrexate (Bourouis et al. 1983 EMBO J. 2(7): 1099-1104), the EPSPS gene, which confers resistance to glyphosate (U.S. Pat. Nos. 4,940,835 and 5,188,642), and the mannose-6-phosphate isomerase gene (also referred to herein as the phosphomannose isomerase,or PMI, gene), which provides the ability to metabolize mannose (U.S. Pat. Nos. 5,767,378 and 5,994,629).

A. Vectors Suitable for *Agrobacterium* Transformation

Many vectors are available for transformation using *Agrobacterium tumefaciens*. These typically carry at least one T-DNA border sequence and include vectors such as pBIN19 (Bevan Nucl. Acids Res. (1984)). Below, the construction of two typical vectors suitable for *Agrobacterium* transformation is described.

1. pCIB200 and pCIB2001

The binary vectors pcIB200 and pCIB2001 are used for the construction of recombinant vectors for use with *Agrobacterium* and are constructed in the following manner. pTJS75kan is created by NarI digestion of pTJS75 (Schmidhauser & Helinski 1985 J. Bacteriol. 164: 446-455) allowing excision of the tetracycline-resistance gene, followed by insertion of an AccI fragment from pUC4K carrying an NPTII (Messing & Vierra 1982 Gene 19: 259-268; Bevan et al. 1983 Nature 304: 184-187; McBride et al. 1990 Plant Molecular Biology 14: 266-276). XhoI linkers are ligated to the EcoRV fragment of PCIB7 which contains the left and right T-DNA borders, a plant selectable nos/nptII chimeric gene and the pUC polylinker (Rothstein et al. 1987 Gene 53: 153-161), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites, also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

2. pCIB10 and Hygromycin Selection Derivatives thereof

The binary vector pCIB10 contains a gene encoding kanamycin resistance for selection in plants and T-DNA right and left border sequences. pCIB10 incorporates sequences from the wide host-range plasmid pRK252 allowing it to replicate in both *E. coli* and *Agrobacterium*. Its construction is described by Rothstein et al. (1987 Gene 53: 153-161). Various derivatives of pCIB10 are constructed, which incorporate the gene for hygromycin B phosphotransferase described by Gritz et al. (1983 Gene 25: 179-188). These derivatives enable selection of transgenic plant cells on hygromycin only (pCIB743), or hygromycin and kanamycin (pCIB715, pCIB717).

B. Vectors Suitable for non-*Agrobacterium* Transformation

Transformation without the use of *Agrobacterium tumefaciens* circumvents the requirement for T-DNA sequences in the chosen transformation vector, and, consequently, vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation), and microinjection. The choice of vector depends largely on the selected transformation method. Below, the construction of typical vectors suitable for non-*Agrobacterium* transformation is described.

1. pCIB3064 pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the published PCT application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 may be obtained from the John Innes Centre, Norwich and the 400 bp SmaI fragment containing the bar gene from *Streptomyces viridochromogenes* is excised and inserted into the HpaI site of pCIB3060 (Thompson et al. 1987 EMBO J 6: 2519-2523). This generated pCIB3064, which comprises the bar gene (for herbicide selection) under the control of the CaMV 35S promoter and terminator, a gene for ampicillin resistance (for selection in *E. coli*), and a polylinker with the unique sites SphI, PstI, HindIII, and BamHI. This vector is suitable for the cloning of plant expression cassettes containing their own regulatory signals.

2. pSOG19 and pSOG35

The plasmid pSOG35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize Adh1 gene (~550 bp), and 18 bp of the GUS untranslated leader sequence from pSOG10. A 250-bp fragment encoding the *E. coli* dihydrofolate reductase type II gene is also amplified by PCR, and these two PCR fragments are assembled with a SacI-PstI fragment from pB1221 (Clontech), which comprises the pUC19 vector backbone and the nopaline synthase terminator. Assembly of these fragments generates pSOG19, which contains the 35S promoter in fusion with the intron 6 sequence, the GUS leader, the DHFR gene, and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

C. Vector Suitable for Chloroplast Transformation

For expression of a nucleotide sequence in plant plastids, plastid transformation vector pPH143 (WO 97/32011, example 36) can be used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

III. Transformation Methods

Target, donor, and other nucleotide sequence cassettes in accordance with the various embodiments of the invention can be introduced into the plant cell in a number of art-recognized ways. Methods for regenerating plants are also well known in the art. For example, Ti plasmid-derived vectors have been utilized for the delivery of foreign DNA, as well as direct DNA uptake, liposomes, electroporation, microinjection, and microprojectiles. In addition, bacteria from the genus *Agrobacterium* can be utilized to transform plant cells.

Once a desired DNA sequence has been transformed into a particular plant species, it may be propagated in that species or moved into other varieties of the same species, particularly including commercial varieties, using traditional breeding techniques.

Below are descriptions of representative techniques for transforming both dicotyledonous and monocotyledonous plants, as well as a representative plastid transformation technique.

A. Transformation of Dicotyledons

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al. 1984 EMBO J 3: 2717-2722, Potrykus et al. 1985 Mol. Gen. Genet. 199: 169-177, Reich et al. 1986 Biotechnology 4: 1001-1004, and Klein et al. 1987 Nature 327: 70-73. In each case, the transformed cells are regenerated into whole plants using standard techniques known in the art.

Agrobacterium-mediated transformation is a preferred technique for the transformation of dicotyledons because of its high transformation efficiency and its broad utility with many different species. Agrobacterium transformation typically involves the transfer of a binary vector carrying a foreign DNA of interest (e.g., pCIB200 or pCIB2001) to an appropriate Agrobacterium strain, which may depend on the complement of vir genes carried by the host Agrobacterium strain either on a co-resident Ti plasmid or chromosomally (e.g., strain CIB542 for pCIB200 and pCIB2001 (Uknes et al. 1993 Plant Cell 5: 159-169). The transfer of the recombinant binary vector to Agrobacterium is accomplished by a triparental mating procedure using E. coli carrying the recombinant binary vector, a helper E. coli strain which carries a plasmid such as pRK2013 and which is able to mobilize the recombinant binary vector to the target Agrobacterium strain. Alternatively, the recombinant binary vector can be transferred to Agrobacterium by DNA transformation (Hofgen & Willmitzer, 1988 Nucl. Acids Res. 16: 9877).

Transformation of the target plant species by recombinant Agrobacterium usually involves co-cultivation of the Agrobacterium with explants from the plant and follows protocols well known in the art. Transformed tissue is regenerated on a selection medium containing the compound (e.g., the antibiotic, herbicide, or carbohydrate source) that corresponds to the selectable marker sequence (e.g., antibiotic or herbicide resistance gene or PMI gene) present between the binary plasmid's T-DNA borders.

Another approach to transforming a plant cell with a gene involves propelling inert or biologically active particles at plant tissues and cells. This technique is disclosed in U.S. Pat. Nos. 4,945,050, 5,036,006, and 5,100,792, all issued to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium, or a bacteriophage, each containing DNA sought to be introduced) can also be propelled into plant cell tissue.

B. Transformation of Monocotyledons

Transformation of most monocotyledon species has now also become routine. Preferred techniques include direct gene transfer into protoplasts using PEG (polyethylene glycol) or electroporation techniques, particle bombardment into callus tissue, and transformation mediated by Agrobacterium. Transformations can be undertaken with a single DNA species or multiple DNA species (i.e., co-transformation), both of which are suitable for use with the methods disclosed herein. Co-transformation may have the advantage of avoiding complete vector construction and of generating transgenic plants with unlinked loci for the gene of interest and either the selectable marker or other sequences, such as those used for improving transformation efficiency, thereby enabling the removal of the selectable marker or other sequences in subsequent generations, should this be regarded as desirable. However, a disadvantage of the use of co-transformation is the less than 100% frequency with which separate DNA species are integrated into the genome (Schocher et al. 1986 Biotechnology 4: 1093-1096).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (1990 Plant Cell 2: 603-618) and Fromm et al. (1990 Biotechnology 8: 833-839) have published techniques for transformation of A188-derived maize line using particle bombardment. Furthermore, WO 93/07278 and Koziel et al. (1993 Biotechnology 11: 194-200) describe techniques for the transformation of elite inbred lines of maize by particle bombardment. This technique utilizes immature maize embryos of 1.5-2.5 mm length excised from a maize ear 14-15 days after pollination and a PDS-1000He device for bombardment.

Transformation of rice can also be undertaken by direct gene transfer techniques utilizing protoplasts or particle bombardment. Protoplast-mediated transformation has been described for Japonica-types and Indica-types (Zhang et al. 1988 Plant Cell Rep 7: 379-384; Shimamoto et al. 1989 Nature 338: 274-277; Datta et al. 1990 Biotechnology 8: 736-740). Both types are also routinely transformable using particle bombardment (Christou et al. 1991 Biotechnology 9: 957-962). Furthermore, WO 93/21335 describes techniques for the transformation of rice via electroporation. Patent Application EP 0 332 581 describes techniques for the generation, transformation, and regeneration of Pooideae protoplasts. These techniques allow the transformation of Dactylis and wheat.

Furthermore, wheat transformation has been described by Vasil et al. (1992 Biotechnology 10: 667-674) using particle bombardment into cells of type C long-term regenerable callus, and also by Vasil et al. (1993 Biotechnology 11: 1553-1558) and Weeks et al. (1993 Plant Physiol. 102: 1077-1084) using particle bombardment of immature embryos and immature embryo-derived callus.

One technique for wheat transformation involves the transformation of wheat by particle bombardment of immature embryos and includes either a high sucrose or a high maltose step prior to gene delivery. Prior to bombardment, any convenient number of embryos (0.75-1 mm in length) can be plated onto MS medium with 3% sucrose (Murashiga & Skoog 1962 Physiologia Plantarum 15: 473-497) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS +1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See, WO 94/00977 and U.S. Pat. No. 5,591,616. Rice transformation using *Agrobacterium* has been described in a number of publications, including Hiei et al. 1994 Plant J. 6:271-282, Dong et al. 1996 Molecular Breeding 2:267-276, and Hiei et al. 1997 Plant Molecular Biol. 35:205-218. Efficient maize transformation using *Agrobacterium* infection of immature embryos and various selection markers also has been described (Ishida et al. Nature Biotechnology 14:745-750; Negrotto et al. 2000 Plant Cell Reports 19:798-803; and Li et al. 2003 Plant Physiol. 133: 736-747).

C. Transformation of Plastids

Seeds of *Nicotiana tabacum* c.v. 'Xanthi nc' are germinated seven per plate in a 1 inch circular array on T agar medium and bombarded 12-14 days after sowing with 1 μm tungsten particles (M10, Biorad, Hercules, Calif.) coated with DNA from plasmids pPH143 and pPH145 essentially as described (Svab and Maliga 1993 *PNAS* 90: 913-917). Bombarded seedlings are incubated on T medium for two days after which leaves are excised and placed abaxial side up in bright light (350-500 μmol photons/m$^2$/s) on plates of RMOP medium (Svab, Hajdukiewicz, and Maliga 1990 *PNAS* 87: 8526-8530) containing 500 μg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al. (1989) *Molecular Cloning: A Laboratory Manual*, Cold Spring Harbor Laboratory, Cold Spring Harbor). BamHI/EcoRI-digested total cellular DNA (Mettler 1987 *Plant Mol Biol Reporter* 5: 346-349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride et al. 1994 *PNAS* 91: 7301-7305) and transferred to the greenhouse.

The foregoing describes various embodiments of the invention and is not intended to limit the scope of the invention as defined in the appended claims. The following Examples are included merely to demonstrate the practice of selected embodiments and should be regarded in an illustrative, rather than a restrictive, manner.

EXAMPLES

Standard recombinant DNA and molecular cloning techniques used here are well known in the art and are described by Ausubel (ed.), CURRENT PROTOCOLS IN MOLECULAR BIOLOGY, John Wiley and Sons, Inc. (1994); J. Sambrook, et al., MOLECULAR CLONING: A LABORATORY MANUAL, 3d Ed., Cold Spring Harbor, N.Y.: Cold Spring Harbor Laboratory Press (2001); and T. J. Silhavy, M. L. Berman, and L. W. Enquist, EXPERIMENTS WITH GENE FUSIONS, Cold Spring Harbor Laboratory, Cold Spring Harbor, N.Y. (1984).

Example 1

Construction of a Modified Neomycin Phosphotransferase II (nptII) Gene with Four *Arabidopsis thaliana* Introns To introduce four *Arabidopsis thaliana* introns into the neomycin phosphotransferase II gene (nptII), which confers kanamycin resistance, individual introns and nptII coding sub-regions (artificial exons) were amplified with PCR and then combined by a second round of PCR to form hybrid fragments containing *Arabidopsis* intron-nptII exon cassettes. Each cassette was cloned individually and combined using standard DNA recombination methods. NptII exon 1 was amplified using primers NPTFA (SEQ ID NO:1: 5'-GAT CTC TAG AAT GAT TGA ACA AGA TGG ATT-3') and NPTRA (SEQ ID NO:2. 5'-TCG CAG CTT GGT ACC TGC AGT TCA TTC AGG GC-3') from pCIB200 (Rothstein et al., Gene 53:153-161, 1987). The PCR product was digested with XbaI/PstI and inserted into XbaI/PstI-digested pNOV2799 to form pNOV205. pNOV2799 was derived from pNOV2711. pNOV2799 was derived from pNOV205 by replacing the SacII/XbaI polylinker with the SpeI/XbaI polylinker from pLITMUS28 (New England Biolab). pNOV204 is a pBluescript vector containing the Smas promoter (Ni et al. 1996 *Plant .J* 7: 661-676.) The intron in the untranslated leader of AtBAF60 was amplified from *A. thaliana* ecotype Columbia DNA with primers IntBAFFW (SEQ ID NO:3: 5'-GCC CTG AAT GAA CTG CAG GTA CCA AGC TGC GA-3') and IntBAFRV (SEQ ID NO:4: 5'-GCC GCG CTG CCT CGT CCT GAA AAA TTC AGA AA-3'). AtBAF60 (CHC1) is a gene that shares homology with the mammalian nucleosome-remodeling factor BAF60. NptII exon 2 was amplified from pCIB200 using primers NPTF2 (SEQ ID NO:5: 5'-TTT CTG AAT TTT TCA GGA CGA GGC AGC GCG GC-3') and NPTR2 (SEQ ID NO:6: 5'-GAA TAG TAC TAA TAC CTG GCA CTT CGC CCA ATA G-3'). A PAL1 intron was amplified from *Arabidopsis thaliana* ecotype Landsberg erecta using primers IntPALFW (SEQ ID NO:7: 5'-TTA GTA CTA TTC TTT TGT TCT CTA ATC AGA-3') and IntPALRV (SEQ ID NO:8: 5'-TGA CAG GAG ATC CTG CCC TGT AAC GAA CAA AAA CAT-3'). NptII exon 3 was amplified from pCIB200 using primers NPTFC (SEQ ID NO:9: 5'-ATG TTT TTG TTC GTT ACA GGG CAG GAT CTC CTG TCA-3') and NPTR3 (SEQ ID NO:10: 5'-ATC GAT TCA TAT ATA TAC CTG GTC GAC AAG ACC GGC-3'). A tubulin-1-β intron (760 bps) was amplified from *Arabidopsis thaliana* ecotype Columbia with primers IntTUBFW (SEQ ID NO:11: 5'-CAG GTA TAT ATA TGA ATC GAT TTC TCC CTT-3') and IntTUBRV (SEQ ID NO:12: 5'-TCG TCC AGA TCA TCC TGT AAT ACA GAA ATG TT-3'). NptII exon 4 was amplified from pCIB200 (Rothstein et al. 1987 Gene 53:153-161) with primers NPTFD (SEQ ID NO:13: 5'-AAC ATT TCT GTA TTA CAG GAT GAT CTG GAC GA) and NPTR4 (SEQ ID NO:14: 5'-GGA AAA GCT TAA TTA CCT CGC CGT CGG GCA TG-3'). A tubulin-1-α intron (560 bps) was amplified from *Arabidopsis thaliana* ecotype Columbia with primers IntTUAFW (SEQ ID NO:15: 5'-GTA ATT AAG CTT TTC CAC CTC TCT TGT T-3') and IntTUARV (SEQ. ID NO:16: 5'-GAT CCT GCA GCA ATG GAA AAA TAT TTC AAT AC-3'). NptII exon 5 was amplified from pCIB200 with primers NPTFE (SEQ ID NO:17: 5'-ATT GCT GCA GGA TCT CGT CGT GAC CCA TGG-3') and NPTR5 (SEQ ID NO:18: 5'-CAT TAG GAT CCT CAG AAG AAC TCG TCA A-3'). All of the above PCR products were gel purified and used as templates for a second round of PCR amplification. All PCR reactions were carried out with a mixture of Taq polymerase and Pfu polymerase (30 to 1, unit/unit) in a Perkin-Elmer thermocycler 9600.

Purified AtBAF60 intron and nptII exon 2 PCR fragments were used as templates for amplification with primers Int-BAFFW and NPTR2, and the resulting PCR product was cloned into a pCR2.1-TOPO vector to form pNOV2708. The PAL1 intron and nptII exon 3 were amplified using primers IntPALFW and NPTR3, and the PCR product was cloned into pCR2.1-TOPO to form pNOV2709. The tubulin-1-β intron and nptII exon 4 PCR fragments were amplified using primers IntTUBFW and NPTR4, and the resulting PCR product was cloned into pCR2.1-TOPO to form pNOV2710. The tubulin-1-α intron and nptIi exon 5 fragments were co-amplified using IntTUAFW and NPTR5 primers, and the resulting PCR product was inserted into pCR2.1-TOPO to form pNOV2712. Plasmid pNOV2708 was digested partially with BglII. A linker was formed by annealing two oligonuleotides, FRT-BGL2 (SEQ ID NO:19: 5'-GAT CTG AAG TTC CTA TTC TCT AGA AAG TAT AGG AAC TTC G-3') and FRTBAM1 (SEQ ID NO:20: 5'-GAT CCG AAG TTC CTA TAC TTT CTA GAG AAT AGG AAC TTC A-3'). This linker, which contained an FRT site, was inserted into the BglII site in the AtBAF60 intron to form pNOV2715. The PAL1 gene 3'-UTR was amplified from *Arabidopsis thaliana* ecotype Landsberg erecta using primers TPALBGLII (SEQ ID NO:21: 5'-TGT TAA GAT CTT AGT CCT CTG TTT TTT TCT-3') and TPALSACI (SEQ ID NO:22: 5'-CTT GAG CTC TTC TAT AAC CCT AGA TGG CTA-3'). The PAL1 3'-UTR PCR product was digested with BglII and SacI and then inserted into BglII/SacI-digested pLITMUS28 to form pNOV2707. All the inserts in the above clones were sequenced to ensure that no mutations were introduced into the coding sequence.

The individual intron-nptII exon cassette was then recombined to form a full-length modified nptII gene. The AtBAF60 intron-nptII exon 2 fragment was removed from pNOV2715 by partial PstI and complete XhoI digestion and inserted into PstI/XbaI-digested pNOV2711 to form pNOV2718. The tubulin-1-β intron-exon 4 fragment was released from pNOV2710 by ClaI/HindIII double-digestion and inserted into ClaI/HindIII-digested pNOV2709 to form pNOV2716, containing PAL1 intron-nptII exon 3-tubulin-1-β intron-nptII exon 4. A BglII/SacI fragment containing the PAL1 3'-UTR was removed from pQD7A1 and inserted into BamHI/SacI-digested pNOV2712 to form pNOV2717. The 1.5 kb XhoI/HindIII and 1.1 kb HindIII/SacI fragments containing intron-exon cassettes were removed from pNOV2716 and pNOV2717, respectively, and inserted into XhoI/SacI-digested pBluescript II KS(+) to form pNOV2719. Plasmid pNOV2719 was digested with SacI and ScaI, and the 2.6 kb SacI/ScaI fragment containing intron-exons and PAL 3'-UTR was isolated into pNOV2718 partially digested with SacI and ScaI to form pNOV2720. Plasmid pNOV2720 then contained the full-length modified nptII gene with four *Arabidopsis* introns (FIG. 14) under the control of a modified super MAS (mSmas) promoter.

Example 2

Construction of a Control Vector for Dicot Plants

Figure 16:
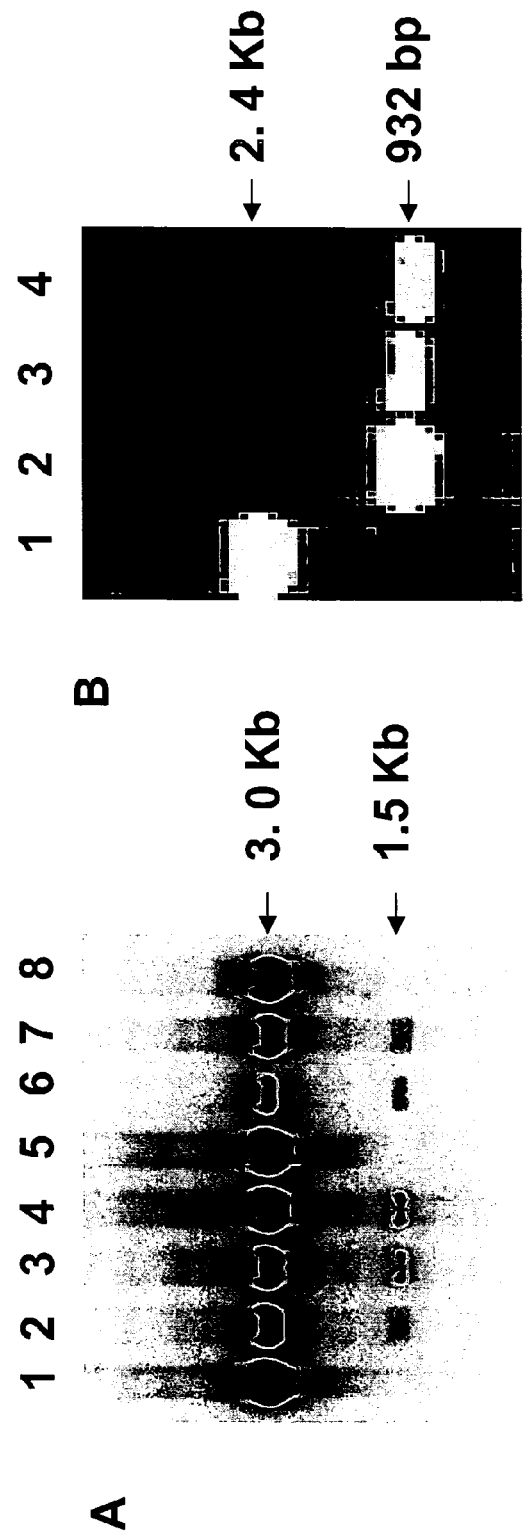
FIGS. 16A-16B represent a PCR analysis of recombinant lines that have been re-transformed with a FLP expression vector.
Figure 16:
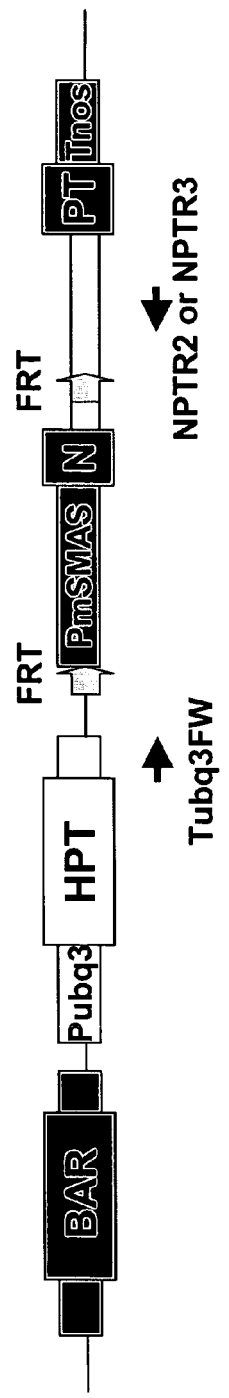

The 4489 base pair SacI/XhoI fragment containing the mSmas promoter-modified nptII-PAL1 3' end cassette was removed from pNOV2720 and inserted into pNOV2722, which was partially digested with SacI and XhoI to form control construct pNOV2731 (FIG. 16). pNOV2731 was transformed into *Agrobacterium* LBA4404, and the resulting *Agrobacterium* strain was used to transform both *Arabidopsis* and tobacco plants. Phosphinothricin (PPT) resistant transformants produced seeds that were highly resistant to kanamycin. The results demonstrate that the modified nptII gene is fully functional and the introns can be spliced out efficiently.

Example 3

Construction of Target Vectors for Dicot Plants

The coding region for the bar gene, which provides resistance to the herbicide glufosinate, was amplified from pGSFR1 (D'Halluin et al. 1992 *Methods Enzymol*. 216: 415-26) using two primers, BARCLA (SEQ ID NO:23: 5'-TCA TAT CGA TGA GCC CAG AAC GAC GCC-3') and BAR-BGL (SEQ ID NO:24: 5'-TTT GAG ATC TTC ATA TCT CGG TGA CGG GCA GG-3'). The gel-purified PCR product was digested with BglII and inserted into SmaI/BamHI-digested pHSPnos to form pNOV2703. pHSPnos is a pSPORT1 base vector (GIBCO BRL, Rockville, MD) containing the *Brassica* HSP80 promoter (see U.S. Pat. No. 5,612,472) followed by the nopaline synthase terminator (Bevan et al. 1983 *Nucleic Acids Res*. 11, 369-385). pNOV2703 was digested with NotI, filled in with a Klenow fragment, and then digested again with XhoI to isolate the 2.4 kb NotI/XhoI fragment containing the Brassica HSP80 promoter-bar-Tnos expression cassette. Binary base vector pHINK078 was digested with ApaI, filled in with a Klenow fragment, and then cut with XhoI. The above-described 2.4 kb NotI/XhoI HSP80 promoter-bar-nos3'UTR fragment was inserted into ApaI/XhoI-digested pHINK078 to form pNOV2797. pNOV2797 was digested with BglII, filled-in with a Klenow fragement, and religated to form pNOV2706. The SacI/NcoI polylinker (88 bps) from pNOV2799 was inserted into SacI/NcoI-digested pNOV2706 to form pNOV2722. pNOV2722 was cut with BglII and then ligated with BglII/BamHI-digested DNA fragments containing a recognition sequence for endonuclease I-SceI, I-CeuI, or HO to form pNOV2723 (I-SceI), pNOV2724 (I-CeuI), and pNOV2725 (HO), respectively. The DNA fragment containing the I-SceI site was synthesized by annealing oligonucleotides ISCEBAM1 (SEQ ID NO:25: 5'-ACT TGG ATC CAT ATT ACC CTG TTA TCC CTA-3') and ISCEBGL2 (SEQ ID NO:26: 5'-TCG AAG ATC TGC TAG GGA TAA CAG GGT AAT -3'), filled-in with a Klenow fragment of *E.coli* DNA polymerase I, and then digested with BglII and BamHI. A DNA fragment for I-CeuI was synthesized similarly with oligonucleotides ICEUBGL2 (SEQ ID NO:27: 5'-TCG AAG ATC TCT ATA ACG GTC GTA AGG TAG-3') and ICEUBAM1 (SEQ ID NO:28: 5'- ACT TGG ATC CTC GCT ACC TTA GGA CCG TTA -3'). The DNA fragment for the HO site was synthesized with oligonucleotides HOBGL2 (SEQ ID NO:29: 5'- TCG AAG ATC TAG CTT TCC GCA ACA GTA TAA-3') and HOBAM1 (SEQ ID NO:30: 5'-ACT TGG ATC CAT TAT ACT GTT GCG GAA AGC -3'). pNOV2720 was digested with BglII and SadI to isolate a 3054 by BglII/SacI fragment containing truncated modified nptII-PAL1-3'-UTR. This fragment was inserted into BglII/SacI-digested pNOV2723, pNOV2724, and pNOV2725 to form pNOV2700 (with I-SceI site), pNOV2729 (with I-CeuI site), and pNOV2701 (with HO site), respectively (FIG. 13C).

Example 4

Generation of Tobacco Plants Containing a Target Construct

*Agrobacterium tumefaciens* strain LBA4404 containing target constructs pNOV2700, pNOV2701, pNOV2729, or control plasmid pNOV2731, respectively, were used to infect leaf explants of *Nicotiana tabacum* c.v. Petit Havana (SR1). Transgenic plants were obtained from the infected leaf explants using PPT (5 mg/L) as a selection agent. Initially, the tobacco leaves were cut into 1-2 mm wide slices, exposed to the *Agrobacterium* resuspended in MS3S for 5 minutes, and then moved to sterile paper to blot away excess liquid and placed on co-cultivation medium (MS3S+NAA (0.1 mg/L) +6-BA (1 mg /L)+gelrite agar (2.4 g /L)) for 3 days. The leaf slices were then moved to selection/regeneration medium (MS3S+NAA (0.1 mg/L)+6-BA (1 mg/L)+Carbenicillin (200 mg/L)+gelrite agar (2.4 g/L)+PPT (5 mg/L)). PPT resistant shoots were rooted in selection/rooting medium (MSB +PPT (5 mg/L)+Carbenicillin (200 mg/L)+phytagar (8 g/L) in GA-7 boxes) and then transplanted to soil. As a control, pNOV2731 was placed in rooting medium that included kanamycin (150 mg/L) as well as PPT (5 mg/L) to screen for the expression of the modified nptII gene with four introns. The plants were selfed or outcrossed with pollens from non-transgenic SR1 plants to produce seeds.

Example 5

Molecular Analysis of Transgenic Plants

The DNA of the transgenic plants was analyzed in accordance with standard molecular biological techniques. DNA was isolated from the leaves of transgenic plants for T-DNA structure analysis using the CTAB protocol (Jorgensen et al. 1996 Plant Mol. Biol. 31:957-973). Samples containing about 5 micrograms of tobacco DNA were digested with a restriction enzyme, such as SacI, NheI, SpeI, KpnI, ScaI, HpaI, EcoRI, and EcoRV, separated on an agarose gel, blotted onto Hybond N+ nylon membrane, and then hybridized with a $^{32}$P-labeled probe. The probes were prepared from either a PPT fragment or the nptII exon 5/Pal terminator fragment, as appropriate.

Example 6

Figure 13D:
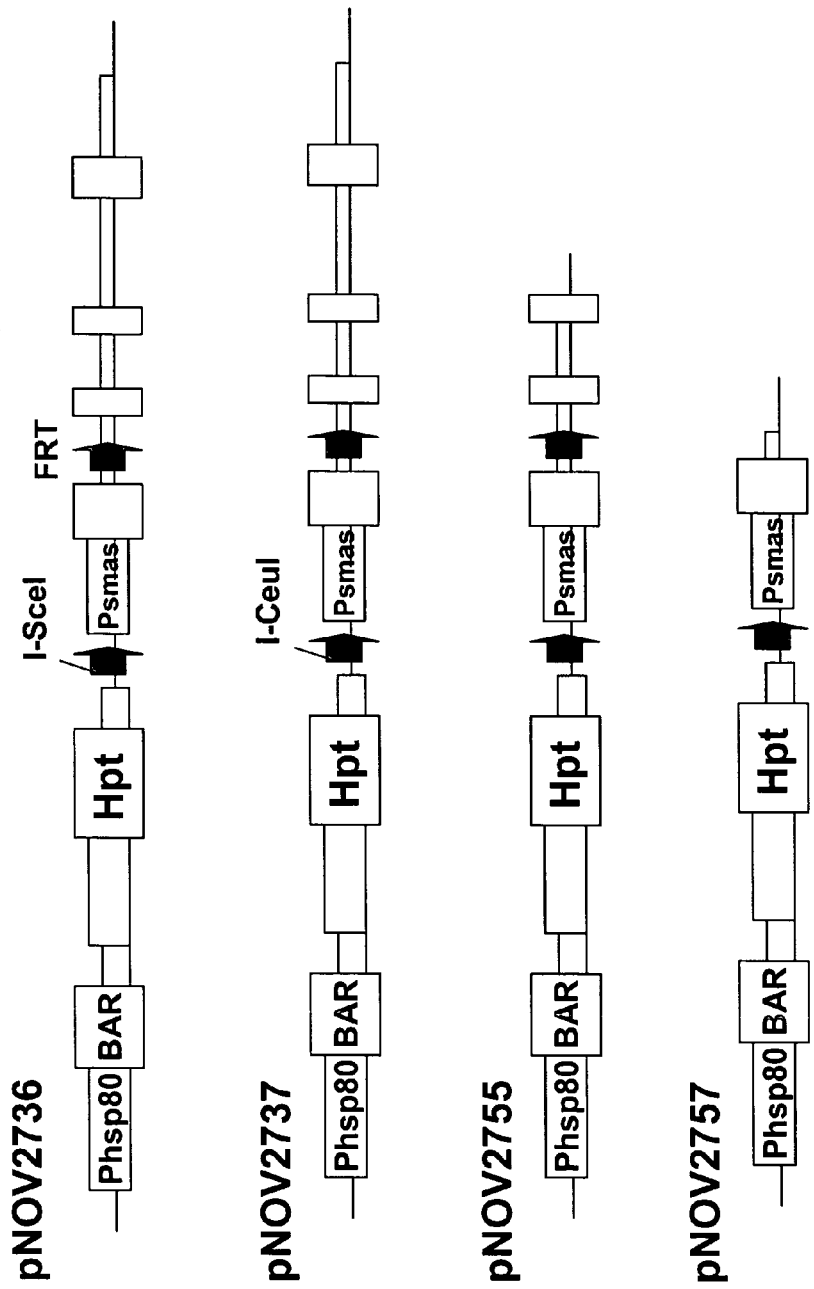

Construction of Donor Vectors pNOV2704 was digested with NotI, blunted with Klenow, cut with XbaI, and ligated with 3.1 kb KpnI/XbaI (blunted) of pNOV2705 containing the UBQ3 5' region (promoter, intron, and leader)-Hyg-TUBG3 to create pNOV2726. pLITMUS28 (New England Biolabs, MA) was digested with BglII and ligated with a fragment containing an FRT site derived from annealed oligonucleotides FRTBGL2 (SEQ ID NO:31: 5'-GAT CTG AAG TTC CTA TTC TCT AGA AAG TAT AGG AAC TTC G-3') and FRTBAM1 (SEQ ID NO:32: 5'-GAT CCG AAG TTC CTA TAC TTT CTA GAG AAT AGG AAC TTC A-3') to create plasmid pNOV2727. pNOV2727 was digested with XhoI, filled-in with a Klenow fragment in the presence of dTTP only, then cut with SacI to isolate a 2.8 kb XhoI/SacI fragment. pNOV2720 was cut with ClaI, filled-in with a Klenow fragment, then digested with SacI to isolate the 4.8 kb SacI/ClaI fragment. The 2.8 kb XhoI/SacI fragment of pNOV2727 was ligated with the 4.8 kb ClaI/SacI fragment of pNOV2720 to create pNOV2732.

pNOV2700 was digested partially with EcoRV and XhoI to isolate the 10 kb EcoRV/XhoI fragment and then ligated with 3.2 kb SacI (blunted)/XhoI fragment of pNOV2726 to create pNOV2733. pNOV2733 was digested with SacI, blunted with T4 DNA polymerase, and then partially cut with BglII to isolate the 10.4 kb BglII/SacI (blunted) fragment. pNOV2732 was digested with NcoI, filled-in with a Klenow fragment, and then partially cut with BglII to isolate the 3.97 kb BglII/ NcoI (blunted) fragment. The donor construct pNOV2736 (FIG. 13D) was created by ligating the 10.4 kb BglII/SacI (blunted) fragment with the 3.97 kb BglII/NcoI fragment.

pNOV2729 was digested partially with EcoRV and XhoI to isolate the 10 kb EcoRV/XhoI fragment. The fragmant was ligated with a 3.2 kb SacI/XhoI fragment of pNOV2726 (SacI site was blunted by a Klenow treatment) to create pNOV2734.

pNOV2734 was digested with SacI, blunted with T4 DNA polymerase treatment, then partially cut with BglII to isolate the 10.4 kb SacI/BglII fragment. This fragment was ligated with the 4 kb NcoI/BglII fragment (NcoI was blunted by a Klenow fragment) of pNOV2732 to create donor construct pNOV2737 (FIG. 13D).

pNOV2701 was digested partially with EcoRV and XhoI to isolate the 10 kb EcoRV/XhoI fragment. This fragment was ligated with the 3.2 kb SacI/XhoI fragement of pNOV2726 (SacI site was blunted by Klenew treatment) to create pNOV2735.

pNOV2735 was digested with SacI, blunted with T4 DNA polymerase, then partially cut with BglII to isolate the 10.4 kb SacI/BglII fragment. This fragment was ligated with the 4 kb NcoI/BglII fragment (NcoI site was blunted) of pNOV2732 to create donor construct pNOV2738.

pNOV2734 was digested partially with Ec1136II and BglII to isolate a 10.4 kb Ec1136II/BglII fragment. This fragment was ligated to a 2.5 kb SalI (Blunted)/BglII fragment of pNOV2732 to form donor construct pNOV2755 (FIG. 13D). The pNOV2734 Ec1136II/BglII (10.4 kb) fragment was ligated with a 1.54 kb MscI/BglII fragment of pNOV2732 to form pNOV2756. The pNOV2734 Ec1136II/BglII (10.4 kb) fragment was ligated with 1.42 kb EcoRI (blunted)/BglII fragment of pNOV2732 to form pNOV2757 (FIG. 13D).

pNOV2733 was digested partially with Ec1136II and BglII to isolate a 10.4 kb Ec1136II/BglII fragment. The fragment was ligated with 3.97 kb NcoI (blunted with Klenow)/BglII fragment of pNOV2732 to form binary donor pNOV2759.

Example 7

Construction of an HO Endonuclease Expression Vector for Dicot Plants

Figure 13E:
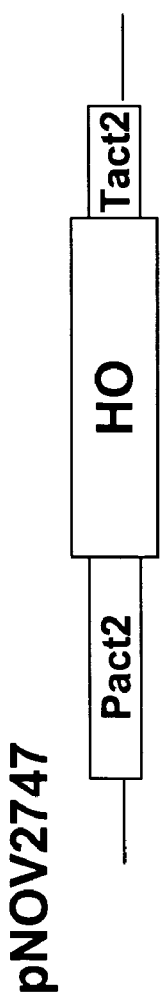
Figure 13F:
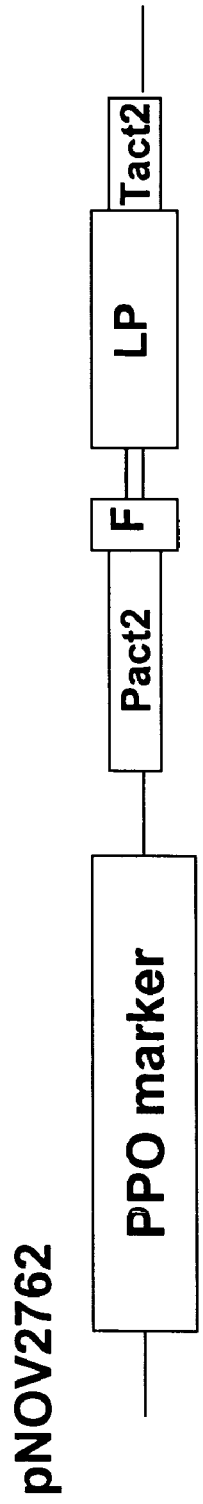

The coding region of the yeast HO endonuclease gene was amplified from *Saccharomyces cereviceae* (ATCC48893) using primers HOATG (SEQ ID NO:33: 5'-CTA CTG TCG ACA AAA ATG CTT TCT GAA AAC-3') and HOBAMH (SEQ ID NO:34: 5'-CTA GGA TCC GAC CTG GTC GTC ACA GTA GCT-3'), and the PCR product was cloned into the pCR2.1-TOPO vector to form pNOV2741. pNOV2741 was digested partially with SalI and BamHI, and the SalI/BamHI fragment containing the HO gene was inserted into (SalI) partial/BamHI-digested pNOV2721 to form pNOV2742. The Act2 promoter-HO-act2 terminator cassette was excised from pNOV2742 by KpnI and SacI digestion and was inserted into KpnI/SacI-digested pHINK078 to form binary vector pNOV2747 (FIG. 13E). The HO expression cassette was also excised from pNOV2742 by KpnI and SacI digestion and inserted into KpnI/SacI-cut pCIB100 (Rothstein et al. 1987 *Gene* 53:153-161) to form pNOV036.

Example 8

Construction of a Synthetic I-CeuI Gene with Maize-Preferred Codons

The amino acid sequence for the homing endonuclease I-CeuI (Gauthier, Turmel, and Lemieux 1991 *Curr. Genet.* 19:

43-47) was back-translated into the DNA sequence shown in SEQ ID NO:35 using maize-preferred codons (see U.S. Pat. No. 6,121,014). The unique restriction endonuclease cut site EagI was identified within this DNA sequence, which allowed the DNA to be cloned as two separate segments or sub-fragments of 340 bp and 346 bp. Because expression of the I-CeuI endonuclease is toxic to *E. coli*, an intron was introduced into the 5'-segment before excision and ligation of the segments to form the complete gene. A 189-bp potato ST-LS 1 intron sequence (Narasimhulu et al. 1996 *Plant Cell* 8:873-886) was also inserted into I-CeuI to facilitate cloning in *E. coli*. Each of the two sub-fragments was constructed from oligonucleotides ranging from 65 to 75 bases in length, with each oligonucletotide overlapping neighboring oligonucleotides by 20 bp.

Segment 1 of synthetic I-CeuI (SynICeuI) included the first 335 bp preceding the EagI site and was constructed from the following oligonucleotides: 1A (SEQ ID NO:36:5'- GGGGA TCCAT GAGCA ACTTC ATCCT GAAGC CCGGC GAGAA GCTGC CCCGG ACAAG CTGGA GGAGC TGAAG AAGA -3') (GG +BamHI site +top strand bases 1-67), 1B (SEQ ID NO:37: 5'-CGCAG GTCGA TCAGG-TACTT GCTGA AGTTC TTGGT CTTCT TCACG GCGTCGTTGA TCTTC TTCAG CTCCT CCAGC-3') (bottom strand bases 48-122), 1C (SEQ ID NO:38: 5'-AAGTA CCTGA TCGAC CTGCG CAAGC TGTTC CAGAT CGACG AGGTG CAGGT GACCA GCGAG AGCAA GCTGT TCCTG-3') (top strand bases 103-177), 1D (SEQ ID NO:39: 5'-TGG CCA GCT TCT TGG TGC TGA TGT TCA GGC TGG CCT CGC CCT CCA GGA AGC CGG CCA GGA ACA GCT TGC TCT CGC-3') (bottom strand bases 158-232), 1E (SEQ ID NO:40: 5'-CAGCA CCAAG AAGCT GGCCA CCAGC AAGTT CGGCC TGGTG GTGGA CCCCG AGTTC AACGT GACCC AGCAC GTGAA-3') (top strand bases 213-287), and 1F (SEQ ID NO:41: 5'-CG-CAG GTCGA TCAGG TACTT GCTGA AGTTC TTGGT CTTCT TCACG GCGTCG TTGAT CTTCT TCAGC TCCTC CAGC-3') (bottom strand bases 268-335+5'CCC).

Segment 1 was constructed in three steps: (1) a Klenow fill-in reaction to form three sets of dimers (AB, CD, and EF); (2) a PCR joining of dimers CD and EF to form a tetramer CDEF; and (3) a second PCR joining of tetramer CDEF to dimer AB, forming hexamer ABCDEF. Three reactions of 50 µl containing 1×DNA polymerase salts and 1 µl each of 20 µM solution of 1A and 1B, 1C and 1D, and 1E and 1F, respectively, were heated at 67° C. for 5 minutes and then allowed to cool slowly to 22° C. To each reaction was added 1 µl of a mix of four deoxynucleotide triphosphates (10 mM each), plus 2 µl (10 units) of a Klenow fragment of DNA polymerase (New England Biolabs). The reaction was incubated at 22° C. for 15 minutes, producing AB, CD, and EF precursors of SynICeuI segment 1. Segment CD was joined to overlapping EF by 10 cycles of PCR. A PCR reaction mixture containing 13 µl water, 5 µl each of the CD and EF Klenow reactions, and 1 µl each of the 20 µM solutions of oligo 1C and 1F as primers was added to a Ready-to-Go PCR bead (Amersham Pharmacia Biotech Inc). The PCR reaction conditions were: 95° C. for 5 minutes; (95° C. for 1 min., 56° C. for 30 sec., 72° C. for 1 min.) 10 cycles; 72° C. for 10 min. The yield of tetrameric product was increased by reamplification of the product of this reaction as follows: A new PCR reaction mixture containing 18 µl water, 5 µl of product of the previous PCR reaction, and 1 µl each of the 20 µM solutions of oligo 1C and 1F as primers was added to a Ready-to-Go PCR bead, and the amplification program described above was re-employed. The tetrameric PCR product was excised from an agarose minigel (2% Seaplaque agarose), and the DNA was purified by the QIAquick Gel Extraction Kit (Qiagen, Vanecia, Calif. 91355).

In order to form the hexameric product, the PCR-mediated joining process was repeated using tetramer CDEF plus dimer AB with oligonucleotides 1A and 1F as primers. The resulting hexameric DNA fragment was isolated and purified as described above and then cloned using the TOPO-TA Cloning Kit (InVitrogen, Carlsbad, Calif.). Clones with hexamer-sized inserts were sequenced to identify one of perfect sequence, which is referred to as pCR2.1 SynICeuI- 1. For assembly of the complete synthetic gene, the fragment was ultimately excised from the TOPO vector with BamHI and EagI, but only after introduction of an intron (see below).

Segment 2 was constructed from the following oligonucleotides: 2G (SEQ ID NO:42: 5'-CCC CGG CCG CAT CCG CCA CAA GAG CGG CAG CAA CGC CAC CCT GGT GCT GAC CAT CGA CAA CCG CCA GAG CCT GGA-3'), 2H (SEQ ID NO:43: 5'-CTC GGG GCT GCT GAA GGC CAC CAC GTA CTG CTC GTA GAA GGG GAT CAC CTT CTC CTC CAG GCT CTG GCG GTT GTC-3'), 2I (SEQ ID NO:44: 5'-TGG CCT TCA GCA GCC CCG AGA AGG TGA AGC GCG TGG CCA ACT TCA AGG CCC TGC TGG AGC TGT TCA ACA ACG ACG -3'), 2J (SEQ ID NO:45: 5'-ATC TGG TCC CAG ATG GGC AGG ATC TTG TTC ACC AGC TGC TCC AGG TCC TGG TGG GCG TCG TTG TTG AAC AGC TCC-3'), 2K (SEQ ID NO:46: 5'-CTG CCC ATC TGG GAC CAG ATG CGC AAG CAG CAG GGC CAG AGC AAC GAG GGC TTC CCC AAC CTG GAG GCC GCC CAG-3'), and 2L (SEQ ID NO:47: 5'-GGG GAA TTC CTA CTT GAT GCC CTT CTT GTA GTT GCG GGC GAA GTC CTG GGC GGC CTC CAG GTT GG-3'). In a manner similar to that described above for segment 1, segment 2 was constructed in three steps: (1) a Klenow fill-in reaction to form three sets of dimers (GH, IJ, and KL); (2) a PCR joining of dimers EF and GH to form a tetramer, EFGH; and (3) a second PCR joining of EFGH with IJ to form a hexamer, EFGHIJ.

The hexamer DNA fragment GHIJKL was cloned into pCR2.1 using the TOPO-TA Cloning Kit (InVitrogen) and was sequenced to identify a clone of perfect sequence, which is referred to as pCR2.1ICeuI-2.

Introduction of an Intron into pCR2.1SynICeuI-1

The potato ST-LS1 intron was PCR-amplified from pBISN1 (Narasimhulu et al. 1996 *Plant Cell* 8:873-886) using an oligonucleotide primer pair (i.e., SEQ ID NO:48: 5'-GGGTA CGTAA GTTTC TGCTT CTACC TTTG-3' and SEQ ID NO:49: 5'-CCCCAG CTGCA CATCA ACAAA TTTTG GTC-3') to form SnaBI and PvuII sites (shown in bold) at the 5' and 3' ends of the intron, respectively. The PCR product was cloned using the TOPO-TA Cloning Kit (Invitrogen), and a perfect copy, referred to as pInt1, was identified through sequencing. The intron was excised from pInt1 as a SnaB1/PvuII fragment, gel-purified, and then extracted from agarose with the QIAquick gel extraction kit. pCR2.1SynICeuI-1 was cleaved at a unique Pm1I site in the insert and, in accordance with methods known in the art, was treated with alkaline phosphatase under appropriately stringent conditions for achieving blunt-end dephosphorylation. The intron fragment was ligated into this vector, and candidate clones were screened by ApoI digestion and sequenced to confirm a clone of perfect sequence with the intron in the correct orientation with respect to the coding sequence of ICeuI. The plasmid so-identified is referred to as pCRSynICeuI-1-int.

Assembly of the SynICeuI Gene

Plasmid pBluescript KS(+) (Stratagene, Inc.) was digested with NotI and EcoRI in the presence of alkaline phosphatase. The 3' end of SynICeuI was excised from pCR2.1IceuI-2 with EagI and EcoRI, gel-purified, and ligated to the bluescript vector, forming pBS-GHIJKL. Because the EagI site of the insert is a half NotI site, the NotI site was reconstituted in the product. This plasmid was next cleaved with NotI in the presence of alkaline phosphatase, and the 5' end of SynICeuI, including the intron excised as an EagI fragment from pCRSynICeuI-1-Int, was ligated into place. Candidate clones were sequenced to identify one with the ABCDEIntF fragment inserted in the correct orientation. The identified clone is referred to as pBS-ICeuI-Int. The sequence of SynICeuI is represented by SEQ ID NO:35, which shows the flanking noncoding DNA between the EcoRI sites in italics.

```
SEQ ID NO:35. I-CeuI endonuclease with maize-
preferred codons and potato ST-LS1 intron
GAATTCGCCCTTGGGGATCCATGAGCAACTTCATCCTGAAGCCCGGCGAG

AAGCTGCCCCAGGACAAGCTGGAGGAGCTGAAGAAGATCAACGACGCCGT

GAAGAAGACCAAGAACTTCAGCAAGTACCTGATCGACCTGCGCAAGCTGT

TCCAGATCGACGAGGTGCAGGTGACCAGCGAGAGCAAGCTGTTCCTGGCC

GGCTTCCTGGAGGGCGAGGCCAGCCTGAACATCAGCACCAAGAAGCTGGC

CACCAGCAAGTTCGGCCTGGTGGTGGACCCCGAGTTCAACGTGACCCAGC

ACGTAAGTTTCTGCTTCTACCTTTGATATATATATAATAATTATCATTAA

TTAGTAGTAATATAATATTTCAAATATTTTTTTCAAAATAAAAGAATGTA

GTATATAGCAATTGCTTTTCTGTAGTTTATAAGTGTGTATATTTTAATTT

ATAACTTTTCTAATATATGACCAAAATTTGTTGATGTGCAGGTGAACGGC

GTGAAGGTGCTGTACCTGGCCCTGGAGGTGTTCAAGACCGGCCGCATCCG

CCACAAGAGCGGCAGCAACGCCACCCTGGTGCTGACCATCGACAACCGCC

AGAGCCTGGAGGAGAAGGTGATCCCCTTCTACGAGCAGTACGTGGTGGCC

TTCAGCAGCCCCGAGAAGGTGAAGCGCGTGGCCAACTTCAAGGCCCTGCT

GGAGCTGTTCAACAACGACGCCCACCAGGACCTGGAGCAGCTGGTGAACA

AGATCCTGCCCATCTGGGACCAGATGCGCAAGCAGCAGGGCCAGAGCAAC

GAGGGCTTCCCCAACCTGGAGGCCGCCCAGGACTTCGCCCGCAACTACAA

GAAGGGCATCAAGTAG GAATTC
```

Example 9

Construction of a Dicot I-CeuI Endonuclease Expression Vector

The pBH37 plasmid, an expression vector containing a modified Smas promoter, a Nos terminator, and cloning sites between these two regions, was digested with BglII, and the BglII site was converted to an MfeI site by the introduction of the following site conversion oligonucleotide: (SEQ ID NO:50: 5'-GATCGGCAATTGCC-3'). The resulting plasmid, pBH37M, was digested with MfeI in the presence of alkaline phosphatase. SynICeuI was excised from its bluescript vector as an EcoRI fragment and was ligated into MfeI-cleaved pBH37M. Candidate clones were digested with BstEII/PstI, and a clone having a correctly oriented fragment containing SynICeuI appropriately flanked by the Smas promoter and the Nos terminator was chosen for further cloning into a binary vector. This fragment, referred to as Smas-ICeuI-Int, was excised as a HindIII/EcoRI fragment, ligated into pHINK078, and then digested with HinndIII/EcoRI in the presence of alkaline phosphatase to form pNOV039. Binary vector pNOV100 was digested with HindIII/EcoRI in the presence of alkaline phosphatase, and the HindIII/EcoRI purified fragment of Smas-ICeuI-Int was ligated with it to form pNOV040.

Example 10

Targeted Integration into a Predetermined Target Loci by Homologous Recombination Single copy T-DNA transgenic tobacco target lines (T2701.6 and T2701.27) were selected and infected with *Agrobacterium tumefaciens* strain LBA4404, which contained a donor vector. Seeds derived from target lines T2701.6 and T2701.27 that had been selfed or backcrossed with untransformed SR1 pollens were germinated on MS3S medium with 5 mg/L PPT. Two different methods for generating targeted events were used. In one method, PPT resistant seedlings were grown in MS3S medium for 3-4 weeks. Leaves of 3 to 6 week old seedlings were used for targeting experiments. The leaves were cut into 1-mm wide slices, exposed for 5 minutes to *Agrobacterium* resuspended in MS3S, moved to sterile paper to blot away excess liquid, and then placed on co-cultivation medium (MS3S+NAA (0.1 mg/L)+6-BA (1 mg/L)+gelrite agar (2.4 g/L) in standard Petri dishes) for 3 days. The leaf slices were then moved to selection/regeneration medium (MS3S+NAA (0.1 mg/L)+6-BA (1 mg/L)+Carbenicillin (200 mg/L)+gelrite agar (2.4 g/L) with kanamycin (200 mg/L)). Kanamycin-resistant shoots were rooted in selection/rooting medium (MSB+PPO (100 nM)+Carbenicillin (200 mg/L)+phytagar (8 g/L) in GA-7 boxes) and then transplanted to soil. PPT-resistant 9-14 days old seedlings were used for *Agrobacterium*-mediated transformation using vacuum-infiltration according to the method described in Puchta et al. 1996 Proc. Natl. Acad. Sci. USA 93:5055-5060. Kanamycin-resistant shoots were further verified by PCR analysis.

Table 1 shows the efficiency of targeted integration in three target lines. Co-delivery of an HO expression vector (pNOV2747 or pNOV036) and an I-CeuI expression vector (pNOV039 or pNOV040) does not increase targeting efficiency. Overall, up to a 1-2% targeted integration efficiency was obtained. It is believed that the insertion of the 4 *Arabidopsis* introns in the nptII gene, which extended the region of homology between the target and donor DNA, contributed to the observed targeting efficiency. The enhancing effect on targeting of a longer region of homology is further substantiated by comparing the effect of three different donor vectors (pNOV2736, pNOV2755, pNOV2757) on the targeting efficiency in both line T2701.6 and T2701.27 (Table 1). On average, 1 to 3 targeted events can be obtained with donor pNOV2736, which flanks both sides of the Hyg cassette with 2.4 kb of sequence homology with the target, but no event was obtained with pNOV2757, which flanks one side of the marker with 2.4 kb of sequence homology with the target and the other side of the marker has no homology to the target.

TABLE 1

Targeting efficiency of two single-copy lines with different vectors

| | Vector(s) | Homology | Explants | Events | PCR+ | South+ |
|---|---|---|---|---|---|---|
| | | Target line T2701.6 | | | | |
| HR-01AB | pNOV2737 | 2.4 & 2.4 kb | 237 | 3 | 2 | 2 |
| HR-01AC | pNOV2737, 2747 | 2.4 & 2.4 kb | 277 | 1 | 1 | 1 |
| HR-01AD | pNOV2755, 2747 | 2.4 & 1.2 kb | 233 | 4 | 2 | 2 |
| HR-02AA | pNOV2736, 036 | 2.4 & 2.4 kb | 347 | 0 | 0 | 0 |
| HR-02AC | pNOV2755, 036 | 2.4 & 1.2 kb | 303 | 1 | 1 | 1 |
| HR-03AB | pNOV2736 | 2.4 & 2.4 kb | 119 | 2 | 2 | 2 |
| HR-03AD | pNOV2737 | 2.4 & 2.4 kb | 91 | 2 | 1 | 1 |
| HR-05AA | pNOV2736 | 2.4 & 2.4 kb | 247 | 5 | 5 | 3/5* |
| HR-05AC | pNOV2755 | 2.4 & 1.2 kb | 194 | 2 | 1 | 1 |
| HR-05AD | pNOV2757 | 2.4 & 0 kb | 204 | 3 | 0 | 0 |
| HR-06AA | pNOV2736 | 2.4 & 2.4 kb | 183 | 2 | 1 | 1 |
| HR-06AB | pNOV2737 | 2.4 & 2.4 kb | 179 | 1 | 1 | 1 |
| HR-11AA# | pNOV2736 | 2.4 & 2.4 kb | 100# | 3 | 3 | ND |
| | | Target line T2701.27 | | | | |
| HR-01CA | pNOV2737 | 2.4 & 2.4 kb | 169 | 5 | 1 | 1 |
| HR-01CC | pNOV2737, 2747 | 2.4 & 2.4 kb | 268 | 4 | 3 | 3 |
| HR-02CA | pNOV2736, 036 | 2.4 & 2.4 kb | 259 | 1 | 0 | 0 |
| HR-02CC | pNOV2755, 036 | 2.4 & 1.2 kb | 211 | 1 | 1 | 1 |
| HR-05CA | pNOV2736 | 2.4 & 2.4 kb | 227 | 8 | 6 | 3/3* |
| HR-05CC | pNOV2755 | 2.4 & 1.2 kb | 183 | 8 | 7 | 2/2* |
| HR-05CD | pNOV2757 | 2.4 & 0 kb | 175 | 2 | 0 | 0 |
| HR-06CB | pNOV2737 | 2.4 & 2.4 kb | 193 | 1 | 1 | ND |
| HR-11CA# | pNOV2736 | 2.4 & 2.4 kb | 100# | 4 | 1 | ND |
| | | Target line T2729.26 | | | | |
| HR-09CC | pNOV2736 | 2.4 & 2.4 kb | 141 | 1 | 1 | ND |
| HR-09CE | pNOV2736 + pNOV040 | 2.4 & 2.4 kb | 183 | 0 | 0 | ND |
| HR-09CF | pNOV2736, pNOV039 | 2.4 & 2.4 kb | 185 | 1 | 1 | ND |
| HR-12CA | pNOV2736 | 2.4 & 2.4 kb | 100 | 1 | 1 | ND |
| HR-12CB | pNOV2736 + pNOV040 | 2.4 & 2.4 kb | 100 | 2 | 2 | ND |
| HR-12CC | pNOV2736, pNOV039 | 2.4 & 2.4 kb | 100 | 1 | 1 | ND |

ND: not determined.
*Number of events analyzed.
13 days-old young seedlings instead of leaf explant tissues were used for transformation.

Example 11

Identification of Recombinant Target Lines

Figure 14A:
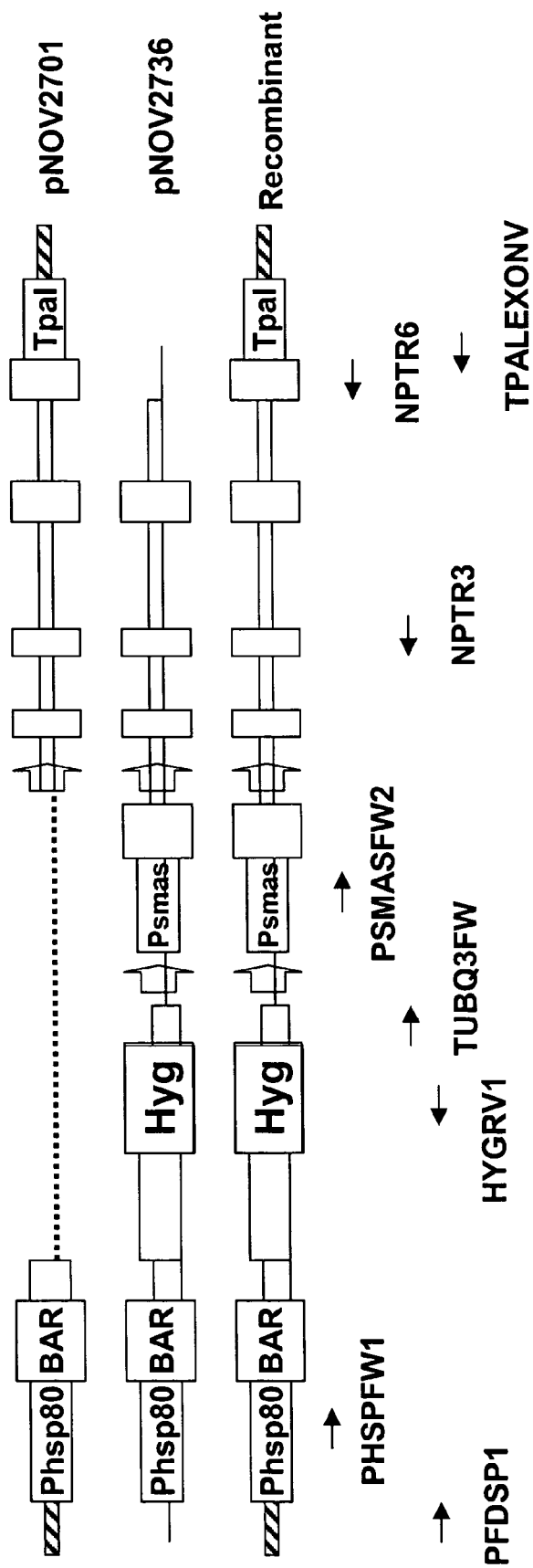
FIGS. 14A-14C illustrate PCR screening and analysis of targeted events.
Figure 14B:
Figure 14C:
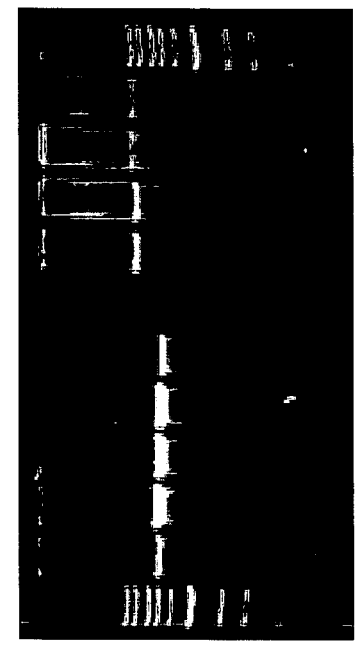

Leaf tissue was collected from these potential recombinants for DNA isolation and PCR analysis (FIG. 14A). In order to identify recombinants, amplification was carried out using the Boehringer Mannheim EXPAND™ High Fidelity PCR system with primers PSMASFW2 (SEQ ID NO:51: 5'-CCG GTG AGT AAT ATT GTA CGG CTA AGA-3') and NPTR6 (SEQ ID NO:52: 5'-AGA TCC TCA GAA GAA CTC GTC AAG AAG -3'). Amplification of recombinant junctions was carried out using Boehringer Mannheim EXPAND™ Long Template PCR system with primers PHSPFWD (SEQ ID NO:53: 5'-AAT ATA GGC GGT ATT CCG GCC ATT ATA ACA -3') and TPalExonV (SEQ ID NO:54: 5'-CTA AGA TCC TCA GAA GAA CTC GTC AAG AAG-3'). FIG. 14B illustrates the identification of targeted events by PCR amplification. FIG. 14C shows recombinants that have successfully integrated a second gene cassette.

Figure 15A:
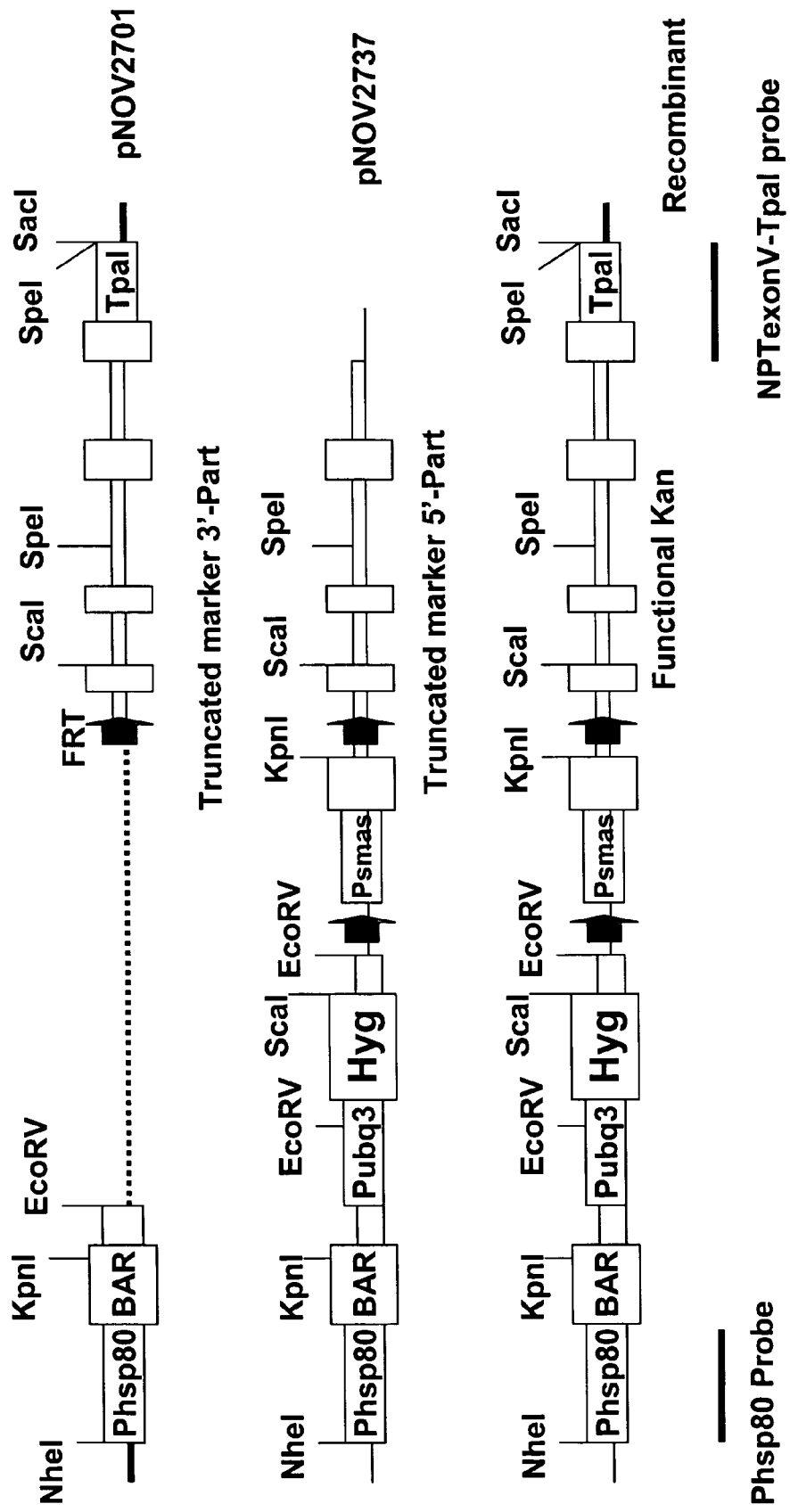

FIGS. 15A, 15B, and 15C illustrate Southern blot analyses of targeted events achieved through homologous recombination. Genomic DNA digested with several enzymes (EcoRV, SacI, NheI, SpeI) was hybridized with two different probes (i.e., the HSP80 promoter and the nptII exonV-PAL1 terminator). The positions of the probes are indicated in FIG. 15A. The HSP80 promoter probe provided information relating to the copy number of the donor sequence (FIG. 15B) and whether recombination occurred at the left end of the target locus (i.e., the end which included the bar gene cassette). Probing with the nptII exonV-PAL1 terminator provided information regarding target sequence copy number and whether there was any rearrangement at the right end of the target locus (i.e., the end which included the nptII gene cassette) (FIG. 15C). If a recombination event derives from recombination at both ends (double crossover recombination), then both probes would be expected to show a shift in the target bands. If a recombination event derives from recombination at a single side (a single crossover recombination), then the target band would be expected to shift with only one probe. If the putatively targeted event is not truly targeted, then none of the bands in the target plant would be expected to shift with either of the probes. FIGS. 15B and 15C illustrate an exemplary analysis of this type.

Target line T2701.6 (lanes 1 to 4, FIGS. 15B and 15C) gave rise to several restriction fragments that were easily separated by regular gel electrophoresis. FIGS. 15B and 15C (lanes 5-8) show that recombinant HR-03AD.2 had a restriction fragment size-shift, which is consistent with a double-sided recombination event. The other two events (HR-05AA.1 and HR-05AA.2, lanes 9-14) show a band shift that is consistent with recombination at only one side. One of the events (HR-05AA.2, lanes 12-14) shows band shifts with both probes, but the band with NheI digestion (lane 14) is smaller than expected, so there might be some rearrangement or deletion close to the HSP80 promoter. Because there is no restriction polymorphism in the region of homology between the target and donor sequences, it is not possible to distinguish whether the recombinants were derived from a reciprocal crossover or a non-reciprocal gene conversion.

Target line T2701.27 gave rise to restriction fragments that were not easily separated (larger than 10 kb NheI, SacI, and ScaI fragments with the nptli exon V-PAL 3'-UTR probe), and events derived from this line are analyzed only minimally, due to difficulty in distinguishing small changes for band sizes larger than 15 kb in normal agarose gel electrophoresis.

Other targeted events were also characterized by Southern blot analysis. The results are summarized as follows: (1) About 70% of the targeted events resulted from single crossover recombination, and about 30% of the recombinants resulted from double crossover recombination. It is not known whether recombinants were the product of a reciprocal crossover or a non-reciprocal gene conversion process using incoming T-DNA as a template. (2) About half of the recombinants had additional copies of the donor sequence inserted elsewhere in the genome. (3) T-DNA is capable of carrying out homologous recombination (by either reciprocal crossover or non-reciprocal gene conversion), and it does not have to be integrated into the host genome first. (4) No unexpected rearrangement of the target locus or ectopic targeting is observed in all of the analyzed events.

Because a Southern blot analysis will not reveal rearrangements that result in relatively small changes in the size of a band, finer restriction mapping of the recombination breakpoints was done. A primer (PFDSP1, FIG. 14A; SEQ ID NO:55: 5'-ACC CTC CGC TAC TTC TCC GGG AAA AGA CGC -3') was created based upon the flanking plant genomic DNA sequences obtained from I-PCR and used to perform long range PCR amplification in nine recombinant lines derived from T2701.6. PCR amplification was done using two primer pairs. The first pair of primers (PFDSP1 and TPa1ExonV, FIGS. 14A and 14C; SEQ ID NO:55 and SEQ ID NO:54) produced a 5.5 kb product from a non-targeted copy, a larger than 5.5 kb product from a targeted copy derived from single-sided recombination, and a 10 kb fragment from a targeted copy derived from double-sided recombination. More particularly, using this pair of primers (PFDSP1 and TPa1ExonV), a ca.10 kb fragment was obtained from one hemizygous recombinant line (HR-03AD.2, see FIG. 14C for examples). A ca. 9 kb fragment was derived from both HR-05AA.2 and HR-01AB.1 and their progeny (FIG. 14C). A ca. 8 kb fragment was amplified from line HR-01AD.1, which is hemizygous for the target transgene locus (not shown). Thus, both HR-01AB.1 and HR-01AD.1 were not the products of a double-crossover recombination. In six other heterozygous lines, only the shorter fragment (5.5 kb) was present, as was predicted from the preferential amplification of the non-targeted copy (result not shown). When the kanamycin resistant progeny of a heterozygous recombinant HR-03AB.1 was subjected to PCR, a 10 kb fragment was produced (FIG. 14C).

Using another pair of primers (PFDSP1, SEQ ID NO:55 and HygRV1, SEQ ID NO:56: 5'-ACT ATC GGC GAG TAC TTC TAC ACA GCC ATC-3') FIG. 14C, lane 1 to 5), the PCR reaction produced a 5.4 kb product. This indicated that the recombinant was derived from double-sided recombination, because the HygRV1 primer could only bind to the Hyg gene present in the donor vector. The 5.4 kb product was present in both hemizygous and heterozygous recombinants derived from double-crossover recombination. A 5.4 kb fragment was obtained from 5 recombinant lines (HR-01AB.1, HR-02AC.1, HR-03AB.1, HR-03AD.2, and HR-05AA.2). No PCR product was derived from five other targeted events (HR-01AB.3, HR-01AC.1, HR-01AD.1, HR-01AD.4, and HR-03AB.2). In these latter recombinants, it is possible that a DNA rearrangement or a repeat structure was present, such that the PCR reaction was unable to amplify the entire region.

Since both HR-01AB.1 and HR-05AA.2 produced a PCR product of only about 9 kb using PFDSP1 and TPa1ExonV (above) but produced a PCR product of about 5.4 kb with PFDSP1 and HygRV1, it is possible that there was an internal rearrangement (such as a deletion, for example) between the hygromcyin phosphotransferase (HPT) gene and the mSmas promoter during targeting. In summary, Southern blot analyses and PCR results demonstrate that at least three events (HR-02AC. 1, HR-03AB. 1, and HR-03AD.2) were derived from double-crossover recombination with no additional rearrangement.

Example 12

Progeny Analysis of Targeted Events

In several recombinants, more than one copy of a donor sequence was integrated into the host cell's genome, as indicated by Southern blot analysis using the HSP80 promoter probe. To study the insertion status of the additional copy(ies) in these lines, plants were pollinated with untransformed SR1. The seeds were plated on PPT, kanamycin, or hygromycin medium. Table 2 shows the number of resistant and sensitive seedlings. In a hemizygous target line, half of the seedlings would be expected to be resistant to PPT, kanamycin, and hygromycin, if all donor copies are integrated into either a single locus or a closely linked locus. Here, all lines had the expected kanamycin resistance segregation ratios, as demonstrated by Southern blot analysis of each plant line. Southern blot analysis indicated that there were several additional copies of the donor sequence present in the HR-01AB.1 genome. The PPT and hygromycin segregation data supported this conclusion.

TABLE 2

Progeny segregation analysis of targeted events

| Crosses | Kan | | PPT | | Hyg | |
|---|---|---|---|---|---|---|
| | R | S | R | S | R | S |
| Hemizygous target* | | | | | | |
| T2701.6 target locus | | | | | | |
| HR-01AB.1 × SR1 | 56 | 64 | 121 | 10 | 80 | 9 |
| HR-03AD.2 × SR1 | 115 | 111 | 50 | 58 | 38 | 35 |
| T2701.27 target locus | | | | | | |
| HR-01CB.4 × SR1 | 43 | 46 | 37 | 42 | 21 | 21 |
| Homozygous target* | | | | | | |
| T2701.6 target locus | | | | | | |
| HR-01AB.3 × SR1 | 46 | 57 | 154 | 0 | NT | |
| HR-03AB.1 × SR1 | 28 | 36 | 78 | 0 | 40 | 37 |
| T2701.27 target locus | | | | | | |
| HR-01CC.4 × SR1 | 65 | 80 | 72 | 0 | 58 | 62 |

*The target status is extrapolated from Southern blot analysis using npt exonV/PAL 3'-UTR as probe. The plants in bold font are most likely derived from double crossover recombination as indicated by Southern blot analysis.
NT: Not tested.

Example 13

Construction of a Site-Specific FLP Recombinase Expression Vector

A 1.6 kb BamHI fragment containing FLP recombinase was excised from pUCFLP/intron (WO 99/55851) and inserted into pNOV2721 linearized with BamHI to create pNOV2760, thereby placing FLP under the control of the *Arabidopsis* Act2 promoter. pNOV2760 was digested with SacI and KpnI to isolate the 3.7 kb Act2 promoter/FLP-intron/Act2 terminator cassette. This fragment was then inserted into SacI/KpnI-digested pNOV1511 to create pNOV2762 (FIG. 13E). The PPO gene was isolated from *Arabidopsis thaliana*, and two mutant amino acids were introduced to obtain PPO(dm) (U.S. Pat. No. 6,308,458), which permitted the selection of transgenic cells with an herbicide (butafenacil, CGA 854,276).

Example 14

Generation of Transgenic Lines Expressing FLP Recombinase

The FLP recombinase binary vector pNOV2762 was transformed into *Agrobacterium* strain LBA4404, and the resulting *Agrobacterium* strain was used to transform tobacco SR1 as described above, with the exception that butafenacil was used as the selection agent. Several FLP-expressing lines were generated. One transgenic line (T2762.2) was selfed to produce progeny lines T2762.2S1 and T2762.2S2.

Example 15

Crossing Recombinant Plant Lines with FLP-Expressing Plant Lines

To regenerate a truncated nptli (with introns) selectable marker for gene stacking, recombinant line HR-03AD.2, which resulted from double-crossover recombination, was chosen for further studies. HR-03AD.2 was crossed with both T2762.2S1 and T2762.2S2 directly. The seeds from these crosses were plated on medium containing both butafenacil and hygromycin. Double-resistant seedlings were transplanted to soil and grown in a greenhouse. Each seedling was analyzed with a PCR assay to determine whether there was a FLP-mediated excision of the sequence flanked by the two FRT sites. The PCR assay (FIG. 16A) was performed with a forward primer (Tubq3FW; SEQ ID NO:57, 5'-GTG TCT CAT GCA CTT GGG AGG TGA TC -3') located at the Ubq3 terminator and a reverse primer at the nptII exon 3 (NPTR3, SEQ ID NO:10). The wild type target locus produced a 3 kb PCR fragment; the same target locus with the Smas promoter and part of the nptII sequence (i.e., exon 1 and part of intron 1) excised by FLP-mediated site-specific recombination produced a 1.5 kb PCR fragment (see FIG. 16A). 72 progeny seedlings were assayed by PCR. 49 of those seedlings had a detectable 1.5 kb PCR fragment. Several lines with an excised nptII sequence (CFP-A7, CFP-B8, CFP-B11, CFP-C3, CFP-C6, CFP-D1, CFP-D5, CFP-E7, and CFP-E9) were crossed with SR1, and the progeny were selected on hygromycin. Hygromycin-resistant seedlings were then assayed by PCR to recover progeny with FLP-mediated excision.

Example 16

Retransformation of Recombinants with a FLP Expression Vector

Truncation of the nptII marker sequence can also be achieved by inserting the recombinase expression construct into the target lines and then allowing the recombinase locus to be lost through segregation. Kanamycin-resistant seedlings resulting from crossing HR-03AB.1 with SR1 and HR-03AD.2 with SR1 were re-transformed with *Agrobacterium* containing pNOV2762 to regenerate a truncated selectable marker gene for gene stacking. In preparation for retransformation with pNOV2762, leaf slices were infected with *Agrobacterium* (pNOV2762) and then selected on hygromycin and butafenacil. Regenerated shoots were rooted in medium with butafenacil. The rooted shoots were transplanted into soil and assayed by PCR, as described above, to determine whether the mSmas promoter and part of the nptII (with introns) gene were deleted (FIG. 16A). Among 44 independent transformants (HR-08AA's) of HR-03AB.1×SR1 kanamycin-resistant seedlings, 19 had a 1.5 kb PCR product. Among 44 transformants (HR-08BA's) of HR-03AD.2×SR1 kanamycin-resistant seedlings, 22 had a 1.5 kb PCR product.

Several lines with an excised nptII sequence (HR-08AA.17, HR-08AA.32, HR-08BA.13 and HR-08BA.20) were crossed with SR1, and the progeny were selected on hygromycin. Hygromycin-resistant seedlings were assayed by PCR to recover progeny with FLP-mediated excision. To facilitate the isolation of lines with complete excision of the nptII sequence, leaves of HR-08AA32 were regenerated. One of the regenerants, HR-08AA32R2, had complete excision of FRT-flanked sequences and was pollinated with pollens from wildtype untransformed SR1. The progeny seedlings were tested for excision of the FRT-flanked mSmas and nptII sequences by PCR. PCR demonstrated that all of the progeny had an mSmas promoter and part of the nptII sequence had been excised (FIG. 16B). Progeny with the regenerated truncated marker gene is then capable of being used to stack additional donor trait cassettes.

The above Examples describe the production of a recombinant line through site-specific recombination-mediated excision of nucleotide sequences flanked by recombinase recognition sequences. This recombinant line, which includes a partially excised (i.e., truncated) selectable marker gene, can be re-used in further rounds of targeting, thereby permitting the use of a single selectable marker gene in combination with a site-specific recombination system to stack an unlimited number of gene cassettes (i.e., donor sequences) at a single locus in the genome of a host cell (see, e.g., FIGS. 12A and 12B).

Example 17a

Construction of a PMI Gene (PMI-Intron) with Four *Arabidopsis* Introns

Four *Arabidopsis* introns were inserted into the phosphomannose isomerase (PMI) gene to form a PMI-intron sequence (FIG. 17), thereby increasing the length of the PMI gene from 1103 bp to 3452 bp. These four introns are from an AtBAF60 homolog, phenylalanine aminolyase (PAL), tubulin-1-alpha, and tubulin-1-beta, as used for constructing the nptII introns in pNOV2720. An R recombinase recognition sequence (RS) was formed by annealing two complementary primers RSFW (SEQ ID NO:58: 5'-GAT CCG CGG TTG ATG AAA GAA TAA CGT ATT CTT TCA TCA A-3') and RSRV (SEQ ID NO:59: 5'-GAT CTT GAT GAA AGA ATA CGT TAT TCT TTC ATC AAC CGC G-3') and inserting them into BglII-digested pNOV2720 to form pNOV2783. PMI intron 1 (488 bps, from AtBAF60 intron) was amplified from pNOV2783 with PMIINTFA (SEQ ID NO:60: 5'-ATG CCG CAG GTA CCA AGC TGC GAA TCT TCG-3') and PMIINTRA (SEQ ID NO:61: 5'-ATC GGG ATA CCT GAA AAA TTC AGA AAC AAA-3'). The other three introns were amplified directly from pNOV2720. PMI intron 2 (from the *Arabidopsis* PAL1 intron) was amplified from pNOV2720 with PMIINTFB (SEQ ID NO:62: 5'-CGG TCG CAG GTA TTA GTA CTA TTC TTT TGT-3') and PMIINTRB (SEQ ID NO:63: 5'-CGG ATG TGC ACC TGT AAC GAA CAA AAA CAT-3'). PMI intron 3 (from the *Arabidopsis* tubulin-1-beta intron) was amplified from pNOV2720 with PMIINTFC (SEQ ID NO:64: 5'-ACC TGC AAG GTA TAT ATA TGA ATC GAT TTC-3') and PMIINTRC (SEQ ID NO:65: 5'-GCG CCA CAC CTG TAA TAC AGA AAT GTT AAG-3'). PMI intron 4 (from the *Arabidopsis* tubulin-1-alpha intron) was amplified from pNOV2720 using PMIINTFD (SEQ ID NO:66: 5'-GTG AAA CAA GGT TAT TAA CGT TTT CCA CCT-3') and PMIINTRD (SEQ ID NO:67: 5'-GTT CTG CAC CTG CAT CAA TGG AAA AAT ATT-3'). PMI exons 1-5 were amplified from pNOV210, which contains the *E. coli* PMI coding sequence in pBluescript KS(+) (Stratagene, La Jolla, Calif.). PMI exon 1 (346 bps) was amplified from pNOV210 with PMIEXF1 (SEQ ID NO:68: 5'-GTG GAT CCG GCA GCA TGC AAA AAC TCA TTA ACT-3') and PMEXR1 (SEQ ID NO:69: 5'-TCG CAG CTT GGT ACC TGC GGC ATT TTC TTT GG-3'). PMI exon 2 (140 bps) was amplified from pNOV210 using PMIEXF2 (SEQ ID NO:70: 5'-AAT TTT TCA GGT ATC CCG ATG GAT GCC GCC-3') and PMIEXR2 (SEQ ID NO:71: 5'-TAG TAC TAA TAC CTG CGA CCG GCT GGA GTA-3'). PMI exon 3 (290 bps) was amplified from pNOV210 with PMIEXF3 (SEQ ID NO:72: 5'-GTT CGT TAC AGG TGC ACA TCC GGC GAT TGC-3') and PMIEXR3 (SEQ ID NO:73: 5'-TCA TAT ATA TAC CTT GCA GGT AAG CGT GCG -3'). PMI exon 4 (146 bps) was amplified from pNOV210 with PMIEXF4 (SEQ ID NO:74: 5'-CTG TAT TAC AGG TGT GGC GCT GGA AGT GAT-3') and PMIEXR4 (SEQ ID NO:75: 5'-TGT TAA TAA CCT TGT TTC ACC GGC TGG GTC-3'). PMI exon 5 (283 bps) was amplified from pNOV210 with PMIEXF5 (SEQ ID NO:76: 5'-CGA TTG ATG CAG GTG CAG AAC TGG ACT TCC C -3') and PMIEXR5 (SEQ ID NO:77: 5'-TGC TCG AGT CAT TAG CAA GAG ATG TTA ATT TT-3').

PMI intron 1 (488 bps) and PMI exon 2 (140 bps) PCR fragments were co-amplified using PMIintFA and PMIEXR2 to form a PMI intron 1::PMI exon 2 PCR fragment (630 bps). PMI exon 1 (346 bps) and PMI intron 1::PMI exon 2 fragment (630 bps) were co-amplified with PMIEXF1 and PMIEXR2 to form a PMI exon 1::PMI intron 1::PMI exon 2 fragment (976 bps), which was then cloned into pCR2.1-TOPO (Invitrogen, Carlsbad, Calif.) to form pNOV2784. PMI intron 2 (449 bps) and PMI exon 3 (290 bps) PCR products were co-amplified with PMIINTFB and PMIEXR3 primers to from a PMI intron 2::PMI exon 3 fragment (740 bps). PMI exon 3 (290 bps) and PMI intron 3 (792 bps) were co-amplified with PMIEXF3 and PMIINTRC primers to form a PMI exon 3::PMI intron 3 fragment (1083 bps). PMI intron 4 (511 bps) and PMI exon 5 (283 bps) PCR products were co-amplified with PMIINTFD and PMIEXR5 to form a PMI intron 4::PMI exon 5 fragment (795 bps). PMI exon 2 (140 bps) and PMI intron 2::PMI exon 3 (740 bps) were co-amplified with PMIEXF2 and PMIEXR3 primers to form a PMI exon 2::PMI intron 2::PMI exon 3 fragment (881 bps). PMI intron 1 (488 bps) and the PMI exon 2::PMI intron 2::PMI exon 3 fragment (881 bps) were co-amplified with PMIINTFA and PMIEXR3 to form a PMI intron 1::PMI exon 2::PMI intron 2::PMI exon 3 PCR product (1370 bps), which was then cloned into pCR2.1-TOPO to form pNOV2785. A PMI exon 3::PMI intron 3 fragment (1083 bps) and PMI exon 4 (146 bps) were co-amplified using PMIEXF3 and PMIEXR4 to form a PMI exon 3::PMI intron 3::PMI exon 4 fragment (1230 bps), which was inserted into pCR2.1-TOPO to form pNOV2786. The PMI exon 4 fragment (146 bps) and the PMI intron 4::PMI exon 5 fragment (795 bps) were co-amplified with PMIEXF4 and PMIEXR5 primers to form a PMI exon 4::PMI intron 4::PMI exon 5 fragment (942 bps), which was inserted into pCR2.1-TOPO to form pNOV2787. pQD84A1 was partially digested with SacI and ScaI to isolate a 4910 bps vector fragment. pQD85B9 was cut with ScaI and SacI to isolate the 789 bp fragment, which was inserted into the 4910 bp pQD84A1 SacI/ScaI vector fragment to form pNOV2788. BstBI/BamHI-digested pQD86A13 was ligated with a BstBI/BamHI fragment (894 bps) of pQD87A19 to form pNOV2789. XhoI/BamHI-digested pBluescript KS(+) (Stratagene, La Jolla, Calif.) was ligated with the BssHI/BamHI fragment (1540 bps) of pQD88A1 and the BssHI/XhoI fragment (1928 bps) of pQD89A7 to form pNOV2790. pNOV2790 contained the full-length PMI sequnce with four *Arabidopsis* introns inserted into pBluescript KS(+).

EXAMPLE 17b

Construction of a GUS Gene with an AtBAF60 Intron

To construct a GUS gene with an *Arabidopsis* intron from the AtBAF60 gene, an AtBAF60 intron (420 bps) was amplified from the *Arabidopsis* genome using two primers, GUS-BAFFW1 (SEQ ID NO:78: 5'- TTG ACT GGC AGG TAC CAA GCT GCG AAT CTT CG-3') and GUSBAFRV1 (SEQ ID NO:79: 5'-ATT GGC CAC CAC CTG AAA AAT TCA GAA ACA AA-3'). AtBAF60 (CHC1) is a gene that shares homology with the mammalian nucleosome-remodeling factor BAF60. GUS exon 1 (645 bps) was amplified from pBI121 (Clonetech) using two primers, GUSBAMHI (SEQ ID NO:80: 5'-GGA TCC AAC CAT GTT ACG TCC TGT AGA AA-3') and BAFGUSRV1 (SEQ ID NO:81: 5'-CAG CTT GGT ACC TGC CAG TCA ACA GAC GCG AC-3'). GUS exon 2 (1200 bps) was amplified from pBI121 using two primers, BAFGUSFW1 (SEQ ID NO:82 5'-TTG ACT GGC AGG TAC CAA GCT GCG AAT CTT CG-3') and GUSSALI (SEQ ID NO:83: 5'-GTC GAC TCA TTG TTT GCC TCC CTG CTG CGG-3'). The GUS exon 1-AtBAF60 intron fragment (1049 bp) was formed by PCR using gel-purified GUS exon 1 (645 bp) and the AtBAF60 intron (420 bp) fragments as a template and two primers, GUSBAMHI (SEQ ID NO:84: 5'- GGA TCC AAC CAT GTT ACG TCC TGT AGA AA -3') and GUSBAFRV1 (SEQ ID NO:85: 5'- ATT GGC CAC CAC CTG AAA AAT TCA GAA ACA AA -3'). The GUS exon 1::AtBAF60 intron fragment (1049 bp) was cloned into the pCR2.1-TOPO vector to form pNOV5001. The AtBAF60 intron-GUS exon 2 fragment (1620 bp) was formed by PCR using the AtBAF60 intron (420 bp) and GUS exon 2 (1200 bp) fragments as templates and GUSBAFFW1 (SEQ ID NO:86: 5'- TTG ACT GGC AGG TAC CAA GCT GCG AAT CTT CG- 3') and GUSSALI (SEQ ID NO:87: 5'-GTC GAC TCA TTG TTT GCC TCC CTG CTG CGG- 3') as primers. The AtBAF60 intron::GUS exon 2 fragment (1620 bp) was cloned into pCR2.1-TOPO to form pNOV5002. pNOV5003 was formed through a tripartite ligation of XhoI/BamHI-digested pBluescript KS(+) with two insert fragments, pNOV5001 BamHI/HindIII fragment (961 bp) and pNOV5002 XhoI/HindIII fragment (1312 bps).

Example 18

Construction of a Monocot Expression Vector Including a PMI-Intron Sequence

Binary backbone vector pNOV2114 was digested with HindIII and Asp718I. The ZmUbi promoter/Nos 3'-UTR fragment was excised from pBH16 as a HindIII/Asp718I fragment and ligated into this vector to form pNOV044. The pBH16 construct contained the ZmUbi promotor-intron linked to the Nos (nopaline synthase) 3'-UTR by a linker with BamHI and SacI sites. pNOV2790 was digested with BamHI/BglII, and the 3011 bp fragment containing the 3'-remainder of the coding region was isolated. This fragment was then ligated into BamHI-digested pNOV044 to form pNOV042, which contained the 5'-truncated PMI-intron sequence. pNOV2790 was also digested with AflII, and an oligonucleotide converter was ligated into the site to change it into BamHI: TTAACGGATCCG, producing pQD90C2BamHI. This plasmid was digested with BamHI, and the 2832 bp fragment containing the 5'-remainder of the coding region was isolated. This fragment was ligated into the BamHI site of pNOV044 to form pNOV043, which contained the 3'-truncated PMI-intron sequence. pNOV2790 was digested with BamHI, and the 3011 bp fragment containing the full-length PMI gene was isolated. This PMI fragment was ligated into BamHI-digested p2114UbiNos to form pNOV041, which contained the full-length PMI-intron sequence.

Example 19

Construction of a PPO-dm Selectable Marker Cassette for Monocots

The rice actin 1 promoter (McElroy et al. 1990 *Plant Cell* 1990 2:163-171) was used to drive PPO-dm expression as a selectable marker. PPO-dm is a mutant form of the *Arabidopsis* PPO gene, which confers tolerance to the herbicide butafenacil. pNOV3010 is a biolistic fragment vector containing a rice actin 1 promoter-PMI expression cassette. pNOV3010 was partially digested with BamHI and filled-in with a Klenow fragment of *E.coli* DNA polymerase I to destroy the BamHI site in the intron of the 5'-region of the rice actin 1 gene, thus forming pNOV5004. The 2175 bp rice actin promoter sequence was removed from pNOV5004 by BamHI/PstI digestion and was inserted into BamHI/PstI-digested pBluescript KS(+) to form pNOV5012. pNOV5012 was digested with BamHI, filled-in with a Klenow fragment, partially cut with SacI, and then treated with calf intestine phosphatase to isolate the 5.1 kb vector. pNOV1511 (U.S. Pat. No. 6,308,458) was digested with NcoI, filled-in with a Klenow fragment, and then digested with SacI to isolate the 1898 bp PPO-dm::35S terminator fragment. This PPO-dm::35S terminator fragment was then inserted into the above pNOV5012 vector (5.1 kb) to form pNOV5013.

Example 20

Construction of a Monocot Target Vector with a PPO Herbicide Resistance Marker Gene Two oligonucleotides, ICEUBGL2 (SEQ ID NO:88: 5'-TCG AAG ATC TCT ATA ACG GTC CTA AGG TAG -3') and ICEUBAMH (SEQ ID NO:89: 5'-ACT TGG ATC CTC GCT ACC TTA GGA CCG TTA -3'), were annealed, filled-in with a Klenow fragment, and digested with BglII and BamHI to isolate a fragment containing I-CeuI cleavage site. The isolated I-CeuI site fragment was inserted into BglII-digested pNOV2790 to form pNOV5006. pNOV5013 was digested with PspOMI, filled-in with a Klenow fragment, then partially cut with BamHI to isolate the 4069 bp rice Act1 promoter::PPO::35S terminator fragment. pNOV5014 was digested with SbfI, blunted with T4 DNA polymerase, and then cut with BglII to isolate the 8972 bp fragment. The 4069 bp rice Act1 promoter::PPO::35S terminator fragment of pNOV5013 was inserted into the SbfI/BglII vector fragment (8972 bps) of pNOV5014 to form target vector pNOV5025 (FIG. 17A). pNOV5014 was constructed by inserting the BglII/SpeI fragment (3034bp) of pNOV5006 into BglII/SpeI-digested pNOV041.

Example 21

Construction of a Monocot Target Vector with the Hygromycin Phosphotransferase (hpt) Gene as an Antibiotic Resistance Marker Target binary vector pADF55 was constructed by the following steps and was used to produce target plants through hygromycin selection. The method herein described may be used with any monocot plant and any of a variety of tranformation methods, as described above. In this example, however, rice plants and *Agrobacterium*-mediated transformation were used (Hiei et al. *Plant Journal* 6:271-282).

Step 1: pAdF50 containing a new promoter-gene fusion (the rice Actin 1 promoter fused to the hygromycin gene) was built through a 3-way ligation of (1) pNEB193 cut with SalI and SphI, (2) the 2212 bp SalI-BamHI fragment of pNOV1100 containing the rice Actin 1 promoter, and (3) a 1029 bp BamHI-SphI PCR fragment containing the hygromycin gene amplified from pNOV 11. Tthe PCR primers for this reaction contained the BamHI and SphI sites: the PCR primer containing the Sphli site also contained an additional restriction site, NotI, located between the SphI site and the 3'end of the hygromycin gene, which restriction site was later used to excise the hygromycin gene.

Step 2: pAdF51 was derived from pAdF50 by adding the CMPS:GIG:Act2 3'-UTR cassette of pQD189A12 and the attP recognition sequence (a phage lambda integrase recognition sequence). pAdF51 was built through a 3-way ligation of (1) pAdF50 cut with PacI and XbaI, (2) the 3224 bp KpnI-XbaI fragment of pQD189A12 carrying the CMPS:GIG: Act2 3' gene, and (3) a 260 bp PacI-KpnI PCR product carrying the attP recognition site, which was amplified from pQD188A7. The PCR primers used for this reaction contained the PacI and KpnI sites.

Step 3: pAdF52, a subclone of the EcoO1091-AscI fragment of pNOV5025, which contains a 35S terminator and the truncated PMI-introns::nos 3' gene fragment, was inserted into pNEB193. The construct was made by subcloning the 4864 bp EcoO1091/blunt with Klenow-AscI fragment of pNOV5025 into vector pNEB193 cut with EcoO1091/blunt with Klenow and AscI.

Step 4: pAdF53 was constructed by insterting the phage lambda integrase recognition site attB into pAdF52, downstream of the 35S terminator, using an NcoI site. The attB sequence was added using two annealed oligonucleotides with ends that were compatible with an NcoI site. A BspHI site was also included in the oligo sequence to conveniently assist in identifying particular clones that contained it.

Step 5: pAdF54 was constructed by adding the *Zygosaccharomyces rouxii* R recombinase recognition site (RS) to plasmid pAdF53, downstream of the truncated PMI::nos 3' gene fragment, in a KpnI site. The RS sequence was added using two annealed oligos with ends that were compatible with a KpnI site. An AgeI site was also included in the oligo sequence to conveniently assist in identifying particular clones that contained it.

Step 6: The final construct, pAdF55, was built through a 3-way ligation of the 5684 bp PacI-AscI vector fragment of pQD199B2 ligated to the 6723 bp PacI-NotI fragment of pAdF51 and the 3566 bp NotI-AscI fragment of pAdF54.

Example 22

Figure 17A:
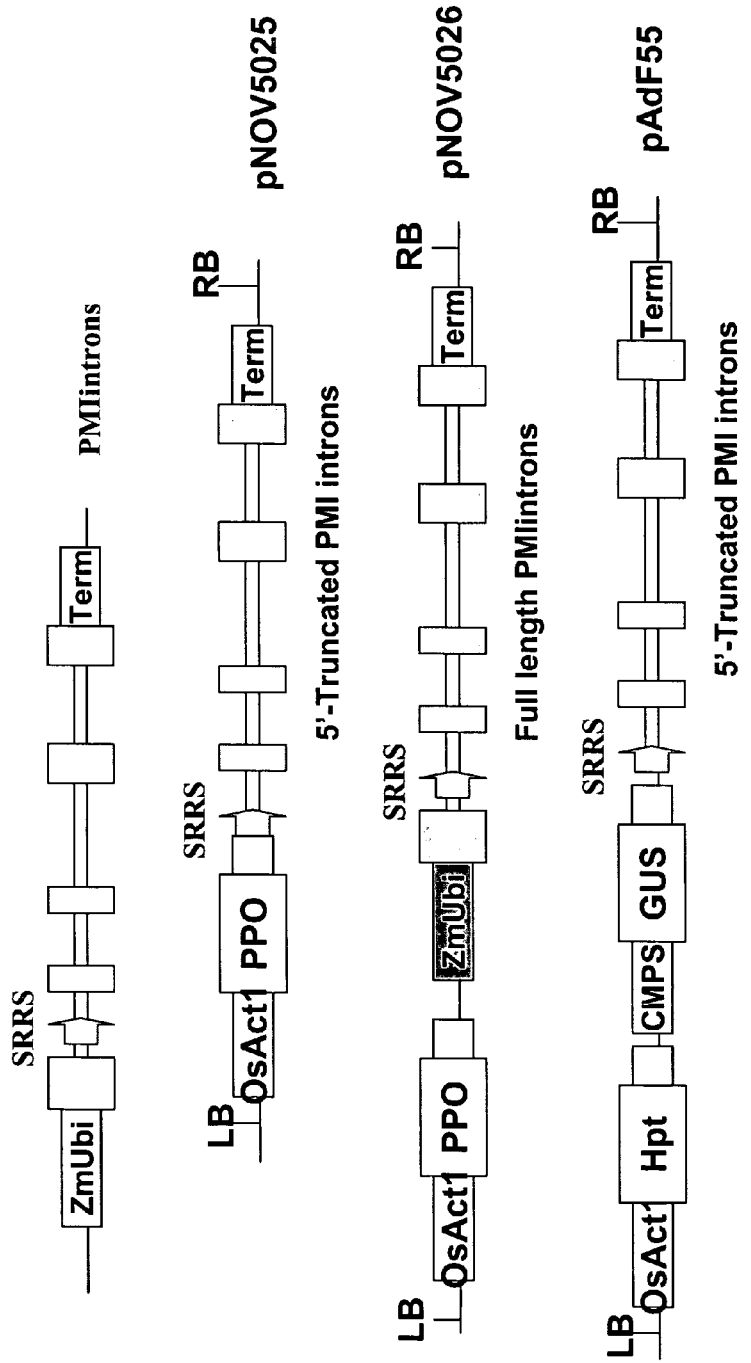
FIGS. 17A-17B illustrate a PMI-intron gene, a monocot target DNA construct, a donor DNA construct, and a positive control vector.

Construction of a Monocot Positive Control Vector pNOV5013 was digested with PspOMI, filled-in with a Klenow fragment, and then partially cut with BamHI to isolate the 4069 bp rice Act1 promoter::PPO::35S terminator fragment. pNOV5015 was digested with SbfI, blunted with T4 DNA polymerase, and then partially cut with BglII to isolate the 11.5 kb vector fragment. The 4069 bp rice ActI promoter::PPO::35S terminator fragment was inserted into the SbfI/BglII vector fragment (11.5 kb) of pNOV5015 to form pNOV5026, the positive control vector for targeting (FIG. 17A).

Example 23

Figure 17B:
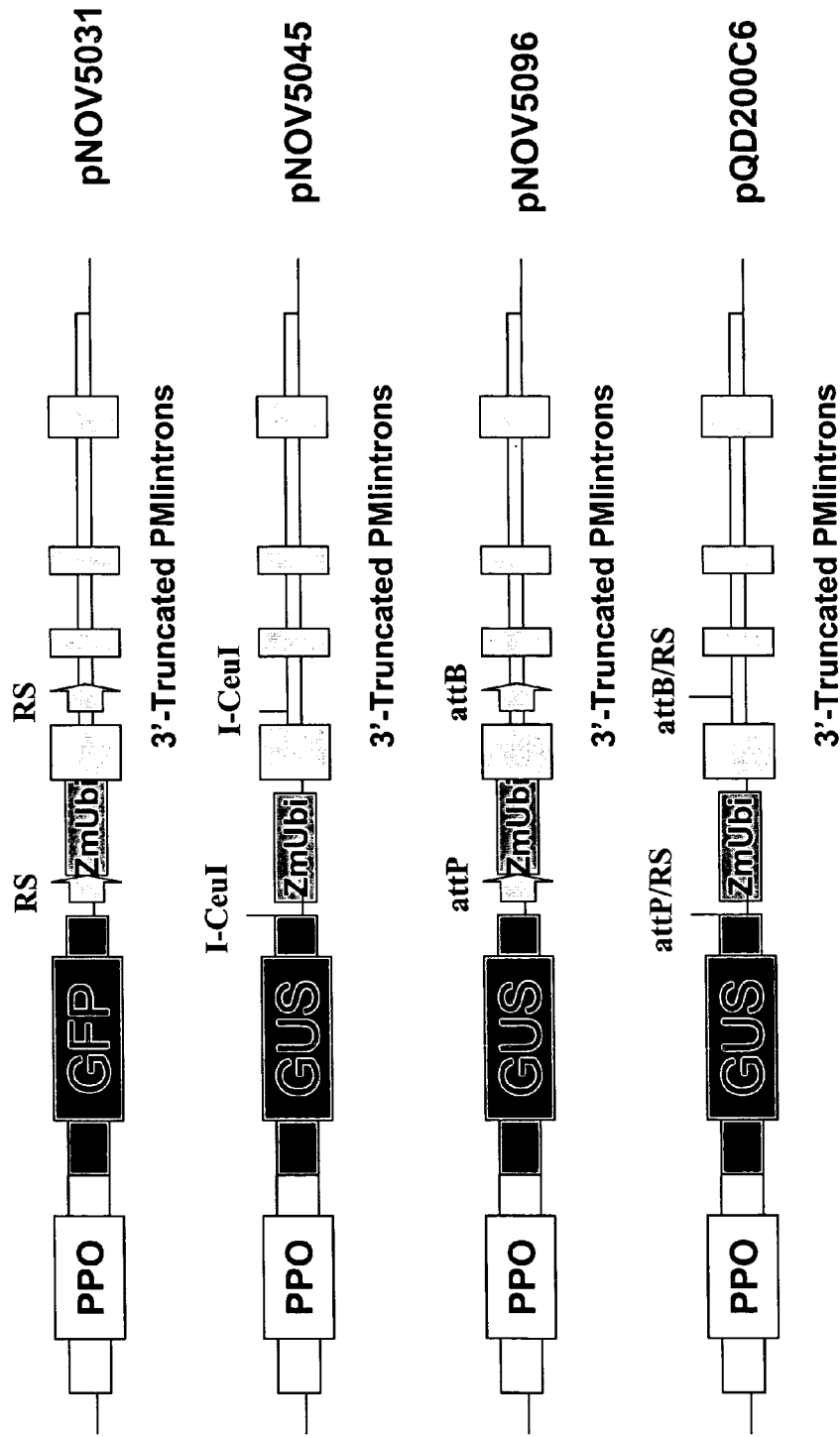
Figure 18:
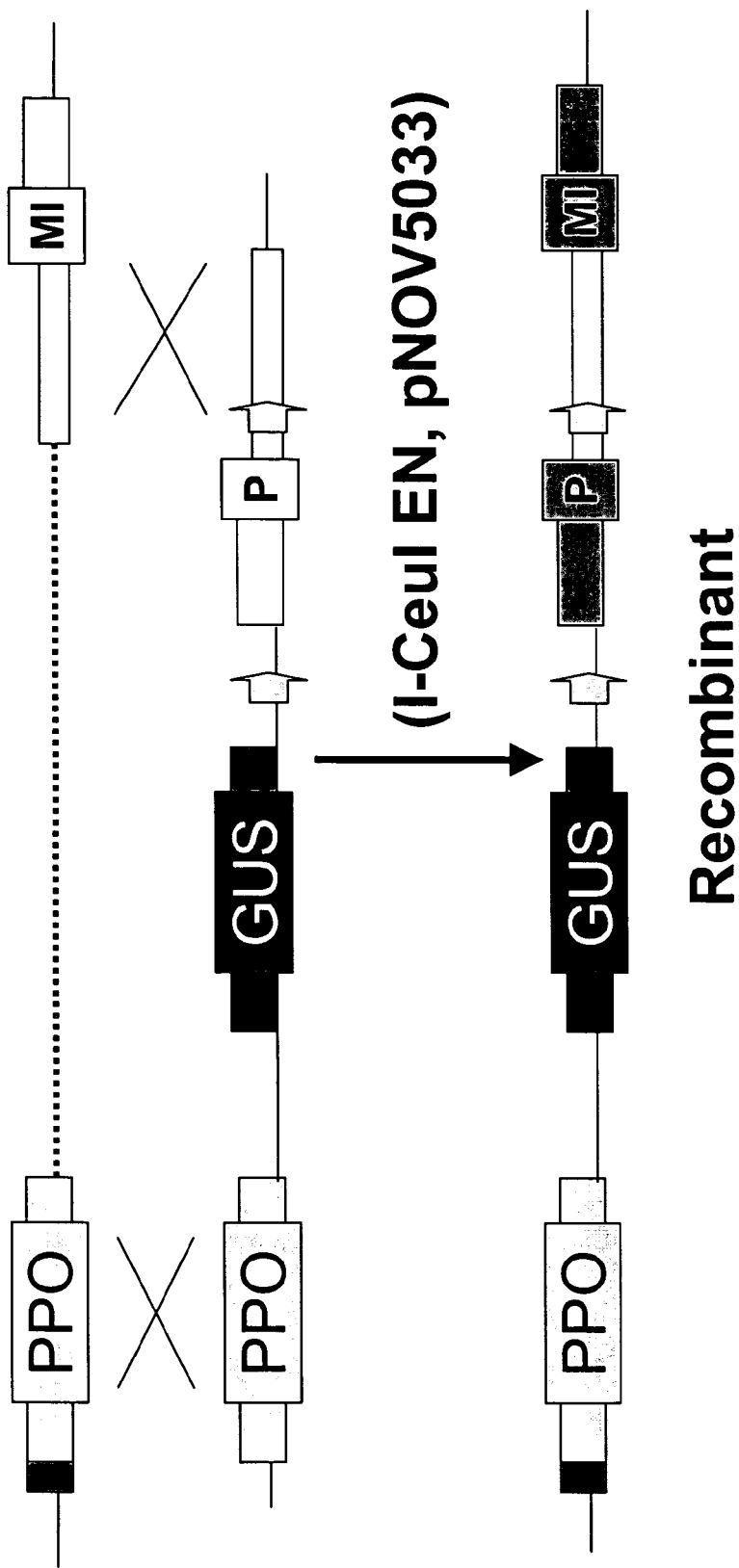
FIG. 18 illustrates an exemplary embodiment of transgene targeting in maize.

Construction of Monocot Donor Vectors pNOV041 was digested with AscI, filled-in with a Klenow fragment, and then cut with BamHI to isolate the 7.7 kb AscIBamHI fragment. pNOV5006 was digested with BstBI, filled-in with a Klenow fragment, cut with BamHI to isolate the 2652 bp BstBI/BamHI fragment. pNOV5016 was constructed by ligating the AscIBamHI fragment (7.7 kb) of pNOV041 with the BstBI/BamHI fragment (2652 bp) of pNOV5006. pNOV5013 was digested with PspOMI, filled-in with a Klenow fragment, and then partially cut with BamHI to isolate the 4069 bp rice Act1 promoter::PPO::35S terminator fragment. pNOV5016 was digested with SbfI, blunted with T4 DNA polymerase, and then partially cut with BglII to isolate the 10.3 kb vector fragment. The 4069 bp rice Act1 promoter::PPO::35S terminator fragment was inserted into an SbfI/BglII-digested pNOV5016 vector (10.3 kb) to form pNOV5027. pNOV5027 was partially digested with SrfI and BsrGI to delete part of the rice ActI promoter, filled-in with a Klenow fragment, and then circularized to form pNOV5030. pNOV5030 was digested with PacI, filled-in with a Klenow fragment, and then partially cut with SalI to isolate a 13,768 bp PacI/SalI fragment as a vector. pNOV5019 is a plasmid derived from pBluescript KS(+) containing a rice α-tubulin promoter::GFPintron::AtAct2 terminator expression cassette. The Ecl136II/XhoI fragment (3286 bp) of pNOV5019 was inserted into the 13,768 bp PacI/SalI vector fragment to form a first monocot donor vector, pNOV5031 (FIG. 17B). pNOV5030 was cut with PacI, blunted with a Klenow fragment, partially digested with PspOMI, and then dephosphorylated with CIP to isolate a 13.8 kb PacI/PspOMI vector fragment. pNOV5044 was cut with Ecl136II and PspOMI to isolate a 3525 bp Ecl136II/PspOMI insert fragment. pNOV5044 contained a CMPS promoter::GUSbafintron:: AtAct2-3'-UTR expression cassette in a pBluescript backbone. The above-described PacI/PspOMI fragment (13.8 kb) of pNOV5030 was ligated with the Ecl136II/PspOMI fragment (3535 bp) of pNOV5044 to form a second monocot donor vector, pNOV5045 (FIG. 17B).

Donor vectors with attB and attP sites were also constructed. These vectors allowed the use of phage lambda integrase to excise the intervening DNA sequences and thereby regenerate the selectable marker target site to permit gene stacking. To do this, complementary oligos ATTB1 (SEQ ID NO:90: 5'-GAT CCG CTC AAG TTA GTA TAA AAA AGC AGG CTT CAT GA-3') and ATTB2 (SEQ ID NO:91: 5'-GAT CTC ATG AAG CCT GCT TTT TTA TAC TAA CTT GAG CG -3') were annealed and inserted into BglII digested- pNOV2790 to form pQD187A8. The phage lambda attP sequence was amplified by PCR from the phage DNA with two primers, ATTPSPOMI (SEQ ID NO:92: 5'-GGG CCC TCT GTT ACA GGT CAC TAA TAC CAT CTA AG-3') and ATTPSPEI (SEQ ID NO:93: 5'-ACT AGT GAA ATC AAA TAA TGA TTT TAT TTT G-3'), and the PCR product was cloned into the pCR2.1-TOPO vector to form pNOV5088. The attP sequence was removed from pNOV5088 by digestion with ApaI, treatment with a Klenow fragment, and then a second digestion with NotI. pNOV5089 was digested with XbaI, filled-in with a Klenow fragment, and then cut with NotI. The above XbaI/NotI fragment of pNOV5089 was then ligated with the ApaI/NotI fragment of pNOV5088 to form pNOV5094. pNOV5089 was derived from pNOV5044 by replacing the BstBI/SnaBI fragment of the GUSBAFintron with the BstBI/SnaBI fragment of the GUSintron from pNOV3603. The KpnI/SpeI fragment of pNOV5031 was replaced with the KpnI/SpeI fragment from pNOV5087 to form pNOV5095. pNOV5094 was cut with Ecl136II and PspOMI to isolate the 3517 bp fragment containing the CMPS promoter::GIG::Tact2::attP site. pNOV5095 was digested with PacI, blunted with a Klenow treatment, and then partially recut with PspOMI to isolate the 13805 bp fragment. The Ecl136II/PspOMI fragment of pNOV5094 was inserted into the above 13.8 kb fragment of pQD195A6 to form a third monocot donor vector, pNOV5096 (FIG. 17B). The 3608 bp Ecl136II/PspOMI of pNOV5098 was inserted into the above PacI/PspOMI-digested pNOV5095 vector to form a fourth monocot donor vector, pQD200C6 (FIG. 17B), which inlcuded RS and FRT sites upstream of the ZmUbi promoter in addition to the attP sequence. A binary vector (pNOV5099) containing a positive control PMI-intron gene with the attB sequence in the first intron was constructed by inserting the 3551 bp BamHI fragment of pQD187A8 into BamHI-digested pNOV041. Another positive control binary vector (pQD203A11) was created by inserting the NcoI(blunt)/PspOMI fragment (3.6 kb) of pNOV5098 into a (PacI)blunt/PspOMI fragment (11535 bps) of pNOV5099.

Example 24

Construction of I-CeuI Expression Vectors for Monocots

An I-CeuI sequence with maize-preferred codons was released from pSmasICeuIintron as a BamHI/KpnI fragment (1154 bps), and a maize ubiquitin promoter (ZmUbi) was released from pNOV2115 as a BamHI/HindIII (2005 bps) fragment. These two fragments (I-CeuI and ZmUbi) were ligated into KpnI/HindIII-digested pNOV2114 to form pNOV5033. pNOV2114 is a binary backbone vector with a VS1 origin, one copy of the VirG gene, and a spectinomycin resistance gene for selection in bacteria. The BamHI/VKpnI fragment of I-CeuI and the ZmUbi fragment were also ligated with KpnI/hindIII-digested pNOV2122 to form pNOV5034. pNOV2122 is a binary backbone vector with an RK2 origin of replication, one copy of the VirG gene, and a kanamycin resistance gene for selection in bacteria. In both pNOV5033 and pNOV5034, I-CeuI expression was under the control of a maize ubiquitin promoter.

Example 25

Generation of Target Maize Plants

Target plants can be generated through *Agrobacterium* or biolistic-mediated transformation using target vector pNOV5025 and pAdF55 with any of several monocot plants, such as maize, rice, wheat, or barley, for example. Maize examples are provided here to demonstrate the feasibility of gene targeting through homologous recombination in monocot plants. The transformation of immature maize embryos was performed essentially as described in Negrotto et al. (2000 Plant Cell Reports 19: 798-803), which describes the use of PMI as the selectable marker gene and mannose as the selection agent, and Li et al (2003 Plant Physiol. 133:736-747), which describes the use of PPO as the selectable marker gene and butafenacil as the selection agent. For this example, all media constituents are as described in Negrotto et al. and Li et al. supra. However, various media constituents described in the literature may be substituted.

Target binary vector pNOV5025 contained the mutant protoporphyrin oxidase (protox) (PPO) gene (U.S. Pat. No. 6,308,458), which permitted the selection of transgenic cells with an herbicide-supplemented media (i.e., butafenacil). See, Li et al. 2003 Plant Physiol. 133:736-747. A positive control vector pNOV5026 was also included.

*Agrobacterium* strain LBA4404 (PSB1) containing pNOV5025 was grown on YEP (yeast extract (5 g/L), peptone 10 g/L), NaCl (5g/L), 15g/l agar, pH 6.8) solid medium for 2-4 days at 28° C. Approximately $0.8 \times 10^9$ Agrobacteria (about 0.75 $A_{660}$) per ml were resuspended in LS-inf media supplemented with 100 µM As (Negrotto et al. 2000 *Plant Cell Rep* 19: 798-803). Bacteria were pre-induced in this medium for 30-60 minutes. For this example, immature embryos from A188×Hi II were excised from 8-12 day old ears into liquid LS-inf+100 µM As. However, immature embryos derived from various other crosses or selfed A188 or HiII plants can be used as transformation targets. The embryos were rinsed once with fresh infection medium and heat-shocked at 45° C. for 5 minutes. The infection medium was replaced with *Agrobacterium* solution, and the embryos were vortexed for 30 seconds and allowed to settle with the bacteria for 5 minutes. The embryos were then transferred scutellum side up to LSAs medium and cultured in the dark for two to three days. Subsequently, between 20 and 25 embryos per petri plate were transferred to LSDc medium supplemented with ticarcillin (250 mg/l) and silver nitrate (1.6 mg/l) and cultured in the dark for 28° C. for 10 days.

Selection was performed essentially as described in Li et al., supra. Silver nitrate was used in both the initiation and selection media, and sucrose was used at 30 g/L. The protox inhibitory herbicide butafenacil was added to the media at 5nM for initiation and primary selection, 500nM for second selection, and 750nM for the final selection. Regeneration 1 was carried out on media supplemented with 50nM herbicide with no herbicide selection in subsequent regeneration media. Maize leaf sample were assayed by Taqman analysis for the copy number of PPO and PMI genes. Maize events (for example, AW286B1A to AW289B1C, AW289B1A to AW289B1C, AW289E2D and AW289F2C etc.) with a single copy of both genes were transplanted into soil and grown in the greenhouse.

Example 26

Targeted Integration of a Donor Sequence by Homologous Recombination in Maize

Once the primary transgenic lines containing the desired T-DNA target (i.e., a target containing single copies of both the PPO and PMI genes) are obtained, various materials derived from these plants and their progeny can be used as target tissue for retransformation to obtain targeted events. These materials can also be used as pollen donors or receptors to produce target tissues for retransformation. For this example, AW289B1A was either selfed or used to pollinate A188 or HiII to produce seeds. Pollen from AW289B1A also was used directly to pollinate untransformed A188 and to generate immature embryos for retransformation with donor vectors pNOV5031, pNOV5045, pNOV5096, and pQD200C6.

Immature embryos (7-10 days post-pollination) were isolated from immature ears and used for *Agrobacterium*-mediated transformation, as described by Negrotto et al., supra. In some experiments, an *Agrobacterium* culture containing an I-CeuI expression vector, pNOV5033, was mixed with an *Agrobacterium* strain containing the donor vector (in a 1:1 ratio). Targeted events were selected from *Agrobacterium*-infected immature maize embryos using mannose as a selection agent. Immature embryos producing embryogenic calli were transferred to LSD1M0.5S medium. The cultures were selected on this medium for 3 weeks, transferred to fresh LSD1M0.5S medium, and then incubated for another 3 weeks. Surviving calli were transferred to Reg1 medium supplemented with mannose. Following a culture period of 1 to 2 weeks in the light (16 hour light/8 hour dark regimen), green tissues were then transferred to Reg2 medium without growth regulators and then incubated for 1-2 weeks. Plantlets were transferred to Magenta GA-7 boxes (Magenta Corp, Chicago Ill.) containing Reg3 medium and grown in the light (16 hour light/8 hour dark regimen). After 2-3 weeks, plants were transferred to the greenhouse for planting in soil. Maize lines HR-18FB.1A to HR-18FB.1N are putative mannose resistant targeted lines. These lines were derived from the targeted integration of donor sequence pNOV5045 by homologous recombination in the presence of pNOV5033.

Example 27

Molecular Characterization of the Targeted Event

Putative mannose-resistant targeted events were confirmed by well-known molecular biological methods, including PCR and Southern blot analysis. For example, a Southern blot was prepared from the DNA of target line AW289B1A and putatively targeted line HR-18FB.1M. DNA samples were digested with various restriction enzymes, including KpnI, ScaI, SacI, SpeI and HpaI, and hybridized with two different target specific probes from 5'-region of the rice actin 1 promoter and 3'-region of the PMIintrons (see FIGS. 20A and 20B for the blot and FIGS. 19A and 19B for the probe location and restriction map). The hybridization patterns were consistent with targeted double crossover recombination of pNOV5045 T-DNA with the target locus, which included T-DNA from pNOV5025.

Figure 19A:
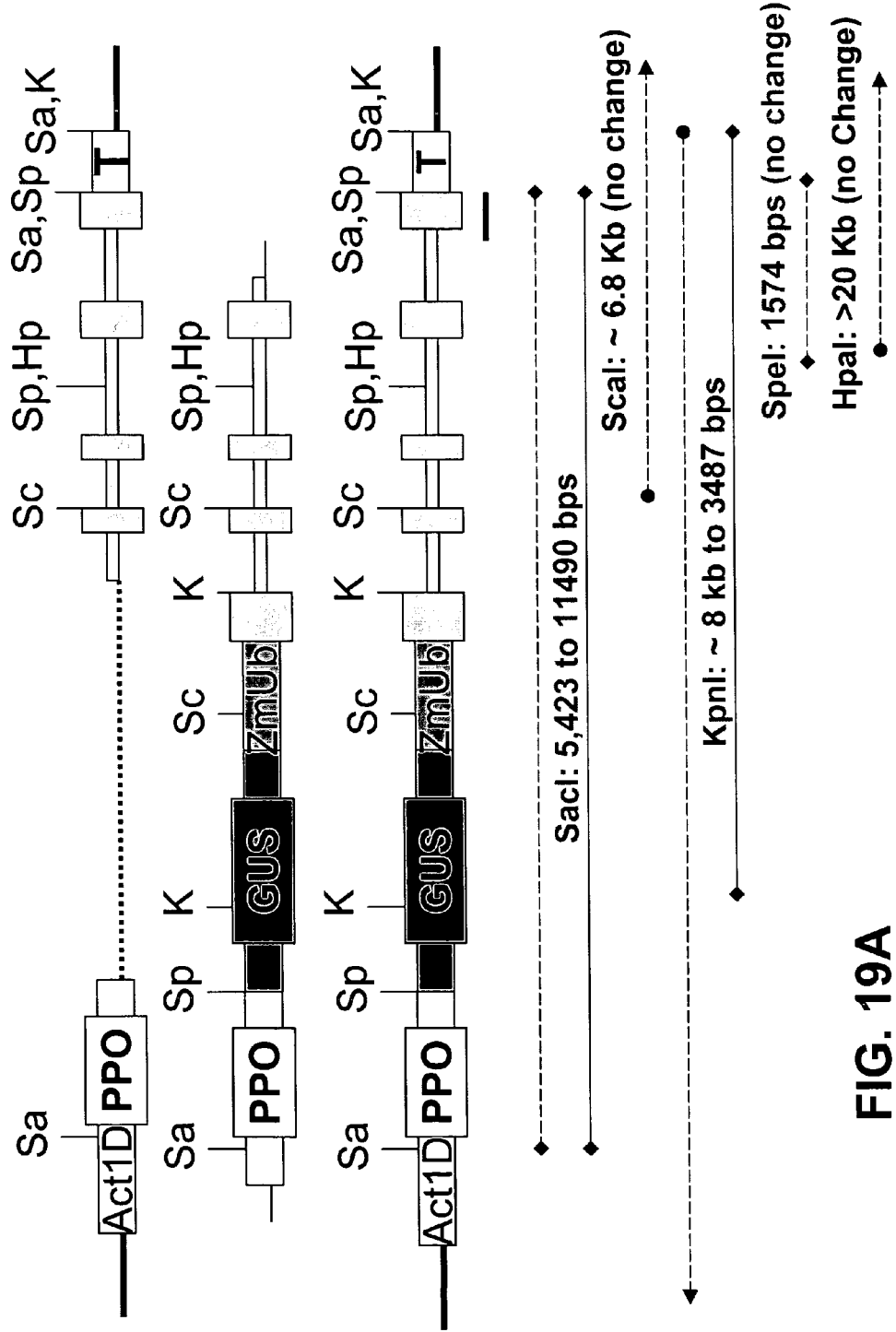
FIGS. 19A-19D represent restriction map and fragment sizes of target locus AW289B1A, T-DNA of donor vector pNOV5045, and putative double crossover recombinant with different probes. The change in size of each restriction fragment is represented in the lower portion with the size in the target locus and recombinant indicated. The short bar under the restriction map represents the location of each probe.
Figure 19B:
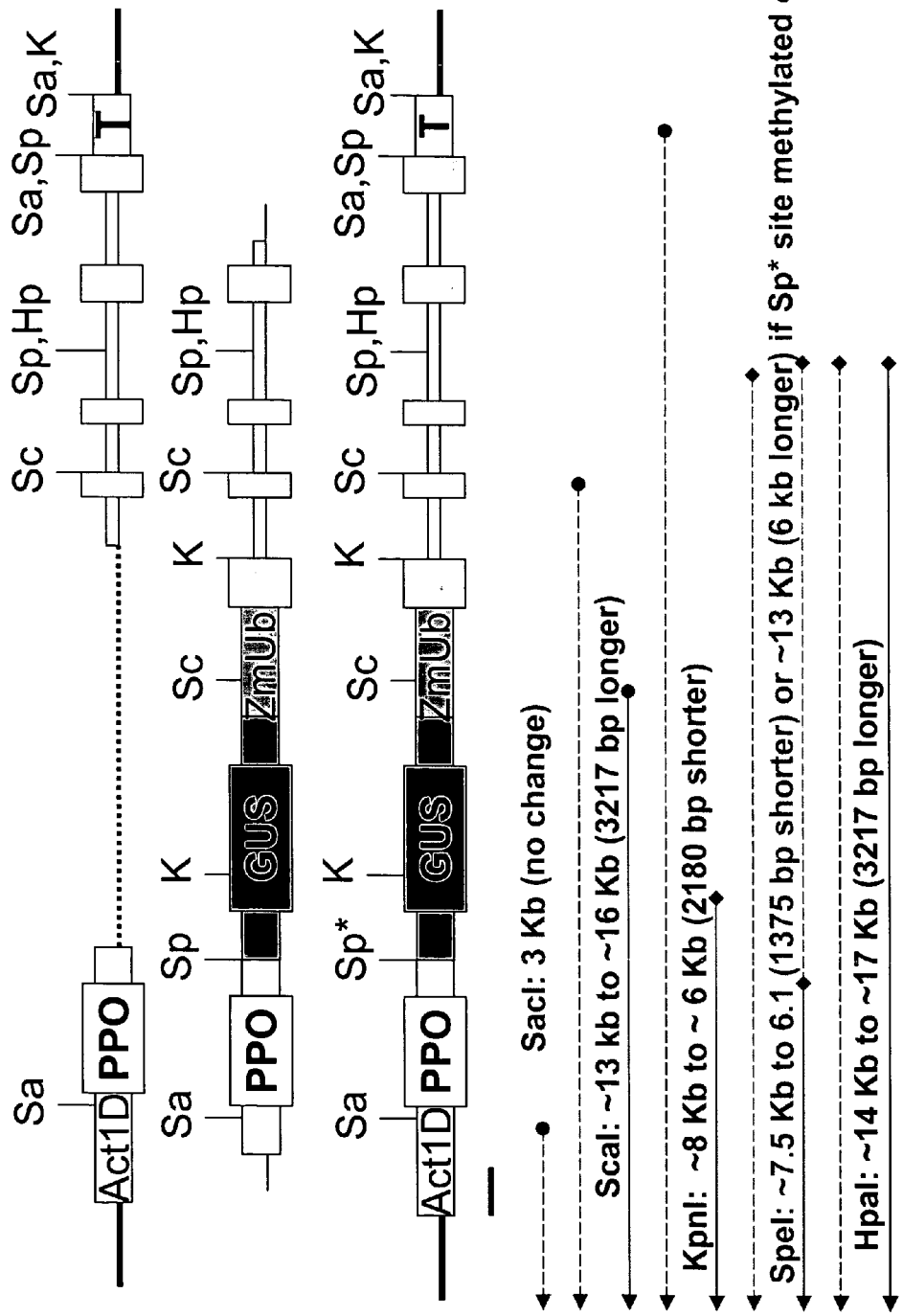
Figure 19C:
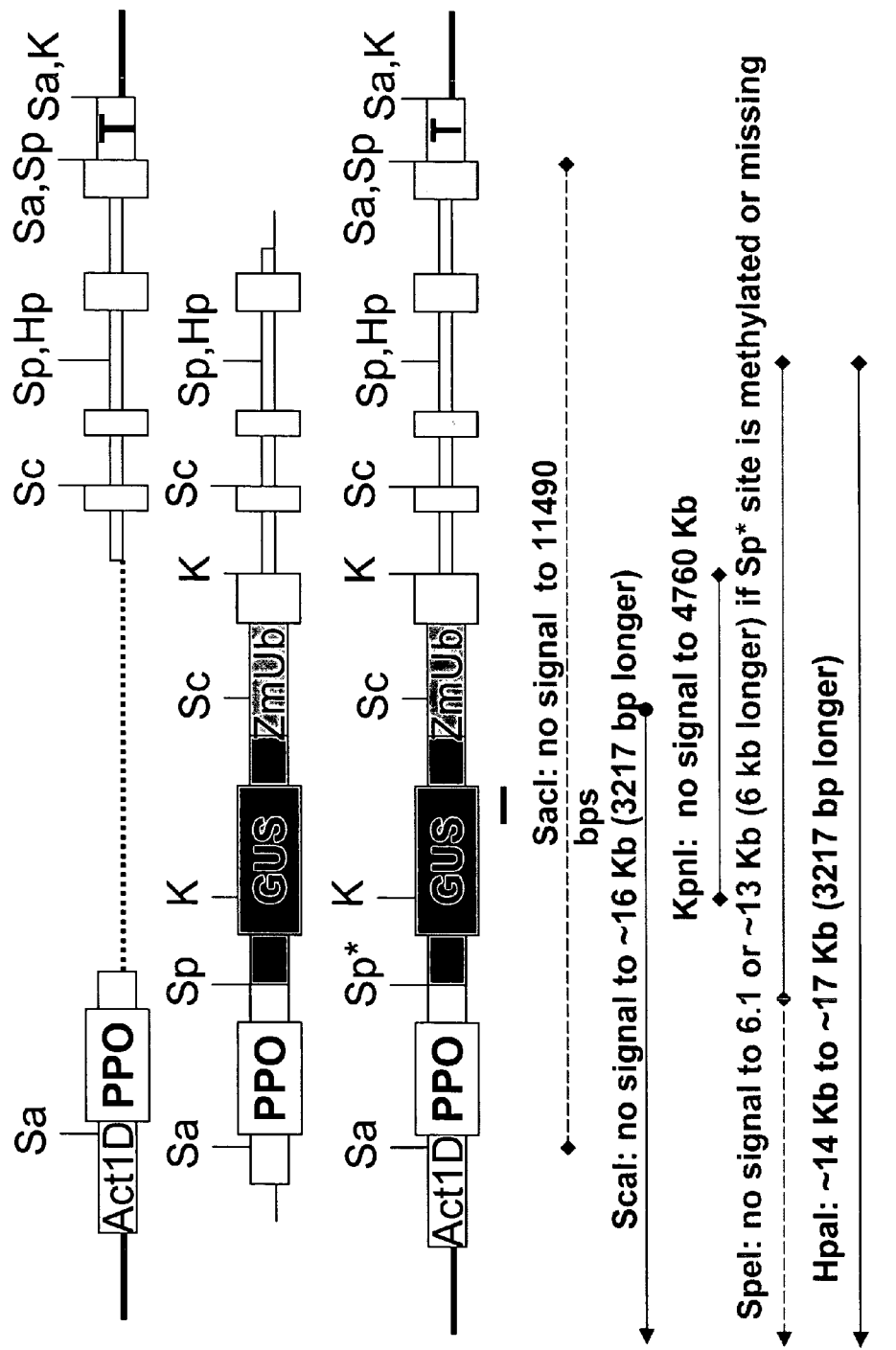
Figure 19D:
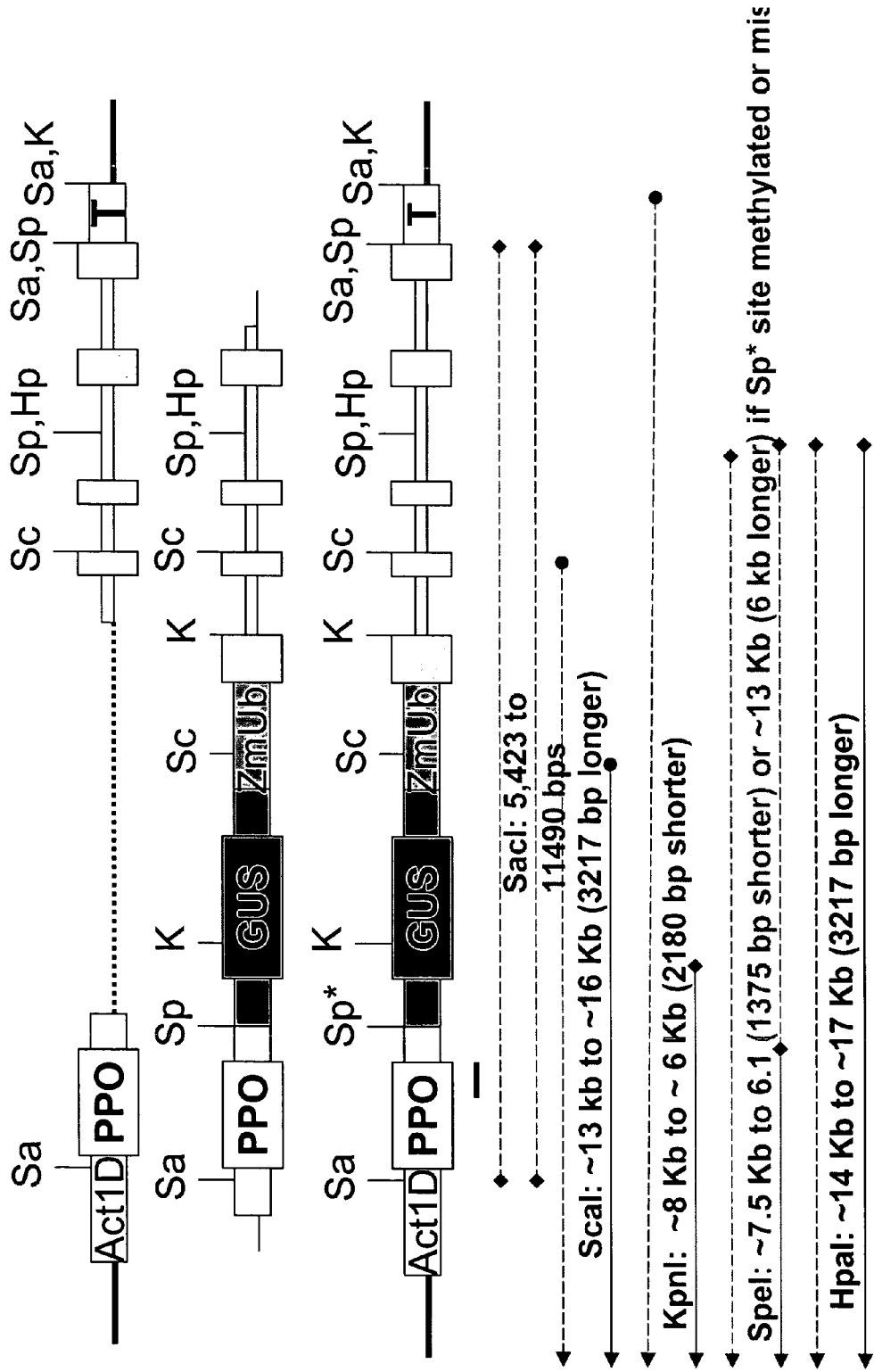

The first target locus-specific probe (i.e., the 5'-region of the rice ActI, FIG. 19B) is from the rice actin 1 promoter 5'-upstream region that is not present in the donor vector pNOV5045 and is used to detect recombination at the LB end of the target locus. The second target locus-specific probe (i.e., PMIintrons 3'-region) hybridizes to the region containing the PMIintrons intron 4/exon 5 and is used to detect recombination at the RB end of the target locus (FIG. 19A).

Figure 20D:
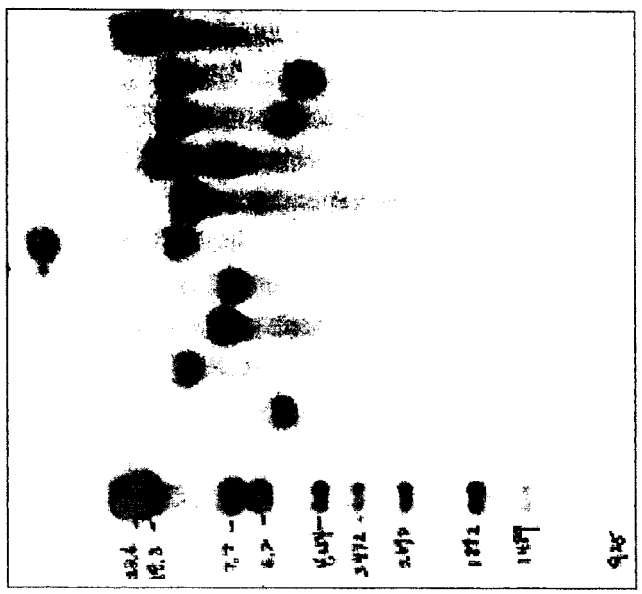
Figure 20C:
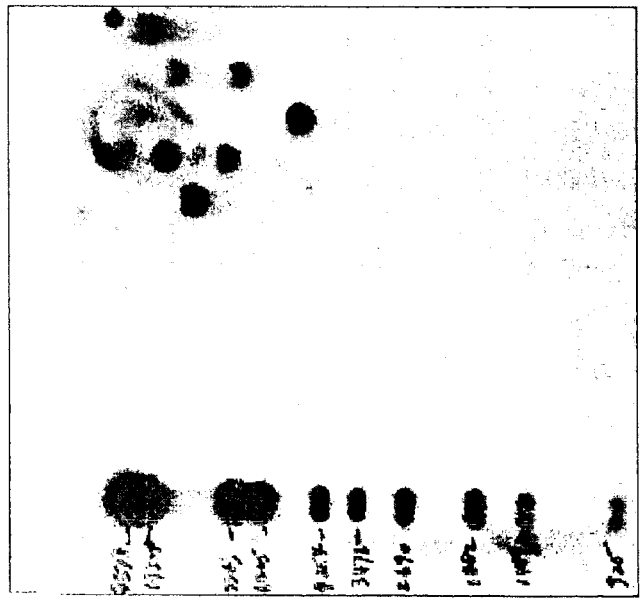

Southern analysis confirmed that HR-18FB.1M is a truly targeted event derived from AW289B1A (FIGS. 19A to 19D and 20A to 20D). SacI digestion of the DNA samples would be expected to release an internal fragment from the target locus that included most of the introduced T-DNA sequences in both the target locus and the expected recombinant, but the size of the SacI band hybridizing to the PMI 3'-end probe would be expected to shift from 5.4 kb to 11.5 kb. As predicted, the size of the SacI fragment shifted from 5.4 kb of the target locus (AW289B1A) to 11.5 kb of the putative targeted line HR-18FB.1M when the PMI-intron 3'-fragment was used as a probe (FIG. 20B, lane 1a vs 6a).

KpnI digestion of the DNA samples resulted in a KpnI fragment that was also decreased in size, as predicted, from about 8 kb in the target locus to 3.5 kb in targeted line HR-18FB.1M when the PMI-intron 3' fragment was used as a probe (FIG. 20B, lane 3a vs 8a).

With ScaI, SpeI, and HpaI digestions, the fragment sizes did not change as predicted when there was targeted integration at the target locus (FIG. 20B, lane 2a vs 7a, lane 4a vs 9a, lane 5a vs 10a). Because ScaI and HpaI digestions hybridized with a PMI-intron 3'-probe detected changes in sequences outside the T-DNA, the results indicated that no DNA rearrangement could be detected on the right border of the T-DNA locus.

With the rice actin-1 5'-region probe, all five digestions indicated that recombination had occurred on the PPO side of the target locus. With the exception of SpeI, all band shifts in the targeted line HR-18FB.1M as compared with the target line AW289B1A were as expected (FIG. 20B). Because SpeI digestion is sensitive to overlapping cytosine methylation, it is possible that the SpeI site between the PPO and GUS genes was methylated. If this were the case, the size of SpeI fragment would have been expected to increase to 13 kb rather than be reduced to 6 kb. Since the SpeI fragment detected by the rice actin-1 probe was in fact 13 kb, methylation was the likely cause of the band shift (FIG. 20B, lane 4b vs 9b). It is also possible that there was a rearrangement, such as a deletion, that lead to the loss of the SpeI site.

Overall, the Southern blot data are consistent with the occurrence of targeted integration of the donor T-DNA into the target locus in line HR-18FB.1M by double crossover homologous recombination.

Example 28

Preparation of a Site-Specific R Recombinase Nucleotide Sequence with Maize-Preferred Codons and Construction of an R Recombinase Expression Vector A site-specific R recombinase amino acid sequence was back-translated into a DNA nucleotide sequence as shown in SEQ ID NO:94 using maize-preferred codons (U.S. Pat. No. 6,121,014). Sequences flanking the synthetic R recombinase (ZmR) coding region are indicated in lower cases letters.

```
SEQ ID NO:94: R recombinase with maize-preferred
codons (ZmR)
ctcgagcaaccATGCAGCTGACCAAGGACACCGAGATCAGCACCATCAAC

CGCCAGATGAGCGACTTCAGCGAGCTGAGCCAGATCCTGCCCCTGCACCA

GATCAGCAAGATCAAGGACATCCTGGAGAACGAGAACCCCCTGCCCAAGG

AGAAGCTGGCCAGCCACCTGACCATGATCATCCTGATGGCCAACCTGGCC

AGCCAGAAGCGCAAGGACGTGCCCGTGAAGCGCAGCACCTTCCTGAAGTA

CCAGCGCAGCATCAGCAAGACCCTGCAGTACGACAGCAGCACCAAGACCG

TGAGCTTCGAGTACCTGAAGGACCCCAGCAAGCTGATCAAGGGCCTG

GAGGACGTGGTGAGCCCCTACCGCTTCGTGGTGGGCGTGCACGAGAAGCC
```

```
-continued
CGACGACGTGATGAGCCACCTGAGCGCCGTGCACATGCGCAAGGAGGCCG

GCCGCAAGCGCGACCTGGGCAACAAGATCAACGACGAGATCACCAAGATC

GCCGAGACCCAGGAGACCATCTGGGGCTTCGTGGGCAAGACCATGGACCT

GATCGAGGCCCGCACCACCCGCCCCACCACCAAGGCCGCCTACAACCTGC

TGCTGCAGGCCACCTTCATGAACTGCTGCCGCGCCGACGACCTGAAGAAC

ACCGACATCAAGACCTTCGAGGTGATCCCCGACAAGCACCTGGGCCGCAT

GCTGCGCGCCTTCGTGCCCGAGACCAAGACCGGCACCCGCTTCGTGTACT

TCTTCCCCTGCAAGGGCCGCTGCGACCCCCTGCTGGCCCTGGACAGCTAC

CTGCAGTGGACCGACCCCATCCCCAAGACCCGCACCACCGACGAGGACGC

CCGCTACGACTACCAGCTGCTGCGCAACAGCCTGCTGGGCAGCTACGACG

GCTTCATCAGCAAGCAGAGCGACGAGAGCATCTTCAAGATCCCCAACGGC

CCCAAGGCCCACCTGGGCCGCCACGTGACCGCCAGCTACCTGAGCAACAA

CGAGATGGACAAGGAGGCCACCCTGTACGGCAACTGGAGCGCCGCCCGCG

AGGAGGGCGTGAGCCGCGTGGCCAAGGCCCGCTACATGCACACCATCGAG

AAGAGCCCCCCCAGCTACCTGTTCGCCTTCCTGAGCGGCTTCTACAACAT

CACCGCCGAGCGCGCCTGCGAGCTGGTGGACCCCAACAGCAACCCCTGCG

AGCAGGACAAGAACATCCCCATGATCAGCGACATCGAGACCCTGATGGCC

CGCTACGGCAAGAACGCCGAGATCATCCCCATGGACGTGCTGGTGTTCCT

GAGCAGCTACGCCCGCTTCAAGAACAACGAGGGCAAGGAGTACAAGCTGC

AGGCCCGCAGCAGCCGCGGCGTGCCCGACTTCCCCGACAACGGCCGCACC

GCCCTGTACAACGCCCTGACCGCCGCCCACGTGAAGCGCCGCAAGATCAG

CATCGTGGTGGGCCGCAGCATCGACACCAGCTGAagctt
```

This synthetic R recombinase with maize preferred codons was synthesized and cloned into pUC19 to form pUC19-ZmR by IDT (Coralville, Iowa 52241). A ZmUbi-R expression cassette was inserted into binary vector pNOV2114 for maize transformation. A ZmR HindIII/BamHI fragment (1493 bp) was then removed from pUC19-ZmR by HindIII digetion, filled-in with a Klenow fragment, and then digested with BamHI and inserted into pNOV3603, which then was cut with SacI, blunted with a Klenow fragment, and digested with BamHI to form pQD204B1. pQD204B1 included the maize ubiquitin promoter to drive expression of ZmR, which was followed by a nopaline synthase terminator. The HindIII/KpnI fragment (3784 bp) of pQD204B1 containing the ZmUbi promoter::ZmR::Tnos cassette was inserted into a HindIII/KpnI-digested pNOV2114 binary backbone vector to form pQD205A1. pQD204B1 was also digested with KpnI, blunted by treatment with a Klenow fragment, and then recut with HindIII to isolate the 3780 bp KpnI/HindIII fragment containing the ZmUbi promoter::ZmR::Tnos expression cassette. This KpnI/HindIII fragment was inserted into pNOV2819, which was cut with SalI, filled-in with a Klenow fragment, and re-digested with HindIII to form binary vector pQD206B1. pQD206B1 contained a ZmR expression cassette (ZmUbi promoter::ZmR::Tnos) and a selectable marker gene cassette (CMPS promoter::PMI::Tnos). ZmR was also placed under the control of several tissue specific promoters, including OsG, RA-8, P19, and OsMADS13 to avoid any potentially undesirable effects of constitutive expression.

These vectors were referred to as pBSC11475 (OsG), pBSC11478 (RA-8), pBSC11479 (P19), and pBSC11480 (OsMADS 13), respectively.

Example 29

Construction of Binary Vectors for Expressing Phage Lambda Integrase, an Integrase Mutant, and an Integration Host Factor Phage lambda integrase, its double amino acid mutant (IntH218), and host factors with maize preferred codons are described in WO/03083045. Binary vector pNOV2114IntIHFs contained maize-optimized lambda integrase (Int) and IHF α and β coding sequences under the control of a CMPS promoter followed by a Tnos terminator. The (HindIII)blunt/AscI fragment (4122 bp) containing the Int and IHF expression cassettes were removed from pNOV2114IntIHFs by HindII digestion, filled-in with a Klenow treatment, recut with HindIII, and ligated with a (BamHI)blunt/AscI fragment (9541 bps) of pWC057 to form pQD208B12. pWC057 is a binary vector containing a ZmUbi promoter::AtPPO(dm)::T35S expression cassette (see U.S. Pat. No. 6,282,837). pQD208B12 is a binary transformation vector containing the CMPS promoter::Int::Tnos, CMPS promoter::IHFα:Tnos, and CMPS promoter::IHFβ::Tnos expression cassettes, as well as the ZmUbi promoter::AtP-POdm::T35S selectable marker cassette. Similarly, binary vector pNOV2114IntH218IHFs contains a maize-optimized lambda integrase mutant (IntH218) and IHF α and β coding sequences under the control of a CMPS promoter followed by a Tnos terminator. The (HindIII)blunt/AscI fragment (4122 bp) containing the IntH218 and IHF expression cassettes were removed from pNOV2114IntH218IHFs by HindIII digestion, filled-in with a Klenow treatment, recut with HindIII, and ligated with a (BamHI)blunt/AscI fragment (9541 bps) of pWC057 to form pQD209B16. pQD209B16 is a binary transformation vector containing the CMPS promoter::IntH218::Tnos, CMPS promoter::IHFα::Tnos, CMPS promoter::IHFβ::Tnos expression cassettes, as well as the ZmUbi promoter::AtPPOdm::T35S selectable marker cassette. Plasmid vector pAdF62A (W003/083045), containing the synthetic XIS gene with maize optimised codons, was cut with SpeI, filled-in with Klenow, and then re-cut with AscI to isolate the SpeI-AscI fragment containing the CMPS promoter, XIS gene, and nos terminator. This fragment was inserted into AscI/SwaI-digested pQD208B12 and pQD209B16 to form pQD35OA7 (aka. pBSC11348) and pQD351A15 (aka. pBSC11349), respectively.

Example 30

Generation of Transgenic Plant Lines Expressing ZmR, IntIHFs, and IntH218IHFs

Binary vectors pQD206B1, pQD208B12, pQD209B16, pBSC11348, pBSC11349, pBSC11475, pBSC11478, pBSC11479, and pBSC11480 were each transformed, individually, into Agrobacterium strain LAB4404(pSB1). The individual cultures of the Agrobacterium strain were then used for co-cultivation with immature maize embryos. The co-cultivated embryos were placed on a selection medium containing an herbicide (butafenacil) to generate transgenic plants. The transgenic plants were crossed directly to target plants or they were self-pollinated to produce seeds, which were used to generate additional plant material to cross with other plants.

Example 31

Removal of the Promoter and Part of the PMI-Intron Sequence to Regenerate a Truncated PMI-Intron Sequence Transgenic maize lines expressing either synthetic R recombinase or phage lambda integrase were obtained by Agrobacterium-mediated transformation using binary pQD208B12, pQD209B16, pBSC11348, pBSC11349, pBSC11475, pBSC11478, pBSC11479, and pBSC11480. R recombinase or integrase-expressing lines can be crossed with desirable targeted recombinants to excise both the promoter sequence and the region of the PMI coding sequence flanked by the RS, attB/attP, or attL/attR sequences to truncate the PMI selectable marker gene. The progeny are screened by PCR for the truncation. Lines with the truncated sequence are backcrossed with a non-transgenic parent line to produce seeds. These seeds are then germinated, and the seedlings are screened by PCR to recover lines with the desired truncated sequence but without the recombinase locus. Lines with a regenerated target site but without the recombinase gene are used for a second round of gene targeting.

Alternatively, recombinant lines can be re-transformed with either an R recombinase or a Lambda integrase expression vector. Transformed lines are screened by PCR for the desired deletion. Lines with the desired deletion are backcrossed with untransformed plants to obtain seeds. These seeds are then germinated, and the seedlings are screened by PCR to recover lines with the desired deletion but without the R recombinase or Lambda integrase locus. Lines with a regenerated target site but without the R recombinase or integrase gene are used for a second round of gene targeting.

Recombinase can also be delivered as a virE2/VirF fusion protein expressed by Agrobacterium (Vergunst et al. 2000 Science 290:979-82). Maize tissues, preferably immature embryo or embryogenic callus, are infected with Agrobacterium cells containing vectors expressing R/integrase::virE2/virF fusion proteins. These fusion proteins are transported into plant cells to mediate a site-specific deletion of the sequence flanked by recombinase recognition sequences in suitable orientation allowing excision of the flanked region, such as Lox, FRT, RS, attB/attP or attL/attR sequences. Regenerated plants are screened by PCR for the deletion. With this method, recombinase or integrase expression vector DNA is delivered into the plant cells. Lines with the desired deletion can be used directly for an additional round of gene targeting.

Example 32

Generation of Target Rice Plants

For this example, the rice (Oryza sativa var. javonica) cultivar "Kaybonnet" was used to generate a target rice plant. However, other rice cultivars also can be used (Hiei et al. (1994) *Plant Journal* 6:271-282; Dong et al. (1996) *Molecular Breeding* 2:267-276; Hiei et al. (1997) *Plant Molecular Biology* 35:205-218). Also, various media constituents described below may be varied or substituted.

Embryogenic responses were initiated and/or cultures were established from mature embryos by culturing on MS-CIM medium (MS basal salts, 4.3 g/liter; B5 vitamins (200×), 5 ml/liter; Sucrose, 30 g/liter; proline, 500 mg/liter; glutamine, 500 mg/liter; casein hydrolysate, 300 mg/liter; 2,4-D (1 mg/ml), 2 ml/liter; adjust pH to 5.8 with 1 N KOH;

Phytagel, 3 g/liter). Either mature embryos at the initial stages of culture response or established culture lines were inoculated and co-cultivated with the Agrobacterium strain LBA4404 containing the desired vector construction (i.e., pNOV5025 or pADF55).

Agrobacterium was cultured from glycerol stocks on solid YP medium (100 mg/L spectinomycin) for 3 days at 28° C., then streaked again and cultured for 1-2 days. Agrobacterium was re-suspended in liquid MS-CIM medium. The Agrobacterium culture was diluted to an OD600 of 0.2-0.3 and acetosyringone was added to a final concentration of 200 µM. Agrobacterium was induced with acetosyringone for at least 30 min before mixing the solution with the rice cultures.

For inoculation, the cultures were immersed in the bacterial suspension for 30 min. The liquid suspension was removed with a vacuum aspirator, and the inoculated cultures were placed on a Whatman paper filter on co-cultivation medium MS-CIM-As (MS-CIM with 200 µM acetosyringone) and incubated at 22° C. for two days. The cultures were then transferred to MS-CIM medium with ticarcillin (400 mg/liter) to inhibit the growth of Agrobacterium. For pNOV5025, a protox inhibitory herbicide (e.g., CGA 856,276 or butafenacil) (U.S. Pat. No. 6,282,837) was used for selection. Cultures are transferred to selection medium containing compound CGA 856,276, MSI/856,276 (MS-CIM with 1000 nM butafenacil, 200 mg/liter timentin) after 14 days and cultured for 28 days in the dark. Resistant colonies were then transferred to regeneration induction medium (MS-CIM with no 2,4-D, 0.5 mg/liter IAA, 1 mg/liter zeatin, 200 mg/liter timentin, and butafenacil) and grown in the dark for 14 days. Proliferating colonies were then transferred to another round of regeneration induction media and moved to the light growth room. Regenerated shoots were transferred to GA7-1 medium (MS without hormones) for 2 weeks and then moved to the greenhouse when they were large enough and had adequate roots. Plants were transplanted to soil in the greenhouse and grown to maturity. For pADF55, a similar protocol was used to generate transgenic plants, except that hygromycin, rather than butafenacil, was used as the selection agent.

Example 33

Targeted Integration of a Donor Construct into Target Rice Lines

Primary transgenic target rice lines, preferably single copy lines, containing T-DNA from target vector pNOV5025 or pADF55 were self-pollinated to obtain seeds. Seeds from selfed progeny of these lines were also used for establishing embryogenic cultures and suspension cultures for targeting experiments. Immature embryos from young seeds or mature embryos from dry seeds are used to establish embryogenic cultures (Hiei et al. 1994 Plant Journal 6:271-282; Dong et al. 1996 Molecular Breeding 2:267-276; Hiei et al. 1997 Plant Molecular Biology 35:205-218). These cultures or suspension cell clusters are then used for Agrobacterium-mediated transformation.

Agrobacterium strain LBA4404 containing the targeting donor vector pQD200C6 or pAdF77 was used for generating targeted events from target lines derived from pNOV5025 or pAdF77, respectively. Other targeting vectors using flanking genomic sequences as a region of homology can also be designed and used. In this case, the length of homology could be increased or decreased, as needed, and the selectable marker gene sequences used to introduce the target sequence can be replaced. Targeted events were selected from Agrobacterium-infected rice embryogenic cultures using the selection and regeneration processes described above, with the exception that 2% mannose is used as a selection agent. Two target lines (RITI2001001226A1A and RITI2001001226A5A, referred later to as lines A1A and A5A) containing 2 copies of T-DNAs were used for targeting study with donor vector pQD200C6. Both lines have 2 copies of T-DNA inserted in the genome, mostly likely at unlinked positions. Two lines derived from pAdF55 (AdF55-15A and AdF55-35A) were aslo randomly selected for gene targeting study with donor vector pADF77. Callus or suspension cell cultures were initiated from mature seeds of target plants and were co-cultured with Agrobacterium cells containing donor vector. Co-cultivations were also done with mixture of two Agrobacterium strains, one containing donor vector and another containing pNOV5033, the expression vector of mega-endonuclease I-CeuI. Co-cultured calli were selected in mannose containing medium to recover targeted events. Mannose resistant callus can be seen within a month after selection. Resistant calli were regenerated into plants. A PCR assay using two primers (PMIExFW1 and PMIExRV5) was used to confirm whether the mannose resistant plants indeed contained a full-length recombinant PMI-intron sequence. Only plants that are derived from recombination between target and donor's truncated PMI-intron gene sequence produce a PCR product of 3.5 Kb. Most of the recovered eventswere tested positive using this assay, suggesting that mannose selection is very effective in recovering targeted events in rice. Co-delivery of I-CeuI expression vector pNOV5033 with donor vector increased the number of targeted events, especially for line A1A. For two target lines derived from pAdF55 (AdF55-15A and AdF55-35A), all targeted events were obtained when the donor vector was co-delivered with the I-CeuI endonuclease expression vector (Table 3).

TABLE 3

Targeted integration of a donor into target rice lines

| Target vector | Target line | Target tissue | Exp. ID. | Donor:I-CeuI vector ratio* | Tissue fresh wt. (g) | No. of mannose resistant events |
|---|---|---|---|---|---|---|
| pNOV5025 | A5A | Suspension culture cells from T2 seeds | 664.154 | 1:0 | 0.96 | 2 |
|  |  |  |  | 1:1 | 1.13 | 0 |
|  |  |  |  | 1:1/2 | 1.09 | 0 |
|  |  |  |  | 1:1/5 | 1.08 | 1 |
|  |  |  |  | Pos. ctrl | 1.13 | 64 |

TABLE 3-continued

Targeted integration of a donor into target rice lines

| Target vector | Target line | Target tissue | Exp. ID. | Donor:I-CeuI vector ratio* | Tissue fresh wt. (g) | No. of mannose resistant events |
|---|---|---|---|---|---|---|
| pNOV5025 | A5A | Suspension culture cells from T2 seeds | 664.165 | 1:0 | 1.10 | 0 |
|  |  |  |  | 1:1 | 1.15 | 2 |
|  |  |  |  | 1:1/2 | 1.58 | 0 |
|  |  |  |  | 1:1/5 | 1.31 | 1 |
|  |  |  |  | Pos. ctrl | 1.13 | 55 |
| pNOV5025 | A5A, T2 | Calli from T2 seeds | 664.162 | 1:0 | 1.18 | 0 |
|  |  |  |  | 1:1 | 1.26 | 2 |
|  |  |  |  | 1:1/2 | 1.31 | 1 |
|  |  |  |  | 1:1/5 | 1.34 | 0 |
|  |  |  |  | Pos. ctrl | 1.15 | 15 |
| pAdF55 | 15A, T1 | Calli from T1 seeds | 664.151 | 1:0 | 2.08 | 0 |
|  |  |  |  | 1:1 | 1.98 | 1 |
|  |  |  |  | 1:1/2 | 1.98 | 2 |
|  |  |  |  | 1:1/5 | 1.98 | 1 |
| pAdF55 | 35A, T1 | Calli from T1 seeds | 664.151 | 1:0 | 1.96 | 0 |
|  |  |  |  | 1:1 | 3.1 | 5 |
|  |  |  |  | 1:1/2 | 1.9 | 0 |
|  |  |  |  | 1:1/5 | 2.07 | 0 |
|  |  |  |  | Pos. ctrl | 1.93 | 49 |

*Note:
Donor vectors used were pQD200C6 and pAdF77 for target lines derived from pNOV5025 and pAdF55 respectively. For I-CeuI endonuclease expression, vector pNOV5033 was used; Pos. ctrl: positive control, pNOV2147 was used for estimating overall transformation (random integration) efficiency.

Example 34

Suppression or Down-Regulation of RecQ Homologs to Enhance Gene Targeting Efficiency 1. Identification of RecQ Homologs in a Plant Genome Plant genomic and cDNA sequence databases can be searched with various bioinformatics programs to identify bacterial, yeast, and animal RecQ homologs. For example, the Arabidopsis genome contains several RecQ homologs (Hartung et al. 2000 Nucleic Acids Res. 21, 4275-4282). To identify RecQ homologs in the rice genome, proprietary Syngenta rice genome (Myriad contigs V8, Nipponbare cultivar) sequences were searched with the TBLASTN program using the E. coli RecQ protein sequence (GenBank accession number: NP_756603) and the mouse RecQ-like protein (GenBank accession number: BC014735) as queries. Two contigs (CLB1350.2, CLB5120.2) produced a high score (517, E value=e-145). Another three contigs (CL003142.76, CL027228.91, and CLC370) produced lower but significant scores. Gene prediction programs (Fgenesh, Genscan, and Genmark) were used to predict the open reading frame of each hit Primers were designed for amplification of the cDNA. OsRecQcfw2 (SEQ ID NO:95: CAC CAT GAA GCA CGG TGT AAT TGA TGA TAA AGA A) and OsRecQcRv1 (SEQ ID NO:96: TCA AGA GGG AAT CTT TAT GCA GTT GTC GCA) amplified a cDNA of 2 kb (OsRecQB) from rice (Oryza sativa, cultivar Kaybonnet) young flowers. OsRecQdFW2 (SEQ ID NO:97: CAC CAT GAT AAA GCC AAG GGT CAA CTG GTC GGA T) and RecQdRV1 (SEQ ID NO:98: CTA GGC TAT TCT GGC GGA CTG CCA CGC AGG) amplified a cDNA of 3.5 kb (OsRecQA) from rice immature flowers. The OsRecQB (2 kb) and OsRecQA (3.5 kb) cDNA PCR products were cloned into pENTR-TOPO vector (Invitrogen) to form pQD356A27 and pQD363C8, respectively. The insert of each clone is sequenced. The OsRecQA cDNA (SEQ ID NO:99) contains an ORF of 3525 bp, which encodes a protein having 1174 amino acid residues (SEQ ID NO:100). The OsRecQB cDNA (SEQ ID NO:101) contains an ORF of 1419 bps, which encodes a protein having 472 amino acid residues (SEQ ID NO:102). When the rice genome open reading frame (ORF) databases (cultivar Nipponbare) were searched, a third homolog, OsRecQC (SEQ ID NO:103), having 4692 bps was also identified. This third homolog encodes a protein having 1563 amino acid residues (SEQ ID NO:104).

```
SEQ ID NO:99: OsRecQA cDNA from Oryza sativa (cultivar Kaybonnet)
DEFINITION      OsRecQA cDNA
SOURCE          Young flower.
ORGANISM        Oryza sativa Cultivar Kaybonnet
REFERENCE       1 (bases 1 to 3525)
AUTHORS         Qiudeng Que
CDS             1 . . . 3525
BASE COUNT      1090 a    736 c    805 g    894 t
ORIGIN
     1 ATGATAAAGC CAAGGGTCAA CTGGTCGGAT CATGCAAATG CTGTTCAAAG CTCCTGTATC

61 AAAGATGAAT TCCTGAGTTC AAGTTTTTTG TTCTCTTTAC CAACACAAAG GCCTAATCAG

121 GAAGCAGATT GTACGGGAAT GCTTCCTTTA AGGTCTGCTG CTTGCAGAAT TCAAGGCCTA

181 GAGCGTCTTC AAGCTCCATC CATTGAGAAG GCCTGGCGTT CTCTACGCAA CACTCAGGTT
```

```
 241 GCACGGAAGA ATTATTTAAG ACCTGGTTTA TCTGGAAAAG TGAAAGATTG TGATAGCGAC

301 CATGCTCATA CTTATGGGAC AAGTTCTTCA TATAATGTTA ACAAAGTGGA CAGTGTGTCC

361 AGAAATAGGA ATCCCACCCA GGAAAGTATG CATCAGACGA CTGAAAGTGG TACTATGGAG

421 AAGAACAGTA GCCATCTGCC TGCAGGCACC AAGTCCTGTA CAAGGACTTA CCTGAACAAT

481 CATGTGGTGC AGGCAGATAC CATTACAACA ACAAATCAAA GTCTTGCAAG AACTGGTCCT

541 GAATTATTCA AGACTGCTCC TTTTATTGAC AACATGTGTG ATGATGCTAA ATTAGATGCC

601 ATGGATGAGG ATGAGCTTCT AGCGAGTATT GATGTGGACC GAATAGTCAT GGAACATTAT

661 CAAGCAACAA ATACACCCAG AGGGTCATCC AAATCTCCAT TAGAGAAGTG CAACTTCAAT

721 GGATTTGATG AGAATAATTT ACCACAAGAA CTCTCTATAA TGTGTGACCA CGGTAGCAAG

781 CTAGCTTTTT GCCCAGAGGC GAAGTCTCAT TTGCTTGAAA TGAAGGATAA CTTGCTTGCA

841 ATATCCCATG AGCTTATTGA CGGTCAACTC AGCCCTCAAC AATCTGATGA TCTTCATCAA

901 AAGAGAGCAC TCCTAAAGAA GCAGATTGAG CTGCTTGGGG AGTATACGGC GAGGTTAACC

961 CAAGATGAAG AGCGACAGCA GTCTCATTCT ATGGCCTCCA ACAGCTCA TCAGGGCCAT

1021 CACCCCACTA GCATCCTAAG TAGCTCTTTT GTAAAGGATA CCAATATATT CCGATCACCG

1081 ATTTACACCA GGAATGAACC TGGGGAGAGT GGTTTATGCT TTTCTTCTGC TCCATATTCC

1141 TATATGGATG GTTTAAGCAT GCCATTACCG TCTGTTCAGA GAGATTACAC TCCAAGGGCT

1201 ATTGATATCA GTTACACTGA AGGTTCTGGT GATAAACAGT GGAGTAGTAC ACACTTTGCA

1261 TGGACTAAGG AACTCGAGGC CAACAACAAA GGAGTATTTG AAACCGTTC TTTTCGCCCA

1321 AATCAACGAG AAATAACCAA CGCCACAATG AGTGGGAATG ATGTTTTTGT TTTGATGCCA

1381 ACTGGTGGTG GAAAAAGTTT GACATATCAG CTTCCAGCAC TCATTTGTAA TGGCGTTACA

1441 TTGGTAGTTT CTCCTCTCGT ATCGCTCATC CAAGACCAGA TCATGCATTT ATTGCAGGCA

1501 AATATTTCTG CAGCTTACCT TAGCGCCAGC ATGGAGTGGT CAGAACAGCA GGAGATATTA

1561 AGAGAATTAA TGTCTCCTAC ATGCACGTAC AAGTTACTGT ATGTTACGCC TGAAAAGATA

1621 GCCAAGAGTG ATGCTCTGTT GAGACAATTG GAAAATTTAT ATTCGCGAGG CCATCTCTCT

1681 AGAATTGTCA TTGATGAAGC CCACTGTGTT AGCCAGTGGG GTCATGATTT CCGACCTGAT

1741 TACCAGCATC TAGGCATTTT AAAACAGAAG TTCCCGCAGA CGCCGGTCCT GGCCTTGACA

1801 GCAACAGCAA CTGCAAGTGT CAAGGAAGAT GTCGTGCAAG TTCTAGGCCT TGCAAACTGC

1861 ATTATTTTCA GACAAGGTTT TAATCGTCCA AATCTGAGGT ATTTTGTATG GCCCAAGACA

1921 AAGAAGTGCC TCGAGGATAT CCATAACTTT ATACATGCAA ATCATAATAA GAATGCGGC

1981 ATCATATATT GCCTTTCGAG GATGGATTGT GAGAAAGTGG CTGCTAAATT AAGGGAATAT

2041 GGGCACCAGG CATCACATTA TCATGGTAGC ATGGATCCTG AGGATAGAGC AAATATCCAG

2101 AAACAGTGGA GCAAGGATAG GATCAACATA ATATGTGCTA CAGTTGCATT TGGGATGGGT

2161 ATTAATAAAC CTGATGTCCG TTTTGTTATC CATCATTCCC TGCCCAAATC AATTGAAGGA

2221 TATCATCAGG AGTGTGGACG TGCTGGTCGT GACAGTCAGC TTTCATCTTG TGTCCTGTTC

2281 TACAATTATT CTGATTATAT TCGTCTCAAA CACATGGTTA CCCAAGGATT TGCGGAGCAA

2341 GGAACATCAG CACCACGAGG AGGTTCTTCG CAGGAACAAG CGCTTGAAAC GCATAAGGAA

2401 AATCTCCTGC GAATGGTTAG TTACTGCGAA AATGATGTGG ACTGCAGACG TCTACTACAG

2461 CTGATCCACT TTGGAGAGAT GTTTAATCCT TCATGTTGTG CAAAAACATG TGATAATTGC
```

-continued

```
2521 TTGAAAGAGT TGAGATGGGT CAAAAAAGAT GTGACCAACA TTGCTAGACA ATTGGTTGAT

2581 CTGGTAATGA TGACAAAGCA AACATATTCA ACTACTCATA TTCTCGAAGT ATACAGAGGT

2641 TCAGTAAACC AAAATGTCAA GAAGCACCGC CATGATACTT TGAGTCTTCA TGGAGCTGGA

2701 AAGCATCTAG CTAAAGGTGA AGCAGCGAGA ATATTGCGCC ATCTAGTAAT TGAGGAAATA

2761 CTCATTGAGG ATGTCAAAAA GAGCGAAAAC TATGGATCTG TATCATCTGT CTTAAAGACT

2821 AATCATAAGA AAAGTGGTGA TCTTCTCTCT GGCAAGCACA ACGTTGTCCT CAAGTTCCCC

2881 ACTCCTGAGA AGGCTCCTAA GATGGGTGTA CTCGATGAAT CGTCAGTTCC ACGAATTAAT

2941 AAGACTAATC AACAGAGTCA AGTGGACGGG AGCCTTGCAG CCGAGCTTTA TGAAGCTTTG

3001 CAATGCCTTA GGACTCAGAT AATGGATGAA AATCCACAAT TATTGGCATA CCACATATTT

3061 AAAAACGAGA CATTGAAGGA AATCAGCAAC CGAATGCCAA GAACGAAAGA GGAACTTGTG

3121 GAGATAAATG GCATCGGCAA GAACAAGCTG AACAAGTACG GGGACCGCGT GCTTGCAACC

3181 ATAGAGGATT TCCTCGCCAG ATATCCAAAT GCGACCAGGA AAACCAGCAG CGGCGGCAGC

3241 AACGAGCACA GCGAGGCGGT CAAGAAGCGA AGAGGCTTCT CCGTCACCAA CACCTCTACC

3301 AACTGTGACG ACTTTGAGGA ACGCACGGTC CAGTCCAAGA AACGCGCTGC AAAGACACGT

3361 ACAAGGCAGG AAATATCTGA TGCTGCCAGC ATCGTCCAGG ACGTCCGCTA CATAGATCTT

3421 GAGCTAGATG GTTGTGAACA AGTCAATGAA GTGCCATACA GTGTACAAAA GCCTGTGGCT

3481 TCTGGTAGGG TTTTACCTGC GTGGCAGTCC GCCAGAATAG CCTAG
//
```

SEQ ID NO:100: Predicted OsRecQA protein sequence
DEFINITION        Predicted OsRecQA protein sequence,
                  1174 amino acid residues
SOURCE            Young flower.
ORGANISM          Oryza sativa Cultivar Kaybonnet

MIKPRVNWSDHANAVQSSCIKDEFLSSSFLFSLPTQRPNQEADCTGMLPLRSAACRIQGL

ERLQAPSIEKAWRSLRNTQVARKNYLRPGLSGKVKDCDSDHAHTYGTSSSYNVNKVDSVS

RNRNPTQESMHQTTESGTMEKNSSHLPAGTKSCTRTYLNNHVVQADTITTTNQSLARTGP

ELFKTAPFIDNMCDDAKLDAMDEDELLASIDVDRIVMEHYQATNTPRGSSKSPLEKCNFN

GFDENNLPQELSIMCDHGSKLAFCPEAKSHLLEMKDNLLAISHELIDGQLSPQQSDDLHQ

KRALLKKQIELLGEYTARLTQDEERQQSHSMASTTAHQGHHPTSILSSSFVKDTNIFRSP

IYTRNEPGESGLCFSSAPYSYMDGLSMPLPSVQRDYTPRAIDISYTEGSGDKQWSSTHFA

WTKELEANNKGVFGNRSFRPNQREITNATMSGNDVFVLMPTGGGKSLTYQLPALICNGVT

LVVSPLVSLIQDQIMHLLQANISAAYLSASMEWSEQQEILRELMSPTCTYKLLYVTPEKI

AKSDALLRQLENLYSRGHLSRIVIDEAHCVSQWGHDFRPDYQHLGILKQKFPQTPVLALT

ATATASVKEDVVQVLGLANCIIFRQGFNRPNLRYFVWPKTKKCLEDIHNFIHANHNKECG

IIYCLSRMDCEKVAAKLREYGHQASHYHGSMDPEDRANIQKQWSKDRINIICATVAFGMG

INKPDVRFVIHHSLPKSIEGYHQECGRAGRDSQLSSCVLFYNYSDYIRLKHMVTQGFAEQ

GTSAPRGGSSQEQALETHKENLLRMVSYCENDVDCRRLLQLIHFGEMFNPSCCAKTCDNC

LKEELRWVKKDVTNIARQLVDLVMMTKQTYSTTHILEVYRGSVNQNVKKHRHDTLSLHGAG

KHLAKGEAARILRHLVIEEILIEDVKKSENYGSVSSVLKTNHKKSGDLLSGKHNVVLKFP

TPEKAPKMGVLDESSVPRINKTNQQSQVDGSLAAELYEALQCLRTQIMDENPQLLAYHIF

KNETLKEISNRMPRTKEELVEINGIGKNKLNKYGDRVLATIEDFLARYPNATRKTSSGGS

NEHSEAVKKRRGFSVTNTSTNCDDFEERTVQSKKRAAKTRTRQEISDAASIVQDVRYIDL

ELDGCEQVNEVPYSVQKPVASGRVLPAWQSARIA
//

-continued

```
SEQ ID NO:101: OsRecQB cDNA from Oryza sativa (cultivar Kaybonnet)
DEFINITION       OsRecQB cDNA 1419 bp
ORGANISM         Oryza sativa Cultivar Kaybonnet
SOURCE           Young flower
REFERENCE        1 (bases 1 to 1419)
AUTHORS          Qiudeng Que
BASE COUNT       427 a   306 c   338 g   348 t
ORIGIN
    1 ATGAAGCACG GTGTAATTGA TGATAAAGAA GTTGAGGTGA GAACTCCTTT GTTCAGACAG

61 GCAGAATCCT CTGCTCGACA GACTCGCATC AATCTGGACT CCTTCGGGTT CTCCTCAGAT

121 GATGACTTTG AAACGTTGGA GTCCCATTGT GATCGTTCAG TCAGTACCCA GAAGAAGGTG

181 AACAGAGGAA ACAATAGATG TGAGTCATCC ACTTCAACTT CAAACAGAGA AACTCTAAGT

241 TATCAGCAGC TCAACATGGA CACCTTTGTG CTTATGCCAA CAGGTGGTGG GAAGAGCTTG

301 TGTTATCAGC TACCTGCAAC ACTGCACCCA GGTGTTACGG TTGTTGTATG CCCTCTACTG

361 TCACTTATTG AGGATCAAAT TGTGGCATTA AACTTCAAGT TTGCTATACC AGCAGCATTT

421 TTGAACTCTC AGCAGACACC TTCACAGTCA TCTGCAGTAA TCCAAGAGCT TAGAAGTGGT

481 AAACCGTCAT TCAAACTCCT CTACGTCACT CCTGAAAGAA TGGCTGGAAA CAGCTCATTT

541 ATTGGGATCC TCATAGGTTT ACACCAGAGG GGTTTACTGG CGAGATTTGT GATTGATGAA

601 GCCCATTGTG TAAGTCAATG GGGACATGAC TTCCGCCCAG ATTACCGAGG CCTGGGATGC

661 CTCAAACAGA ACTTCCCTCG AGTACCAATT ATGGCTTTAA CAGCTACAGC GACTGCATCT

721 GTCTGCAAGG ACATACTAAG TACCTTGAGG ATCCCTAATG CAACGGTACT CAAGAGGAGC

781 TTTGACAGAA CAAACCTGAA TTATGAGGTG ATTGGCAAGA CAAAAACTCC ACAGAAGCAG

841 CTGGGTGATA TCCTAAAAGA GCGTTTCATG AACATGTCTG GTATCGTGTA CTGTCTGTCC

901 AAAAATGAAT GTGCTGACAC TGCCAAGTTC TTGAGGGAGA AGTACAAGAT AAAATGCGCA

961 CATTACCACG CTGGCTTGGC TGCTCGTCAA CGATCCAATG TACAAGGAAA ATGGCACAGC

1021 GGAGAGGTCA AAGTCATTTG TGCGACCATA GCATTTGGCA TGGGAATAGA CAAACCTGAT

1081 GTGCGCTTTG TTATCCACAA CACCATGTCA AAATCGATAG AAAGCTACTA TCAGGAGTCA

1141 GGGAGAGCAG GAAGAGACAA TCTTCCGGCA CATTGCATTG TGTTATATCA GAAAAAGGAC

1201 CTCGGTCGAA TTGTATGCAT GCTGAGGAAT TCAGGGAACT TCAAGAGTGA GAGCTTCAAG

1261 GTTGCAATGG AGCAAGCAAA GAAAATGCAA ACATATTGCG AGCTGAAGAC AGAATGCCGG

1321 AGGCAAACTC TTCTTGGCCA CTTCGGTGAG CAGTATGACA GGCAAAGGTG CAAACATGGT

1381 TGTAGCCCTT GCGACAACTG CATAAAGATT CCCTCTTGA
//

SEQ ID No:102: Predicted OsREcQB protein sequence
DEFINITION       OsRecQB protein 472 amino acids
ORGANISM         Oryza sativa Cultivar Kaybonnet
MKHGVIDDKEVEVRTPLFRQAESSARQTRINLDSFGFSSDDDFETLESHCDRSVSTQKKV

NRGNNRCESSTSTSNRETLSYQQLNMDTFVLMPTGGGKSLCYQLPATLHPGVTVVVCPLL

SLIEDQIVALNFKFAIPAAFLNSQQTPSQSSAVIQELRSGKPSFKLLYVTPERMAGNSSF

IGILIGLHQRGLLARFVIDEAHCVSQWGHDFRPDYRGLGCLKQNFPRVPIMALTATATAS

VCKDILSTLRIPNATVLKRSFDRTNLNYEVIGKTKTPQKQLGDILKERFMNMSGIVYCLS

KNECADTAKFLREKYKIKCAHYHAGLAARQRSNVQGKWHSGEVKVICATIAFGMGIDKPD

VRFVIHNTMSKSIESYYQESGRAGRDNLPAHCIVLYQKKDLGRIVCMLRNSGNFKSESFK

VAMEQAKKMQTYCELKTECRRQTLLGHFGEQYDRQRCKHGCSPCDNCIKIPS
//
```

-continued

```
SEQ ID NO:103: OsRecQC cDNA from Oryza sativa (cultivar Nipponbare)
DEFINITION      OsRecQC Open Reading Frame 4692 bp DNA
SOURCE          Oryza sativa cv Nipponbare
REFERENCE       1 (bases 1 to 4692)
CDS             1 . . . 4692
BASE COUNT      817 a   1669 c   1511 g   695 t
ORIGIN
    1 ATGGCTTCCC GTCCCGCGCA CGACCTGCTT CAACGCGTCT TTGGTTACGA CGATTTCCGT

61 GGTCCGCAGC AGGACATCGT GGAGCATGTG GCTGCCGGTC ACGACGCCCT GGTGCTGATG

121 CCCACCGGCG GCGGCAAATC GCTGTGCTAC CAGGTCCCAG CCCTGCTGCG TGACGGTTGC

181 GGCATCGTCA TCTCGCCGCT GATCGCACTG ATGCAGGACC AGGTCGAAGC CCTGCGCCAG

241 CTCGGCGTGC GCGCCGAGTA CCTGAATTCA CCCCTGGACG CCGAGACCGC CGGCCGCGTC

301 GAGCGCGAGC TGCTCGCCGG CGAACTGGAC ATGCTGTATG TCGCCCCTGA GCGGCTGCTG

361 AGCGGGCGTT TCCTGTCGCT GCTGTCGCGC AGCCAGATCG CCCTGTTCGC CATCGACGAA

421 GCACACTGCG TGTCGCAGTG GGGCCATGAC TTCCGCCCCG AATATCGCCA GTTGACCGTG

481 CTGCACGAGC GTTGGCCGCA GATCCCGCGG ATCGCGCTGA CCGCCACCGC CGATCCGCCG

541 ACCCAGCGCG AGATCGCCGA CGCCTCGAT CTGCAGGAAG CGCGCCATTT TGTCAGTTCC

601 TTCGACCGCC CAACATCCG CTACACCGTC GTGCAGAAGG ACAACGCCCG CAAGCAGCTG

661 ACCGACTTCC TGCGCGGCCA CCGTGGCGAG GCCGGCATCG TCTACTGCAT GTCGCGGCGC

721 AAGGTCGAGG AGACCGCTGA ATTCCTCTGC GGCCAAGGCG TCAACGCTCT GCCTTACCAC

781 GCCGGCCTGC CGCCGGAAGT GCGCGCCAGC AACCAGCGCC GCTTCCTGCG CGAGGACGGC

841 ATCGTGATGT GTGCCACCAT CGCCTTCGGC ATGGGCATCG ACAAGCCGGA CGTGCGTTTC

901 GTCGCGCATA CCGACCTGCC CAAGTCGATG GAGGGCTACT ACCAGGAAAC CGGACGCGCA

961 GGCCGCGATG GCGAAGCCGC CGAGGCCTGG CTGTGCTACG CCTGGGTGA TGTGGTACTG

1021 CTCAAGCAGA TGATCGAGCA GTCCGAGGCG GGCGAAGAGC GCAAGCAGCT GGAACGGGCC

1081 AAGCTCGACC ATCTGCTGGG CTACTGCGAA TCGATGCAGT GCCGCCGCCA GGTGCTGCTG

1141 GCCGGCTTCG GCGAAACCTA CCCCCAACCG TGCGGCAACT GCGACAACTG CCTGACGCCA

1201 CCGGCCTCGT GGGACGCGAC CATACCGGCA CAGAAGGCGC TGAGCTGCGT CTACCGCAGC

1261 GGCCAGCGCT TCGGTGTCGG CCACCTGATC GACATCCTGC GCGGCAGCGA GAACGAGAAG

1321 GTGAGGCAGC AGGGCCACGA CAAGCTGAGC ACTTATGCCA TCGGCCGCGA CCTGGATGCA

1381 CGCACCTGGC GCAGCGTGTT CCGCCAGCTG GTCGCGGCCA GCCTGCTGGA GTGGACAGC

1441 GAGGGCCACG GCGGCCTGCG CCTGACCGAC GCCAGCCGCG ACGTGCTGAC CGGCCGCCGC

1501 CAGATCAGCA TGCCGCCGCGA CCCGGCCAGC AGCAGCAGCG GACGCGAGCG CAGTGCGCAG

1561 CGCACCGGCC TGTCGGTACT GCCGCAGGAC CTGGCCCTGT TCAACGCGCT GCGCGGCCTG

1621 CGCGCCGAAC TGGCCCGGGA ACAGAACGTA CCGGCGTTCG TGATCTTCCA CGACAGCACC

1681 CTGCGCAACA TCGCCGAGCG GCGCCCGACC AGCCTGGATG AACTGGCCCG GGTCGGCGGC

1741 ATCGGCGGTA CCAAGCTGAG CCGCTATGGC CGCGCCTGG TCGAGATCGT GCGCGAAGAA

1801 GGCCTGTTGC TCAACGGGCT GAACGCGGCC ATGGCCCGTG GTCACGAAGA AATGGGGCGG

1861 ATGGCCCACG CCGCAGCCGC TGCTGTTGAT GGCGGCACTG CCGACTGCCA CCACCACGCC

1921 GCCATGCAGG CCGACCCGGC CCCGCAGGCC AAGGCCCCGG CCCACGACGC CCACTGCCAG

1981 ATCAAGGACT GCGTGCGCAG CTGCGCCCAG CACCCGCTGC TGGTGGTGCA GCCGTTGCCG

2041 TTCATGGCCG GACCGGCACT GTCGCTGGCC CCGCAGCCGA TGCCGGCCAC CGGCCGGCCG

2101 GCGCCCCCGT CTGCCGCCGA CTCACGCCC TCCCATCGGC TGATTCCACA CGCACCGGCC

2161 TGGCCGCCGG TGGCGTGGTT GCCGGCATCG CCGCTGTCGG CGTGCCGCAG CGCGTGCTCG
```

```
2221 CCGCCGCCAC TGCCGCCCCA CGCCTGGCCG GCGCCCCCGC CGTGCTCAGC GACACCCGCA
2281 TCGAACTGGC CATCGGCGAA TCGCTGGCCA ACTTTCACTG GCCGCACCCG TCCGGCGATC
2341 ACCGTCAATG GATCGCTGCC GGCACCGATC CTGCGCTGGC GCGAAGGCCA GACCGTGGAC
2401 CTGTTCGTGC GCAACACGCT GGACCGCCAC CCGACCTCGA TCCATTGGCA CGGCATTCTG
2461 CTGCCGGCCA ACATGGACGG CGTGCCCGGC CTGAGCTTCA ATGGCATCGG CCCCGGTGAG
2521 ACCTACCACT ACCACTTCGA ACTGAAGCAG TCGGGTACCT ACTGGTACCA CAGCCACTCG
2581 ATGTTCCAGG AGCAGGCCGG CCTGTACGGA GCGCTGATCA TCGACCCGGC CGAGCCGGCG
2641 CCCTACCAGC ACGACCGCGA GCACGTGATC CTGCTGTCCG ACTGGACCGA CATGGACCCC
2701 GGCGCGCTGT TCCGGCGCAT GAAGAAGCTC GCCGAGCATG ACAACTACTA CAAGCGCACC
2761 CTGCCCGACT TCCTGCGTGA CGTGAAGCGC GACGGTTGGT CGGCCGCGTT GTCCGACCGT
2821 GGCATGTGGG GGCGGATGCG GATGACGCCC ACCGACATCT CCGACATCAA TGCGCACACC
2881 TACACCTACC TGATGAATGG CACCGCGCCG GCCGGCAACT GGACCGGGCT GTTCCGCAGC
2941 GGCGAGAAAG TACTGCTGCG CTTCATCAAC GGCGCCTCGA TGACCTACTT CGACGTGCGC
3001 ATTCCCGGCC TGAAGATGAC CGTGGTCGCC GCCGACGGCC AGTACATCCA TCCGGTCAGC
3061 ATCGACGAGT TCCGCATCGC GCCGGCCGAA ACCTACGACG TGCTGGTGGA ACCGACCGGG
3121 CAGGACGCGT TCACCATCTT CTGCCAGGAC ATGGGCCGCA CCGGTTCCCG CGCGCGACCC
3181 ACGCCCGTTG CTGACGATAG CGACATGGGG CACGACATGG GTAGTGGTGG CCATGGTGGC
3241 CACGACATGG CCGCGATGAA GGGCATGGAA GGCGGCTGCG GCGCCAGCAT GGACCACGGT
3301 GCGCACGGCG GTAGCGATGC CGCCAGCAAG GCACCGAAGC ACCCGGCCAG CGAACGCAAC
3361 AACCCGCTGG TGGACATGCA GAGCTCGGCC ACCGAACCGA AGCTGGACGA TCCCGGCATC
3421 GGCCTGCGCG ACAACGGTCG CCAGGTACTC ACCTACGGCG CGATGCGCAG CCTGTTCGAG
3481 GACCCCGATG CCGCGAGCC GAGCCGCGAG ATCGAGCTGC ACCTGACCGG CCATATGGAG
3541 AAGTTCTCCT GGTCATTCGA TGGCATTCCG TTCGCCAGCG CCGAGCCGCT GCGGCTGAAC
3601 TACGGCGAGC GCATGCCATC TGATCTGGAG AACGCGCAGG GCGAATTCCA GCTGCGCAAG
3661 CACACCATCG ACATGCCACC CGGCACCCGC CGCAGTTACC GCGTGCGCGC CGATGCGCTC
3721 GGTCGCTGGG CCTACCACTG CCATCTGCTC TACCACATGG AAGCGGGCAT GATGCGCGAA
3781 AACAGCACCG GCCAGGCCTG GGAGGCCACC GGCTGGATCG GTGGCAACAT CAACCGCCTG
3841 TGGTTGCGCA CCGATGGCGA ACGCAGCCGC GGCCGCACGG AATCGTCGTC ACTGGAAGCA
3901 CTGTATGGTC GCAGCGTATC GCCGTGGTGG GACGTGCTGG GCGGCGTGCG CCAGGACTTC
3961 CGGCCGGCCG ACTCGCGCAC CTGGGCGGCC ATCGGCATCC AGGGCCTTGC ACCGTACAAG
4021 TTCGAGAGCT CGGCAACGCT GTACATGGGT TCCGGCGGCC AGGTGCTGGC CAAGGCCGAG
4081 GTCGAGTACG ACGTGCTGCT GACCAACCGC CTGATCCTGC AGCCGCTGCT GGAAGCCACC
4141 ATCGCAGCCA AGGATGAACC GGAGTACGGC ATTGGTCGCG GACTGAACAA GATCCGCCGC
4201 GCCACCCTTG CCGATGTCGA CGCGCTGTCG ACCATCGCCA TCACCACCTA CAACGAAACC
4261 TGGGGCGACT CGTATCCGGC GCAGGAGCTG CAGGATTTCC TGCAGGCGCA CTACAGCAGC
4321 GAACCGCAGC GCGCCGAGTT GTCCGACCCG CGCAGTGCGA TCTGGCTGCT GTTGGACGGC
4381 GACAACGTGG TCGGCTACCT GGCCGCCGGT GCCAACACCC TGCCGCATGC CGAAGCCCGC
4441 GAGGGCGACA TCGAACTGAA GCGCTTCTAC ATCCTGGCCG ACTACCAGAA CGGCGGCCAC
```

```
4501 GGCGCGCGCC TGATGGACGC GTTCATGGCC TGGCTGGACC AGCCGCAGCG CCGCACCCTG

4561 TGGGTGGGCG TCTGGGAGGA GAACTTCGGC GCGCAGCGCT CTACGCGCG CTACGGCTGC

4621 AGCAAGGTCG GCGAGTACGA CTTCATCGTC GGGGATACGC GCGACCGCGA GTTCATCCTG

4681 CGCCGGCTGT GA
//

SEQ ID NO:104 Amino Acid Sequence of OsRecQC
DEFINITION         OsRecQC protein 1563 amino acids
ORGANISM           Oryza sativa Cultivar Nipponbare
MASRPAHDLLQRVFGYDDFRGPQQDIVEHVAAGHDALVLMPTGGGKSLCYQVPALLRDGC

GIVISPLIALMQDQVEALRQLGVRAEYLNSTLDAETAGRVERELLAGELDMLYVAPERLL

SGRFLSLLSRSQIALFAIDEAHCVSQWGHDFRPEYRQLTVLHERWPQIPRIALTATADPP

TQREIAERLDLQEARHFVSSFDRPNIRYTVVQKDNARKQLTDFLRGHRGEAGIVYCMSRR

KVEETAEFLCGQGVNALPYHAGLPPEVRASNQRRFLREDGIVMCATIAFGMGIDKPDVRF

VAHTDLPKSMEGYYQETGRAGRDGEAAEAWLCYGLGDVVLLKQMIEQSEAGEERKQLERA

KLDHLLGYCESMQCRRQVLLAGFGETYPQPCGNCDNCLTPPASWDATIPAQKALSCVYRS

GQRFGVGHLIDILRGSENEKVRQQGHDKLSTYAIGRDLDARTWRSVFRQLVAASLLEVDS

EGHGGLRLTDASRDVLTGRRQISMRRDPASSSSGRERSAQRTGLSVLPQDLALFNALRGL

RAELAREQNVPAFVIFHDSTLRNIAERRPTSLDELARVGGIGGTKLSRYGPRLVEIVREE

GLLLNGLNAAMARGHEEMGRMAHAAAAAVDGGTADCHHHAAMQADPAPQAKAPAHDAHCQ

IKDCVRSCAQHPLLVVQPLPFMAGPALSLAPQPMPATGRPAPPSAADLTPSHRLIPHAPA

WPPVAWLPASPLSACRSACSPPPLPPHAWPAPPPCSATPASNWPSANRWPTFTGRTRPAI

TVNGSLPAPILRWREGQTVDLFVRNTLDRHPTSIHWHGILLPANMDGVPGLSFNGIGPGE

TYHYHFELKQSGTYWYHSHSMFQEQAGLYGALIIDPAEPAPYQHDREHVILLSDWTDMDP

GALFRRMKKLAEHDNYYKRTLPDFLRDVKRDGWSAALSDRGMWGRMRMTPTDISDINAHT

YTYLMNGTAPAGNWTGLFRSGEKVLLRFINGASMTYFDVRIPGLKMTVVAADGQYIHPVS

IDEFRIAPAETYDVLVEPTGQDAFTIFCQDMGRTGSRARPTPVADDSDMGHDMGSGGHGG

HDMAAMKGMEGGCGASMDHGAHGGSDAASKAPKHPASERNNPLVDMQSSATEPKLDDPGI

GLRDNGRQVLTYGAMRSLFEDPDGREPSREIELHLTGHMEKFSWSFDGIPFASAEPLRLN

YGERMPSDLENAQGEFQLRKHTIDMPPGTRRSYRVRADALGRWAYHGHLLYHMEAGMMRE

NSTGQAWEATGWIGGNINRLWLRTDGERSRGRTESSSLEALYGRSVSPWWDVLGGVRQDF

RPADSRTWAAIGIQGLAPYKFESSATLYMGSGGQVLAKAEVEYDVLLTNRLILQPLLEAT

IAAKDEPEYGIGRGLNKIRRATLADVDALSTIAITTYNETWGDSYPAQELQDFLQAHYSS

EPQRAELSDPRSAIWLLLDGDNVVGYLAAGANTLPHAEAREGDIELKRFYILADYQNGGH

GARLMDAFMAWLDQPQRRTLWVGVWEENFGAQRFYARYGCSKVGEYDFIVGDTRDREFIL

RRL
//
```

In a similar manner, orthologs of the above rice OsRecQ genes were identified in maize (SEQ ID NO:105 and SEQ ID NO:106). As will be appreciated by those of skill in the art, others of such orthologs can be identified in other monocot or dicot species using the rice OsRecQ amino acid sequence as a query. Standard molecular methods can be used to clone these sequences from other plants.

```
SEQ ID NO:105  ZmRecQa cDNA from Zea mays
LOCUS              ZmRecQa 1185 bp
ORGANISM           Zea mays
REFERENCE          1 (bases 1 to 1185)
BASE COUNT         347 a    258 c    277 g    303 t
ORIGIN
    1 GCACGAGCGC AAGGCAAGCT TTCCGCTTCC TATTTCGGAT TGGGATCATC AGCGGCTGTA
   61 GCGTGGACCC GACGGGGGTG TCCGGACCAC ATCCCTATTT CATCTTGGTA CCCCGTCCGT
  121 CTCCGATTTC AGAAGCACGG CGGGCTCCCC GGCAGCCTCT ACCGAGCAGA AAGCTGAGTT
  181 CTACCCCAGA ACCGAGGCAT GGAGGACGAA GAAAACATCG AGGGAGAACT GTTGCTCGTG
  241 GAGTCACAAC TCCACGACAT CCAAGGACAA ATTAAAACAT TACTCGATCG CCAAGAGGAG
  301 TTGTATGAAC GCCAGGCACA GTTGAAGGCT TTGCTCGAAG CATCTAAATT GACCAGAAAT
  361 ACAACAATTA ACACATCTTC AGTTGCTCCG GAAGATTGGT CTGGGAGCTT CCCATGGGAT
  421 CTGGAGGCTG ACGATACCAG GTTCAATATA TTTGGCATTT CCTCCTACCG ATCAAATCAA
  481 CGAGAAATAA TTAATGCAGT CATGAGTGGA AGAGATGTTC TGGTCATAAT GGCAGCTGGT
  541 GGAGGGAAGA GTCTATGTTA CCAGCTCCCA GCTGTACTTC GTGATGGAAT TGCACTGGTT
  601 GTCAGTCCTT TACTTTCCCT TATTCAGGAC CAGGTCATGG GACTGTCAGC TTTAGGTATA
  661 CCAGCATACA TGCTAACTTC AACTACCAAC AAGGAAGTTG AGAAGTTCAT CTATAAGACA
  721 CTTGATAAAG GAGAAGGAGA ACTAAAGATA TTATATGTGA CACCTGAAAA GATCTCAAAA
  781 AGTAAAAGGT TCATGTCTAA GCTCGAGAAA TGCCATCATG CCGGTCGTCT TTCTCTGATT
  841 GCAATAGATG AGGCTCACTG CTGTAGCCAA TGGGGTCATG ATTTTCGTCC TGACTACAAG
  901 AATCTTGGCA TTTTGAAAAT TCAATTTCCC AGTGTTCCAA TGATAGCTTT AACTGCAACT
  961 GCAACAAGTA AGGTCCAAAT GGATTTAATG GAGATGCTCC ACATCCCGAG ATGCATCAAG
 1021 TTTGTCAGCA CAGTTAACAG GCCCAACCTT TTTTATAAGG TGTCTGAGAA ATCGCCAGTT
 1081 GGAAAGGTTG TCATTGATGA GATCACAAAG TTTATAAGTG AATCATACCC AAATAATGAG
 1141 TCTGGAATTA TATACTGCTT TTCAAGGAAG GAATGTGAAC AGGTT
//

SEQ ID NO:106  ZmRecQb cDNA from Zea mays
LOCUS              ZmRecQb 870 bp
ORGANISM           Zea mays
REFERENCE          1 (bases 1 to 870)
BASE COUNT         239 a    200 c    242 g    189 t
ORIGIN
    1 CTTGAGGATC CCCAACGCTG TGGTACTGAA GAGGAGCTTC GACAGACTGA ACCTCAACTA
   61 CGAGGTAATC GGCAAGACGA AAACTTTCCA GAAGCAGCTG GGCGATCTCC TGAAAGAGCG
  121 CTTCATGAAC GAATCTGGTA TCGTGTACTG TCTCTCGAAG AACGAGTGTG CAGACACTGC
  181 CAAGTTTTTG AGGAAGAAAT ACAAGATCAA ATGCGCGCAC TACCACGCTA GCCTGGCAGC
  241 TCGTCAGCGA ACCAGTGTCC AGGAGAAATG GCACAACGGG GAGGTTAAGG TCATCTGCGC
  301 TACCATAGCC TTCGGCATGG GGATCGACAA ACCTGACGTG CGTTTTGTTA TCCACAACAC
  361 ATTGTCCAAG TCAATAGAAA GCTACTACCA GGAGTCCGGG AGGGCAGGGC GAGATGAGCT
  421 TCCGGCACAC TGTATCGTCT TGTACCAGAA GAAAGACTTC AGCCGTATCG TGTGCATGTT
  481 GAGGAACGGT GAGAACTTCA GGAGCGAGAG CTTCAGGGTT GCGATGGAGC AAGCTAAGAA
  541 GATGCAGGCA TACTGCGAGC TCAAGACCGA GTGCCGGAGA CAGGCACTTC TGCAGCACTT
```

```
601 CGGCGAACAG TACGACAGGC GAAGGTGCCG AGACGGGCCT AGCCCCTGCG ACAACTGCCT

661 CAAGACATAG TTTAGGGTAA TAAACTATGG CGATAAAAAA TGCCATGACG CTTGGTTATG

721 CTCTGAACTT GTGAGGTGTG TGCCACTTCC ACAGTACATT CGTCTGTGTA TATGTAGCAT

781 CCATAGCTCA AACAAGTGGC CGCAACTGCA CTGTGTGTAA CGATGGTCTT TGTTTTCAGT

841 TGGATTGTGA GGTTCGGGGC TTTAAAAAAA
//
```

2. Suppression or Down-Regulation of the OsRecQ gene expression to enhance the efficiency of targeted integration through homologous recombination: antisense suppression, sense co-suppression, dsRNAi, gene knock-out, and the use of dominant negative mutants.

E. coli and yeast cells deficient in RecQ show an elevated level of homologous recombination activity (Nakayama et al. 1985 Mol. Gen. Genet. 200, 266-271; Watt et al. 1995 Genetics 144, 935-945). The above rice and maize RecQ sequence homologs can be used to down-regulate RecQ expression levels and thereby enhance targeting frequency in the previously described target maize and rice lines. Similarly, RecQ homologs from other plants can be used to enhance the frequency and efficiency in those plants of targeted integration through homologous recombination. (See, Bagherieh-Najjar, de Vries, Hille, and Dijkwel, "Increased Homologous Recombination and Altered DNA Damage Response in the *Arabidopsis* recQ14A Mutant," attached hereto and forming a part hereof).

Down-regulation can be achieved ectopically by a transgene using methods in the art, including homology dependent gene silencing (antisense suppression, sense suppression, dsRNAi, virus mediated silencing) and dominant-negative mutants of the gene. For homology-dependent silencing, only part of the gene is needed to initiate silencing of the gene. For example, a segment of sense and/or antisense OsRecQ mRNA sequence can be placed under the control of a constitutive or tissue-specific promoter to initiate gene silencing of native genomic OsRecQ genes. Dominant negative mutants are defective variants of a protein, usually deficient in one or more functions that the protein normally has. For example, RecQ has a helicase domain and also interacts with other proteins to carry out its normal biological functions. A dominant negative mutant RecQ may lose its helicase activity but still retain its interactions with other proteins. Sometimes a dominant negative mutant is a truncated protein.

A particular RecQ gene can also be knocked out totally, and plant lines with a RecQ gene knock-out can be used in gene targeting. In plants, mutagenesis methods such as transposon, T-DNA insertion, UV, gamma rays, X-rays, and chemicals can be used to inactivate these genes. The materials with reduced RecQ expression obtained by the above methods are then used as target tissue when the targeting methods disclosed herein are carried out. For example, rice transgenic target lines with a pNOV5025 or pAdF55 T-DNA insertion locus can be introgressed into lines with the OsRecQ dsRNAi knockout locus, and the resulting lines containing both loci can be re-transformed with the targeting donor vector pQD20OC6 or pAdF77, with or without another recombination enhancing vector (e.g., pNOV5033, which expresses the I-CeuI endonuclease to make a dsDNA break at the target locus). Similarly, maize transgenic target lines with a pNOV5025 T-DNA insertion locus can be introgressed into lines with the ZmRecQ dsRNAi knockout locus, and the resulting lines containing both loci can be re-transformed with the targeting donor vector pQD200C6, with or without the recombination enhancing vector pNOV5033, which expresses the I-CeuI endonuclease to make a dsDNA break at the target locus. Down-regulation of the RecQ gene can also be carried out transiently by introducing the interfering protein or RNA or RNA expression cassette during the targeting process, such as, for example, during the *Agrobacterium*-mediated delivery and transformation of the donor T-DNA into the host cell.

Example 35

Over-Expression or Up-Regulation of OsRad54, OsBRCA1, OsBRCA2, and OsSPO11 to Enhance the Efficiency of Targeted Integration Through Homologous Recombination Some genes encode proteins that are involved in the recombination machinery of the cell or that are positive regulators of the recombination process. To clone some of these genes, proprietary Syngenta rice genome (Myriad contigs V8, Nipponbare cultivar) and public rice genome sequence databases were searched with the TBLASTN program using the protein sequences of human BRCA1, BRCA2, RAD54, and yeast SPO11. Primers were designed to amplify predicted cDNAs encoding homologs of these sequences. The following cDNAs were cloned from young rice flowers or mitomycin C-treated callus tissue: OsRad54A (SEQ ID NO:107), OsRad54B (SEQ ID NO:108), OsBRCA1 (SEQ ID NO:109), OsBRCA2 (SEQ ID NO:110), OsSPO1A (SEQ ID NO:111), and OsSPO11B (SEQ ID NO:112). These cDNA sequences are useful for increasing targeting efficiency, since over-expression of these genes can increase the frequence of homologous recombination in plant cells.

Each of these genes can be put under the control of a regulated promoter, such as a tissue-specific or inducible promoter, for example, so that their expression is tissue-specific or transient. In one embodiment, the recombination enhancing genes is expressed when the donor sequence is delivered to the target cell. In another embodiment, several of the above recombination enhancing genes are co-expressed in the host cell to increase the targeting efficiency. The proteins encoded by these genes (the predicted amino acid sequences of which are shown in SEQ ID NOs:113, 114, 115, 116, 117, and 118) can be introduced into the host cell by any means described herein (such as the methods described above with reference to a mega-endonuclease or a recombinase) or methods that are otherwise known in the art. Such other methods include, for example, introducing the protein (or a fusion protein containing the protein) into the cell through physical or biological means, e.g., electroporation or *Agrobacterium*. For example, rice target lines with a pNOV5025 or pAdF55 T-DNA insertion locus are introgressed with a line having a transgenic locus for the over-expression of these genes, and the resulting lines containing both loci are re-transformed with a donor vector, such as pQD200C6 or pAdF77, with or without another recombination enhancing vector pNOV5033 which expresses the I-CeuI endonucleases to make a dsDNA break at the target locus. Similarly, maize target lines with a pNOV5025 T-DNA insertion locus can be introgressed into a line with a transgenic locus for the over-expression of these genes, and the resulting lines containing both loci are re-transformed with a donor vector, such as pQD200C6, with or without the recombination enhancing vector pNOV5033 which expresses the I-CeuI endonucleases to make a dsDNA break at the target locus.

```
SEQ ID NO:107: OsRad54A cDNA from Oryza sativ, (cultivar Kaybonnet)
LOCUS          OsRad54A cDNA 3569 bp
ORGANISM       Rice, Oryza sativa cv Kaybonnet
SOURCE         Young flower
REFERENCE      1 (bases 1 to 3569)
AUTHORS        Qiudeng Que
CDS            1 . . . 3564
BASE COUNT     1072 a     771 c     865 g     861 t
ORIGIN
       1 ATGGAGGACG ATGACGATGA CCAACGCTTG CTTCACAGCC TTGGTGTCAC GTCCGCAGAC

61 ATCCACGATA TTGAAAGGAG AATCATATCA CAGGCAACAA CTGATCCTGC CGACTCATCT

121 GGACCAACCA TCAATGGAGG TCATCAGCCT GATGATGCTC TCGCCAAACT GCATCACAAA

181 CTGCGCTCTG TGCAAATTGA AATTGATGCT GTAGCCTCCA CCATCAAAGG AGCTAAGCTT

241 AAGCAACCAT CCGGAAATAA ACCACATGAG CATAAAGGCA AGGACCAGCC AGATCATCAT

301 GGAGCAGGAC ACCTCCAGCA AGCCCTTGCT GCCGACCGTC TTACAAGCCT CAGGAAAGCT

361 AAAGCACAGA TACAGAAAGA GATACTACAG TCACATCTTT CTCCATCTGC CTCCAATCGA

421 AAAGATAAAA TGCTGGCCAT GCTGGTCCAA GACGAGCCGA GGCACAAAAA GCCACCCGTA

481 GGGCCTAAAA ACATCGTGAA ACGCCCGATG AAAACTGTCA CCTATGATGA TGACAACAAC

541 TTCGATGCAG TGCTTGATGG AGCCTCTGCG GGATTTATGG AAACTGAAAG GGAAGAACTG

601 ATCAGGAAGG GTTTGTTGAC ACCATTCCAT AAGTTGAAGG GCTTCGAGAA ACGTGTGGAA

661 CTACCCGAAC CTTCTCATAG ACAAGATGAT TCTGCAGGAC AAACTGAAGA AGCCATGGAA

721 GCTTCCAGGA TTGCTAGAGT TGCTCAGTCG CTAAAGCAGA TTGCACAGAA CCGCCCAGCA

781 ACCAAATTGC TTGATTCAGA GTCTTTACCT AAGCTAGATG CACCTGCTGC CCCATTTCAG

841 AGACTTGGAA AACCCCTAAA GCGTCCTGTC TCTCCCAGTT CAGATGAGCA GGAAAAGAAG

901 AGACCAAGAA ATAAGACCAA AAGACCACTG CCTGGCAAGA ATGGAGGAA AGCAAACTCA

961 ATTAAGGAAT CATCATTGGA TGACAACGAT GTTGGAGAGG CAGCTGTGTC AGTTTCAGAT

1021 GATGATGAAG ATCAGGTTAC AGAAGGCTCT GATGAGTTAA CTGATGTTAC CCTTGAAGGA

1081 GGTTTGAGAA TTCCTGGCAC ACTTTACACG CAACTATTTG ACTACCAGAA AGTGGGAGTG

1141 CAGTGGCTAT GGGAGTTGCA TTGTCAAAGG GCTGGTGGAA TAATTGGAGA TGAAATGGGC

1201 CTGGGAAAGA CTGTGCAGGT CTTGTCATTT CTTGGTTCCT TGCATAACAG TGGGCTCTAC

1261 AAGCCTAGCA TTGTTGTTTG TCCTGTAACC CTTTTGCAAC AGTGGCGAAG GGAGGCCAGT

1321 AGATGGTATC CAAAGTTCAA GGTTGAGATC TTACATGACT CTGCAAACAG TTCATCTAAA

1381 AAGAGCAAGA GGTCTAGTGA TTCTGACAGT GAAGCTTCCT GGGATAGTGA TCAGGAAGAA

1441 GCGGTTACAT GTTCAAAACC CGCAAAGAAG TGGGATGACT TGATTTCACG TGTTGTGAGT

1501 TCAGGATCAG GTTTGCTTCT GACCACATAT GAGCAGTTAA GGATCCTAGG GGAGAAGTTG

1561 CTTGATATAG AATGGGGATA TGCTGTATTG GATGAGGGTC ACCGCATTAG GAATCCTAAT

1621 GCTGAGATTA CTCTTGTGTG CAAGCAATTG CAGACCGTGC ACAGGATAAT TATGACAGGT

1681 GCACCTATTC AAAACAAACT TTCGGAGCTT TGGTCTCTCT TTGATTTTGT GTTCCCTGGA

1741 AAACTAGGTG TCCTGCCTGT GTTTGAGGCT GAGTTTTCTG TTCCAATTAC TGTTGGTGGG

1801 TACGCTAATG CAACACCATT GCAAGTGTCC ACGGCGTATC GATGTGCTGT TGTCCTACGT

1861 GACCTGGTCA TGCCGTACCT TCTTAGAAGA ATGAAAGCTG ATGTCAATGC ACAGCTTCCC
```

```
1921 AAGAAAACAG AGCATGTTCT TTTCTGTAGT CTAACTACTG AGCAACGTGC TACTTATCGT

1981 GCATTTCTTG CTAGTTCGGA GGTGGAACAA ATCTTTGATG GTAACAGAAA TTCCCTTTAT

2041 GGGATAGATG TTCTAAGGAA GATATGCAAT CATCCTGATC TACTTGAGAG AGAACATGCT

2101 GCTCAGAATC CTGACTATGG GAATCCAGAA AGAAGTGGAA AGATGAAAGT GGTTGAGCAA

2161 GTTCTTAAAG TATGGAAAGA ACAAGGTCAT CGTGTTCTTC TTTTCACTCA GACACAACAA

2221 ATGCTTGACA TTATGGGGAA CTTCTTGACA GCTTGCGAAT ACCAATACCG AAGAATGGAT

2281 GGACTTACAC CTGCAAAGCA AGAATGGCA CTTATTGATG AATTCAATAA CACAGATGAA

2341 ATTTTTATTT TCATTCTGAC CACGAAAGTT GGTGGACTGG GTACGAATTT GACTGGTGCA

2401 AACCGGATTA TTATATATGA TCCTGACTGG AATCCTTCAA CTGACATGCA GGCTAGGGAA

2461 CGTGCATGGC GAATTGGGCA AACTAGAGAT GTGACAGTTT ATAGACTGAT CACGCGTGGG

2521 ACAATAGAGG AGAAAGTCTA CCATCGTCAG GTATACAAGC ATTTCCTCAC AAACAAAGTA

2581 CTGAAAGACC CTCAGCAGAG GCGGTTTTTT AAAGCCAGAG ACATGAAGGA TTTGTTTACG

2641 CTGCAAGATG ATGACAATAA TGGCTCAACT GAAACATCAA ATATTTTCAG CCAATTGTCT

2701 GAGGATGTGA ATATCGGAGT TCCGAGTGAC AAGCAACAAG ACCAGCTATA TGCAGCCTCT

2761 GCTACACCGA CAACCTCTGG GACTGAACCG AGCTCATCCA GGCATGGACA GGGTAAAGAA

2821 GACCATTGCC CTGACCAAGC AGATGAAGAA TGCAACATTT TGAAGAGCCT TTTTGATGCT

2881 CAAGGCATTC ATAGTGCGAT CAATCATGAT GCCATAATGA ACGCTAATGA TGACCAGAAG

2941 CTGCGCCTAG AAGCAGAAGC TACACAGGTG GCACAAAGGG CAGCTGAAGC TTTACGCCAA

3001 TCACGGATGC TCAGAAGTCA TGAAAGTTTT TCTGTTCCTA CATGGACTGG AAGAGCTGGT

3061 GCTGCGGGGG CACCATCCTC TGTCCGCAGG AAGTTTGGGT CAACACTCAA TACCCAGTTG

3121 GTTAATTCTT CTCAGCCATC AGAAACTTCA ATGGCAGGG GCCAAAGTCT TCAGGTGGGT

3181 GCTCTAAATG GCAAAGCACT GTCCTCCGCT GAGCTTCTGG CCAGGATACG TGGAACCCGA

3241 GAGGGAGCAG CTTCAGATGC ACTAGAACAT CAACTCAACC TGGGATCAGC TTCCAATCAC

3301 ACATCGAGTT CATCAGGGAA TGGCCGTGCA TCAAGCTCTT CTACTAGGAG CATGATCGTA

3361 CAGCCTGAAG TCCTAATCCG CCAATTGTGC ACCTTCATAC AGCAGCATGG TGGTTCCGCC

3421 AGCTCAACAA GTATAACTGA ACACTTCAAG AACCGGATAC TGTCCAAGGA TATGCTGCTG

3481 TTTAAGAATC TGCTGAAGGA AATAGCTACG TTGCAAAGAG GTGCAAATGG TGCAACGTGG

3541 GTGCTGAAAC CTGACTACCA GTAACTAGT
//

SEQ ID NO:108: OsRad54B cDNA from Oryza sativa (cultivar Kaybonnet)
DEFINITION      OsRad54B CDNA 3453
ORGANISM        Oryza sativa cv Kaybonnet
SOURCE          Young flower
REFERENCE       1 (bases 1 to 3453)
AUTHORS         Qiudeng Que
CDS             1 . . . 3447
BASE COUNT      1134 a    655 c    776 g    888 t
ORIGIN
   1 ATGCGCACAA GCACCACATC AGATAGCCCA TCCCCATCTC CACAAAACAA AGCCTCTTTT

61 AACACATCAC GTGGTGCTGC ATTTAGGGAT GAAGAACCAG GTGCAAAAGA CAATGAAGTT

121 GAGAAAAGGA AACCATTGAT ATTACATTTG AAGAAGCGTT CAACCAAGGA ACTATCTACA

181 GATACCACAT CATCAAAGTC AGGGTTACTT GGAAAGTCTT CAGAAGAGAA ACAGGAGAAA

241 CACGGAAGTG CTTTGAAAGT GAAGAAACAT CTGCATCCCA TGGAATTATC TCCAAAGAAA

301 TATAAGAACA AGAAGCAACA CAATCACAGA GACAGTAAGA GATCCGAAGC AAAAAAGGTC

361 CAATATTTGG CATCAGATGT GGACAGTGAT TCTTCAATGG AACCATCTAC TTCTCTTGAG

421 CACAGCGAAT CGCCGCCCCC AAAAAGAAAA TCGTTGGATG GAAGAACACC TGCATCAAGT
```

-continued

```
 481 ACCAAGAAAG GAAAAAAGAA AGTGAAATTT ATTGATAAAA AGCACCCTGA GAATGCTGTT

541 CATATAACTG AAAAGGAGCA TGGTGGTGCA GGAGACAAAA TAACAACTCA GGGGGATCTG

601 CAGGTTGATC GCATCCTAGG CTGTCGACTT CAGACAAGCC AAATCATTTC ACCTGCCCAT

661 GCTTCATCAG AGCAGATTGA TATGGCCCCT CCTAGTGCAT CCGGTGCAAC AGAACCTAGT

721 CAAGCCCTTT CAAAAGGACT TCATGAAGAA ATTCAGTCTT CTAATAGTGA TACTAATGTG

781 ACAGAGGATG CATGTGCTGA TGAATTAGCA ACGATGGTG GGGAAAATAA TTTGGATTGT

841 TCTGATGCTC AAAAGGAGAG TAATGTTAGA TCCCATGGAC ACAAGGAATC ACTTAACGCA

901 AAAGAAATCA TGAATACAGC ATCAGCATGT TCCGCTGATC AAATTGTCAC AGTTAAGGAT

961 GCTGGAGCAG TACAGACATA TGTAACGGCT TCAGTAAATG GTGAATATGA GACAGTAACT

1021 GATATTCCAG AAGAAAAGAA TGACACCAAA CATCCAGTTT CCAAAGCTGA CACAGAAGTC

1081 CACACTAAAC AAGAACATAC ACCTGATAGT AAATTGCATG GAAACTAGA AAACTACAAA

1141 GCAAAGTACG GAACAGGTTT GATAAACATC TGCAAAGAAC AATGGTGCCA ACCGCAACGA

1201 GTTATTGCTC TGCGCACTTC TTTAGATGAA ATAGAAGAGG CTTTGATCAA ATGGTGTGCC

1261 CTTCCATATG ACGAATGCAC GTGGGAAAGA TTAGATGAAC CTACAATGGT GAAGTATGCA

1321 CATTTGGTCA CTCAGTTCAA AAAATTTGAA TCCCAGGCTT TGGATAAGGA TAAGGGAGGT

1381 AGCCATGCAA AGCCAAGGGA ACACCAAGAG TTTAATATGC TGGTTGAGCA GCCAAAAGAA

1441 CTCCAGGGAG GCATGCTCTT CCCTCATCAA CTGGAAGCAT TGAACTGGCT ACGCAAATGC

1501 TGGTACAAGT CAAAAAATGT TATCCTTGCT GATGAGATGG GTCTTGGAAA GACTGTGTCT

1561 GCCTGTGCTT TTCTATCATC CCTATGTTGT GAATATAAGA TTAACTTGCC ATGTCTTGTC

1621 TTGGTTCCTC TTTCTACTAT GCCCAACTGG ATGGCTGAAT TGCATCATG GCACCTCAT

1681 TTAAATGTTG TGGAGTATCA TGGTTCTGCA CGGGCAAGAT CTATTATTCG TCAATATGAG

1741 TGGCATGAGG GTGATGCAAG CCAGATGGGT AAAATCAAGA ATCTCATAA GTTCAATGTA

1801 TTGCTCACTA CTTATGAAAT GGTGCTTGTT GATGCTGCAT ATCTTCGGTC TGTGTCATGG

1861 GAGGTTCTTA TAGTCGATGA GGGTCATCGT CTGAAGAATT CTAGCAGCAA ACTTTTCAGT

1921 TTACTCAATA CATTATCATT TCAGCATAGA GTTTTGCTGA CTGGAACTCC GTTACAGAAT

1981 AACATTGGTG AAATGTATAA CTTATTGAAC TTCTTACAAC CTGCTTCTTT CCCTTCTCTA

2041 GCTTCATTTG AGGAGAAATT CAATGACCTT ACAACAACAG AGAAAGTGGA GGAGCTGAAG

2101 AACCTTGTAG CTCCACATAT GCTTCGAAGA CTGAAAAAGG ATGCAATGCA AAATATCCCT

2161 CCAAAGACTG AACGAATGGT GCCTGTTGAA TTGACATCAA TCCAGGCTGA ATACTACCGT

2221 GCTATGCTTA CAAAGAACTA CCAAGTATTG CGCAATATTG GAAAGGTGG TGCTCACCAG

2281 TCATTGTTGA ACATAGTAAT GCAACTTCGG AAAGTCTGCA ATCATCCGTA TCTTATTCCT

2341 GGAACTGAAC CTGAATCAGG ATCACCAGAG TTCTTGCATG AAATGCGAAT AAAGGCCTCA

2401 GCAAAGTTAA CTTTGTTGCA CTCTATGCTT AAAATCCTAC ACAAGGATGG TCATCGAGTT

2461 CTTATTTTTT CTCAGATGAC AAAGCTTCTT GACATCCTTG AAGATTACCT GACCTGGGAG

2521 TTTGGTCCGA AAACATTTGA AAGAGTGGAT GGTTCAGTAT CTGTGGCAGA ACGCCAGGCA

2581 GCAATTGCTC GTTTTAATCA GGACAAGAGT CGTTTTGTAT TCCTGCTATC TACGCGGTCA

2641 TGTGGGCTTG GAATTAATTT GGCAACTGCA GATACTGTTA TCATATATGA TTCTGATTTC

2701 AATCCACATG CTGATATACA GGCAATGAAC AGAGCACACA GAATTGGACA GTCAAACAGA

2761 CTTTTAGTTT ACAGGCTTGT CGTGCGTGCT AGTGTTGAGG AGCGTATCTT GCACCTTGCG

2821 AAGAAAAAAT TGATGCTTGA TCAACTTTTT GTTAACAAAT CAGAATCACA GAAGGAAGTG
```

-continued

```
2881 GAAGATATCA TTCGCTGGGG AACAGAGGAA CTCTTCAGGA ATAGCGATGT TGCAGTTAAA

2941 GATAATAATG AAGCTTCTGG TGCTAAAAAT GATGTAGCAG AGGTTGAGTT TAAGCATAAA

3001 AGAAAAACTG GTGGACTAGG CGATGTTTAT GAAGACAGAT GTGCTGATGG TTCTGCTAAA

3061 TTTAATTGGG ATGAAAATGC TATCACAAAG CTTCTTGACA GATCCAACGT TCCATCAACA

3121 GTAGCTGAAA GCACTGATGG GGACTTGGAC AATGATATGC TTGGCACTGT AAAGTCAATA

3181 GATTGGAACG ATGAGCTGAA TGATGACCCT GGTGCCACCG AGGACATCCC AAATATTGAT

3241 AATGATGGTT GCGAGCAGGC ATCTGAAGCA AAGCAGGATG CAGCTAATCG TGTTGAAGAA

3301 AATGAATGGG ATAAACTCTT ACGTGTCAGA TGGGAGCAGT ATCAAACTGA GGAGGAAGCA

3361 TCTCTTGGTC GAGGTAAGCG TTTAAGGAAG GCTGTTTCTT ACAGGGAAAC ATTTGCAACC

3421 ATTCCTAATG AAGCTTTAAG CGAGTAGAAC TAG
//

SEQ ID NO:109: OsBRCA1 cDNA from Oryza sativa (cultivar Kaybonnet)
DEFINITION    OsBRCA1 cDNA 2964 bp
ORGANISM      Oryza sativa cv Kaybonnet
SOURCE        Young flower
AUTHORS       Qiudeng Que
CDS           1 . . . 2964
BASE COUNT    957 a    623 c    694 g    690 t
ORIGIN
    1 ATGGCGGACA CGGGGAGCCT GGAGAAGATG GGGCGAGAGC TCAAGTGCCC CATCTGCCTG

61 AGCCTTCTCA GTTCGGCGGT ATCCATCTCC TGCAACCACG TCTTCTGCAA TGATTGCCTC

121 ACGGAATCGA TGAAATCCAC GTCGAGCTGC CCCGTGTGCA AGGTCCCGTT CCGACGACGA

181 GAAATGCGAC CAGCACCTCA CATGGACAAT CTGGTCAGCA TTTTCAAAAG CATGGAGGCT

241 GCAGCAGGTA CCAATGTTGT CTCAACACAG GAGGCTCCTG TGGTAAAACT TGCAGATGGA

301 TCAGATTGTG TCAACAGCGG GAAAAATTCC AAAAGGTCAC AAAAATCATT GACACGAAAA

361 AGGAAGGTAA CATCCGAGAT GGAAAAAAAT ACAGCAAAGG ATGCTACAGC TTCTGCATCC

421 CAACCTACTA CAAAGCCTTC CTTCTCTACT AACAAAAGAA TACAAGTGAA ACCATTCCCT

481 GAATCTGAGA CACCAATAAG AGCTGAGAAG ATTATGAAGC TGAAGAGCC AAAAAATAAT

541 CTGAATAATG ATGTTGAAGG AAAGAATAAA GCAGTGGCAT CGGGTCAACC TGGAAGTCCT

601 TCATTGTCAC CCTTTTTTTG GCTAAGGGAA CAAGAAGAAC AAGAAGGCTG TACCGCTGAG

661 ACGTTAAGTG AAACGCAATC TTTAGACACA CCCTTGCGTC ATAATGCACC CTCTTTTAGC

721 GATATTAAAG ATTCTGATGA CGAAATCCCT TTAAATACAA CTCCAAATAG CAAAGCTGCG

781 GCTACAGAAC TCTTTGACAG TGAAATATTT GAATGGACCC AGAGACCATG CTCTCCTGAA

841 TTGTATTCCA CTCCATTGAA AAAGCAGAGT AAAGCTAAGA GTAAACTAGA TCAAATTGAA

901 GAGAAGGGTG ATGAAGAAGA TGTGCATATT GGTGGTTCAT TTGATAAGCT GGGCAGTGCA

961 AGTAATGCAG CTCAGCTTGT CAATACAAAA GCAACAAAGC AGAAGAGAAA GAAAACAAGT

1021 CCCAGTAACA AAAACAGTGC AAAATTGTCC AATCGTGCTG AGCCCTGCAT AAAAAAGTCT

1081 GATGCCAATC AACAAGGTTC AAATAGACGT AAAAGTGCTG CCCTAAAATC TTGTCAGAAA

1141 AGCAGCAGTG CTGTAGGGAG GAATACTTCA GGTAGAAGAA ACAAGGCCTC TAGCAACAGC

1201 AAGCCAATTC ATGGCTCTAG TGATAACTCC CCAGAGTCAT ATCTTCCTAA GGAGGGTTTG

1261 GATGTTGAAG CACCTGACAA ACCCCTTTCT GAAAGGATCC AAAACTTGGA GAAAACTAGT

1321 CGACGAAAGG GAAGTGCAAG GAAGCTGGAA ATGGCAGGGA AACTATTTC AGATACTACA

1381 GAGAAGAATA GTGAGCCAAG AAGTAAGAGA GTCAGAAGAA TGTCTGACCA CGCTATAGCT

1441 AAACCGGTTG AAGTTCCTTC AGGATCTGGA AATGAAACAG AAATACCACA GCTTCACACC

1501 CTCACAAAAG GCAGCATTCA ACGCAAATCC TCCAACGCTA GAAGACATAG CAAAGTTTGT
```

-continued

```
1561 GGAGAACAGG AAGGTAAGAA TAAACTTGAG AACACGACAA TGACACCTAT TATTTTACAT

1621 GGGAAATGCC AAAATAAAGA GGCAGTATGT ACAGCTCCTT CAGTAAGGAC TGCATCTGTT

1681 AAGTACAAGC AAGCAAAATT TAGCGAACAA CCAGATTGTT TTGGAACGGA GAACTTTGGA

1741 AACCTTCAAG CATGCCCTGC ACGTAATGTT TTACTGAAGA AGTGTGAGGT ATCTACTTTG

1801 AAGGTTTCCT GTGCTTTCTG CCAGACCGAT GTCATCACAG AGGAGTCTGG AGAGATGGTT

1861 CATTATCAAA ATGGGAAGCA AGTCCCTGCA GAGTTCAATG GAGGAGCCAA TGTGGTGCAC

1921 TCTCACAAGA ACTGCCTTGA GTGGGCTCCT GATGTCTACT TCGAAGATGA TTCTGCCTTT

1981 AATCTTACAA CTGAATTGGC GAGAAGCAGA CGGATCAAAT GTGCTTGCTG TGGAATTAAA

2041 GGAGCTGCAC TTGGATGCTT TGAGATGAGT TGTCGGAGAA GTTTCCACTT CACCTGTGCT

2101 AAACTAATCC CAGAATGCAG ATGGGATAAT GAAAATTTTG TGATGTTATG CCCTCTACAT

2161 CGGTCTACAA AGTTACCCAA TGAAAATTCT GAACAGCAAA AGCAACCTAA AAGGAAAACA

2221 ACACTCAAAG GGTCATCTCA AATAGGATCC AATCAAGATT GTGGTAATAA CTGGAAATGG

2281 CCATCTGGAT CACCACAGAA GTGGGTTCTC TGCTGCTCAT CACTTTCTAG TTCTGAGAAG

2341 GGACTTGTAT CAGAATTTGC AAAGTTAGCT GGCGTGCCTA TTTCGGCAAC TTGGAGTCCA

2401 AATGTTACCC ATGTTATTGC ATCAACTGAT CTCTCTGGTG CTTGCAAACG GACGCTGAAG

2461 TTTCTCATGG CAATCTTGAA TGGCAGATGG ATTGTCTCCA TAGATTGGGT TAAAACTTGC

2521 ATGGAGTGCA TGGAACCAAT TGATGAGCAC AAATTTGAAG TCGCTACTGA TGTTCATGGG

2581 ATCACTGATG GTCCTAGGTT AGGAAGATGC AGGGTTATTG ACAGGCAACC TAAGCTGTTC

2641 GACAGCATGA GGTTCTACCT CCATGGGGAC TACACAAAAT CCTACAGAGG CTACCTGCAA

2701 GATCTCGTGG TTGCAGCAGG TGGAATAGTT CTTCAGAGGA AGCCCGTATC AAGAGACCAG

2761 CAAAAGCTTC TTGATGACAG CTCTGACCTC CTCATCGTTT ACAGCTTCGA GAATCAAGAT

2821 AGGGCAAAAT CCAAGGCCGA AACCAAGGCT GCTGATCGCA GGCAGGCTGA TGCTCAGGCT

2881 CTTGCTTGCG CTTCTGGAGG CAGAGTTGTG AGCAGTGCAT GGGTGATTGA CTCAATTGCA

2941 GCCTGCAATC TGCAACCTCT TTGA
//

SEQ ID NO:110: OsBRCA2 cDNA from Oryza sativa (cultivar Kaybonnet)
DEFINITION    OsBRCA2 cDNA 4500 bp
ORGANISM      Oryza sativa cv Kaybonnet
SOURCE        Oryza sativa cv. Kaybonnet Mitomycin-C treated calli
REFERENCE     1 (bases 1 to 4500)
BASE COUNT    1379 a    856 c    1102 g    1163 t
ORIGIN
    1 ATGGCTGACC TCTTCAACCA AGCTTTGGAT AAGCTGGTTG CTGCTGATGG AATGGCCGAA

61 GCGATCGAGG ATTCAGGGAA AGGTGCGGTG TTCTGCACTG GGTTGGGGGG ATCAGTTGCC

121 GTCAGCGAGA GGGCTGTAGA GAGGGCCAAG GCATTGGTTG GGGAGGTCGC GGAGGAGATA

181 AGTAATGAGA GGAGGCAACC ATTTGGTGAT GGTTCTAATT TGGAGTGCGG ATTGGGAGAA

241 AGTAATGTTT CATTTAAAGG TGGTGTACAT AAAGATAGTT TGTCTCCGAT GTTCCAAACC

301 GGATCGGGTA AAATGGTTTC GCTGAGCAAG GGCTCAATTC AGAAGGCTAG AGCTGTTTTA

361 GAAGGAAATG CCGAGAATTC TTCTGTCATT GCTGTACAGT CTATGTTCCA TACTGGATTG

421 GTTAGGCCAG ACCCAGTCAG CAGGAGCTCC ACTGATAATG CAATGACTGT TTTGGAGGGA

481 CAAACAAATC CAAACAAGG AGATGTGGCA GATGTGTATG ACAAGGAAAA TTTTCCATTG

541 TTCCAAACTG GTTCAGGTAA AGCTGTATCG GTCAGTGTAG CATCTATCCA GAAAGCTAAG

601 GCTGTCCTGG AGCAAAATAA TACAGAAAAC ACGGAAGATT TGGTAGGCC TGACCAATCT

661 CTGATTTTCC AAACTGGTTC GCGAAGACCA GTCTTGATCA GTGAAAGATC TAGCTCTGTG

721 GTGAAGGATG GAGGTGCTGA AAATATTGTG TTCCAAACGG GGTTAGGGAG GCCTGTTGTG
```

```
 781 GTGAGCCAGA CCTCAATTCA AAAGGCAAGG ACAGTATTAG ATCAAGAATG TGCCAAAAGA

841 AGTGGACATG GAGATACTAA TGTCTCCACC ACTACTTTTC AAACTGAAAC ACCAACGCCT

901 GTTCTGATGA GTGGTGGCCT GACTATGAAT GATAGATCTG TTACACCTGA GGGGGGTGTT

961 TCAATGCAAG GAAATTTTTT GGAGGCTGAT GGTCACTTGC CATTATTTCA AACTGGGTTA

1021 GGGAGGTCCA TTTCAGTAAG TAAAGGCTCA ATTAAGAGAG CAAGTGCACT TCTGGAGCCA

1081 AGGAACATTA CAAAAGAACT GGAAGATGAA GCTCACTCAG ATGATGGCTG TGCCACTCCA

1141 ATGTTCAAAA CTGGATCAGG AAGGTCTATC ACAGCAAGTG AAAATTCTAG AAAGAAAGCC

1201 CACGTTGTCT TAGAGGGCGA GGAACCAGTA AAAAATGTAA ATAATGACAC TGGAGAAGCC

1261 ATTGCTCCAA TGCTCCATGC TGGAATGCAG AAGTTTGCAC CCCAAAATAG AAACTCAAGT

1321 CATAAGGCGA TCACCCTCAT GGAGCAAGGG AGCTCTATGG AAGAAGACCG TGGAAACGAA

1381 CCACCAATGT TTCGAACTGG ATCTGGGAAG TCAGTCTTGA TTAGTCACAG CTCCGTGCAG

1441 AAGGCAAGGG CGGTTCTGGA GGAAGAAGGC AATATGAAGA AAGAAAATCA CAAACAACTT

1501 AGCAATGTGG ACAAATATAT TCCGATCTTT ACTTCACCTC TCAAGACAAG CTATGCAAGG

1561 ACTGTACATA TATCTTCAGT TGGTGTTTCT CGAGCTGCAA CTTTGTTGGG TTTGGAGGAG

1621 AATACCCTTT CAACACAACT TTTAGGACAT GTGGGTGATA AGCTAGGTAC AAAGATAACT

1681 GTTGAGAGGG AAAATTCAGA GCACCAGTTT GGTGTAGCAT CAGTCAGTGG AATTTCTGGT

1741 GGCTGCCCTA TAAGCTCTGG CCCAGCTGAA AACCAAGTAC TTATGGATCC ACATCAGCAT

1801 TTTGCATTTT CTAAAACAAC GTTCTCTGAT TCCAGTGAGC AAGCTATCAG GTTCAGCACT

1861 GCTGGCGGCA GAACAATGGC TATTCCTAGT GATGCACTTC AGCGTGCGAA AAATCTTCTG

1921 GGTGAATCGG ATTTAGAGGT TTCACCAAAT AATTTATTAG GCCACTCTTC AGCATCTGCT

1981 TGTAAAGAGA ATATACAAAA TTCAACTGGT CTGCGAAAAG AAGGTGAACC TGATTTATTG

2041 AAAAGTAGGG GGAACAGCAA AACTGAGCCA GCACAATTTT CCATTCCAGC AAAACCTGAT

2101 AGGAAGCACA CAGATTCCTT GGAATATGCT GTACCTGATG CCACTTTGGC TAACGGAAAC

2161 TCCGTCAGGC TTCATGCGGC AAGAGATTTT CATCCTATCA ATGAAATTCC AAAGATATCC

2221 AAGCCTTCTT CCAGATGTTC ATTTGGAACT GAAAATGCAA GTGACACTAA AGATAAGGCT

2281 CGAAGACTCC AAATGCCATC TGGACCATTG ATTGACATCA CTAATTACAT CGATACACAT

2341 TCTGTTAATA CTGACTACCT GGCCGGTGAG AAGAGAAGAT TTGGGGGAAG AAACTCCATA

2401 TCTCCCTTTA AACGTCCTCG TTCTTCCAGG TTCATCGCAC CTATCAACAT CAATAATCCA

2461 TCCCCTTCTG GAGTATCCAA ACTACCTATT CAGATTAATC CCTGTCGAAC AAAGCTATCT

2521 TCATGCTATC CTTTTCAACA TCAAAGAAAA TCGTGTGAAG AGTATTTTGG TGGTCCCCCA

2581 TGCTTCAAAT ATTTGACAGA AGATGTAACA GATGAAGTGA AGCTCATGGA TGCAAAAAAG

2641 GCTGAGAAGT ACAAGTTTAA AACAGATACT GGTGCAGAAG AATTTCAGAA GATGCTTCTT

2701 GCCTGTGGTG CTTCATTGAC ATACACAACT AAAGAATGGG TCAGCAACCA CTACAAATGG

2761 ATTGTTTGGA AGCTTGCTTC ATTGGAGAGA TGCTATCCAA CTAGAGCTGC TGGCAAATTC

2821 TTAAAAGTTG GTAATGTTTT GGAAGAGCTG AAGTACAGGT ATGACAGAGA AGTGAACAAT

2881 GGCCACCGCT CAGCCATAAA GAAAATTTTG GAAGGGAATG CTTCACCATC TTTGATGATG

2941 GTGCTGTGCA TTTCTGCTAT TTACTCTTGT CCTGACCTAA ACAACAGTAA GCCAGAGGAT

3001 GATAGGGCAC ATACAGACGA CGACAACAGT GAGAATAAAA GCTTGAGACC TGCTAAAAGG

3061 AACATGTCTA CAAAGATTGA ACTAACTGAT GGATGGTATT CTCTAGATGC GTCATTAGAT

3121 CTGGCACTTT TGGAGCAACT AGAGAAAAGA AAACTTTTTA TAGGACAGAA GCTTCGGATA
```

```
3181 TGGGGAGCTT CACTATGTGG GTGGGCTGGG CCTGTGTCAT TCATGAGGC ATCGGGTACC

3241 GTCAAATTAA TGATCCACAT AAATGGCACC TATCGTGCAA GATGGGATGA GACTTTGGGG

3301 TTATGCAAGC ATGCTGGAGT CCCACTGGCA TTCAAGTGCA TAAAAGCTTC AGGTGGCAGA

3361 GTTCCTAGGA CACTGGTTGG AGTTACAAGG ATTTATCCTG TTATGTACAG GGAGAGGTTT

3421 TCTGACGGTC GTTTTGTGGT GAGGTCTGAA AGGATGGAAA GAAAAGCACT ACAGCTGTAT

3481 CACCAGAGAG TGTCTAAGAT TGCAGAAGAC ATTCAGTCAG AACATGGAGA CACTGCGAC

3541 AACACTGATG ATAACGATGA AGGGGCAAAA ATATGCAAAA TGCTAGAGAG GGCAGCTGAG

3601 CCTGAAATTC TTATGTCCAG CATGAGTTCA GAGCAGCTGC TGTCTTTCTC ATATTATCAA

3661 GAAAAGCAAA AGATTGTCAG GCAAAATGAA GTAGCTAAGA AGGTTGAAAA TGCTCTTAAA

3721 GTTGCTGGGC TTAGTTCAAG AGATGTTACA CCATTTTTGA AAGTGAGGGT GACGGGCCTT

3781 ATCAGCAAAC ACTCCGCCAC AAAATCTGGC TGCAGGGAAG GGTTAATAAC AATTTGGAAC

3841 CCTACCGAGA AGCAAAAATC CGACCTGGTG GAGGGACAAA TTTATTCTGT CACAGGACTG

3901 TTGGCTTCAA GCTACTTTAC AGAAGTATCC TACTTGAGTG GTAGAGGATC ATCTACAGCA

3961 TGGACGCCTT TAGCAACCGC ACAGACTACA AATTTTGAAC CATTTTTCAC CCCTCGTAAA

4021 GCAGTTGAAT TGTCACATTT TGGTGAAGTG CCACTTACAA GCGAATTTGA CATTGCAGGT

4081 GTTATTTTGT ATGTTGGGAA TGTTTATTTA TTGAACAACC AGAATAGGCA GTGGCTCTTT

4141 TTGACAGATG GATCTAAATT TATCTCTGGA GAAAAGTATG AAGAGCAAGA TGACTGTCTT

4201 CTGGCAGTTA GCTTTTCTTC CAAACCCACT GGCGAGGATT CTGCATTCTT CAATTATGCC

4261 CTTTCTGGAC ATATAGTTGG TTTTAGTAAT CTGGTCAAGC GAGATAAAGA CCAGATGAGG

4321 CACGTGTGGG TAGCTGAGGC GACAGAGAGC TCCACCTATA GTCTCTCCCA CGAGATACCT

4381 AAAAAATCAC ATCTCAAAGA GGCTGCCACT TCTGCTGAAA AATGGGCTTC AAATTCTCAT

4441 CCTATGATTC AGCATCTGAA GGAAAGAGTT CTGCAAATAG TTGGTGACAG TGGTGGCTGA
//

SEQ ID NO:111: OsSPO11A cDNA from Oryza sativa (cultivar Kaybonnet)
DEFINITION      OsSPO11A cDNA 1329 bp
ORGANISM        Oryza sativa cv Kaybonnet
SOURCE          Young flower
AUTHORS         Qiudeng Que
CDS             1 . . . 1329
BASE COUNT       225 a    460 c    405 g    239 t
ORIGIN
    1 ATGTCGGAGA AGAAGCGCCG CGGCGGGGCA GGCGCGGGGG CCGCGTCGGG CTCCGCCTCC

61 AAGAAGCCGC GGGTCTCCAC GGCGGCGTCG TACGCCGAGT CGCTCCGCTC GAAGCTCCGC

121 CCCGACGCCT CCATCCTCGC CACCCTCCGC TCCCTGGCCT CCGCCTGCTC CAAACCCAAG

181 CCCGCGGGGT CGTCGTCGTC GTCGTCGTCC GCCTCGAAGG CGCTCGCAGC CGAGGACGAC

241 CCGGCCGCCA GCTACATCGT GGTGGCCGAC CAGGACTCCG CCTCCGTCAC CTCCCGCATC

301 AACCGCCTCG TGCTCGCCGC GGCGCGCAGC ATCCTGTCCG GCCGGGGCTT CTCCTTCGCG

361 GTGCCCTCCC GCGCCGCCTC CAACCAGGTC TACCTCCCGG ACCTCGACCG CATCGTGCTC

421 GTCCGCCGCG AGTCCGCCAG GCCCTTCGCC AACGTCGCCA CCGCGCGGAA GGCCACCATC

481 ACCGCGCGCG TCCTCTCCTT GGTCCACGCC GTCCTCCGCA GGGGGATCCA CGTCACCAAG

541 CGTGACCTCT TCTACACCGA CGTCAAGCTC TTCGGCGACC AGGCGCAGTC CGACGCCGTC

601 CTCGACGACG TCTCCTGTAT GCTCGGCTGC ACCCGCTCCT CCCTCCACGT CGTCGCGTCC

661 GAGAAGGGCG TCGTCGTCGG GCGCCTCACC TTCGCCGACG ACGGCGACCG GATCGACTGC

721 ACGCGCATGG GCGTCGGCGG GAAGGCCATC CCGCCCAACA TCGACAGGGT CTCAGGCATC

781 GAGAGCGACG CTCTCTTCAT CTTGCTGGTG GAGAAGGACG CCGCGTTCAT GCGTCTCGCC
```

```
 841 GAGGACCGGT TCTACAACCG CTTCCCGTGC ATCATCTTGA CGGCGAAGGG GCAGCCGGAT

901 GTCGCCACAC GGCTGTTCTT GCGGCGGCTT AAGGTGGAGC TGAAGCTGCC AGTGCTGGCA

961 TTGGTGGACT CCGACCCATA TGGGCTGAAG ATCTTGTCAG TGTACATGTG TGGTTCCAAG

1021 AACATGTCAT ATGACAGTGC CAACCTGACA CACCGGATA TCAAGTGGCT CGGAGTGCGG

1081 CCAAGCGATC TGGACAAGTA TCGGGTGCCG GAGCAGTGCC GGCTTCCGAT GACTGATCAC

1141 GATATCAAGG TGGGGAAGGA GCTGCTTGAG GAGGACTTTG TGAAGCAGAA TGAAGGATGG

1201 GTGAAGGAGC TGGAGACGAT GTTGCGGACG AGGCAGAAGG CTGAGATACA GGCTCTCAGT

1261 TCATTTGGTT TCCAGTATCT CACTGAGGTC TATCTACCTC TCAAGCTGCA GCAACAGGAC

1321 TGGATTTGA
//

SEQ ID NO:112: OsSPO11B gDNA from Oryza sativa (cultivar Kaybonnet)
DEFINITION    OsSpo11B gDNA 1456 bp
ORGANISM      Oryza sativa cv Kaybonnet
SOURCE        Oryza sativa cv. Kaybonnet calli
REFERENCE     1 (bases 1 to 1456)
CDS           1 . . . 1444
BASE COUNT    452 a    268 c    326 g    410 t
ORIGIN
    1 AGCAACCATG GATGATTCAA CGGATGACGA TTCGTATCAT CCAAGAAAAC ACTATGCTTA

61 TGATCGTCAG GTTTCTTCAA GCAGATGGCG TACCAGCCGC GAGTATATCA GAGGTCCCGG

121 CCCCGAAACT CATACTACTG AGAGTGCTCA AGATGGACAG GATCCACCTG CTGGAGTATA

181 TTCCTATGGT TATTTTTCTG GCAGTGGTAA TGATCCTCAA GTTCAAGGAC ACTTTGTTCC

241 GGAGATTCAA AAGTACAACC CTTACGTGAT TTTCAAAGGT GAACAACTCC CGGTTCCTAT

301 ATGGGAACTG CCAGAGGAGA AGGTCCAAGA TTTTCATGAT AGGTACTTTA TTGCAAAAGA

361 CAAGAGTCGA GTTGAAGCCA GGAAGACTCT GAATAGGTTG TTAGAGGGGA ACATCAATAC

421 AATTGAAAGG GGACATGGAT ATAAATTCAA TATTCCAAAA TATACAGATA ACATGGAGTT

481 TAATGAGGAA GTCAAGGTTT CTCTAGCAAA AGCAGGCAAG ACCATAAGCC GTTCCTTTTG

541 CAATGCGAAT CAGCGGGAAG TTGCATCTAG GACTGGCTAT ACCATTGATC TAATAGAACG

601 GACACTTGGG GCTGGATTGA ACATCTCGAA GAGAACTGTC TTATACACAA ACAAGGATCT

661 GTTTGGGGAT CAAAGTAAAT CAGATCAAGC GATCAATGAC ATCTGCGCTT TGACAAATAT

721 CAGAAGGGGC TCTTTGGGTA TAATAGCAGC TGAAAAAGGA ATTGTAGTTG GAAACATTTT

781 CCTGGAATTG ACAAATGGCA AATCGATTAG TTGTTCTATT GGAGTGCAGA TACCACACAG

841 GCTTGACCAG ATCAAAGATG TTTGTGTTGA ATAGGTTCA CGCAACATAG AGTATATTCT

901 TGTTGTGGAA AAGCATACAA TGTTGAATTA TCTACTAGAG ATGGACTATC ACACCAATAA

961 CAACTGTATA ATTCTGACAG GATGTGGCAT GCCAACCCTC CAAACAAGGG ATTTCCTCAG

1021 ATTCTTGAAA CAACGCACTG GACTACCTGT CTTTGGACTT TGTGATCCAG ATCCTGAAGG

1081 TATAAGTATT CTTGCTACGT ATGCTAGAGG GTCTTGCAAT TCAGCATATG ACAATTTCAA

1141 TATTTCCGTG CCATCTATTT GTTGGGTTGG ATTGTCATCC TCAGACATGA TAAAGTTGAA

1201 TTTGTCTGAG ACCAACTACT CACGTTTGTC TCGCGAGGAC AAAACTATGT TGAAGAACCT

1261 TTGGCAGGAC GATTTGTCCG ATGTATGGAA ACGCAGAATC GAAGAAATGA TAAGTTTTGA

1321 CAAGAAGGCC TCTTTTGAAG CTATTCATAG TTTGGGGTTT GATTATTTTG CAACCAATTT

1381 GCTTCCGGAT ATGATTAACA AAGTACGAGA AGGCTATGTT CAGGTATATT TCTCACTCCT

1441 ATAGCAACTT GTATTT
//
```

SEQ ID NO:113: OsRad54A protein sequence
LOCUS           OsRad54A protein 1187 amino acid residues
ORGANISM        Rice, Oryza sativa cv Kaybonnet
MEDDDDDQRLLHSLGVTSADIHDIERRIISQATTDPADSSGPTINGGHQPDDALAKLHHK

LRSVQIEIDAVASTIKGAKLKQPSGNKPHEHKGKDQPDHHGAGHLQQALAADRLTSLRKA

KAQIQKEILQSHLSPSASNRKDKMLAMLVQDEPRHKKPPVGPKNIVKRPMKTVTYDDDNN

FDAVLDGASAGFMETEREELIRKGLLTPFHKLKGFEKRVELPEPSHRQDDSAGQTEEAME

ASRIARVAQSLKQIAQNRPATKLLDSESLPKLDAPAAPFQRLGKPLKRPVSPSSDEQEKK

RPRNKTKRPLPGKKWRKANSIKESSLDDNDVGEAAVSVSDDDEDQVTEGSDELTDVTLEG

GLRIPGTLYTQLFDYQKVGVQWLWELHCQRAGGIIGDEMGLGKTVQVLSFLGSLHNSGLY

KPSIVVCPVTLLQQWRREASRWYPKFKVEILHDSANSSSKKSKRSSDSDSEASWDSDQEE

AVTCSKPAKKWDDLISRVVSSGSGLLLTTYEQLRILGEKLLDIEWGYAVLDEGHRIRNPN

AEITLVCKQLQTVHRIIMTGAPIQNKLSELWSLFDFVFPGKLGVLPVFEAEFSVPITVGG

YANATPLQVSTAYRCAVVLRDLVMPYLLRRMKADVNAQLPKKTEHVLFCSLTTEQRATYR

AFLASSEVEQIFDGNRNSLYGIDVLRKICNHPDLLEREHAAQNPDYGNPERSGKMKVVEQ

VLKVWKEQGHRVLLFTQTQQMLDIMGNFLTACEYQYRRMDGLTPAKQRMALIDEFNNTDE

IFIFILTTKVGGLGTNLTGANRIIIYDPDWNPSTDMQARERAWRIGQTRDVTVYRLITRG

TIEEKVYHRQVYKHFLTNKVLKDPQQRRFFKARDMKDLFTLQDDDNNGSTETSNIFSQLS

EDVNIGVPSDKQQDQLYAASATPTTSGTEPSSRHGQGKEDHCPDQADEECNILKSLFDA

QGIHSAINHDAIMNANDDQKLRLEAEATQVAQRAAEALRQSRMLRSHESFSVPTWTGRAG

AAGAPSSVRRKFGSTLNTQLVNSSQPSETSNGRGQSLQVGALNGKALSSAELLARIRGTR

EGAASDALEHQLNLGSASNHTSSSSGNGRASSSSTRSMIVQPEVLIRQLCTFIQQHGGSA

SSTSITEHFKNRILSKDMLLFKNLLKEIATLQRGANGATWVLKPDYQ
//

SEQ ID NO:114: OsRad54B Protein sequence
DEFINITION      OsRad54B protein 1148 amino acid residues
ORGANISM        Oryza sativa cv Kaybonnet
MRTSTTSDSPSPSPQNKASFNTSRGAAFRDEEPGAKDNEVEKRKPLILHLKKRSTKELST

DTTSSKSGLLGKSSEEKQEKHGSALKVKKHLHPMELSPKKYKNKKQHNHRDSKRSEAKKV

QYLASDVDSDSSMEPSTSLEHSESPPPKRKSLDGRTPASSTKKGKKKVKFIDKKHPENAV

HITEKEHGGAGDKITTQGDLQVDRILGCRLQTSQIISPAHASSEQIDMAPPSASGATEPS

QALSKGLHEEIQSSNSDTNVTEDACADELANDGGENNLDCSDAQKESNVRSHGHKESLNA

KEIMNTASACSADQIVTVKDAGAVQTYVTASVNGEYETVTDIPEEKNDTKHPVSKADTEV

HTKQEHTPDSKLHGKLENYKAKYGTGLINICKEQWCQPQRVIALRTSLDEIEEALIKWCA

LPYDECTWERLDEPTMVKYAHLVTQFKKFESQALDKDKGGSHAKPREHQEFNMLVEQPKE

LQGGMLFPHQLEALNWLRKCWYKSKNVILADEMGLGKTVSACAFLSSLCCEYKINLPCLV

LVPLSTMPNWMAEFASWAPHLNVVEYHGSARARSIIRQYEWHEGDASQMGKIKKSHKFNV

LLTTYEMVLVDAAYLRSVSWEVLIVDEGHRLKNSSSKLFSLLNTLSFQHRVLLTGTPLQN

NIGEMYNLLNFLQPASFPSLASFEEKFNDLTTTEKVEELKNLVAPHMLRRLKKDAMQNIP

PKTERMVPVELTSIQAEYYRAMLTKNYQVLRNIGKGGAHQSLLNIVMQLRKVCNHPYLIP

GTEPESGSPEFLHEMRIKASAKLTLLHSMLKILHKDGHRVLIFSQMTKLLDILEDYLTWE

FGPKTFERVDGSVSVAERQAAIARFNQDKSRFVFLLSTRSCGLGINLATADTVIIYDSDF

NPHADIQAMNRAHRIGQSNRLLVYRLVVRASVEERILHLAKKKLMLDQLFVNKSESQKEV

EDIIRWGTEELFRNSDVAVKDNNEASGAKNDVAEVEFKHKRKTGGLGDVYEDRGADGSAK

```
-continued
FNWDENAITKLLDRSNVPSTVAESTDGDLDNDMLGTVKSIDWNDELNDDPGATEDIPNID

NDGCEQASEAKQDAANRVEENEWDKLLRVRWEQYQTEEEASLGRGKRLRKAVSYRETFAT

IPNEALSE
//

SEQ ID NO:115: OsBRCA1 protein sequence
DEFINITION    OsBRCA1 protein 987 amino acid residues
ORGANISM      Oryza sativa cv Kaybonnet
MADTGSLEKMGRELKCPICLSLLSSAVSISCNHVFCNDCLTESMKSTSSCPVCKVPFRRR

EMRPAPHMDNLVSIFKSMEAAAGTNVVSTQEAPVVKLADGSDCVNSGKNSKRSQKSLTRK

RKVTSEMEKNTAKDATASASQPTTKPSFSTNKRIQVKPFPESETPIRAEKIMKPEEPKNN

LNNDVEGKNKAVASGQPGSPSLSPFFWLREQEEQEGCTAETLSETQSLDTPLRHNAPSFS

DIKDSDDEIPLNTTPNSKAAATELFDSEIFEWTQRPCSPELYSTPLKKQSKAKSKLDQIE

EKGDEEDVHIGGSFDKLGSASNAAQLVNTKATKQKRKKTSPSNKNSAKLSNRAEPCIKKS

DANQQGSNRRKSAALKSCQKSSSAVGRNTSGRRNKASSNSKPIHGSSDNSPESYLPKEGL

DVEAPDKPLSERIQNLEKTSRRKGSARKLEMAGKTISDTTEKNSEPRSKRVRRMSDHAIA

KPVEVPSGSGNETEIPQLHTLTKGSIQRKSSNARRHSKVCGEQEGKNKLENTTMTPIILH

GKCQNKEAVCTAPSVRTASVKYKQAKFSEQPDCFGTENFGNLQACPARNVLLKKCEVSTL

KVSCAFCQTDVITEESGEMVHYQNGKQVPAEFNGGANVVHSHKNCLEWAPDVYFEDDSAF

NLTTELARSRRIKCACCGIKGAALGCFEMSCRRSFHFTCAKLIPECRWDNENFVMLCPLH

RSTKLPNENSEQQKQPKRKTTLKGSSQIGSNQDCGNNWKWPSGSPQKWVLCCSSLSSSEK

GLVSEFAKLAGVPISATWSPNVTHVIASTDLSGACKRTLKFLMAILNGRWIVSIDWVKTC

MECMEPIDEHKFEVATDVHGITDGPRLGRCRVIDRQPKLFDSMRFYLHGDYTKSYRGYLQ

DLVVAAGGIVLQRKPVSRDQQKLLDDSSDLLIVYSFENQDRAKSKAETKAADRRQADAQA

LACASGGRVVSSAWVIDSIAACNLQPL
//

SEQ ID NO:116: OsBRCA2 Protein sequence
DEFINITION    OsBRCA2 protein 1499 amino acid resisues
ORGANISM      Oryza sativa cv Kaybonnet
MADLFNQALDKLVAADGMAEAIEDSGKGAVFCTGLGGSVAVSERAVERAKALVGEVAEEI

SNERRQPFGDGSNLECGLGESNVSFKGGVHKDSLPMFQTGSGKMVSLSKGSIQKARAVL

EGNAENSSVIAVQSMFHTGLVRPDPVSRSSTDNAMTVLEGQTNPKQGDVADVYDKENFPL

FQTGSGKAVSVSVASIQKAKAVLEQNNTENTEDFGRPDQSLIFQTGSRRPVLISERSSSV

VKDGGAENIVFQTGLGRPVVVSQTSIQKARTVLDQECAKRSGHGDTNVSTTTFQTETPTP

VLMSGGLTMNDRSVTPEGGVSMQGNFLEADGHLPLFQTGLGRSISVSKGSIKRASALLEP

RNITKELEDEAHSDDGCATPMFKTGSGRSITASENSRKKAHVVLEGEEPVKNVNNDTGEA

IAPMLHAGMQKFAPQNRNSSHKAITLMEQGSSMEEDRGNEPPMFRTGSGKSVLISHSSVQ

KARAVLEEEGNMKKENHKQLSNVDKYIPIFTSPLKTSYARTVHISSVGVSRAATLLGLEE

NTLSTQLLGHVGDKLGTKITVERENSEHQFGVASVSGISGGCPISSGPAENQVLMDPHQH

FAFSKTTFSDSSEQAIRFSTAGGRTMAIPSDALQRAKNLLGESDLEVSPNNLLGHSSASA

CKENIQNSTGLRKEGEPDLLKSRGNSKTEPAQFSIPAKPDRKHTDSLEYAVPDATLANGN

SVRLHAARDFHPINEIPKISKPSSRCSFGTENASDTKDKARRLQMPSGPLIDITNYIDTH

SVNTDYLAGEKRRFGGRNSISPFKRPRSSRFIAPININNPSPSGVSKLPIQINPCRTKLS

SCYPFQHQRKSCEEYFGGPPCFKYLTEDVTDEVKLMDAKKAEKYKFKTDTGAEEFQKMLL

ACGASLTYTTKEWVSNHYKWIVWKLASLERCYPTRAAGKFLKVGNVLEELKYRYDREVNN

GHRSAIKKILEGNASPSLMMVLCISAIYSCPDLNNSKPEDDRAHTDDDNSENKSLRPAKR
```

-continued

```
NMSTKIELTDGWYSLDASLDLALLEQLEKRKLFIGQKLRIWGASLCGWAGPVSFHEASGT

VKLMIHINGTYRARWDETLGLCKHAGVPLAFKCIKASGGRVPRTLVGVTRIYPVMYRERF

SDGRFVVRSERMERKALQLYHQRVSKIAEDIQSEHGEHCDNTDDNDEGAKICKMLERAAE

PEILMSSMSSEQLLSFSYYQEKQKIVRQNEVAKKVENALKVAGLSSRDVTPFLKVRVTGL

ISKHSATKSGCREGLITIWNPTEKQKSDLVEGQIYSVTGLLASSYFTEVSYLSGRGSSTA

WTPLATAQTTNFEPFFTPRKAVELSHFGEVPLTSEFDIAGVILYVGNVYLLNNQNRQWLF

LTDGSKFISGEKYEEQDDCLLAVSFSSKTTGEDSAFFNYALSGHIVGFSNLVKRDKDQMR

HVWVAEATESSTYSLSHEIPKKSHLKEAATSAEKWASNSHPMIQHLKERVLQIVGDSGG
//

SEQ ID NO:117: OsSPO11A protein
DEFINITION     OsSPO11A protein, 442 amino acids
ORGANISM       Oryza sativa cv Kaybonnet
MSEKKRRGGAGAGAASGSASKKPRVSTAASYAESLRSKLRPDASILATLRSLASACSKPK

PAGSSSSSSASKALAAEDDPAASYIVVADQDSASVTSRINRLVLAAARSILSGRGFSFA

VPSRAASNQVYLPDLDRIVLVRRESARPFANVATARKATITARVLSLVHAVLRRGIHVTK

RDLFYTDVKLFGDQAQSDAVLDDVSCMLGCTRSSLHVVASEKGVVVGRLTFADDGDRIDC

TRMGVGGKAIPPNIDRVSGIESDALFILLVEKDAAFMRLAEDRFYNRFPCIILTAKGQPD

VATRLFLRRLKVELKLPVLALVDSDPYGLKILSVYMCGSKNMSYDSANLTTPDIKWLGVR

PSDLDKYRVPEQCRLPMTDHDIKVGKELLEEDFVKQNEGWVKELETMLRTRQKAEIQALS

SFGFQYLTEVYLPLKLQQQDWI
//

SEQ ID NO:118: OsSPO11B
DEFINITION     OsSpo11B protein, 478 amino acid residues
ORGANISM       Oryza sativa cv Kaybonnet
MDDSTDDDSYHPRKHYAYDRQVSSSRWRTSREYIRGPGPETHTTESAQDGQDPPAGVYSY

GYFSGSGNDPQVQGHFVPEIQKYNPYVIFKGEQLPVPIWELPEEKVQDFHDRYFIAKDKS

RVEARKTLNRLLEGNINTIERGHGYKFNIPKYTDNMEFNEEVKVSLAKAGKTISRSFCNA

NQREVASRTGYTIDLIERTLGAGLNISKRTVLYTNKDLFGDQSKSDQAINDICALTNIRR

GSLGIIAAEKGIVVGNIFLELTNGKSISCSIGVQIPHRLDQIKDVCVEIGSRNIEYILVV

EKHTMLNYLLEMDYHTNNNCIILTGCGMPTLQTRDFLRFLKQRTGLPVFGLCDPDPEGIS

ILATYARGSCNSAYDNFNISVPSICWVGLSSSDMIKLNLSETNYSRLSREDKTMLKNLWQ

DDLSDVWKRRIEEMISFDKKASFEAIHSLGFDYFATNLLPDMINKVREGYVQVYFSLL
//
```

All publications, published patent documents, and patent applications cited in this specification are indicative of the level of skill in the art(s) to which the invention pertains. All publications, published patent documents, and patent applications cited herein are hereby incorporated by reference to the same extent as though each individual publication, published patent document, or patent application was specifically and individually indicated as being incorporated by reference.

The foregoing describes the invention with reference to various embodiments and examples. No particular embodiment, example, or element of a particular embodiment or example is to be construed as a critical, required, or essential element or feature of any or all of the claims. As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter. Further, no element described herein is required for the practice of the invention unless expressly described as "essential" or "critical."

It will be appreciated that various modifications and substitutions can be made to the disclosed embodiments without departing from the scope of the invention as set forth in the claims below. The specification, including the drawings and examples, is to be regarded in an illustrative manner, rather than a restrictive one, and all such modifications and substitutions are intended to be included within the scope of the invention. Accordingly, the scope of the invention should be determined by the appended claims and their legal equivalents, rather then by the examples given above. For example, the steps recited in any of the method or process claims may be executed in any feasible order and are not limited to an order presented in any of claims.

I claim:

1. A method for targeted nucleotide sequence stacking in a genome of a host cell, the method comprising the steps of:
   (a) providing a host cell having a genome with a target sequence comprising:
      (i) a first heterologous sequence of interest;
      (ii) a truncated functional sequence;
      (iii) a host homology sequence located between the first heterologous sequence of interest and the truncated functional sequence; and
      (iv) a target recombinase recognition site located between the first heterologous sequence of interest and the host homology sequence;
   (b) introducing into the host cell a donor sequence comprising:
      (i) a second heterologous sequence of interest or fragment thereof homologous to the first heterologous sequence of interest;
      (ii) a donor homology sequence homologous to the host homology sequence;
      (iii) a sequence that completes the truncated functional sequence, which is located between the second heterologous sequence of interest or fragment thereof and the donor homology sequence;
      (iv) a first donor recombinase recognition site located between the donor homology sequence and the sequence that completes the truncated functional sequence;
      (v) a second donor recombinase recognition site located between the sequence that completes the truncated functional sequence and the second heterologous sequence of interest or fragment thereof; and further wherein the first and second donor recombinase recognition sites are oriented relative to one another such that the sequence that completes the truncated functional sequence is excisable in the presence of a recombinase; and
      (vi) a third heterologous sequence of interest located between the second heterologous sequence of interest and the second donor recombinase recognition site;
   (c) obtaining in the host cell a first recombination product comprising:
      (i) a first recombined sequence resulting from homologous recombination of the first heterologous sequence of interest and the second heterologous sequence of interest;
      (ii) a second recombined sequence resulting from homologous recombination of the host homology sequence and the donor homology sequence;
      (iii) a restored functional sequence comprising the sequence that completes the truncated functional sequence, the truncated functional sequence, the second recombined sequence located between the sequence that completes the truncated functional sequence and the truncated functional sequence, and the first donor recombinase recognition site located between the sequence that completes the truncated functional sequence and the the second recombined sequence;
      (iv) the third heterologous sequence of interest located between the first recombined sequence and the restored functional sequence; and
      (v) the second donor recombinase recognition site located between the third heterologous sequence of interest and the sequence that completes the restored functional sequence.

2. The method of claim 1, wherein the host homology sequence comprises one or more introns.

3. The method of claim 1, wherein the second heterologous sequence of interest or fragment thereof comprises one or more introns.

4. The method of claim 1, wherein the restored functional sequence encodes a selectable marker.

5. The method of claim 4, wherein the selectable marker is selected from the group consisting of NPTII, HPT, PAT, BAR, EPSPS, GAT, HPPD, ALS, PPO, and PMI.

6. The method of claim 4, wherein the restored functional sequence encodes a visible marker.

7. The method of claim 6, wherein the visible marker is selected from the group consisting of GUS, LUC, GFP, RFP, and CFP.

8. The method of claim 1, further comprising selecting the first recombination product by identifying a product encoded by the restored functional sequence.

9. The method of claim 1, wherein the first donor recombinase recognition site is located within a transcribed region of the restored functional sequence.

10. The method of claim 1, wherein the target sequence further comprises a mega-endonuclease recognition site located between the first heterologous sequence of interest and the host homology sequence.

11. The method of claim 10, further comprising:
(d) introducing into the host cell a mega-endonuclease or a mega-endonuclease-encoding sequence.

12. The method of claim 11, wherein the mega-endonuclease is a naturally occurring mega-endonuclease.

13. The method of claim 12, wherein the mega-endonuclease is selected from the group consisting of I-Ceu, I-CreI, I-DmoI, I-SceI, I-SceII, I-PpoI, I-Tevl, PI-PfuI, PI-PspI, PI-Scel, and HO.

14. The method of claim 13, wherein the mega-endonuclease is I-CeuI encoded by the nucleotide sequence of SEQ ID NO:35.

15. The method of claim 11, wherein the mega-endonuclease is a mutant or heterologous mega-endonuclease.

16. The method of claim 1, wherein the donor sequence further comprises a mega-endonuclease recognition site located between the third heterologous sequence of interest and the second donor recombinase recognition site.

17. The method of claim 16, further comprising:
(d) introducing into the host cell a mega-endonuclease or a mega-endonuclease-encoding sequence.

18. The method of claim 17, wherein the mega-endonuclease is a naturally occurring mega-endonuclease.

19. The method of claim 18, wherein the mega-endonuclease is selected from the group consisting of I-Ceu, I-CreI, I-DmoI, I-SceI, I-SceII, I-PpoI, I-Tevl, PI-PfuI, PI-PspI, PI-Scel, and HO.

20. The method of claim 19, wherein the mega-endonuclease is I-CeuI encoded by the nucleotide sequence of SEQ ID NO:35.

21. The method of claim 17, wherein the mega-endonuclease is a mutant or heterologous mega-endonuclease.

22. The method of claim 1, further comprising:
(d) suppressing expression of RecQ in the host cell.

23. The method of claim 1, wherein the host cell is a plant cell.

24. The method of claim 23, wherein the plant cell is a monocotyledonous plant cell.

25. The method of claim 23, wherein the plant cell is a dicotyledonous plant cell.

26. The method of claim 23, further comprising growing the host cell comprising the first recombination product into a plant.

27. A plant comprising the first recombination product of claim 26.

28. The method of claim 1, further comprising:
(d) introducing into the host cell of step (c) a recombinase or recombinase coding sequence to thereby excise the sequence that completes the truncated functional sequence and to thereby yield a second recombination product comprising:
(i) the first recombined sequence;
(ii) the truncated functional sequence;
(iii) the second recombined sequence;
(iv) a regenerated target recombinase recognition site located between the first recombined sequence and the second recombined sequence; and
(v) the third heterologous sequence of interest located between the first recombined sequence and the regenerated target recombinase recognition site.

29. The method of claim 28, wherein the recombinase is selected from the group consisting of FLP, Cre, R recombinase, Gin, β recombinase, bacteriophage-λ integrase, HK022 integrase, ΦC31 integrase, and R4 integrase.

30. The method of claim 29, wherein the recombinase is encoded by the nucleotide sequence of SEQ ID NO:94.

31. The method of claim 28, wherein the recombinase is a mega-endonuclease.

32. The method of claim 28, wherein the host cell is a plant cell.

33. The method of claim 32, wherein the plant cell is a monocotyledonous plant cell.

34. The method of claim 32, wherein the plant cell is a dicotyledonous plant cell.

35. The method of claim 32, further comprising growing the host cell comprising the second recombination product into a plant.

36. A plant comprising the second recombination product of claim 35.

37. The method of claim 28, further comprising repeating steps (a)-(c) to thereby obtain a host cell comprising three heterologous sequences of interest.

38. The method of claim 28, further comprising repeating steps (a)-(d) one or more times to thereby obtain a host cell comprising greater than 2 heterologous sequences of interest.

39. A method for targeted nucleotide sequence stacking in a genome of a host cell, the method comprising the steps of:
(a) providing a host cell having a genome with a target sequence comprising:
(i) a first heterologous sequence of interest;
(ii) a truncated functional sequence;
(iii) a host homology sequence located between the first heterologous sequence of interest and the truncated functional sequence; and
(iv) a target recombinase recognition site located between the first heterologous sequence of interest and the host homology sequence;
(b) introducing into the host cell a donor sequence comprising:
(i) a second heterologous sequence of interest or fragment thereof homologous to the first heterologous sequence of interest;
(ii) a donor homology sequence homologous to the host homology sequence;
(iii) a sequence that completes the truncated functional sequence, which is located between the second heterologous sequence of interest or fragment thereof and the donor homology sequence;
(iv) a third heterologous sequence of interest located between the second heterologous sequence of interest or fragment thereof and the sequence that completes the truncated functional sequence;
(c) obtaining in the host cell a recombination product comprising:
(i) a first recombined sequence resulting from homologous recombination of the first heterologous sequence of interest and the second heterologous sequence of interest;
(ii) a second recombined sequence resulting from homologous recombination of the host homology sequence and the donor homology sequence;
(iii) a restored functional sequence comprising the sequence that completes the truncated functional sequence, the truncated functional sequence, and the second recombined sequence located between the sequence that completes the truncated functional sequence and the truncated functional sequence; and (iv) the third heterologous sequence of interest located between the first recombined sequence and the restored functional sequence.

40. The method of claim 39, wherein the host cell is a plant cell.

41. The method of claim 40, further comprising growing the host cell comprising the recombination product into a plant.

42. A plant comprising the recombination product of claim 41.

* * * * *

UNITED STATES PATENT AND TRADEMARK OFFICE
CERTIFICATE OF CORRECTION

| | | |
|---|---|---|
| PATENT NO. | : 7,935,862 B2 | Page 1 of 1 |
| APPLICATION NO. | : 11/001346 | |
| DATED | : May 3, 2011 | |
| INVENTOR(S) | : Que | |

It is certified that error appears in the above-identified patent and that said Letters Patent is hereby corrected as shown below:

At column 218, line 42, delete "the" in between "the" and "second"

At column 219, line 15, delete "I-Tev1" and insert therefor --I-TevI--

At column 219, lines 15-16, delete "PI-Sce1" and insert therefor --PI-SceI--

At column 219, line 34, delete "I-Tev1" and insert therefor --I-TevI--

At column 219, lines 34-35, delete "PI-Sce1" and insert therefor --PI-SceI--

Signed and Sealed this
Fifth Day of July, 2011

David J. Kappos
*Director of the United States Patent and Trademark Office*